US007015351B2

(12) United States Patent
Haupfear et al.

(10) Patent No.: US 7,015,351 B2
(45) Date of Patent: Mar. 21, 2006

(54) REACTION SYSTEMS FOR MAKING N-(PHOSPHONOMETHYL) GLYCINE COMPOUNDS

(75) Inventors: Eric Haupfear, O'Fallon, MO (US); Jerald D. Heise, St. Louis, MO (US); Amy L. Jorgenson, Richmond Heights, MO (US); Michael Rogers, Maryland Heights, MO (US); Henry Chien, St. Louis, MO (US); Eduardo Casanova, Chesterfield, MO (US); William Hooper, St. Louis, MO (US); William Scholle, St. Louis, MO (US); Juan Arhancet, Creve Coeur, MO (US); Mark A. Leiber, St. Peters, MO (US); Kent Wittler, deceased, late of Muscatine, IA (US); by Karen A. Wittler, legal representative, Muscatine, IA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/863,885

(22) Filed: May 22, 2001

(65) Prior Publication Data
US 2002/0068836 A1  Jun. 6, 2002

Related U.S. Application Data

(60) Provisional application No. 60/230,240, filed on Sep. 1, 2000, provisional application No. 60/220,140, filed on Jul. 21, 2000, provisional application No. 60/206,562, filed on May 22, 2000.

(51) Int. Cl.
 C07F 9/28  (2006.01)
(52) U.S. Cl. .................................................. 562/17
(58) Field of Classification Search ................... 562/17
 See application file for complete search history.

(56) References Cited

U.S. PATENT DOCUMENTS

| 3,288,846 A | 11/1966 | Irant et al. |
| 3,340,097 A | 9/1967 | Hess et al. |
| 3,799,758 A | 3/1974 | Franz |
| 3,835,000 A | 9/1974 | Frazier et al. |
| 3,927,080 A | 12/1975 | Gaertner |
| 3,950,402 A | 4/1976 | Franz |
| 3,954,848 A | 5/1976 | Franz |
| 3,956,370 A | 5/1976 | Parry et al. |
| 3,969,398 A | 7/1976 | Hershman |
| 3,977,860 A | 8/1976 | Franz |
| 4,026,950 A | 5/1977 | Le Ludec |
| 4,147,719 A | 4/1979 | Franz |
| 4,186,110 A | 1/1980 | Jalan et al. |
| 4,190,065 A | 2/1980 | Kulpa |
| 4,237,065 A | 12/1980 | Ehrat |
| 4,264,776 A | 4/1981 | Hershman et al. |
| 4,405,531 A | 9/1983 | Franz |
| 4,415,479 A | 11/1983 | Puskas et al. |
| 4,486,356 A | 12/1984 | Bakel |
| 4,486,359 A | 12/1984 | Brendel nee Hajnoczki et al. |
| 4,507,250 A | 3/1985 | Bakel |
| 4,525,294 A | 6/1985 | Sartori et al. |
| 4,579,689 A | 4/1986 | Hershman et al. |
| 4,582,650 A | 4/1986 | Felthouse |
| 4,624,937 A | 11/1986 | Chou |
| 4,654,429 A | 3/1987 | Balthazor et al. |
| 4,696,772 A | 9/1987 | Chou |
| 4,724,103 A | 2/1988 | Gentilcore |
| 4,775,498 A | 10/1988 | Gentilcore |
| 4,810,426 A | 3/1989 | Fields, Jr. et al. |
| 4,851,131 A | 7/1989 | Grabiak et al. |
| 4,921,991 A | 5/1990 | Lacroix |
| 4,978,649 A | 12/1990 | Surovikin et al. |
| 5,023,369 A | 6/1991 | Fields, Jr. |
| 5,077,431 A | 12/1991 | Fields, Jr. |
| 5,087,740 A | 2/1992 | Smith |
| 5,091,561 A | 2/1992 | Riley et al. |
| 5,095,140 A | 3/1992 | Fields, Jr. |
| 5,179,228 A | 1/1993 | Martin Ramon et al. |
| 5,202,479 A * | 4/1993 | Fujiwara et al. |

(Continued)

FOREIGN PATENT DOCUMENTS

AU  58285/80 B  11/1980

(Continued)

OTHER PUBLICATIONS

Affidavit of Thomas J. Richard, dated Jul. 16, 1985, filed Aug. 14, 1985 in the Austrailian Patent Office in connection with the Opposition of Australian Application No. 58285/80 (Acceptance No. 542716) by Monsato Company, including Exhibits TJR-1 through TJR-7.

(Continued)

Primary Examiner—Paul A. Zucker
(74) Attorney, Agent, or Firm—Senniger Powers; Joseph A. Schaper

(57)  ABSTRACT

This invention generally relates to liquid phase oxidation processes for making N-(phosphonomethyl)glycine (also known in the agricultural chemical industry as glyphosate) and related compounds. This invention, for example, particularly relates to processes wherein an N-(phosphonomethyl)iminodiacetic acid (NPMIDA) substrate (i.e., N-(phosphonomethyl)iminodiacetic acid, a salt of N-(phosphonomethyl)iminodiacetic acid, or an ester of N-(phosphonomethyl)iminodiacetic acid) is continuously oxidized to form an N-(phosphonomethyl)glycine product (i.e., N-(phosphonomethyl)glycine, a salt of N-(phosphonomethyl)glycine, or an ester of N-(phosphonomethyl)glycine). This invention also, for example, particularly relates to processes wherein an N-(phosphonomethyl)iminodiacetic acid substrate is oxidized to form an N-(phosphonomethyl) glycine product, which, in turn, is crystallized (at least in part) in an adiabatic crystallizer.

249 Claims, 35 Drawing Sheets

U.S. PATENT DOCUMENTS

| | | | |
|---|---|---|---|
| 5,292,936 A | 3/1994 | Franczyk | |
| 5,356,849 A | 10/1994 | Matviya et al. | |
| 5,367,112 A | 11/1994 | Franczyk | |
| 5,385,650 A | 1/1995 | Howarth et al. | |
| 5,410,085 A | 4/1995 | Birkenstock et al. | |
| 5,500,485 A | 3/1996 | Hodgkinson | |
| 5,543,383 A * | 8/1996 | Parker et al. ............... | 504/360 |
| 5,585,083 A | 12/1996 | Kielin et al. | |
| 5,602,276 A | 2/1997 | Stern et al. | |
| 5,606,107 A | 2/1997 | Smith | |
| 5,627,125 A | 5/1997 | Ebner et al. | |
| 5,650,537 A | 7/1997 | Beller et al. | |
| 5,658,839 A | 8/1997 | de Agudelo et al. | |
| 5,688,994 A | 11/1997 | Baysdon et al. | |
| 5,874,612 A | 2/1999 | Baysdon et al. | |
| 5,876,867 A | 3/1999 | Itoh et al. | |
| 5,882,619 A | 3/1999 | Heineke et al. | |
| 5,898,082 A | 4/1999 | Hodgkinson | |
| 5,948,938 A | 9/1999 | Nakano et al. | |
| 5,962,729 A | 10/1999 | Hayden et al. | |
| 5,994,269 A | 11/1999 | Bugg et al. | |
| 6,005,140 A | 12/1999 | Morgenstern et al. | |
| 6,130,351 A | 10/2000 | Stern et al. | |
| 6,232,494 B1 * | 5/2001 | Morgenstern et al. | |
| 6,365,772 B1 | 4/2002 | Cullen et al. | |
| 6,417,133 B1 * | 7/2002 | Ebner et al. | |
| 6,586,621 B1 | 7/2003 | Leiber et al. | |

FOREIGN PATENT DOCUMENTS

| | | |
|---|---|---|
| DE | 199 38 622 A1 | 2/2001 |
| EP | 0 019 445 A2 | 11/1980 |
| EP | 0 019 445 A3 | 11/1980 |
| EP | 0 055 695 A1 | 7/1982 |
| EP | 0 019 445 B1 | 5/1983 |
| EP | 0 098 034 A2 | 1/1984 |
| EP | 0 162 035 A2 | 11/1985 |
| EP | 0 164 923 A2 | 12/1985 |
| EP | 0 019 445 B2 | 10/1988 |
| EP | 0 323 821 A1 | 7/1989 |
| EP | 0 408 528 A1 | 1/1991 |
| EP | 0 413 672 A2 | 2/1991 |
| EP | 0 472 693 A1 | 3/1992 |
| EP | 0 595 124 A1 | 5/1994 |
| EP | 0 680 948 A1 | 11/1995 |
| EP | 0 801 978 A1 | 10/1997 |
| EP | 0 806 428 A1 | 11/1997 |
| GB | 1 601 715 | 11/1981 |
| GB | 2 224 505 A | 5/1990 |
| WO | WO 96/19485 | 6/1996 |
| WO | WO 96/38455 | 12/1996 |
| WO | WO 96/40592 | 12/1996 |
| WO | WO 97/05149 | 2/1997 |
| WO | WO 99/43430 | 9/1999 |
| WO | WO 00/01707 | 1/2000 |
| WO | WO 01/60830 A1 | 8/2001 |
| WO | WO 01/66508 A2 | 9/2001 |
| WO | WO 99/43430 A1 | 10/2001 |

OTHER PUBLICATIONS

Declaration of Dr. Peter Hajdu, dated May 28, 1986, filed in the Australian Patent Office in connection with the Opposition of Australian Application No. 58285/80 (Acceptance No. 542716) by Monsanto Company, including Exhibits PH1 through PH5.

International Search Report (Form PCT/ISA/210) for International Application No. PCT/US 01/10826, dated Jan. 25, 2002, pp. 1-3 and 1-4.

Andrew, M.R. et al., "The Characterization of Pt/Sn Catalyst for the Electrochemical Oxidation of Methanol,", *Journal of Applied Electrochemistry*, 6, pp. 99-106, 1976.

Anonymous, "Recycle Process", *Research Disclosure*, Dec. 1997, 942, No. 4.

Aricò, A.S. et al., "Methanol Oxidation on Carbon-Supported Pt-Sn Electrodes in Silicotungstic Acid", *Electrochimica Acta.*, 1994, pp. 691-700, vol. 39, No. 5, Elsevier Science Ltd., Great Britain.

Balakrishnan, Krishnan et al., "Chemisorption and XPS Study of Bimetallin Pt-Sn/Al$_2$O$_3$ Catalysts", *Journal of Catalysis*, 1991, pp. 287-306, vol. 127, Academic Press, Inc.

Burch, R., "The Oxidation State of Tin and the Interaction between Platinum and Tin", *Journal of Catalysis*, 1981, pp. 348-359, Academic Press, Inc.

Cameron, D.S. et al., "Carbons as Supports for Precious Metal Catalysts", *Catalysis Today*, 1990, pp. 113-137, vol. 7, Elsevier Science Publishers B.V., Amsterdam, The Netherlands.

Campbell, Stephan A. et al., "Effect of Bi and Sn Adatoms on Formic Acid and Methanol Oxidation at Well Defined Platinum Surfaces", *Journal of Chemical Society Faraday Trans.*, 1992, pp. 833-841, vol. 88, No. 6.

Cathro, K.J., "The Oxidation of Water-Soluble Organic Fuels Using Platinum-Tin Catalysts", *J. Electrochem. Soc.: Electrochemical Technology*, 1969, pp. 1608-1611, vol. 116, No. 11.

Coloma, F. et al., "Heat-Treated Carbon Blacks as Supports for Platinum Catalysts", *Journal of Catalysis*, 1995, pp. 299-305, vol. 154, Academic Press, Inc.

Coloma, F. et al., "Preparation of Platinum Supported on Pregraphitized Carbon Blacks", *Langmuir*, 1994, pp. 750-755, vol. 10, No. 3, American Chemical Society.

Dubinn, M.M., "Microporous Structures of Carbonaceous Adsorbents", *Carbon*, 1982, pp. 195-200, vol. 20, No. 3, Pergamon Press Ltd., Great Britain.

Franklin, Thomas C., et al., "The Effect of Anionic Poisons on the Catalytic Oxidationof Formaldehyde on Platinum", *Journal of Catalysis*, 1976, vol. 42, No. 3.

Franz, J.E. et al., "Glyphosate: A Unique Global Herbicide", Chapter 8 —Methods of Preparing Glyphosate, 1997, pp. 233-262, American Chemical Society, New York, NY.

Gallezot, Pierre, et al., "Catalytic Oxidations with Air for Clean and Selective Transformations of Polyols", *Catalysis of Organic Reactions*, 1994, pp. 331-340.

Gökağaç, Gülsün et al., "Characterisation of Carbon-supported Pt-Sn Bimetallic Catalysts for the Electrochemical Oxidation of Methanol", *Journal of Chemical Society Faraday Trans.*, 1993, pp. 151-157, vol. 89, No. 1.

Kimura, Hiroshi et al., " Palladium Based Multi-Component Catalytic Systems for the Alcohol to Carboxylate Oxidation Reaction", *Applied Catalysis A: General*, 1993, pp. 143-169, vol. 95, Elsevier Science Publishers B.V., Amsterdam.

Kimura, Hiroshi, "Selective Oxidation of Glycerol on a Platinum-Bismuth Catalyst by Using a Fixed Bed Reactor", *Applied Catalysis A: General*, 1993, pp. 147-158, vol. 105, Elsevier Science Publishers B.V., Amsterdam.

Kim, Kyong Tae et al., "Preparation of Carbon-Supported Platinum Catalysts: Absorption Mechanism of Anionic Platinum Precursor Onto Carbon Support", *Carbon*, 1992, pp. 467-475, vol. 30, No. 3, Pergamon Press Ltd., Great Britain.

Kim, Kyong Tae et al., "Surface and Catalytic Properties of Iron-Platinum/Carbon Electrocatalysts for Cathodic Oxygen Reduction in PAFC", *J. Electrochem. Soc.*, 1993, pp. 31-36, vol. 140, No. 1, The Electrochemical Society, Inc.

Lide, David R. (Editor-in-Chief), "CRC Handbook of Chemistry and Physics", *CRC Press LLC*, 1998-1999, pp. 10-175 and 10-177, 79th Edition, CRC Press, Boca Raton, FL.

Luk'Yanova, Z.V. et al., "Determination of the Surface Area of Platinum in Absorption Catalysts from the Amount of 'Soluble' Platinum", *Russian Journal of Physical Chemistry*, 1979, pp. 225-227, vol. 53, No. 2.

Maier, Ludwig, "Organic Phosphorous Compounds 95. A Simple Method for the Preparation of N-Dihydroxyphosphonylmethyl-Glycine (Glyphosate)", *Phosphorous, Sulfur, and Silicon*, 1991, pp. 65-67, vol. 61, Gordon and Breach Science Publishers S.A., United Kingdom.

Mallat, T. et al., "Preparation of Promoted Platinum Catalysts of Designed Geometry and the Role of Promoters in the Liquid-Phase Oxidation of 1-Methoxy-2-Propanol", *Journal of Catalysis*, 1993, pp. 237-253, vol. 142, Academic Press, Inc.

Margitfalvi, J. et al., "Supported Bimetallic Catalysts Prepared by Controlled Surface Reactions", pp. 373-409, Chapter 11.

Merlen, E. et al., "Characterization of Bimetallic Pt-Sn/$Al_2O_3$ Catalysts: Relationship between Particle Size and Structure", *Journal of Catalysis*, 1996, pp. 178-188, vol. 159, Academic Press, Inc.

Perry, Robert H. (editor), "Crystallization Equipment", *Chemical Engineers' Handbook Fifth Edition*, pp. 19-26 to 19-33.

Ponec, Vladimir et al., "Catalysis By Metals and Alloys", Chapter 7—Preparation and Characterization of Metal and Alloy Catalysts, *Studies in Surface Science and Catalysis*, 1995, pp. 299-391, vol. 95, Elsevier Science B.V. Amsterdam.

Prado-Burguete, C et al., "Effect of Carbon Support and Mean Pt. Particle Size on Hydrogen Chemisorption by Carbon-Supported Pt Catalysts", *Journal of Catalysis*, 1991, pp. 397-404, vol. 128, Academic Press, Inc.

Prado-Burguete, C. et al., "The Effect of Oxygen Surface Groups of the Support on Platinum Dispersion in Pt/Carbon Catalysts", *Journal of Catalysis*, 1989, pp. 98-106, vol. 115, Academic Press, Inc.

Riley, Dennis P. et al., "Homogeneous Catalysts for Selective Molecular Oxygen Driven Oxidative Decarboxylations", *J. Am. Chem. Soc.*, 1991, pp. 3371-3378, vol. 113, American Chemical Society.

Riley, Dennis P. et al., "Vanadium (IV, V) Salts as Homogeneous Catalysts for the Oxygen Oxidation of N-)Phosphonomethyl)iminodiacetic Acid to N-(Phosphonomethyl)glycine", *Inorg. Chem.*, 1991, pp. 4191-4197, vol. 30, American Chemical Society.

Rodriguez-Reinoso, F. et al., "Platinum Catalysts Supported on Activated Carbons", *Journal of Catalysis*, 1986, pp. 171-183, vol. 99.

Shekhobalova, V.I., "Effect of Small Additions of KI on the Properties of Pt Adsorption Catalysts", *Russian Journal of Physical Chemistry*, 1984, pp. 1759-1760, vol. 58, No. 11.

Shekhobalova, V.I. et al., "Deactivation Mechanism of Platinum Catalysts During the Liquid-phase Decomposition of Hydrogen Peroxide", *Russian Journal of Physical Chemistry*, 1979, pp. 1308-1309, vol. 53, No. 9.

Shekhobalova, V.I. et al., "Relationship between the Shape of the Kinetic Curves for the Catalytic Decomposition of Hydrogen Peroxide and the Amount of 'Soluble' Metal in the Catalyst", *Russian Journal of Physical Chemistry*, 1979, pp. 917-918, vol. 53, no. 6.

van Dam, H.E. et al., "Preparation of Platinum on Activated Carbon", *Journal of Catalysis*, 1991, pp. 335-349, vol. 131, Academic Press, Inc.

van Dierendonck, Laurent L. et al., "Loop Venturi Reactor-A Feasible Alternative to Stirred Tank Reactors?", *Ind. Eng. Chem. Res.*, 1998, pp. 734-738, vol. 37, American Chemical Society.

Vértes, Cs. et al., "Mössbauer Spectroscopy Studies of Sn-Pt/$Al_2O_3$ Catalysts Prepared by Controlled Surface Reactions", *Applied Catalysis*, 1991, pp. 149-159, vol. 68, Elsevier Science Publishers B.V., Amsterdam.

Watanabe, M. et al., "Electrocatalysis by AD-Atoms—Part XIII, Preparation of AD-Electrodes with Tin AD-Atoms for Methanol, Formaldehyde and Formic Acid Fuel Cells" *J. Electroanal Chem.*, 1985, pp. 367-375, vol. 191, Elsevier Sequoia S.A., Lausanne, The Netherlands.

Disclosed Anonymously, "40466 Recycle Process", *Research Disclosure*, Dec. 1997, pp. 4, 942/No. 404, Kenneth Mason Publications, Ltd., Hampshire, England.

* cited by examiner

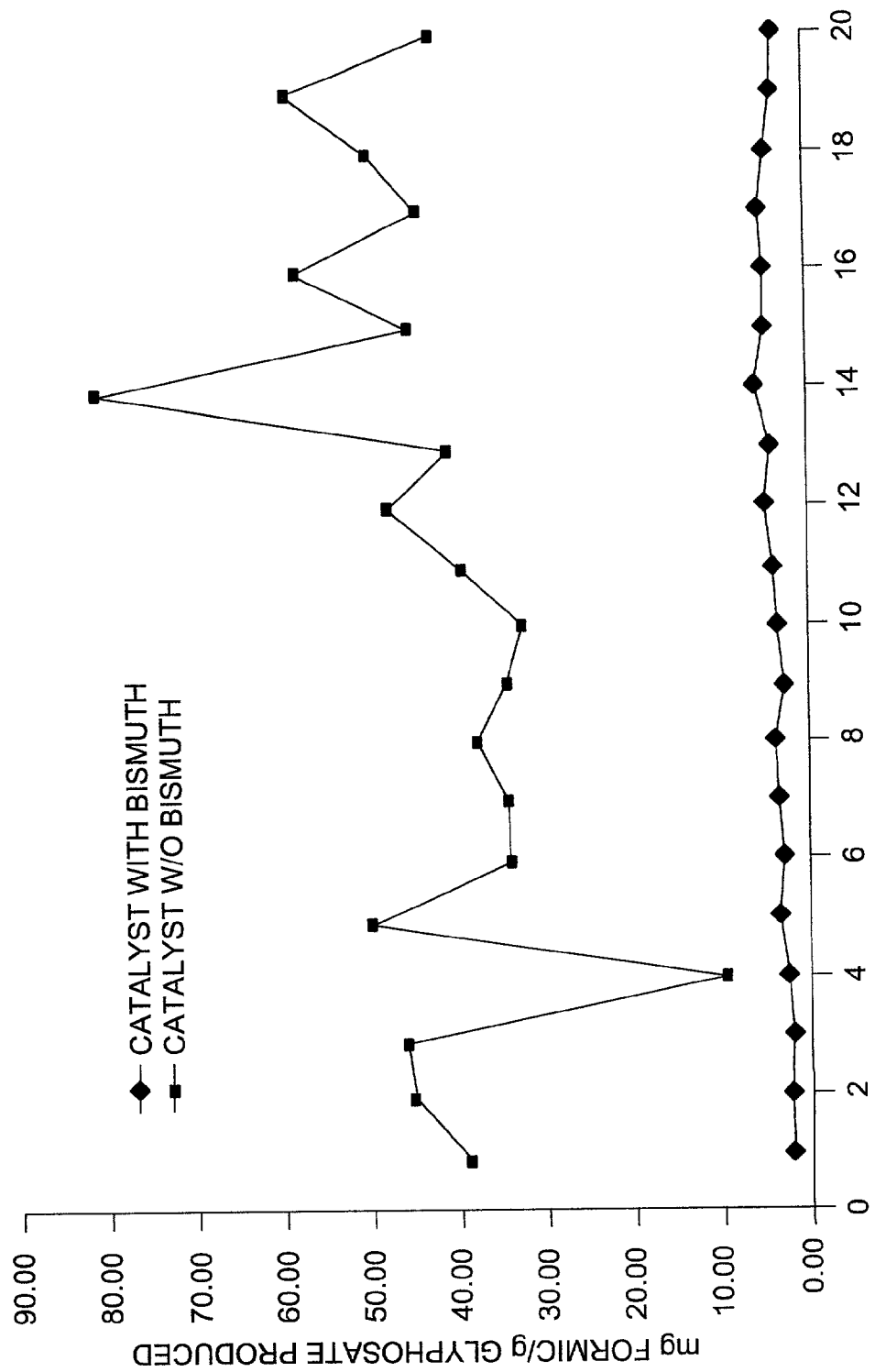

Block Flow Diagram

Block Flow Diagram

Glyphosate Slurry

REACTION SYSTEMS FOR MAKING N-(PHOSPHONOMETHYL) GLYCINE COMPOUNDS

This application claims the benefit of U.S. provisional application Ser. No. 60/206,562, filed May 22, 2000, U.S. provisional application Ser. No. 60/220,140, filed Jul. 21, 2000, and U.S. provisional application Ser. No. 60/230,240, filed Sep. 1, 2000, the entire disclosures of which are incorporated herein by reference.

FIELD OF THE INVENTION

This invention generally relates to liquid phase oxidation processes for making N-(phosphonomethyl)glycine (also known in the agricultural chemical industry as glyphosate) and related compounds. This invention, for example, particularly relates to processes wherein an N-(phosphonomethyl)iminodiacetic acid (NPMIDA) substrate (i.e., N-(phosphonomethyl)iminodiacetic acid, a salt of N-(phosphonomethyl)iminodiacetic acid, or an ester of N-(phosphonomethyl)iminodiacetic acid) is continuously oxidized to form an N-(phosphonomethyl)glycine product (i.e., N-(phosphonomethyl)glycine, a salt of N-(phosphonomethyl)glycine, or an ester of N-(phosphonomethyl)glycine). This invention also, for example, particularly relates to processes wherein an N-(phosphonomethyl)iminodiacetic acid substrate is oxidized to form an N-(phosphonomethyl) glycine product, which, in turn, is crystallized (at least in part) in an adiabatic crystallizer.

BACKGROUND OF THE INVENTION

N-(phosphonomethyl)glycine is described by Franz in U.S. Pat. No. 3,799,758. N-(phosphonomethyl)glycine and its salts are conveniently applied as a post-emergent herbicide in an aqueous formulation. It is a highly effective and commercially important broad-spectrum herbicide useful in killing or controlling the growth of a wide variety of plants, including germinating seeds, emerging seedlings, maturing and established woody and herbaceous vegetation, and aquatic plants.

One of the more widely accepted methods of making N-(phosphonomethyl)glycine compounds comprises oxidatively cleaving a carboxymethyl substituent from an N-(phosphonomethyl)iminodiacetic acid substrate. Over the years, a wide variety of methods have been disclosed for conducting this oxidation. See generally, Franz, et al., *Glyphosate: A Unique Global Herbicide* (ACS Monograph 189, 1997) at pp. 233–62 (and references cited therein); Franz (U.S. Pat. No. 3,950,402); Hershman (U.S. Pat. No. 3,969,398); Chou (U.S. Pat. No. 4,624,937); Chou (U.S. Pat. No. 4,696,772); Ramon et al. (U.S. Pat. No. 5,179,228); Felthouse (U.S. Pat. No. 4,582,650); Siebenhaar et al. (PCT/EP99/04587); and Ebner et al. (International Publication No. WO 99/43430). Although many of these processes produce suitable yields of various N-(phosphonomethyl)glycine products, a need continues to exist for an improved process for oxidizing N-(phosphonomethyl)iminodiacetic acid substrates. Desirable improvements include increased throughput, reduced cost per unit of N-(phosphonomethyl)glycine product, and reduced concentrations of undesirable by-products (e.g., formaldehyde, formic acid, N-methyl-N-(phosphonomethyl)glycine (NMG), and aminomethylphosphonic acid (AMPA)).

SUMMARY OF THE INVENTION

This invention provides, in part, for economical processes for oxidizing N-(phosphonomethyl)iminodiacetic acid, salts of N-(phosphonomethyl)iminodiacetic acid, and esters of N-(phosphonomethyl)iminodiacetic acid to form N-(phosphonomethyl)glycine, salts of N-(phosphonomethyl)glycine, and esters of N-(phosphonomethyl)glycine. This invention also provides effective methods for purifying and/or concentrating the N-(phosphonomethyl)glycine product obtained in the oxidation reaction mixture.

Briefly, therefore, the present invention is directed to a process for making an N-(phosphonomethyl)glycine product. The process comprises introducing an aqueous feed stream comprising an N-(phosphonomethyl)iminodiacetic acid substrate into an oxidation reactor system in which the N-(phosphonomethyl)iminodiacetic acid substrate is oxidized in the presence of an oxidation catalyst to produce a reaction product solution comprising N-(phosphonomethyl)glycine product. The reaction product solution is divided into plural fractions comprising a primary fraction and a secondary fraction. N-(phosphonomethyl)glycine product crystals are precipitated from the primary fraction to produce a primary product slurry comprising precipitated N-(phosphonomethyl)glycine product crystals and a primary mother liquor, while N-(phosphonomethyl)glycine product crystals are also precipitated from an aqueous secondary crystallization feed mixture comprising N-(phosphonomethyl)glycine product contained in the secondary fraction to produce a secondary product slurry comprising precipitated N-(phosphonomethyl)glycine product crystals and a secondary mother liquor.

In another embodiment, the process for making an N-(phosphonomethyl)glycine product comprises introducing an aqueous feed stream comprising an N-(phosphonomethyl)iminodiacetic acid substrate into an oxidation reactor system and oxidizing the N-(phosphonomethyl)iminodiacetic acid substrate in the oxidation reactor system in the presence of an oxidation catalyst to produce a reaction product solution containing N-(phosphonomethyl)glycine product. N-(phosphonomethyl)glycine product crystals are precipitated from the reaction product solution to produce a primary product slurry comprising precipitated N-(phosphonomethyl)glycine product crystals and a primary mother liquor. Water is then evaporated from the primary mother liquor to thereby precipitate additional N-(phosphonomethyl)glycine product crystals and produce a secondary mother liquor.

In another embodiment, the process for making an N-(phosphonomethyl)glycine product comprises introducing an aqueous feed stream comprising an N-(phosphonomethyl)iminodiacetic acid substrate into a primary oxidation reactor system comprising one or more oxidation reaction zones. The N-(phosphonomethyl)iminodiacetic acid substrate is oxidized in the primary oxidation reactor system to produce a reaction product solution comprising N-(phosphonomethyl)glycine product and unreacted N-(phosphonomethyl)iminodiacetic acid substrate. The reaction product solution is divided into plural fractions comprising a primary fraction and a secondary oxidation reactor feed fraction. N-(phosphonomethyl)glycine product crystals are precipitated from the primary fraction to produce a primary product slurry comprising precipitated N-(phosphonomethyl)glycine product crystals and a primary mother liquor. The secondary oxidation reactor feed fraction is introduced into a secondary oxidation reactor system comprising one or more oxidation reaction zones. The N-(phosphonomethyl)iminodiacetic acid substrate is oxidized in the secondary oxidation reactor system to produce a secondary oxidation reactor effluent comprising N-(phosphonomethyl)glycine product. Thereafter, N-(phosphonomethyl)glycine product crystals are precipitated from the secondary oxidation reactor effluent to produce a secondary product slurry comprising precipitated N-(phosphonomethyl)glycine product crystals and a secondary mother liquor.

The present invention is also directed to a process for preparing an N-(phosphonomethyl)glycine product by oxidizing an N-(phosphonomethyl)iminodiacetic acid substrate. The process comprises introducing the N-(phosphonomethyl)iminodiacetic acid substrate into a liquid reaction medium comprising the N-(phosphonomethyl)glycine product within an oxidation reaction zone. The oxidation reaction zone is substantially back-mixed in the liquid phase and contains a catalyst for the oxidation reaction in contact with the liquid reaction medium. An oxidizing agent is also introduced into the oxidation reaction zone wherein the N-(phosphonomethyl)iminodiacetic acid substrate is continuously oxidized to form the N-(phosphonomethyl)glycine product. A reaction mixture effluent comprising the N-(phosphonomethyl)glycine product is continuously withdrawn from the oxidation reaction zone.

In another embodiment, the process comprises introducing the N-(phosphonomethyl)iminodiacetic acid substrate into a liquid reaction medium within an oxidation reaction zone. The liquid reaction medium comprises the N-(phosphonomethyl)glycine product and has a particulate heterogeneous catalyst for the oxidation reaction suspended therein. An oxidizing agent is also introduced into the oxidation reaction zone wherein the N-(phosphonomethyl)iminodiacetic acid substrate is continuously oxidized in the liquid reaction medium to form the N-(phosphonomethyl)glycine product. A reaction mixture effluent comprising the N-(phosphonomethyl)glycine product is continuously withdrawn from said oxidation reaction zone. The particulate catalyst is continuously separated from the reaction mixture effluent to form a catalyst recycle stream comprising the separated catalyst. At least a portion of the particulate catalyst contained in the catalyst recycle stream is introduced into said oxidation reaction zone.

The present invention is further directed to a continuous process for preparing an N-(phosphonomethyl)glycine product by oxidizing an N-(phosphonomethyl)iminodiacetic acid substrate in a reactor system. The process comprises introducing an aqueous feed stream comprising the N-(phosphonomethyl)iminodiacetic acid substrate and an oxidizing agent into a first oxidation reaction zone. The N-(phosphonomethyl)iminodiacetic acid substrate is continuously oxidized in the first oxidation reaction zone to form the N-(phosphonomethyl)glycine product. An intermediate reaction mixture effluent comprising the N-(phosphonomethyl)glycine product and unreacted N-(phosphonomethyl)iminodiacetic acid substrate is continuously withdrawn from the first oxidation reaction zone. An intermediate aqueous feed stream comprising N-(phosphonomethyl)glycine product and unreacted N-(phosphonomethyl)iminodiacetic acid substrate obtained in the intermediate reaction mixture effluent is continuously introduced into a second oxidation reaction zone along with an oxidizing agent wherein N-(phosphonomethyl)iminodiacetic acid substrate is continuously oxidized to form additional N-(phosphonomethyl)glycine product. A reaction mixture effluent comprising the N-(phosphonomethyl)glycine product is continuously withdrawn from the second oxidation reaction zone.

The present invention is also directed to processes for concentrating and recovering the N-(phosphonomethyl)glycine product. In one embodiment, a process for removing water from an aqueous starting solution comprising N-(phosphonomethyl)glycine product and crystallizing N-(phosphonomethyl)glycine product therefrom is provided. The process comprises introducing an aqueous evaporation feed mixture comprising the aqueous starting solution into an evaporation zone. Water is evaporated from the feed mixture in the evaporation zone in the presence of solid particulate N-(phosphonomethyl)glycine product, thereby producing a vapor phase comprising water vapor, precipitating N-(phosphonomethyl)glycine product from the aqueous liquid phase, and producing an evaporation product comprising N-(phosphonomethyl)glycine product solids and a mother liquor that is substantially saturated or supersaturated in N-(phosphonomethyl)glycine product. A ratio of particulate N-(phosphonomethyl)glycine product solids to mother liquor is maintained in the evaporation zone which exceeds the ratio of N-(phosphonomethyl)glycine product solids incrementally produced by the effects of evaporation to mother liquor incrementally produced thereby.

In a further embodiment, the process comprises introducing an evaporation feed mixture comprising the aqueous starting solution into a vapor/liquid separation zone wherein the pressure is below the vapor pressure of the mixture. This allows water to flash from the evaporation feed mixture, producing a vapor phase comprising water vapor and increasing the concentration of N-(phosphonomethyl)glycine product in the remaining liquid phase to a concentration in excess of the solubility of N-(phosphonomethyl)glycine product. As a result, N-(phosphonomethyl)glycine product precipitates from the liquid phase to produce a first slurry stream comprising particulate N-(phosphonomethyl)glycine product in a saturated or supersaturated mother liquor. The vapor phase is separated from the first slurry stream and the first slurry stream is introduced into a decantation zone in which a supernatant liquid comprising a fraction of the mother liquor is separated from a second slurry stream comprising precipitated N-(phosphonomethyl)glycine product and mother liquor. The decantation zone has an inlet for the first slurry, a decantation liquid exit for the supernatant liquid spaced above the inlet, and an exit for the second slurry vertically spaced above the inlet but below the supernatant liquid exit. The relative rates at which the first slurry is introduced into the decantation zone, the second slurry is drawn off through the second slurry exit and the supernatant liquid is drawn off through the decantation liquid exit are maintained such that the upward flow velocity in a lower region of the decantation zone below the second slurry exit is sufficient to maintain precipitated N-(phosphonomethyl) glycine product in suspension (i.e., entrained) in the liquid phase while the upward flow velocity in an upper region of the decantation zone above the second slurry exit is below the sedimentation velocity of at least 80% by weight of the N-(phosphonomethyl)glycine product particles in the lower region.

In a still further embodiment, the process comprises introducing an aqueous evaporation feed mixture comprising the aqueous starting solution into an evaporation zone. Water is evaporated from the feed mixture in the evaporation zone in the presence of solid particulate N-(phosphonomethyl)glycine product, thereby producing a vapor phase comprising water vapor, precipitating N-(phosphonomethyl) glycine product from the aqueous liquid phase, and producing an evaporation product comprising N-(phosphonomethyl)glycine product solids and a mother liquor that is substantially saturated or supersaturated in N-(phosphonomethyl)glycine product. The evaporation product is divided to provide an N-(phosphonomethyl)glycine product solids fraction that is relatively depleted in mother liquor and a mother liquor fraction that is relatively depleted in N-(phosphonomethyl)glycine product solids. A ratio of particulate N-(phosphonomethyl)glycine product solids to mother liquor is maintained in the evaporation zone that exceeds the ratio of N-(phosphonomethyl)glycine product solids incrementally produced by the effects of evaporation to mother liquor incrementally produced thereby.

The present invention is also directed to integrated processes for the preparation of an oxidation reaction mixture effluent comprising the N-(phosphonomethyl)glycine product and thereafter concentrating and recovering the product. In one embodiment, the process comprises introducing an aqueous feed mixture comprising N-phosphonomethyl)iminodiacetic acid substrate into a liquid reaction medium and catalytically oxidizing the N-(phosphonomethyl)iminodiacetic acid substrate in the aqueous liquid reaction medium thereby producing an oxidation reaction mixture comprising N-(phosphonomethyl)glycine product. A primary crystallization feed mixture comprising N-(phosphonomethyl)glycine product produced in the reaction mixture is cooled, thereby precipitating N-(phosphonomethyl)glycine product and producing a primary mother liquor comprising N-(phosphonomethyl)glycine product. After separating precipitated N-(phosphonomethyl)glycine product from the primary mother liquor, primary mother liquor is recycled and introduced into the liquid reaction medium wherein N-(phosphonomethyl)iminodiacetic acid substrate is oxidized to N-(phosphonomethyl)glycine product.

In a further embodiment of the present invention, the process comprises introducing an aqueous feed mixture comprising an N-(phosphonomethyl)iminodiacetic acid substrate into a catalytic reactor system comprising one or more catalytic reaction zones. The N-(phosphonomethyl)iminodiacetic acid substrate is catalytically oxidized to N-(phosphonomethyl)glycine product in the catalytic reactor system to produce a product mixture which is then divided into a primary fraction and a secondary fraction. N-(phosphonomethyl)glycine product from the primary fraction is crystallized to produce a solid N-(phosphonomethyl)glycine product fraction and a primary mother liquor. Primary mother liquor is recycled for use as a source of water in the preparation of the feed mixture introduced into the catalytic reactor system.

The present invention is further directed to a continuous processes for the catalytic oxidation of an N-(phosphonomethyl)iminodiacetic acid substrate to produce an N-(phosphonomethyl)glycine product. In one embodiment, the process comprises introducing a liquid phase feed stream comprising an aqueous feed stream comprising the N-(phosphonomethyl)iminodiacetic acid substrate into a primary oxidation reaction zone, the primary oxidation reaction zone comprising a primary fixed bed containing an oxidation catalyst. An oxidizing agent is introduced into the primary oxidation reaction zone wherein the N-(phosphonomethyl)iminodiacetic acid substrate is continuously oxidized to the N-(phosphonomethyl)glycine product, thereby producing a primary reaction mixture comprising the N-(phosphonomethyl)glycine product and unreacted N-(phosphonomethyl)iminodiacetic acid substrate. The primary reaction mixture is withdrawn from the primary oxidation reaction zone. The difference in unit weight sensible heat content between the reaction mixture and the aqueous feed stream is maintained less than the exothermic reaction heat generated in the reaction zone per unit weight of the aqueous feed stream.

In another embodiment, the continuous process comprises introducing an aqueous feed stream comprising the N-(phosphonomethyl)iminodiacetic acid substrate into the first of a series of oxidation reaction zones, each of the series of oxidation reaction zones comprising an oxidation catalyst. The N-(phosphonomethyl)iminodiacetic acid substrate is oxidized in the first oxidation reaction zones to produce an intermediate oxidation reaction product. The intermediate oxidation reaction product is introduced into a second oxidation reaction zone comprising a fixed bed containing a noble metal on carbon catalyst, wherein by-product formaldehyde and/or formic acid is oxidized.

In a further embodiment, the continuous process comprises introducing a first component feed stream comprising an N-(phosphonomethyl)iminodiacetic acid substrate into the first of a series of continuous reaction zones, each of the series of reaction zones comprising an oxidation catalyst. An oxidant is introduced into the first of the series of reaction zones wherein the substrate is catalytically oxidized to produce an intermediate reaction mixture stream containing N-(phosphonomethyl)glycine product. The intermediate reaction mixture exiting the first reaction zone is transferred to the second of the series of reaction zones wherein the substrate is catalytically oxidized. An intermediate reaction mixture is withdrawn from each of the reaction zones and introduced into each succeeding reaction zone. An additional component feed stream is introduced into each of one or more of the reaction zones succeeding the first reaction zone in the series, each the additional feed stream comprising an N-(phosphonomethyl)iminodiacetic acid substrate. An oxidant is introduced into one or more of the reaction zones succeeding the first reaction zone in the series. A final reaction product is withdrawn from the last in the series of reaction zones.

In a further embodiment, the continuous process comprises introducing an aqueous feed stream comprising the N-(phosphonomethyl)iminodiacetic acid substrate into an oxidation reaction zone comprising a fixed bed containing an oxidation catalyst. An $O_2$-containing gas is introduced into the oxidation reaction zone wherein the N-(phosphonomethyl)iminodiacetic acid substrate is continuously oxidized to the N-(phosphonomethyl)glycine product, thereby producing an oxidation reaction mixture comprising the N-(phosphonomethyl)glycine product. The ratio of the mass flow rate of the liquid phase to the mass flow rate of gas phase in the fixed bed is between about 20 and about 800.

In a further embodiment, the continuous process comprises introducing an aqueous feed stream comprising the N-(phosphonomethyl)iminodiacetic acid substrate into an oxidation reaction zone comprising a fixed bed containing an oxidation catalyst. An $O_2$-containing gas is introduced into the oxidation reaction zone wherein the N-(phosphonomethyl)iminodiacetic acid substrate is continuously oxidized to N-(phosphonomethyl)glycine product, thereby producing an oxidation reaction mixture comprising the N-(phosphonomethyl)glycine product. The volumetric ratio of the liquid phase holdup in the fixed bed to the total bed volume is between about 0.1 and about 0.5.

In another embodiment, the continuous process comprises introducing an aqueous feed stream comprising the N-(phosphonomethyl)iminodiacetic acid substrate into an oxidation reaction zone comprising a fixed bed containing an oxidation catalyst. An $O_2$-containing gas is introduced into the oxidation reaction zone wherein the N-(phosphonomethyl)iminodiacetic acid substrate is continuously oxidized to the N-(phosphonomethyl)glycine product, thereby producing an oxidation reaction mixture comprising the N-(phosphonomethyl)glycine product. The partial pressure of oxygen at the liquid exit of the fixed bed is not greater than about 100 psia.

In a further embodiment, the continuous process comprises introducing an aqueous feed stream comprising the N-(phosphonomethyl)iminodiacetic acid substrate into an oxidation reaction zone comprising a fixed bed containing an oxidation catalyst. An $O_2$-containing gas is introduced into the oxidation reaction zone wherein the N-(phosphonomethyl)iminodiacetic acid substrate is continuously oxidized to the N-(phosphonomethyl)glycine product, thereby producing an oxidation reaction mixture comprising the N-(phosphonomethyl)glycine product. The partial pressure of oxygen is not greater than about 50 psia at any location in the fixed bed at which the concentration of N-(phosphonomethyl)iminodiacetic acid substrate in the liquid phase is lower than about 0.1 ppm.

In a further embodiment, the continuous process comprises introducing an aqueous feed stream comprising the N-(phosphonomethyl)iminodiacetic acid substrate into an oxidation reaction zone comprising a fixed bed containing an oxidation catalyst. The catalyst surface area to liquid holdup in the fixed bed is between about 100 and about 6000 $m^2/cm^3$. An oxidizing agent is introduced into the oxidation reaction zone wherein the N-(phosphonomethyl)iminodiacetic acid substrate is continuously oxidized to the N-(phosphonomethyl)glycine product, thereby producing an oxidation reaction mixture comprising the N-(phosphonomethyl)glycine product.

In a further embodiment, the continuous process comprises introducing an aqueous feed stream comprising the N-(phosphonomethyl)iminodiacetic acid substrate into an oxidation reaction zone comprising a fixed bed containing an oxidation catalyst. An $O_2$-containing gas is introduced into the oxidation reaction zone wherein the N-(phosphonomethyl)iminodiacetic acid substrate is continuously oxidized to the N-(phosphonomethyl)glycine product, thereby producing an oxidation reaction mixture comprising the N-(phosphonomethyl)glycine product. The integrated average partial pressure of oxygen along the liquid flow path in the fixed bed is at least about 50 psia and the integrated average temperature of the liquid phase in the fixed bed being between about 80° C. and about 130° C.

In a still further embodiment, the continuous process comprises introducing an aqueous feed stream comprising the N-(phosphonomethyl)iminodiacetic acid substrate into an oxidation reaction zone comprising a fixed bed containing oxidation catalyst bodies and other means for promoting gas/liquid mass transfer. An $O_2$-containing gas is introduced into the oxidation reaction zone wherein the N-(phosphonomethyl)iminodiacetic acid substrate is continuously oxidized to the N-(phosphonomethyl)glycine product, thereby producing an oxidation reaction mixture comprising the N-(phosphonomethyl)glycine product.

In yet a further embodiment, the continuous process comprises introducing a liquid phase feed stream comprising an aqueous feed mixture comprising the N-(phosphonomethyl)iminodiacetic acid substrate into a primary oxidation reaction zone comprising a fixed bed containing an oxidation catalyst. An oxidizing agent is introduced into the primary oxidation reaction zone wherein the N-(phosphonomethyl)iminodiacetic acid substrate is continuously oxidized to the N-(phosphonomethyl)glycine product, thereby producing a liquid phase exit stream comprising a primary reaction mixture comprising the N-(phosphonomethyl)glycine product and unreacted N-(phosphonomethyl)iminodiacetic acid substrate. The liquid phase exit stream is withdrawn from the primary oxidation reaction zone. The rate of introduction of the liquid phase feed stream and withdrawal of the liquid phase exit stream is such that the liquid phase hourly space velocity in the fixed bed based on total bed volume is between about 0.5 $hr^{-1}$ and about 20 $hr^{-1}$.

Other features of this invention will be in part apparent and in part pointed out hereinafter.

BRIEF DESCRIPTION OF THE DRAWINGS

FIG. 15 shows the effect on the formic acid by-product concentration profile over 20 batch reaction runs caused by a one-time introduction of bismuth oxide directly into an N-(phosphonomethyl)iminodiacetic acid oxidation reaction mixture. Here, the catalyst concentration in the reaction mixture was 0.5% by weight, and the catalyst contained 5% by weight platinum and 0.5% by weight iron.

DETAILED DESCRIPTION OF THE PREFERRED EMBODIMENTS

Figure 1:
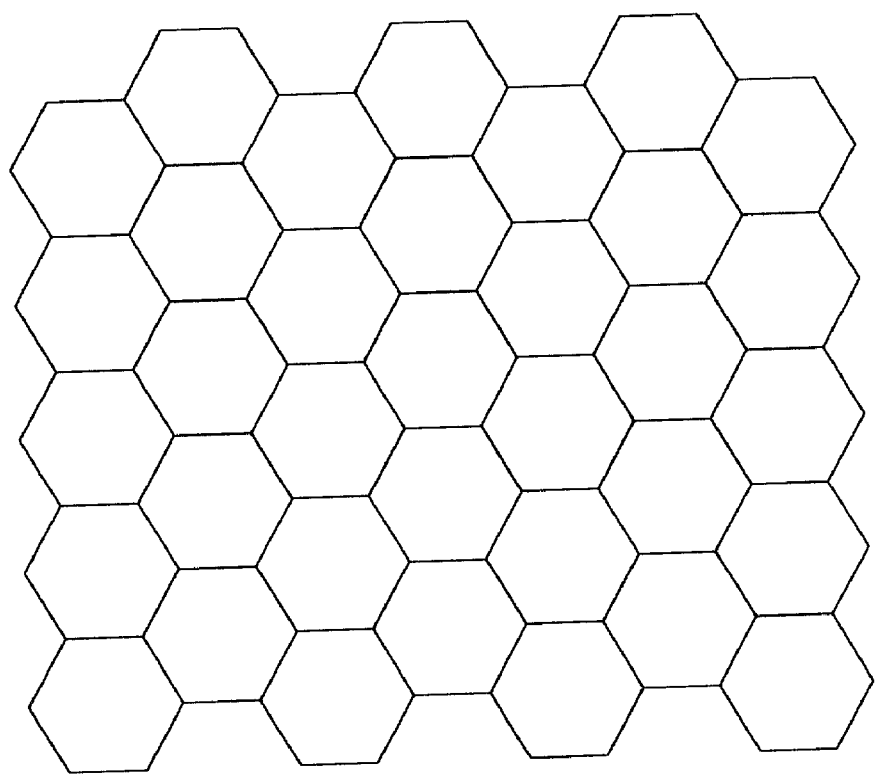
FIG. 1 shows an example of a cross-section of a honeycomb catalyst support.

In general, the processes of this invention comprise (1) oxidizing an N-(phosphonomethyl)iminodiacetic acid substrate in one or more oxidation reaction zones to form an N-(phosphonomethyl)glycine product, and/or (2) concentrating and/or purifying the N-(phosphonomethyl)glycine product. These steps, along with several other features of the more preferred embodiments, are outlined below.

The N-(phosphonomethyl)iminodiacetic acid substrate is oxidized by introducing the substrate and an oxidizing agent (i.e., oxygen source) into a reactor system comprising one or more oxidation reaction zones containing an oxidation catalyst. The oxidation reaction proceeds generally in accordance withe the following equation:

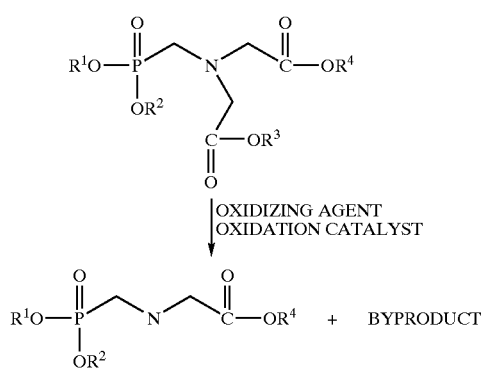

wherein $R^1$, $R^2$, $R^3$, and $R^4$ are each independently hydrogen, an agronomically acceptable cation, hydrocarbyl, or substituted hydrocarbyl.

A hydrocarbyl is any group consisting exclusively of carbon and hydrogen. The hydrocarbyl may be branched or unbranched, may be saturated or unsaturated, and may comprise one or more rings. Suitable hydrocarbyl groups include alkyl, alkenyl, alkynyl, and aryl groups. They also include alkyl, alkenyl, alkynyl, and aryl groups substituted with other aliphatic or cyclic hydrocarbyl groups, such as alkaryl, alkenaryl, and alkynaryl.

A substituted hydrocarbyl is any hydrocarbyl wherein at least one hydrogen atom has been substituted with (a) an atom other than hydrogen, or (b) a group of atoms containing at least one atom other than hydrogen. For example, the hydrogen atom may be substituted with a halogen atom, such as a chlorine or fluorine atom. The hydrogen atom alternatively may be substituted with an oxygen atom or a group containing an oxygen atom to form, for example, a hydroxy group, an ether, an ester, an anhydride, an aldehyde, a ketone, or a carboxylic acid. The hydrogen atom also may be replaced with a group containing a nitrogen atom to form, for example, an amide or a nitro group. In addition, the hydrogen atom may be substituted with a group containing a sulfur atom to form, for example, —$SO_3H$.

An agronomically acceptable cation is a cation that allows agriculturally and economically useful herbicidal activity of an N-(phosphonomethyl)glycine anion. Such a cation may be, for example, an alkali metal cation (e.g., a sodium or potassium ion), an ammonium ion, an isopropyl ammonium ion, a tetra-alkylammonium ion, a trialkyl sulfonium ion, a protonated primary amine, a protonated secondary amine, or a protonated tertiary amine.

In a particularly preferred embodiment, $R^1$, $R^2$, $R^3$, and $R^4$ are each independently hydrogen or an agronomically acceptable cation, with hydrogen often being most preferred.

Various oxidizing agents may be used in accordance with this invention. These include, for example, peroxides (e.g., $H_2O_2$, benzoyl peroxide), hydroperoxides, peroxy acids, $O_2$-containing gases, and liquids comprising dissolved oxygen. Typically, $O_2$-containing gases are especially preferred. As used herein, an $O_2$-containing gas is any gaseous mixture comprising $O_2$ and optionally one or more diluents which are non-reactive with the oxygen or with the substrate or product under the reaction conditions. Examples of such gases are air; pure $O_2$; or $O_2$ diluted with He, Ar, $N_2$, and/or other non-oxidizing gases. The oxygen source is most preferably an $O_2$-containing gas containing at least about 95 mole % $O_2$, more preferably about at least about 98 mole % $O_2$, with the remainder being one or more non-oxidizing gases (particularly $N_2$ and/or Ar).

Preferred Oxidation Catalysts

A wide variety of oxidation catalysts may be used in accordance with this invention. These include both homogeneous and heterogeneous catalysts.

Various water-soluble tungsten salts, for example, can be used to catalyze the oxidation of N-(phosphonomethyl) iminodiacetic acid substrates with $H_2O_2$. N-(phosphonomethyl)iminodiacetic acid also can be oxidized to a N-oxide intermediate with $H_2O_2$ in the presence of an acid (e.g., $H_2SO_4$) and heat. This N-oxide intermediate, in turn, can be decomposed to form N-(phosphonomethyl)glycine in the presence of heat and various water-soluble ferrous, cuprous, tungsten, molybdenum, and vanadium salt catalysts. A general discussion related to the use of such homogeneous catalysts for the conversion of N-(phosphonomethyl)iminodiacetic acid to N-(phosphonomethyl)glycine can be found, for example, in Franz, et al., *Glyphosate: A Unique Global Herbicide* (ACS Monograph 189, 1997) at pp. 240–41.

It is typically more preferred to use a heterogeneous catalyst. This preference stems, at least in part, from the ease with which a heterogeneous catalyst can normally be separated from the reaction mixture following the oxidation. The literature is replete with suitable heterogeneous catalysts.

One of the first heterogeneous catalysts used for catalyzing the oxidative cleavage of N-(phosphonomethyl)iminodiacetic acid is disclosed by Franz in U.S. Pat. No. 3,950,402. Franz discloses that N-(phosphonomethyl)glycine may be prepared by the liquid phase oxidative cleavage of N-(phosphonomethyl)iminodiacetic acid with $O_2$ in the presence of a catalyst comprising a noble metal deposited on the surface of an activated carbon support.

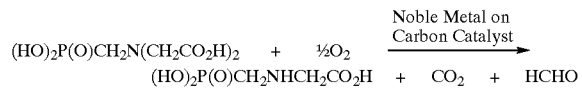

$$(HO)_2P(O)CH_2N(CH_2CO_2H)_2 + \tfrac{1}{2}O_2 \xrightarrow{\text{Noble Metal on Carbon Catalyst}} (HO)_2P(O)CH_2NHCH_2CO_2H + CO_2 + HCHO$$

Even though Franz's process generally produces an acceptable yield and purity of N-(phosphonomethyl)glycine, it also suffers from a number of problems:

1. The costly noble metal in Franz's catalyst tends to be lost into the reaction solution (i.e., leaching). This noble metal leaching is the result of at least two factors: (a) under the oxidation conditions of the reaction, some of the noble metal is oxidized into a more soluble form; and (b) both the N-(phosphonomethyl)iminodiacetic acid substrate and the N-(phosphonomethyl)glycine product act as ligands that solubilize the noble metal.
2. The N-(phosphonomethyl)glycine product often oxidizes to form aminomethylphosphonic acid (AMPA), particularly as the concentration of the N-(phosphonomethyl)iminodiacetic acid substrate decreases. This obviously reduces yield of the desired N-(phosphonomethyl)glycine product.

In U.S. Pat. No. 3,969,398, Hershman discloses that activated carbon alone, without the presence of a noble metal, may be used to effect the oxidative cleavage of N-(phosphonomethyl)iminodiacetic acid to form N-(phosphonomethyl)glycine. In U.S. Pat. No. 4,624,937, Chou further discloses that the activity of the carbon catalyst disclosed by Hershman may be increased by removing the oxides from the surface of the carbon catalyst before using it in the oxidation reaction. See also, U.S. Pat. No. 4,696,772 (providing a separate discussion by Chou regarding increasing the activity of the carbon catalyst by removing oxides from the surface of the carbon catalyst). Although these processes obviously do not suffer from noble metal leaching, they do tend to produce greater concentrations of formaldehyde and formic acid by-product when used to effect the oxidative cleavage of N-(phosphonomethyl)iminodiacetic acid.

Optimally, the formaldehyde and formic acid are simultaneously oxidized to carbon dioxide and water as the N-(phosphonomethyl)iminodiacetic acid substrate is oxidized to N-(phosphonomethyl)glycine, thus giving the following reaction:

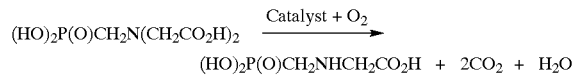

$$(HO)_2P(O)CH_2N(CH_2CO_2H)_2 \xrightarrow{\text{Catalyst} + O_2} (HO)_2P(O)CH_2NHCH_2CO_2H + 2CO_2 + H_2O$$

Much attention has focused on catalysts comprising a noble metal on a carbon support for at least two reasons. With such catalysts, the carbon component primarily effects the oxidation of N-(phosphonomethyl)iminodiacetic acid to form N-(phosphonomethyl)glycine and formaldehyde, while the noble metal component primarily effects the oxidation of formaldehyde and formic acid to form carbon dioxide and water. The noble metal component also tends to reduce the rate of deactivation of the carbon. More specifically, when activated carbon is used alone, it tends to deactivate by as much as 10% per cycle or more. Without being bound by any particular theory, it is believed that the deactivation of the activated carbon alone arises because the surface of the carbon support oxidizes under the reaction conditions. See Chou, U.S. Pat. No. 4,624,937. See also, Chou, U.S. Pat. No. 4,696,772 (providing a separate discussion related to deactivation of activated carbon by oxidation of the surface of the carbon). In the presence of the noble metal, however, the rate of deactivation of the activated carbon is diminished. It is believed that the noble metal reacts with the oxidant at a faster rate than the activated carbon surface, and, thus, preferentially removes the oxidant from solution before extensive oxidation of the carbon surface can occur. Further, unlike many oxide species which form at activated carbon surfaces and require high temperature treatments to be reduced, oxide species which form at the surface of a noble metal typically are easily reduced by the reducing agents present in or added to the reaction mixture (e.g., the amine fragment cleaved, formaldehyde, formic acid, $H_2$, etc.), thus restoring the noble metal surface to a reduced state. In this manner, the catalyst advantageously exhibits significantly longer life as long as the noble metal is not lost by leaching or sintered (i.e., in the form of undesirably thick layers or clumps) by processes such as dissolution and re-deposition or noble metal agglomeration.

Ramon et al. (U.S. Pat. No. 5,179,228) disclose an example of using a noble metal deposited on the surface of a carbon support. To reduce the problem of leaching (which Ramon et al. report to be as great as 30% noble metal loss per cycle), Ramon et al. disclose flushing the reaction mixture with $N_2$ under pressure after the oxidation reaction is completed to cause re-deposition of the noble metal onto the surface of the carbon support. According to Ramon et al., $N_2$ flushing reduces the noble metal loss to less than 1%.

Felthouse (U.S. Pat. No. 4,582,650) discloses using 2 catalysts: (i) an activated carbon to effect the oxidation of N-(phosphonomethyl)iminodiacetic acid to N-(phosphonomethyl)glycine, and (ii) a co-catalyst to concurrently effect the oxidation of formaldehyde to carbon dioxide and water. The co-catalyst is an aluminosilicate support having a noble metal located within its pores. The pores are sized to exclude N-(phosphonomethyl)glycine and thereby prevent the noble metal of the co-catalyst from being poisoned by N-(phosphonomethyl)glycine. According to Felthouse, use of these 2 catalysts together allows for the simultaneous oxidation of N-(phosphonomethyl)iminodiacetic acid to N-(phosphonomethyl)glycine and of formaldehyde to carbon dioxide and water.

Ebner et al., International Publication No. WO 99/43430, the entire disclosure of which is incorporated herein by references, disclose oxidizing N-(phosphonomethyl)iminodiacetic acid substrates using a deeply reduced catalyst comprising a noble metal on a carbon support. Such a catalyst tends to exhibit improved resistance to noble metal leaching and increased destruction of undesirable by-products (e.g., formaldehyde). The advantages of such catalysts make them particularly preferred. Thus, much of the following discussion will focus on such catalysts. Nevertheless, it should be recognized that the features of this invention may be generally applied using the wide variety of homogeneous and heterogeneous catalysts described above.

Oxygen-containing functional groups (e.g., carboxylic acids, ethers, alcohols, aldehydes, lactones, ketones, esters, amine oxides, and amides) at the surface of the carbon support tend to increase noble metal leaching and potentially increase noble metal sintering during liquid phase oxidation reactions, and, thus, reduce the ability of the catalyst to oxidize oxidizable substrates, particularly formaldehyde and formic acid during the N-(phosphonomethyl)iminodiacetic acid oxidation reaction. As used herein, an oxygen-containing functional group is at the surface of the carbon support if it is bound to an atom of the carbon support and is able to chemically or physically interact with compositions within the reaction mixture or with the metal atoms deposited on the carbon support.

Many of the oxygen-containing functional groups that reduce noble metal resistance to leaching and sintering and reduce the activity of the catalyst desorb from the carbon support as carbon monoxide when the catalyst is heated at a high temperature (e.g., 900° C.) in an inert atmosphere (e.g., helium or argon). Thus, measuring the amount of CO desorption from a fresh catalyst (i.e., a catalyst that has not previously been used in a liquid phase oxidation reaction) under high temperatures is one method that may be used to analyze the surface of the catalyst to predict noble metal retention and maintenance of catalyst activity. One way to measure CO desorption is by using thermogravimetric analysis with in-line mass spectroscopy (TGA-MS). Preferably, no greater than about 1.2 mmole of carbon monoxide per gram of catalyst desorb from the catalyst when a dry, fresh sample of the catalyst in a helium atmosphere is subjected to a temperature which is increased from 20 to 900° C. at 10° C. per minute, and then held constant at 900° C. for 30 minutes. More preferably, no greater than about 0.7 mmole of carbon monoxide per gram of fresh catalyst desorb under those conditions, even more preferably no greater than about 0.5 mmole of carbon monoxide per gram of fresh catalyst desorb, and most preferably no greater than about 0.3 mmole of carbon monoxide per gram of fresh catalyst desorb. A catalyst is considered dry when the catalyst has a moisture content of less than 1% by weight. Typically, a catalyst may be dried by placing it into a $N_2$ purged vacuum of 25 inches of Hg and a temperature of 120° C. for 16 hours.

Measuring the number of oxygen atoms at the surface of a fresh catalyst support is another method which may be used to analyze the catalyst to predict noble metal retention and maintenance of catalytic activity. Using, for example, x-ray photoelectron spectroscopy, a surface layer of the support which is about 50 Å in thickness is analyzed. Presently available equipment used for x-ray photoelectron spectroscopy typically is accurate to within ±20%. Typically, a ratio of carbon atoms to oxygen atoms at the surface (as measured by presently available equipment for x-ray photoelectron spectroscopy) of at least about 20:1 (carbon atoms:oxygen atoms) is suitable. Preferably, however, the ratio is at least about 30:1, more preferably at least about 40:1, even more preferably at least about 50:1, and most preferably at least about 60:1. In addition, the ratio of oxygen atoms to metal atoms at the surface (again, as measured by presently available equipment for x-ray photoelectron spectroscopy) preferably is less than about 8:1 (oxygen atoms:metal atoms). More preferably, the ratio is less than 7:1, even more preferably less than about 6:1, and most preferably less than about 5:1.

In general, the carbon supports used in the present invention are well known in the art. Activated, non-graphitized carbon supports are preferred. These supports are characterized by high adsorptive capacity for gases, vapors, and colloidal solids and relatively high specific surface areas. The support suitably may be a carbon, char, or charcoal produced by means known in the art, for example, by destructive distillation of wood, peat, lignite, coal, nut shells, bones, vegetable, or other natural or synthetic carbonaceous matter, but preferably is activated to develop adsorptive power. Activation usually is achieved by heating to high temperatures (800–900° C.) with steam or with carbon dioxide which brings about a porous particle structure and increased specific surface area. In some cases, hygroscopic substances, such as zinc chloride and/or phosphoric acid or sodium sulfate, are added before the destructive distillation or activation, to increase adsorptive capacity. Preferably, the carbon content of the carbon support ranges from about 10% for bone charcoal to about 98% for some wood chars and nearly 100% for activated carbons derived from organic polymers. The non-carbonaceous matter in commercially available activated carbon materials normally will vary depending on such factors as precursor origin, processing, and activation method. Many commercially available carbon supports contain small amounts of metals. Carbon supports having the fewest oxygen-containing functional groups at their surfaces are most preferred.

The form of the support used in fixed bed reactors may vary considerably. For example, the carbon support may be in the form of a monolithic support. Suitable monolithic supports may have a wide variety of shapes. A monolithic support may, for example, be in the form of a reactor impeller. Even more preferably, such a support may also be, for example, in the form of a screen or honeycomb having parallel channels through which the feed mixture is passed. FIG. 1 shows an example of a cross-section of a honeycomb support. Although the cross-sections of the channels in the honeycomb support of FIG. 1 are hexagonal in shape, a honeycomb support as defined herein may alternatively (or additionally) comprise channels having other cross-section shapes (e.g., circular, oval, square, triangular rectangular, and the like). The channels of the honeycomb support are preferably straight, and/or have a cross-section large enough so that they will not be clogged by a slurry containing solid N-(phosphonomethyl)iminodiacetic acid substrate. Alternatively, the flow channels in a monolithic support may be irregular and without a uniform flow direction (e.g., a random network of interconnecting flow channels).

In a particularly preferred embodiment, the support is in the form of particulates. Because particulate supports are especially preferred, most of the following discussion focuses on embodiments which use a particulate support. It should be recognized, however, that this invention is not limited to the use of particulate supports.

Suitable particulate supports may have a wide variety of shapes. For example, such supports may be in the form of pellets, granules and powders. Pellet supports typically have a particle size of from about 1 mm to about 10 mm. Preferably, the support is in the form of a powder. These particulate supports may be used in a reactor system as free particles, or, alternatively, may be bound to a structure in the reactor system, such as a screen or an impeller.

Typically, a support which is in particulate form comprises a broad size distribution of particles. For powders, preferably at least about 95% of the particles are from about 2 to about 300 $\mu$m in their largest dimension, more preferably at least about 98% of the particles are from about 2 to about 200 $\mu$m in their largest dimension, and most preferably about 99% of the particles are from about 2 to about 150 $\mu$m in their largest dimension with about 95% of the particles being from about 3 to about 100 $\mu$m in their largest dimension. Particles greater than about 200 $\mu$m in their largest dimension tend to fracture into super-fine particles (i.e., less than 2 $\mu$m in their largest dimension), which are difficult to recover.

The specific surface area of the carbon support, measured by the BET (Brunauer-Emmett-Teller) method using $N_2$, is preferably from about 10 to about 3,000 m²/g (surface area of carbon support per gram of carbon support), more preferably from about 500 to about 2,100 m²/g, and still more preferably from about 750 to about 2,100 m²/g. In some embodiments, the most preferred specific area is from about 750 to about 1,750 m²/g.

The pore volume of the support may vary widely. Using the measurement method described in Example 1, the pore volume preferably is from about 0.1 to about 2.5 ml/g (pore volume per gram of catalyst), more preferably from about 0.2 to about 2.0 ml/g, and most preferably from about 0.4 to about 1.7 ml/g. Catalysts comprising supports with pore volumes greater than about 2.5 ml/g tend to fracture easily. On the other hand, catalysts comprising supports having pore volumes less than 0.1 ml/g tend to have small surface areas and therefore low activity.

Carbon supports for use in the present invention are commercially available from a number of sources. The following is a listing of some of the activated carbons which may be used with this invention: Darco G-60 Spec and Darco X (ICI-America, Wilmington, Del.); Norit SG Extra, Norit EN4, Norit EXW, Norit A, Norit Ultra-C, Norit ACX, and Norit 4 X 14 mesh (Amer. Norit Co., Inc., Jacksonville, Fla.); G1-9615, VG-8408, VG-8590, NB-9377, XZ, NW, and JV (Barnebey-Cheney, Columbus, Ohio); BL Pulv., PWA Pulv., Calgon C 450, and PCB Fines (Pittsburgh Activated Carbon, Div. of Calgon Corporation, Pittsburgh, Pa.); P-100 (No. Amer. Carbon, Inc., Columbus, Ohio); Nuchar CN, Nuchar C-1000 N, Nuchar C-190 A, Nuchar C-115 A, and Nuchar SA-30 (Westvaco Corp., Carbon Department, Covington, Va.); Code 1551 (Baker and Adamson, Division of Allied Amer. Norit Co., Inc., Jacksonville, Fla.); Grade 235, Grade 337, Grade 517, and Grade 256 (Witco Chemical Corp., Activated Carbon Div., New York, N.Y.); and Columbia SXAC (Union Carbide New York, N.Y.).

The carbon support preferably has one or more noble metal(s) at its surface. Preferably, the noble metal(s) is selected from the group consisting of platinum (Pt), palladium (Pd), ruthenium (Ru), rhodium (Rh), iridium (Ir), silver (Ag), osmium (Os), and gold (Au). In general, platinum and palladium are more preferred, and platinum is most preferred. Because platinum is presently the most preferred noble metal, the following discussion will be directed primarily to embodiments using platinum. It should be understood, however, that the same discussion is generally applicable to the other noble metals and combinations thereof. It also should be understood that the term noble metal as used herein means the noble metal in its elemental state as well as the noble metal in any of its various oxidation states.

The concentration of the noble metal deposited at the surface of the carbon support may vary within wide limits. Preferably, it is in the range of from about 0.5 to about 20 wt. % ([mass of noble metal÷total mass of catalyst]×100%), more preferably from about 2.5 to about 10 wt. %, and most preferably from about 3 to about 7.5 wt. %. If concentrations less than 0.5 wt. % are used during the N-(phosphonomethyl)iminodiacetic acid oxidation reaction, there tends to be less formaldehyde oxidized, and therefore a greater amount of N-methyl-N-(phosphonomethyl)glycine produced, thereby reducing the N-(phosphonomethyl)glycine yield. On the other hand, at concentrations greater than about 20 wt. %, layers and clumps of noble metal tend to form. Thus, there are fewer surface noble metal atoms per total amount of noble metal used. This tends to reduce the activity of the catalyst and is an uneconomical use of the costly noble metal.

The dispersion of the noble metal at the surface of the carbon support preferably is such that the concentration of surface noble metal atoms is from about 10 to about 400 $\mu$mole/g ($\mu$mole of surface noble metal atoms per gram of catalyst), more preferably, from about 10 to about 150 $\mu$mole/g, and most preferably from about 15 to about 100 $\mu$mole/g. This may be determined, for example, by measuring chemisorption of $H_2$ or CO using a Micromeritics ASAP 2010C (Micromeritics, Norcross, Ga.) or an Altamira AMI100 (Zeton Altamira, Pittsburgh, Pa.).

Preferably, the noble metal is at the surface of the carbon support in the form of metal particles. At least about 90% (number density) of the noble metal particles at the surface of the carbon support are preferably from about 0.5 to about 35 nm in their largest dimension, more preferably from about 1 to about 20 nm in their largest dimension, and most preferably from about 1.5 to about 10 nm in their largest dimension. In a particularly preferred embodiment, at least about 80% of the noble metal particles at the surface of the carbon support are from about 1 to about 15 nm in their largest dimension, more preferably from about 1.5 to about 10 nm in their largest dimension, and most preferably from about 1.5 to about 7 nm in their largest dimension. If the noble metal particles are too small, there tends to be an increased amount of leaching when the catalyst is used in an environment that tends to solubilize noble metals, as is the case when oxidizing N-(phosphonomethyl)iminodiacetic acid to form N-(phosphonomethyl)glycine. On the other hand, as the particle size increases, there tends to be fewer noble metal surface atoms per total amount of noble metal used. As discussed above, this tends to reduce the activity of the catalyst and is also an uneconomical use of the costly noble metal.

In addition to the noble metal, at least one promoter may be at the surface of the carbon support. As defined herein, a promoter is a metal that tends to increase catalyst selectivity, activity, and/or stability. A promoter additionally may reduce noble metal leaching. Although the promoter usually is deposited onto the surface of the carbon support in a promoter deposition step, the carbon support itself may also (or alternatively) naturally contain a promoter. A promoter which is deposited or exists naturally on the catalyst surface before the carbon support surface is finally reduced (described below) is referred to herein as a catalyst-surface promoter.

The catalyst-surface promoter may, for example, be an additional noble metal(s) at the surface of the carbon support. For example, depending on the application, ruthenium and palladium may act as catalyst-surface promoters on a catalyst comprising platinum deposited at a carbon support surface. The catalyst-surface promoter(s) alternatively may be, for example, a metal selected from the group consisting of tin (Sn), cadmium (Cd), magnesium (Mg), manganese (Mn), nickel (Ni), aluminum (Al), cobalt (Co), bismuth (Bi), lead (Pb), titanium (Ti), antimony (Sb), selenium (Se), iron (Fe), rhenium (Re), zinc (Zn), cerium (Ce), zirconium (Zr), tellurium (Te), and germanium (Ge). Preferably, the catalyst-surface promoter is selected from the group consisting of bismuth, iron, tin, tellurium and titanium. In a particularly preferred embodiment, the catalyst-surface promoter is tin. In another particularly preferred embodiment, the catalyst-surface promoter is iron. In an additional preferred embodiment, the catalyst-surface promoter is titanium. In a further particularly preferred embodiment, the catalyst comprises both iron and tin at its surface. Use of iron, tin, or both generally (1) reduces noble metal leaching for a catalyst used over several cycles, and (2) tends to increase and/or maintain the activity of the catalyst when the catalyst is used to effect the oxidation of an N-(phosphonomethyl)iminodiacetic acid substrate. Catalysts comprising iron generally are most preferred because they tend to have the greatest activity and stability with respect to formaldehyde and formic acid oxidation.

In a preferred embodiment, the catalyst-surface promoter is more easily oxidized than the noble metal (in instances where the catalyst-surface promoter is a noble metal as well, the catalyst-surface promoter noble metal preferably is more easily oxidized than the non-promoter noble metal). A promoter is more easily oxidized if it has a lower first ionization potential than the noble metal. First ionization potentials for the elements are widely known in the art and may be found, for example, in the *CRC Handbook of Chemistry and Physics* (CRC Press, Inc., Boca Raton, Fla.).

The amount of catalyst-surface promoter at the surface of the carbon support (whether associated with the carbon surface itself, metal, or a combination thereof) may vary within wide limits depending on, for example, the noble metal(s) and catalyst-surface promoter(s) used. Typically, the weight percentage of the catalyst-surface promoter is at least about 0.05% ([mass of catalyst-surface promoter÷total mass of the catalyst]×100%). The weight percent of the catalyst-surface promoter preferably is from about 0.05 to about 10%, more preferably from about 0.1 to about 10%, still more preferably from about 0.1 to about 2%, and most preferably from about 0.2 to about 1.5%. When the catalyst-surface promoter is tin, the weight percent most preferably is from about 0.5 to about 1.5%. Catalyst-surface promoter weight percentages less than 0.05% generally do not promote the activity of the catalyst over an extended period of time. On the other hand, weight percents greater than about 10% tend to decrease the activity of the catalyst.

The molar ratio of noble metal to catalyst-surface promoter (and, in instances where the catalyst-surface promoter is a noble metal as well, the molar ratio of the non-promoter noble metal to the catalyst-surface promoter noble metal) may also vary widely, depending on, for example, the noble metal(s) and catalyst-surface promoter(s) used. Preferably, the ratio is from about 1000:1 to about 0.01:1; more preferably from about 150:1 to about 0.05:1; still more preferably from about 50:1 to about 0.05:1; and most preferably from about 10:1 to about 0.05:1. For example, a catalyst comprising platinum and iron preferably has a molar ratio of platinum to iron of about 3:1.

In a particularly preferred embodiment of this invention, the noble metal (e.g., Pt) is alloyed with at least one catalyst-surface promoter (e.g., Sn, Fe, or both) to form alloyed metal particles (and, in instances where the catalyst-surface promoter is a noble metal as well, the non-promoter noble metal preferably is alloyed with the catalyst-surface promoter noble metal). A catalyst comprising a noble metal alloyed with at least one catalyst-surface promoter tends to have all the advantages discussed above with respect to catalysts comprising a catalyst-surface promoter in general. Catalysts comprising a noble metal alloyed with at least one catalyst-surface promoter also tend to exhibit greater resistance to catalyst-surface promoter leaching and further stability from cycle to cycle with respect to formaldehyde and formic acid oxidation (See, e.g., Example 17).

The term alloy encompasses any metal particle comprising a noble metal and at least one catalyst-surface promoter, irrespective of the precise manner in which the noble metal and catalyst-surface promoter atoms are disposed within the particle (although it is generally preferable to have a portion of the noble metal atoms at the surface of the alloyed metal particle). The alloy may be, for example, any of the following:

1. An intermetallic compound. An intermetallic compound is compound comprising a noble metal and a promoter (e.g., $Pt_3Sn$).
2. A substitutional alloy. A substitutional alloy has a single, continuous phase, irrespective of the concentrations of the noble metal and promoter atoms. Typically, a substitutional alloy contains noble metal and promoter atoms which are similar in size (e.g., platinum and silver; or platinum and palladium). Substitutional alloys are also referred to as monophasic alloys.
3. A multiphasic alloy. A multiphasic alloy is an alloy that contains at least two discrete phases. Such an alloy may contain, for example $Pt_3Sn$ in one phase, and tin dissolved in platinum in a separate phase.
4. A segregated alloy. A segregated alloy is a metal particle wherein the particle stoichiometry varies with distance from the surface of the metal particle.
5. An interstitial alloy. An interstitial alloy is a metal particle wherein the noble metal and promoter atoms are combined with non-metal atoms, such as boron, carbon, silicon, nitrogen, phosphorus, etc.

Preferably, at least about 80% (number density) of the alloyed metal particles are from about 0.5 to about 35 nm in their largest dimension, more preferably from about 1 to about 20 nm in their largest dimension, still more preferably from about 1 to about 15 nm in their largest dimension, and most preferably from about 1.5 to about 7 nm in their largest dimension.

The alloyed metal particles need not have a uniform composition; the compositions may vary from particle to particle, or even within the particles themselves. In addition, the catalyst may further comprise particles consisting of the noble metal alone or the catalyst-surface promoter alone. Nevertheless, it is preferred that the composition of metal particles be substantially uniform from particle to particle and within each particle, and that the number of noble metal atoms in intimate contact with catalyst-surface promoter atoms be maximized. It is also preferred, although not essential, that the majority of noble metal atoms be alloyed with a catalyst-surface promoter, and more preferred that substantially all of the noble metal atoms be alloyed with a catalyst-surface promoter. It is further preferred, although not essential, that the alloyed metal particles be uniformly distributed at the surface of the carbon support.

Regardless of whether the catalyst-surface promoter is alloyed to the noble metal, it is presently believed that the catalyst-surface promoter tends to become oxidized if the catalyst is exposed to an oxidant over a period of time. For example, an elemental tin catalyst-surface promoter tends to oxidize to form $Sn(II)O$, and $Sn(II)O$ tends to oxidize to form $Sn(IV)O_2$. This oxidation may occur, for example, if the catalyst is exposed to air for more than about 1 hour. Although such catalyst-surface promoter oxidation has not been observed to have a significant detrimental effect on noble metal leaching, noble metal sintering, catalyst activity, or catalyst stability, it does make analyzing the concentration of detrimental oxygen-containing functional groups at the surface of the carbon support more difficult. For example, as discussed above, the concentration of detrimental oxygen-containing functional groups (i.e., oxygen-containing functional groups that reduce noble metal resistance to leaching and sintering, and reduce the activity of the catalyst) may be determined by measuring (using, for example, TGA-MS) the amount of CO that desorbs from the catalyst under high temperatures in an inert atmosphere. However, it is presently believed that when an oxidized catalyst-surface promoter is present at the surface, the oxygen atoms from the oxidized catalyst-surface promoter tend to react with carbon atoms of the support at high temperatures in an inert atmosphere to produce CO, thereby creating the illusion of more detrimental oxygen-containing functional groups at the surface of the support than actually exist. Such oxygen atoms of an oxidized catalyst-surface promoter also can interfere with obtaining a reliable prediction of noble metal leaching, noble metal sintering, and catalyst activity from the simple measurement (via, for example, x-ray photoelectron spectroscopy) of oxygen atoms at the catalyst surface.

Thus, when the catalyst comprises at least one catalyst-surface promoter which has been exposed to an oxidant and thereby has been oxidized (e.g., when the catalyst has been exposed to air for more than about 1 hour), it is preferred that the catalyst-surface promoter first be substantially reduced (thereby removing the oxygen atoms of the oxidized catalyst-surface promoter from the surface of the catalyst) before attempting to measure the amount of detrimental oxygen-containing functional groups at the surface of the carbon support. This reduction preferably is achieved by heating the catalyst to a temperature of 500° C. for 1 hour in an atmosphere consisting essentially of $H_2$. The measurement of detrimental oxygen-containing functional groups at the surface preferably is performed (a) after this reduction, and (b) before the surface is exposed to an oxidant following the reduction. Most preferably, the measurement is taken immediately after the reduction.

The preferred concentration of metal particles at the surface of the carbon support depends, for example, on the size of the metal particles, the specific surface area of the carbon support, and the concentration of noble metal on the catalyst. It is presently believed that, in general, the preferred concentration of metal particles is roughly from about 3 to about 1,500 particles/$\mu m^2$ (i.e., number of metal particles per $\mu m^2$ of surface of carbon support), particularly where: (a) at least about 80% (number density) of the metal particles are from about 1.5 to about 7 nm in their largest dimension, (b) the carbon support has a specific surface area of from about 750 to about 2100 $m^2/g$ (i.e., $m^2$ of surface of carbon support per gram of carbon support), and (c) the concentration of noble metal at the carbon support surface is from about 1 to about 10 wt. % ([mass of noble metal÷total mass of catalyst]×100%). In more preferred embodiments, narrower ranges of metal particle concentrations and noble metal concentrations are desired. In one such embodiment, the concentration of metal particles is from about 15 to about 800 particles/$\mu m^2$, and the concentration of noble metal at the carbon support surface is from about 2 to about 10 wt. %. In an even more preferred embodiment, the concentration of metal particles is from about 15 to about 600 particles/$\mu m^2$, and the concentration of noble metal at the carbon support surface is from about 2 to about 7.5 wt. %. In the most preferred embodiment, the concentration of the metal particles is from about 15 to about 400 particles/$\mu m^2$, and the concentration of noble metal at the carbon support surface is about 5 wt. %. The concentration of metal particles at the surface of the carbon support may be measured using methods known in the art.

The surface of the carbon support preferably is deoxygenated before the noble metal is deposited onto it. Preferably, the surface is deoxygenated using a high-temperature deoxygenation treatment. Such a treatment may be a single-step or a multi-step scheme which, in either case, results in an overall chemical reduction of oxygen-containing functional groups at the surface of the carbon support.

In a two-step high-temperature deoxygenation treatment, the carbon support preferably is first treated with a gaseous or liquid phase oxidizing agent to convert oxygen-containing functionalities in relatively lower oxidation states (e.g., ketones, aldehydes, and alcohols) into functionalities in relatively higher oxidation states (e.g., carboxylic acids), which are easier to cleave from the surface of the catalyst at high temperatures. Representative liquid phase oxidizing agents include nitric acid, $H_2O_2$, chromic acid, and hypochlorite, with concentrated nitric acid comprising from about 10 to about 80 grams of $HNO_3$ per 100 grams of aqueous solution being preferred. Representative gaseous oxidants include molecular oxygen, ozone, nitrogen dioxide, and nitric acid vapors. Nitric acid vapors are the preferred oxidizing agent. With a liquid oxidant, temperatures of from about 60 to about 90° C. are appropriate, but with gaseous oxidants, it is often advantageous to use temperatures from about 50 to about 500° C. or even greater. The time during which the carbon is treated with the oxidant can vary widely from about 5 minutes to about 10 hours. Preferably, the reaction time is from about 30 minutes to about 6 hours. Experimental results indicate that carbon load, temperature, oxidant concentration, etc. in the first treatment step are not narrowly critical to achieving the desired oxidation of the carbon material and thus may be governed by convenience over a wide range. The highest possible carbon load is preferred for economic reasons.

In the second step, the oxidized carbon support is pyrolyzed (i.e., heated) at a temperature preferably in the range of from about 500 to about 1500° C., and more preferably from about 600 to about 1,200° C., in a nitrogen, argon, helium, or other non-oxidizing environment (i.e., an environment consisting essentially of no oxygen) to drive off the oxygen-containing functional groups from the carbon surface. At temperatures greater than 500° C., an environment may be used which comprises a small amount of ammonia (or any other chemical entity which will generate $NH_3$ during pyrolysis), steam, or carbon dioxide which aid in the pyrolysis. As the temperature of the carbon support is cooled to temperatures less than 500° C., however, the presence of oxygen-containing gases such as steam or carbon dioxide may lead to the reformation of surface oxides and thus, is preferably avoided. Accordingly, the pyrolysis is preferably conducted in a non-oxidizing atmosphere (e.g., nitrogen, argon, or helium). In one embodiment, the non-oxidizing atmosphere comprises ammonia, which tends to produce a more active catalyst in a shorter time as compared to pyrolysis in the other atmospheres. The pyrolysis may be achieved, for example, using a rotary kiln, a fluidized-bed reactor, or a conventional furnace.

The carbon support generally is pyrolyzed for a period of from about 5 minutes to about 60 hours, preferably from about 10 minutes to about 6 hours. Shorter times are preferred because prolonged exposure of the carbon at elevated temperatures tends to reduce the activity of the catalyst. Without being bound to any particular theory, it is presently believed that prolonged heating at pyrolytic temperatures favors the formation of graphite, which is a less preferred form of a carbon support because it normally has less surface area. As discussed above, a more active catalyst typically may be produced in a shorter time by using an atmosphere which comprises ammonia.

In a preferred embodiment of this invention, high-temperature deoxygenation is carried out in one step. This one-step treatment may consist of merely performing the pyrolysis step of the two-step high-temperature deoxygenation treatment discussed above. More preferably, however, the single-step treatment consists of pyrolyzing the carbon support as described above while simultaneously passing a gas stream comprising $N_2$, $NH_3$ (or any other chemical entity which will generate $NH_3$ during pyrolysis), and steam over the carbon. Although it is not a critical feature of this invention, the flow rate of the gas stream preferably is fast enough to achieve adequate contact between the fresh gas reactants and the carbon surface, yet slow enough to prevent excess carbon weight loss and material waste. A non-reactive gas may be used as a diluent to prevent severe weight loss of the carbon.

Methods used to deposit the noble metal onto the surface of the carbon support are generally known in the art, and include liquid phase methods such as reaction deposition techniques (e.g., deposition via reduction of noble metal compounds, and deposition via hydrolysis of noble metal compounds), ion exchange techniques, excess solution impregnation, and incipient wetness impregnation; vapor phase methods such as physical deposition and chemical deposition; precipitation; electrochemical deposition; and electroless deposition. See generally, Cameron, D. S., Cooper, S. J., Dodgson, I. L., Harrison, B., and Jenkins, J. W. "Carbons as Supports for Precious Metal Catalysts," *Catalysis Today*, 7, 113–137 (1990). Catalysts comprising noble metals at the surface of a carbon support also are commercially available, e.g., Aldrich Catalog No. 20,593-1, 5% platinum on activated carbon (Aldrich Chemical Co., Inc., Milwaukee, Wis.); Aldrich Catalog No. 20,568-0, 5% palladium on activated carbon.

Preferably, the noble metal is deposited via a reactive deposition technique comprising contacting the carbon support with a solution comprising a salt of the noble metal, and then hydrolyzing the salt. An example of a suitable platinum salt which is relatively inexpensive is hexachloroplatinic acid ($H_2PtCl_6$). The use of this salt to deposit platinum onto a carbon support via hydrolytic deposition is illustrated in Example 3.

In one embodiment of this invention, the noble metal is deposited onto the surface of the carbon support using a solution comprising a salt of a noble metal in one of its more reduced oxidation states. For example, instead of using a salt of Pt(IV) (e.g., $H_2PtCl_6$), a salt of Pt(II) is used. In another embodiment, platinum in its elemental state (e.g., colloidal platinum) is used. Using these more reduced metal precursors leads to less oxidation of the carbon support and, therefore, less oxygen-containing functional groups being formed at the surface of the support while the noble metal is being deposited onto the surface. One example of a Pt(II) salt is $K_2PtCl_4$. Another potentially useful Pt(II) salt is diamminedinitrito platinum(II). Example 11 shows that using this salt to deposit the noble metal produces a catalyst which is more resistant to leaching than a catalyst prepared using $H_2PtCl_6$ as the metal precursor. Without being bound by any particular theory, it is believed that this is due to the fact that diamminedinitrito platinum(II) generates ammonia in-situ during reduction which further promotes removal of the oxygen-containing functional groups at the surface of the carbon support. This benefit, however, should be weighed against a possible explosion danger associated with the use of diamminedinitrito platinum(II).

A catalyst-surface promoter(s) may be deposited onto the surface of the carbon support before, simultaneously with, or after deposition of the noble metal onto the surface. Methods used to deposit a promoter onto the surface of the carbon support are generally known in the art, and include the same methods used to deposit a noble metal discussed above. In one embodiment, a salt solution comprising a promoter is used to deposit the catalyst-surface promoter. A suitable salt that may be used to deposit bismuth is $Bi(NO_3)_3 \cdot 5H_2O$, a suitable salt that may be used to deposit iron is $FeCl_3 \cdot 6H_2O$, and a suitable salt that may be used to deposit tin is $SnCl_2 \cdot 2H_2O$. It should be recognized that more than one catalyst-surface promoter may be deposited onto the surface of the carbon support. Examples 13, 14, 15, and 17 demonstrate depositing a promoter onto a carbon surface with a salt solution comprising a promoter. Example 18 demonstrates depositing more than one promoter (i.e., iron and tin) onto a carbon surface using salt solutions comprising the promoters.

As noted above, a catalyst comprising a noble metal alloyed with at least one catalyst-surface promoter is particularly preferred. There are a variety of possible preparative techniques known in the art which may be used to form a multi-metallic alloy at support surfaces. See, e.g., V. Ponec & G. C. Bond, *Catalysis by Metals and Alloys*, "Studies in Surface Science and Catalysis," Vol. 95 (B. Delmon. & J. T. Yates, advisory eds., Elsevier Science B.V., Amsterdam, Netherlands).

In one of the more preferred embodiments, reactive deposition is used to form metal particles containing a noble metal alloyed with a catalyst-surface promoter. Reactive deposition may comprise, for example, reductive deposition wherein a surface of a carbon support is contacted with a solution comprising: (a) a reducing agent; and (b) (i) a compound comprising the noble metal and a compound comprising the promoter, or (ii) a compound comprising both the noble metal and the promoter. A wide range of reducing agents may be used, such as sodium borohydride, formaldehyde, formic acid, sodium formate, hydrazine hydrochloride, hydroxylamine, and hypophosphorous acid. Compounds comprising a noble metal and/or a promoter include, for example:

1. Halide compounds. These include, for example, $H_2PtCl_6$, $K_2PtCl_4$, $Pt_2Br_6^{2-}$, $K_2PdCl_4$, $AuCl_4^{1-}$, $RuCl_3$, $RhCl_3 \cdot 3H_2O$, $K_2RuCl_6$, $FeCl_3 \cdot 6H_2O$, $(SnCl_3)^{1-}$, $SnCl_4$, $ReCl_6$, $FeCl_2$, and $TiCl_4$.
2. Oxide and oxy chloride compounds. These include, for example, $RuO_4^{2-}$ and $M_2SnO_4$.
3. Nitrate compounds. These include, for example, $Fe(NO_3)_3$.
4. Amine complexes. These include, for example, [Pt(NH$_3$)$_4$]Cl$_2$, [Pd(NH$_3$)$_4$]Cl$_2$, Pt(NH$_3$)$_2$Cl$_2$, Pt(NH$_3$)$_4$]PtCl$_4$, Pd(NH$_2$CH$_2$CH$_2$NH$_2$)Cl$_2$, Pt(NH$_2$CH$_2$CH$_2$NH$_2$)$_2$Cl$_2$, and [Ru(NH$_3$)$_5$Cl]Cl$_2$.
5. Phosphine complexes. These include, for example, Pt(P(CH$_3$)$_3$)$_2$Cl$_2$; IrClCO(P(C$_6$H$_5$)$_3$)$_2$; PtClH(PR$_3$)$_2$, wherein each R is independently a hydrocarbyl, such as methyl, ethyl, propyl, phenyl, etc
6. Organometallic complexes. These include, for example, Pt$_2$(C$_3$H$_6$)$_2$Cl$_4$; Pd$_2$(C$_2$H$_4$)$_2$Cl$_4$; Pt(CH$_3$COO)$_2$, Pd(CH$_3$COO)$_2$; K[Sn(HCOO)$_3$]; Fe(CO)$_5$; Fe$_3$(CO)$_{12}$; Fe$_4$(CO)$_{16}$; Sn$_3$(CH$_3$)$_4$; and Ti(OR)$_4$, wherein each R is independently a hydrocarbyl, such as methyl, ethyl, propyl, phenyl, etc.
7. Noble metal/promoter complexes. These include, for example, Pt$_3$(SnCl$_3$)$_2$(C$_8$H$_{12}$)$_3$ and [Pt(SnCl$_3$)$_5$]$^{3-}$.

In a particularly preferred embodiment, hydrolysis reactions are used to deposit a noble metal alloyed with a catalyst-surface promoter. In this instance, ligands containing the noble metal and promoter are formed, and then hydrolyzed to form well-mixed, metal oxide and metal hydroxide clusters at the surface of the carbon support. The ligands may be formed, for example, by contacting the surface of the support with a solution comprising (a) a compound comprising the noble metal and a compound comprising the promoter, or (b) a compound comprising both the noble metal and the promoter. Suitable compounds comprising a noble metal and/or a promoter are listed above with respect to reductive deposition. Hydrolysis of the ligands may be achieved, for example, by heating (e.g., at a temperature of at least about 60° C.) the mixture. Example 17 further demonstrates the use of hydrolysis reactions to deposit a noble metal (i.e., platinum) alloyed with a catalyst-surface promoter (i.e., iron).

In addition to the above-described reactive deposition techniques, there are many other techniques which may be used to form the alloy. These include, for example:

1. Forming the alloy by introducing metal compounds (which may be simple or complex, and may be covalent or ionic) to the surface of the support via impregnation, adsorption from a solution, and/or ion exchange.
2. Forming the alloy by vacuum co-deposition of metal vapors containing the noble metal and promoter onto the surface.
3. Forming the alloy by depositing one or metals onto a pre-deposited metal belonging to Group 8, 9, or 10 of the Periodic Table of the Elements (i.e., Fe, Co, Ni, Ru, Rh, Pd, Os, Ir, and Pt) via, for example, electrolytic or electroless plating.
4. Forming the alloy by: (a) depositing metal complexes containing metals in the zero valence state (e.g., carbonyl, pi-allyl, or cyclopentadienyl complexes of the noble metal and of the promoter) at the surface of the carbon support; and (b) removing the ligands by, for example, heating or reduction to form the alloy particles at the surface.
5. Forming the alloy by contacting a solution containing a metal compound (e.g., a metal chloride or a metal alkyl compound) with a pre-deposited metal hydride containing a metal belonging to Group 8, 9, or 10 of the Periodic Table of the Elements.
6. Forming the alloy by co-depositing, either simultaneously or sequentially, metal complexes (either pre-formed or formed in situ) containing the noble metal(s) and promoter(s) at the surface of the carbon support.
7. Forming the alloy by preforming alloy particles as colloids or aerosols, and then depositing the preformed alloy particles at the surface of the carbon support. To illustrate, colloidal particles containing platinum and iron may be easily formed by boiling a dilute solution of $H_2PtCl_6$ and $SnCl_2.2H_2O$ with a sodium citrate solution. Protecting agents (e.g., carbohydrates, polymers, lipophilic quaternary nitrogen salts) may be used to effectively control metal alloy particle growth. This technique, therefore, is often useful to form a narrow distribution of alloy particle sizes.

It should be recognized that the above-discussed techniques for forming an alloy are simply illustrative, and not exhaustive. Using the teachings of this specification and the general knowledge of the art, one of ordinary skill in the art may routinely determine which of the numerous alloy preparation techniques known in the art are suitable to a particular use.

Regardless of the technique used to form the alloy, after the metals have been deposited at the surface of the carbon support, it is often preferable to dry the support using, for example, a sub-atmospheric, non-oxidizing environment (preferably, $N_2$, a noble gas, or both). Use of a drying step is particularly preferred where the surface of the support is to be subsequently reduced by heating the surface (and even more preferred where the heating is to be conducted in a non-oxidizing environment). Preferably, the support is dried to reduce the moisture content of the support to less than about 5% by weight.

It should be recognized that reducing the surface of the carbon support after deposition of the noble metal(s) and catalyst-surface promoter(s) typically increases the extent of noble metal alloyed with a catalyst-surface promoter. Such reduction also often tends to increase the number of particles falling within the preferred size range.

After the carbon support has been impregnated with the noble metal(s) (and catalyst-surface promoter(s), if any), the surface of the catalyst preferably is reduced. The surface of the catalyst suitably may be reduced, for example, by heating the surface at a temperature of at least about 400° C. It is especially preferable to conduct this heating in a non-oxidizing environment (e.g., nitrogen, argon, or helium). It is also more preferred for the temperature to be greater than about 500° C. Still more preferably, the temperature is from about 550 to about 1,200° C., and most preferably from about 550 to about 900° C. Temperatures less than 400° C. tend to be unsatisfactory for removing the oxygen-containing functional groups from the surface of the carbon support. On the other hand, temperatures greater than 1,200° C. tend to reduce the activity of the catalyst. Temperatures of from about 400 to about 500° C. preferably are used only if the surface of the carbon support has a carbon atom to oxygen atom ratio of at least about 20:1 before the noble metal is deposited onto the surface.

In a particularly preferred embodiment, the surface of the catalyst is reduced by a process comprising exposing the surface to a reducing environment. For example, before the heating, the catalyst sample may be pre-treated with a liquid phase reducing agent, such as formaldehyde or formic acid. Even more preferably, the heating is conducted in the presence of a gas-phase reducing agent (the method of heating the catalyst in the presence of a gas-phase reducing agent will sometimes be referred to as high-temperature gas-phase reduction). Various gas-phase reducing agents may be used during the heating, including but not limited to $H_2$, ammonia, and carbon monoxide. Hydrogen gas is most preferred because the small molecular size of hydrogen allows better penetration into the deepest pores of the carbon support. Preferably, the remainder of the gas consists essentially of a non-oxidizing gas, such as nitrogen, argon, or helium. The gas may comprise any finite concentration of $H_2$, although $H_2$ concentrations of less than 1.0% are disadvantageous because of the time they tend to require to reduce the surface of the support. Preferably, the gas comprises from about 5 to about 50 volume % $H_2$, and most preferably from about 5 to about 25 volume % $H_2$.

The preferred amount of time that the catalyst surface is heated depends on the mass transfer of the reducing agent to the catalyst surface. When the reducing agent is a non-oxidizing gas comprising from about 10 to about 20 volume % $H_2$, the surface preferably is heated for from about 15 minutes to about 24 hours at from about 550 to about 900° C. with a space velocity of from about 1 to about 5,000 $hour^{-1}$. More preferably, the space velocity is from about 10 to about 2,500 $hour^{-1}$, and even more preferably from about 50 to about 750 $hour^{-1}$. In the most preferred embodiment, the heat treatment is conducted at the above preferred temperatures and space velocities for from about 1 to about 10 $hours^{-1}$. Heating the surface at space velocities of less than 1 $hour^{-1}$ is disadvantageous because the oxygen-containing functional groups at the surface of the carbon support may not be sufficiently destroyed. On the other hand, heating the surface at space velocities greater than 5,000 hour$^{-1}$ is uneconomical.

Pre-existing oxygen-containing functional groups at the surface of the carbon support generally are not necessary, or even desired, to obtain adequate noble metal dispersion and retention. Without being bound by any particular theory, it is believed that this heating step enhances the platinum-carbon interaction on the catalyst by removing oxygen-containing functional groups at the surface of the carbon support, including those formed by depositing the noble metal onto the surface. It is believed that these oxygen-containing functional groups are unstable anchor sites for the noble metal because they tend to interfere with the potentially stronger π interactions between the noble metal and the carbon support. Heating alone will decompose and thereby remove many of the oxygen-containing functional groups at the surface of the carbon support. However, by heating the surface in the presence of a reducing agent (e.g., $H_2$), more oxygen-containing functional groups are able to be eliminated.

If the carbon atom to oxygen atom ratio at the surface of the carbon support is less than about 20:1 before the noble metal is deposited onto the surface of the support, the surface preferably is reduced using the above-described high-temperature gas-phase reduction treatment at a temperature greater than 500° C., although the surface may optionally be treated with other reduction environments in addition to high-temperature gas-phase reduction. On the other hand, if the surface of the carbon support has a carbon atom to oxygen atom ratio which is at least about 20:1 before the noble metal is deposited onto the surface, various alternative reduction environments may be used instead of high-temperature gas-phase reduction.

The surface of the catalyst may be reduced, at least in part, by treating it with an amine, such as urea, a solution comprising ammonium ions (e.g., ammonium formate or ammonium oxalate), or ammonia gas, with ammonia gas or a solution comprising ammonium ions being most preferred. This amine treatment preferably is used in addition to other reduction treatments, and most preferably is used before high-temperature gas-phase reduction. In one such embodiment, the noble metal is deposited onto the surface by treating it with a noble metal precursor solution comprising ammonium ions. Alternatively, after the noble metal is deposited onto the surface of the support, the support may be washed with a solution comprising ammonium ions or placed into contact with a gas comprising ammonia. Most preferably, the catalyst surface is washed with diluted aqueous ammonia after depositing the noble metal. In this instance, the catalyst is added to pure water and stirred for a few hours to wet the surface of the catalyst. Next, while continuing to stir the catalyst slurry, a solution comprising ammonium ions is added to the catalyst slurry in an amount sufficient to produce a pH of greater than 7, more preferably from about 8 to about 12, and most preferably from about 9.5 to about 11.0. Because the temperature and pressure are not critical, this step preferably is performed at room temperature and atmospheric pressure. Example 10 further demonstrates this reduction treatment.

Sodium borohydride ($NaBH_4$) also may be used to reduce the surface of the catalyst. As with the amine treatment, this treatment preferably is used in addition to other reduction treatments, and most preferably is used before high-temperature gas-phase reduction. Preferably, after depositing the noble metal onto the surface of the support, the support is washed with a solution of $NaBH_4$ in the presence of NaOH at a pH of from about 8 to about 14 for about 15 to about 180 minutes. The amount of $NaBH_4$ used preferably is sufficient to reduce all the noble metal. Because the temperature and pressure are not critical, this step preferably is performed at room temperature and atmospheric pressure. Example 12 further demonstrates this reduction treatment.

It should be recognized that any of the above treatments which may be used to reduce the surface of the catalyst also may be used to deoxygenate the surface of the carbon support before the noble metal is deposited onto the surface.

In many processes, when it is desirable for a catalyst to contain a promoter, the promoter is pre-deposited onto the catalyst surface by, for example, the promoter deposition techniques described above (this deposition step is often performed by the manufacturer of the catalyst). This promoter deposition step, however, tends to add costs to the catalyst preparation process. To avoid these additional costs, it has been found that the benefits of a promoter (e.g., increased selectivity, activity, and/or catalyst stability) may be obtained by merely mixing a promoter (i.e., a supplemental promoter) directly with a carbon-supported, noble-metal-containing catalyst (particularly with the reduced catalysts described above). This mixing may, for example, be conducted directly in an oxidation reaction zone where the N-(phosphonomethyl)iminodiacetic acid substrate is oxidized. Alternatively, for example, this mixing may take place separately from the oxidation reaction, such as in a catalyst holding tank.

Particularly, it has been discovered that certain metals and/or metal compounds function as supplemental promoters in the oxidation of an N-(phosphonomethyl)iminodiacetic acid substrate catalyzed by a carbon-supported, noble-metal-containing catalyst. It has been found that such supplemental promoters are effective in enhancing the capability of noble metal on carbon catalysts for the oxidation of an N-(phosphonomethyl)iminodiacetic acid substrate to an N-(phosphonomethyl)glycine product wherein they are effective in enhancing catalysis of the desired conversion to N-(phosphonomethyl) glycine, the oxidation of by-product formaldehyde to formic acid, and the oxidation of by-product formic acid to carbon dioxide.

Depending on the application, the supplemental promoter(s) may be, for example, tin, cadmium, magnesium, manganese, ruthenium, nickel, copper, aluminum, cobalt, bismuth, lead, titanium, antimony, selenium, iron, rhenium, zinc, cerium, zirconium, tellurium, sodium, potassium, vanadium, gallium, tantalum, niobium, rubidium, cesium, lanthanum, and/or germanium. It is often more preferred for the supplemental promoter(s) to be bismuth, lead, germanium, tellurium, titanium, copper and/or nickel.

In an especially preferred embodiment, the supplemental promoter is bismuth. It has been found in accordance with this invention that the presence of bismuth is especially effective in enhancing the selectivity of a carbon-supported, noble-metal-containing catalyst (particularly the reduced catalyst described above) when it is used to catalyze the oxidation of an N-(phosphonomethyl)iminodiacetic acid substrate to form an N-(phosphonomethyl)glycine product. More specifically, it has been found that the presence of bismuth causes an increase in the amount of formic acid by-product that is catalytically oxidized. In some instances (particularly where the catalyst comprises tin as a catalyst-surface promoter), the presence of bismuth also has been found to cause an increase in the amount of formaldehyde by-product that is catalytically oxidized. This increased destruction of one or both of these by-products, in turn, causes less N-methyl-N-phosphonomethyl)glycine by-product to be formed (it is believed that this stems from the fact that the formation of each molecule of N-methyl-N (phosphonomethyl)glycine by-product requires either (a) two formaldehyde molecules, or (b) a formic acid molecule and a formaldehyde molecule). Further, it has been found that in some instances (particularly where more than one supplemental promoter is used) that the presence of bismuth may also reduce the amount of noble metal that leaches from the carbon support of the catalyst during the oxidation of an N-(phosphonomethyl)iminodiacetic acid substrate.

In another preferred embodiment of this invention, tellurium is used as a supplemental promoter. As in the above embodiment incorporating bismuth as a supplemental promoter, it has been found that the presence of tellurium is also effective in enhancing the selectivity of a carbon-supported, noble-metal-containing catalyst (particularly the reduced catalyst described above) when it is used to catalyze the oxidation of an N-(phosphonomethyl)iminodiacetic acid substrate to form an N-(phosphonomethyl)glycine product. More particularly, it has been further found that tellurium may increase the activity of the catalyst in the oxidation of an N-(phosphonomethyl)iminodiacetic acid substrate. Further, it has also been found that noble metal leaching from the carbon support of the catalyst may be reduced during the oxidation of an N-(phosphonomethyl)iminodiacetic acid substrate by the presence of tellurium in the reaction medium (particularly when bismuth is also present).

In a most preferred embodiment, both bismuth and tellurium are used as supplemental promoters.

The mixing of the supplemental promoter and catalyst preferably is conducted in a liquid medium. As noted above, this mixing may, for example, be conducted directly in a liquid reaction medium where the N-(phosphonomethyl) iminodiacetic acid substrate is being oxidized. Where, however, the oxidation reaction is carried out under pressure, the reaction vessel is normally sealed and it is consequently often more preferred to mix the catalyst with the supplemental promoter separately from the reaction vessel, such as in a catalyst holding or recycle tank.

Typically, the supplemental promoter is introduced into the mixing liquid in the form of an inorganic or organic compound containing the supplemental promoter. The promoter-containing compound may be soluble or insoluble in the liquid, but most typically is at least partially soluble. The functional group attached to the supplemental promoter atom is generally not critical (although it preferably is an agronomically acceptable functional group). Typically, for example, suitable compounds include oxides, hydroxides, salts of inorganic hydracids, salts of inorganic oxy-acids, salts of aliphatic or aromatic organic acids, and phenates.

Suitable bismuth-containing compounds, for example, include inorganic or organic compounds wherein the bismuth atom(s) is at an oxidation level greater than 0 (e.g., 2, 3, 4 or 5), most preferably 3. Examples of such suitable bismuth compounds include:

1. Bismuth oxides. These include, for example, BiO, $Bi_2O_3$, $Bi_2O_4$, $Bi_2O_5$, and the like.
2. Bismuth hydroxides. These include, for example, $Bi(OH)_3$ and the like.
3. Bismuth salts of inorganic hydracids. These include, for example, bismuth chloride (e.g., $BiCl_3$), bismuth bromide (e.g., $BiBr_3$), bismuth iodide (e.g., $BiI_3$), bismuth telluride (e.g., $Bi_2Te_3$), and the like. Bismuth halides are typically less preferred because they tend to be corrosive to the process equipment.
4. Bismuth salts of inorganic oxy-acids. These include, for example, bismuth sulphite (e.g., $Bi_2(SO_3)_3 \cdot Bi_2O_3 \cdot 5H_2O$), bismuth sulphate (e.g., $Bi_2(SO_4)_3$), bismuthyl sulfate (e.g., $(BiO)HSO_4$), bismuthyl nitrite (e.g., $(BiO)NO_2 \cdot 0.5H_2O$), bismuth nitrate (e.g., $Bi(NO_3)_3 \cdot 5H_2O$, also known as bismuth nitrate pentahydrate), bismuthyl nitrate (e.g., $(BiO)NO_3$, also known as bismuth subnitrate, bismuth nitrate oxide, and bismuth oxynitrate), double nitrate of bismuth and magnesium (e.g., $2Bi(NO_3)_3 \cdot 3Mg(NO_3)_2 \cdot 24H_2O$), bismuth phosphite (e.g., $Bi_2(PO_3H)_3 \cdot 3H_2O$), bismuth phosphate (e.g., $BiPO_4$), bismuth pyrophosphate (e.g., $Bi_4(P_2O_7)_3$), bismuthyl carbonate (e.g., $(BiO)_2CO_3$, also known as bismuth subcarbonate), bismuth perchlorate (e.g., $Bi(ClO_4)_3 \cdot 5H_2O$), bismuth antimonate (e.g., $BiSbO_4$), bismuth arsenate (e.g., $Bi(AsO_4)_3$), bismuth selenite (e.g., $Bi_2(SeO_2)_3$), bismuth titanate (e.g., $Bi_2O_3 \cdot 2TiO_2$), and the like. These salts also include bismuth salts of oxy-acids derived from transition metals, including, for example, bismuth vanadate (e.g., $BiVO_4$), bismuth niobate (e.g., $BiNbO_4$), bismuth tantalate (e.g., $BiTaO_4$), bismuth chromate (e.g., $Bi_2(CrO_4)$), bismuthyl dichromate (e.g., $(BiO)_2Cr_2O_7$), bismuthyl chromate (e.g., $H(BiO)CrO_4$), double chromate of bismuthyl and potassium (e.g., $K(BiO)CrO_4$), bismuth molybdate (e.g., $Bi_2(MoO_4)_3$), double molybdate of bismuth and sodium (e.g., $NaBi(MoO_4)_2$), bismuth tungstate (e.g., $Bi_2(WO_4)_3$), bismuth permanganate (e.g., $Bi_2O_2(OH)MnO_4$), bismuth zirconate (e.g., $2Bi_2O_3 \cdot 3ZrO_2$), and the like.
5. Bismuth salts of aliphatic or aromatic organic acids. These include, for example, bismuth acetate (e.g., $Bi(C_2H_3O_2)_3$), bismuthyl propionate (e.g., $(BiO)C_3H_5O_2$), bismuth benzoate (e.g., $C_6H_5CO_2Bi(OH)_2$), bismuthyl salicylate (e.g., $C_6H_4CO_2(BiO)(OH)$), bismuth oxalate (e.g., $(C_2O_4)_3Bi_2$), bismuth tartrate (e.g., $Bi_2(C_4H_4O_6)_3 \cdot 6H_2O$), bismuth lactate (e.g., $(C_6H_9O_5)OBi \cdot 7H_2O$), bismuth citrate (e.g., $C_6H_5O_7Bi$), and the like.
6. Bismuth phenates. These include, for example, bismuth gallate (e.g., $C_7H_7O_7Bi$), bismuth pyrogallate (e.g., $C_6H_3(OH)_2(OBi)(OH)$), and the like.
7. Miscellaneous other organic and inorganic bismuth compounds. These include, for example, bismuth phosphide (e.g., BiP), bismuth arsenide (e.g., $Bi_3As_4$), sodium bismuthate (e.g., $NaBiO_3$), bismuth-thiocyanic acid (e.g., $H_2(Bi(BNS)_5) \cdot H_3(Bi(CNS)_6)$), sodium salt of bismuth-thiocyanic acid, potassium salt of bismuth-thiocyanic acid, trimethylbismuthine (e.g., $Bi(CH_3)_3$), triphenylbismuthine (e.g., $Bi(C_6H_5)_3$), bismuth oxychloride (e.g., BiOCl), bismuth oxyiodide (e.g., BiOI), and the like.

In a preferred embodiment, the bismuth compound is a bismuth oxide, bismuth hydroxide, or bismuth salt of an inorganic oxy-acid. More preferably, the bismuth compound is bismuth nitrate (e.g., $Bi(NO_3)_3 \cdot 5H_2O$), bismuthyl carbonate (e.g., $(BiO)_2CO_3$), or bismuth oxide (e.g., $Bi_2O_3$), with bismuth (III) oxide (i.e., $Bi_2O_3$) being most preferred because it contains no counterion which can contaminate the final reaction product.

Suitable tellurium-containing compounds, for example, include inorganic or organic compounds wherein the tellurium atom(s) is at an oxidation level greater than 0 (e.g., 2, 3, 4, 5 or 6), most preferably 4. Examples of such suitable tellurium compounds include:

1. Tellurium oxides. These include, for example, $TeO_2$, $Te_2O_3$, $Te_2O_5$, $TeO_3$, and the like.
2. Tellurium salts of inorganic hydracids. These include, for example, tellurium tetrachloride (e.g., $TeCl_4$), tellurium tetrabromide (e.g., $TeBr_4$), tellurium tetraiodide (e.g., $TeI_4$), and the like.
3. Tellurium salts of inorganic oxy-acids. These include, for example, tellurious acid (e.g., $H_2TeO_3$), telluric acid (e.g., $H_2TeO_4$ or $Te(OH)_6$), tellurium nitrate (e.g., $Te_2O_4.HNO_3$), and the like.
4. Miscellaneous other organic and inorganic tellurium compounds. These include, for example, dimethyl tellurium dichloride, lead tellurium oxide, tellurium isopropoxide, ammonium tellurate, tellurium thiourea, and the like.

In a preferred embodiment, the tellurium compound is a tellurium oxide or tellurium salt of an inorganic hydracid. More preferably, the tellurium compound is tellurium dioxide (e.g., $TeO_2$), tellurium tetrachloride (e.g., $TeCl_4$), or telluric acid (e.g., $Te(OH)_6$), with tellurium tetrachloride being most preferred.

The preferred amount of the supplemental promoter introduced into the reaction zone depends on, for example, the mass of the carbon-supported, noble-metal-containing catalyst (i.e., the total mass of the carbon support, noble metal, and any other component of the catalyst); mass of the total reaction feed mixture; and the concentration of the N-(phosphonomethyl) iminodiacetic acid substrate.

In general, the ratio of the mass of the supplemental promoter to the mass of the carbon-supported, noble-metal-containing catalyst charged to the reactor(s) is preferably at least about 1:15000; more preferably at least about 1:5000; even more preferably at least about 1:2500; and most preferably at least about 1:1000. Although it is feasible to practice the present invention without detriment to the oxidation reaction when ratios of the mass of supplemental promoter to the mass of the carbon-supported, noble-metal-containing catalyst are as great as about 1:750, about 1:500, about 1:300, and even greater than about 1:50 or 1:40, the preferred lower ratios described above have been found to be effective for most applications, and particularly for the oxidation of an N-(phosphonomethyl) iminodiacetic acid substrate.

The ratio of the mass of the supplemental promoter to the total reaction mass charged to the reactor is preferably at least about 1:1,000,000; more preferably at least about 1:100,000; even more preferably at least about 1:40,000; and most preferably from about 1:40,000 to about 1:15,000. Although ratios greater than 1:8000 may normally be used without detriment to the oxidation reaction, it is generally preferred for the ratio to be less than 1:8000 (particularly where bismuth is the supplemental promoter).

The ratio of the mass of the supplemental promoter to the mass of the N-(phosphonomethyl)iminodiacetic acid substrate charged to the reactor is preferably at least about 1:100,000; more preferably 1:10,000; even more preferably at least about 1:4000; and most preferably from about 1:4000 to about 1:2000. Although ratios greater than 1:1000 may normally be used without detriment to the oxidation reaction, it is generally preferred for the ratio to be less than 1:1000 (particularly where bismuth is the supplemental promoter).

Where a particulate noble metal on carbon catalyst is used for the oxidation of an N-(phosphonomethyl)iminodiacetic acid substrate, both the catalyst and the supplemental promoter may be charged to an aqueous reaction medium containing the N-(phosphonomethyl)iminodiacetic acid substrate and oxygen. The supplemental promoter may be charged in a mass ratio to the catalyst charge of at least about 1:15,000, preferably at least about 1:5000, more preferably at least about 1:2500, and most preferably at least about 1:1000. As oxidation of the N-(phosphonomethyl)iminodiacetic acid substrate proceeds, formaldehyde and formic acid by-products are generated. The catalyst is effective to catalyze not only the oxidation of the N-(phosphonomethyl) iminodiacetic acid substrate but also the further oxidation of formaldehyde to formic acid, and formic acid to carbon dioxide. The presence of the supplemental promoter is effective to enhance the catalytic oxidation of these by-products, especially for the conversion of formic acid to $CO_2$.

Where the oxidation reaction is conducted in a stirred tank reactor in which catalyst is slurried in the reaction medium, the catalyst is separated from the reaction mixture, preferably by filtration, and recycled to the reactor for further oxidation of the N-(phosphonomethyl)iminodiacetic acid substrate and the aforesaid by-products. Such a stirred tank reactor system may be operated in either a batch or continuous mode. Alternatively, a fixed or fluid catalyst bed can be used. In a continuous process, the N-(phosphonomethyl) iminodiacetic acid substrate, formaldehyde and formic acid are all oxidized in a continuous reaction zone to which an aqueous reaction medium comprising the N-(phosphonomethyl)imindiacetic acid substrate is continuously or intermittently supplied and a reaction mixture comprising an N-(phosphonomethyl)glycine product is continuously or intermittently withdrawn, the supplemental promoter being continuously or intermittently introduced into the reaction zone.

It has been observed that addition of a discrete charge of supplemental promoter to the first batch of series of successive batch reaction cycles is effective to enhance the activity of the catalyst for oxidation of formaldehyde and formic acid throughout the series of reaction cycles, without further addition of supplemental promoter from any external source. It has further been observed that the supplemental promoter is present in the recycled catalyst, apparently having been deposited thereon by adsorption to the noble metal and/or the carbon support. Only a fraction of the supplemental promoter added to the first batch of the series can be found on the catalyst after multiple cycles. However, when supplemental promoter is introduced into the first batch in the amounts described above, the fraction remaining on the catalyst is apparently sufficient for promoting the oxidation of formaldehyde and formic acid throughout the series of batches in which the catalyst recycled from an earlier batch is substantially the sole source of supplemental promoter for the successive batch reaction cycles of the series. It has been found that a single addition of supplemental promoter in a mass ratio to the catalyst of approximately 1:2500 is effective for promotion of by-product oxidation in series of 20 or more, typically 50 or more, more typically over 100, batch reaction cycles. Thereafter, a further discrete charge of supplemental promoter optionally may be added to the reaction medium for a subsequent batch constituting the first of another series of batch oxidation reaction cycles in which the recycle catalyst from an earlier batch of such further series becomes substantially the sole source of promoter for the successive batch reaction cycles of the further series of batch reactions.

Similarly, where supplemental promoter is added to the reaction medium in a continuous stirred tank reactor, addition of supplemental promoter in a single discrete amount is effective to enhance the effectiveness of the catalyst for formaldehyde and formic acid oxidation throughout multiple reactor turnovers of a continuous reaction run. No further addition of supplemental promoter is made until the start of a second reaction run. For this purpose, a reaction run consists of the period of oxidation of formaldehyde and formic acid from the time of any discrete addition of supplemental promoter to the reaction zone until the time of the next succeeding addition of supplemental promoter to the reaction zone, and may consist of 50 or more, typically 100 or more, turnovers of the working volume of the reactor.

As noted, only a fraction of the supplemental promoter added to the first batch of a cycle remains on the catalyst after multiple cycles of a series of batch reaction runs, or after multiple turnovers of a continuous reaction run. However, the supplemental promoter remains effective to enhance the oxidation of the N-(phosphonomethyl)iminodiacetic acid substrate, formaldehyde and formic acid when the substrate is contacted with the oxidizing agent in a reaction zone which comprises the liquid reaction medium and wherein the mass ratio of supplemental promoter to the catalyst in such reaction zone is at least about 1:200,000, preferably at least about 1:70,000, more preferably at least about 1:30,000, most preferably at least about 1:15,000. Inasmuch as substantially the sole source of supplemental promoter for the reactor may be recycle catalyst, it is further preferred that the supplemental promoter be present on or in the recycle catalyst in the same mass ratios, i.e., at least about 1:200,000, preferably at least about 1:70,000, more preferably at least about 1:30,000, most preferably at least about 1:15,000.

The supplemental promoter content of the reaction zone can also be expressed as a mass ratio to the noble metal component of the catalyst. For example, for a 5% noble metal on carbon catalyst, the ratio of supplemental promoter to noble metal should be at least about 1:10,000, more preferably 1:3500, more preferably 1:1800, most preferably 1:700. These preferences generally prevail over the range of noble metal content of the noble metal on carbon catalyst, which is typically from about 0.5 to 20% noble metal. However, where the noble metal content is relatively high, e.g., approaching 20%, the supplemental promoter may be effective in relatively lower mass ratios to the noble metal component, even as low as 1:40,000.

Where the supplemental promoter is added in a discrete charge at the start of a series of batch reaction cycles, or at the beginning of a continuous reaction run as defined above, it is added in a mass ratio to the noble metal component of the catalyst of at least about 1:750, preferably at least about 1:250, more preferably at least about 1:125, most preferably at least about 1:50. As indicated above, the preferred ratio of supplemental promoter to noble metal may vary with the noble metal content of the catalyst. Thus, e.g., when the noble metal content of the catalyst approaches 20% by weight, the supplemental promoter may be effective when added at a mass ratio to noble metal of 1:3000 or higher, more preferably at least about 1:1000, 1:500 or 1:200.

Periodic discrete additions of supplemental promoter may be advantageous because excessive proportions of supplemental promoter, while maximizing the effectiveness of the catalyst for the oxidation of formaldehyde and formic acid, may retard the oxidation of the N-(phosphonomethyl)iminodiacetic acid substrate. By adding supplemental promoter only periodically, the proportions of supplemental promoter deposited on the catalyst and present in the reaction zone may decay fairly rapidly to a residual quasi-steady state range wherein the supplemental promoter remains effective to enhance catalytic activity for the oxidation of formaldehyde or formic acid without significantly retarding the rate or extent of oxidation of the N-(phosphonomethyl)iminodiacetic acid substrate. Thus, the optimum supplemental promoter content within the oxidation reaction zone for oxidizing the N-(phosphonomethyl)iminodiacetic acid substrate, and on the recycle catalyst for such reaction, may be lower than 1:15,000, for example, in a range of 1:65,000 to 1:25,000.

Deposit of supplemental promoter on the surface of a noble metal on carbon catalyst in the reaction medium results in formation of a novel catalyst complex comprising the catalyst and the promoter. The catalyst component of the catalyst complex may further comprise a surface promoter comprising a metal different from the supplemental promoter or, in some instances, comprising the same metal. The supplemental promoter is believed to be deposited by adsorption from the reaction medium, and remains desorbable from the catalyst surface into the catalyst medium. While an operative fraction of residual supplemental promoter resists desorption to remain adhered to the catalyst through multiple reaction cycles (or through an extended run of a continuous reaction system) as explained hereinabove, the supplemental promoter is typically more desorbable than the surface promoter which is applied in the catalyst preparation process.

As described above, the catalyst is prepared in the first instance by depositing noble metal and optionally surface promoter onto a carbon support to form a catalyst precursor, then reducing the catalyst precursor to produce the reaction catalyst. The novel catalyst complex is formed by subsequent deposition of supplemental promoter on the oxidation catalyst, typically by adsorption to the carbon or noble metal surface. Advantageously, the supplemental promoter is mixed with the oxidation catalyst in the reaction medium so that the promoter is deposited from the reaction medium onto the catalyst surface. However, it will be understood that, in the alternative, the supplemental promoter can be premixed with the oxidation catalyst in another liquid medium to form the catalyst complex, after which the catalyst complex may be introduced into the reaction medium for use in conducting the oxidation reaction.

It should be recognized that, depending on the desired effects, more than one supplemental promoter may be used. In addition, each supplemental promoter may come from more than one source. Further, the carbon-supported, noble-metal-containing catalyst may already contain an amount of metal on its surface which is the same metal as the supplemental promoter, such as where (a) the catalyst is manufactured with a such a metal on its surface to act as a catalyst-surface promoter, or (b) the catalyst is a used catalyst which has been recovered from a previous reaction mixture where the metal was present (e.g., as a supplemental promoter).

In a particularly preferred embodiment, the carbon-supported, noble-metal-containing catalyst itself also comprises one or more catalyst-surface promoters on its surface, as described above. Where the catalyst is being used in the oxidation of an N-(phosphonomethyl)iminodiacetic acid substrate and the supplemental promoter is bismuth, it is particularly preferred for the catalyst to contain tin and/or iron (the presence of tin tends to be particularly useful for increasing the oxidation of the formaldehyde by-product in addition to increasing the oxidation of the formic acid by-product).

In many instances, after a supplemental promoter (particularly bismuth) and a carbon-supported, noble-metal-containing catalyst have been combined, at least a portion of the supplemental promoter deposits onto the surface of the carbon support and/or noble metal of the catalyst, and is consequently retained by the catalyst. Because the catalyst retains the promoter, the catalyst may typically be recycled for use in catalyzing the oxidation of subsequent amounts of the oxidation substrate (e.g., the catalyst may be used to oxidize additional batches of the oxidation substrate, or may be used in a continuous oxidation process) while still retaining the benefits of the supplemental promoter. And, as the effects of the supplemental promoter decrease over time with use, replenishing amounts of fresh supplemental promoter may periodically be mixed with the catalyst to revive the effects and/or achieve other desired results (e.g., decreased formic acid levels). Where, for example, the catalyst is used in multiple batch reactions, such periodic replenishing may, for example, be conducted after the catalyst has been used in at least about 20 batch oxidation reactions (more preferably after it has been used in at least about 30 batch oxidation reactions, and most preferably after it has been used in at least about 100 or more batch oxidation reactions). Where a catalyst is periodically replenished with fresh supplemental promoter, the mixing for replenishment may be conducted in or separately from the oxidation reaction zone(s).

In a particularly preferred embodiment, a supplemental promoter is mixed with a used catalyst (i.e., a catalyst that has been used in one or more previous oxidation reactions). Typically, the activity and/or desired selectivity of a catalyst decreases with use. Thus, for example, the activity of a carbon-supported, noble-metal-containing catalyst for oxidizing by-products (e.g., formaldehyde and/or formic acid) of the oxidation of an N-(phosphonomethyl)iminodiacetic acid substrate often tends to decrease as the catalyst is used, thereby causing less formaldehyde and/or formic acid to be destroyed and, consequently, a greater amount of N-methyl-N-(phosphonomethyl)glycine to be produced. Eventually, in fact, this activity will decrease to a level where an unacceptable amount of formaldehyde and/or formic acid is not oxidized, consequently often causing an unacceptable amount of N-methyl-N-(phosphonomethyl)glycine compounds to be produced (i.e., the selectivity of the catalyst for making N-(phosphonomethyl)glycine compounds from N-(phosphonomethyl)iminodiacetic acid substrates will decrease to an unacceptable level). Traditionally, when the catalyst activity for oxidizing the by-products reaches such a point, the catalyst has been deemed unuseable, and, consequently, has either been recycled (i.e., reactivated) through a time-consuming and sometimes costly process, or discarded altogether. It has been discovered in accordance with this invention, however, that such a catalyst can be revived (i.e., the selectivity of the catalyst for making N-(phosphonomethyl)glycine product can be increased to an acceptable level) by mixing the catalyst with a supplemental promoter, particularly bismuth or tellurium. In other words, the supplemental promoter can be used to modify the catalyst performance and extend the life of the catalyst.

It has been observed that a supplemental promoter (particularly bismuth) may cause a slight decrease in the oxidation rate of an N-(phosphonomethyl)iminodiacetic acid substrate. In such an instance, the oxidation rate may typically be increased, at least in part, by increasing the amount of oxygen fed into the reacting mixture, maintaining a relatively high oxygen flowrate for an extended period during the reaction, and/or increasing the pressure. Where, however, the oxygen flow is increased, it preferably is not increased to an extent which causes the catalyst surface to become detrimentally over-oxidized. Thus, the increased oxygen feed rate preferably is maintained at a level such that at least about 40% (more preferably at least about 60%, even more preferably at least about 80%, and most preferably at least about 90%) of the fed oxygen is utilized.

Preferred Oxidation Reactor Systems

The oxidation reaction zone(s) may comprise a wide range of reactor configurations, including those that have back-mixed characteristics, in the liquid phase and optionally in the gas phase as well, and those that have plug flow characteristics. Suitable reactor configurations having back-mixed characteristics include, for example, stirred tank reactors, ejector nozzle loop reactors (also known as venturi-loop reactors) and fluidized bed reactors. Suitable reactor configurations having plug flow characteristics include those having a packed or fixed catalyst bed (e.g., trickle bed reactors and packed bubble column reactors) and bubble slurry column reactors. Fluidized bed reactors may also be operated in a manner exhibiting plug flow characteristics.

In a broad sense, the oxidation reaction may be practiced in accordance with the present invention at a wide range of temperatures, and at pressures ranging from sub-atmospheric to super-atmospheric. Use of mild conditions (e.g., room temperature and atmospheric pressure) has commercial advantages in that less expensive equipment may be used in the reactor system. However, operating at higher temperatures and super-atmospheric pressures, tends to improve mass transfer between the liquid and gas phase (e.g., the oxygen source), increase the N-(phosphonomethyl)iminodiacetic acid oxidation reaction rate and increase the N-(phosphonomethyl)glycine product solubility, thereby reducing the amount of water requiring separation to precipitate and recover the product. Accordingly, use of more aggressive oxidation conditions can actually reduce the overall costs of a plant and reduce operating costs per unit of N-(phosphonomethyl)glycine product produced. Preferably, the N-(phosphonomethyl)iminodiacetic acid oxidation reaction is conducted at a temperature of from about 20° C. to about 180° C., more preferably from about 50° C. to about 140° C., still more preferably from about 80° C. to about 110° C., and yet still more preferably from about 95° C. to about 105° C. At temperatures greater than about 180° C., the feed materials tend to slowly decompose. Moreover, the selectivity toward the desired N-(phosphonomethyl)glycine product tends to worsen as the oxidation reaction temperature increases much above about 90° C. For example, the production of the undesired by-product-methyl-N-(phosphonomethyl)glycine (NMG) tends to increase roughly 2- to 4-fold for each 10° C. increase in reaction temperature above 90° C. Lower temperatures (i.e., temperatures less than about 95° C.) often tend to be less advantageous because the solubility of some N-(phosphonomethyl)iminodiacetic acid substrates and N-(phosphonomethyl)glycine products are reduced at such temperatures. The total pressure maintained in the oxidation reaction zone(s) generally depends on the temperature used and the reactor configuration. The total pressure in each oxidation reaction zone is preferably at least equal to atmospheric pressure and sufficient to prevent the liquid reaction medium in the oxidation zone from boiling. Preferred oxidation reaction conditions for particular reactor systems are discussed in greater detail below.

In a preferred embodiment, the oxidation of the N-(phosphonomethyl)iminodiacetic acid substrate is conducted in one or more continuous oxidation reaction zones, wherein the substrate is continuously oxidized to form the N-(phosphonomethyl)glycine product. Continuous oxidation provides the opportunity for greater process throughput and lower production costs. Moreover, because the oxidation of the N-(phosphonomethyl)iminodiacetic acid substrate is exothermic, after startup of a continuous oxidation reactor system, typically no heat input to the aqueous feed stream introduced into the oxidation zone is required to maintain the desired oxidation reaction temperature.

Various reactor configurations may be suitably employed to provide the continuous oxidation reaction zone(s). In accordance with one preferred embodiment, continuous oxidation of the N-(phosphonomethyl)iminodiacetic acid substrate is carried out in one or more substantially back-mixed oxidation reaction zones (i.e., back-mixed in at least the liquid phase) utilizing a heterogeneous particulate catalyst, preferably the deeply reduced noble metal on carbon particulate catalyst described above, suspended in contact with the liquid reaction medium. However, it should be understood that the practice of the present invention is not limited to use of such a deeply reduced catalyst, nor to a catalyst in particulate form. Moreover, it should be understood that the catalyst used in the reactor systems of the present invention may comprise a mixture of different catalysts and/or the catalyst may vary from one oxidation reaction zone to the next within the reactor system.

Figure 2:
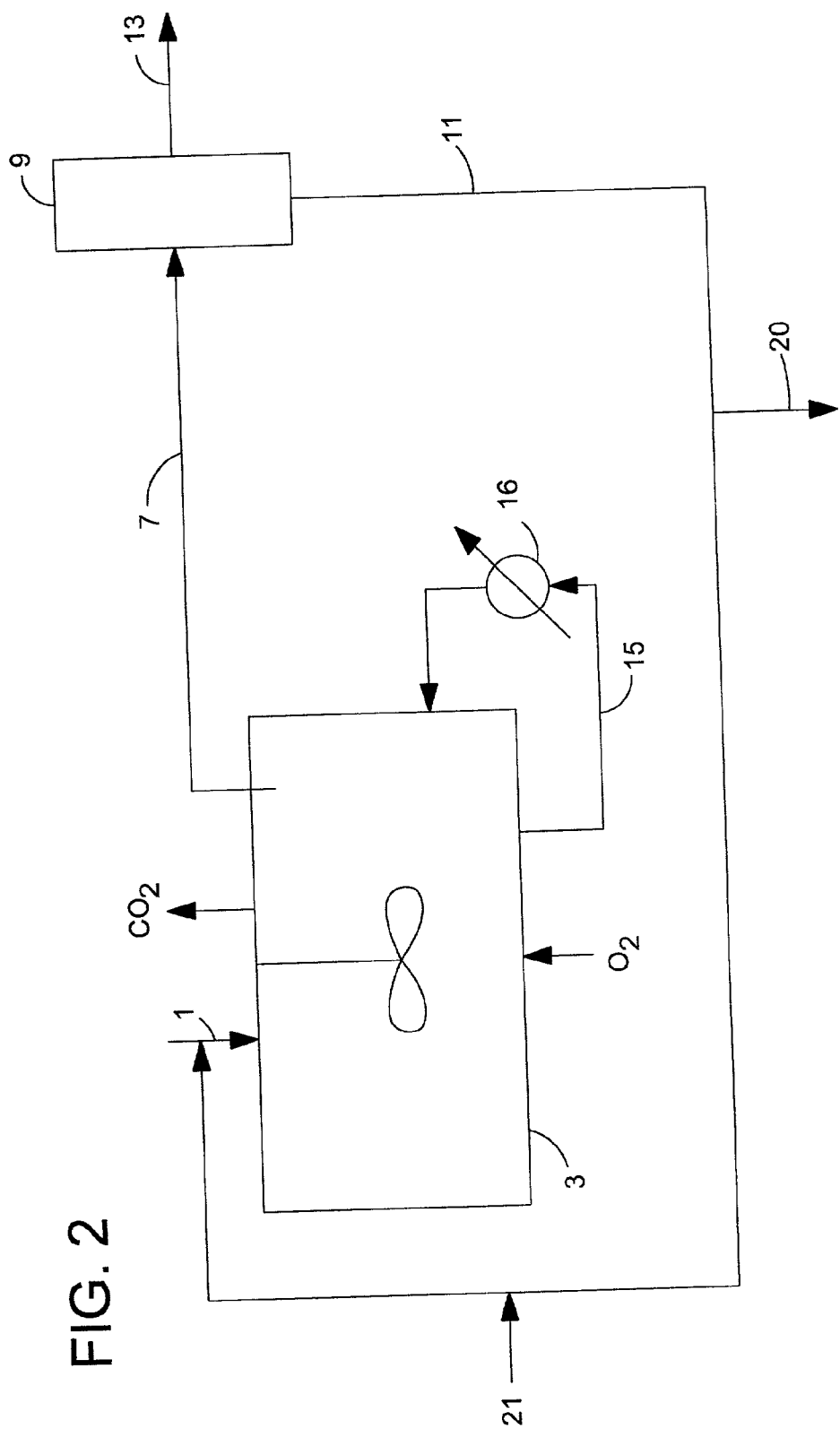
FIG. 2 is a schematic flow sheet of a continuous oxidation reactor system for oxidizing an N-(phosphonomethyl)iminodiacetic acid substrate to form an N-(phosphonomethyl)glycine product. The reactor system comprises a back-mixed oxidation reaction zone utilizing a heterogeneous particulate catalyst slurry recycled in a loop independent from a heat transfer recirculation loop.

FIG. 2 shows an example of a reactor system that may be used to carry out the continuous oxidation process of the present invention. The system shown in FIG. 2 comprises a continuous stirred tank reactor 3 providing mechanical agitation of the liquid reaction medium contained therein, typically by a rotating impeller. Stirred tank reactors suitably back-mix the liquid phase within the reaction zone, are relatively simple in design, and operation can be scaled to the desired process capacity. Various impeller designs may be employed, including systems with multiple blades rotated on a common shaft. The reactor vessel may include internal baffles and/or draft tubes to modify mixing characteristics and prevent swirling of the liquid reaction medium as is well-known to those skilled in the art.

Although the reactor system shown in FIG. 2 comprises a single continuous stirred tank reactor, in many instances, a reactor system comprising two or more back-mixed oxidation reaction zones staged in series is preferred as will be described in greater detail below. The back-mixed oxidation reaction zone(s) may be suitably provided by reactor configurations other than continuous stirred tank reactors (e.g., ejector nozzle loop reactors and fluidized bed reactors). Moreover, different reactor configurations may be combined in a reactor system comprising multiple oxidation reaction zones. For example, one or more reactors having back-mixed characteristics may be combined with a reactor configuration having plug flow characteristics such as a fixed catalyst bed reactor.

An aqueous feed stream 1 comprising the N-(phosphonomethyl)iminodiacetic acid substrate is continuously or intermittently introduced into a liquid reaction medium within the stirred tank reactor 3 along with an oxygen source. The heterogeneous particulate catalyst is also present within the oxidation reaction zone in contact with the liquid reaction medium and used to catalyze the oxidation of the N-(phosphonomethyl)iminodiacetic acid substrate in the aqueous feed. Vapor comprising $CO_2$ evolved as the oxidation reaction proceeds is vented from the headspace above the reaction mixture in the stirred tank reactor 3. A reaction mixture effluent 7 containing the N-(phosphonomethyl)glycine product and the heterogenous particulate catalyst is continuously or intermittently withdrawn from the stirred tank reactor 3 and transferred to a catalyst filter 9, wherein substantially all the catalyst is separated from the reaction mixture to form: (1) a catalyst recycle stream 11 comprising substantially all the catalyst and a residual amount of the N-(phosphonomethyl)glycine product; and (2) a filtrate 13 containing much of the N-(phosphonomethyl)glycine product. The catalyst recycle stream 11 is reintroduced into the stirred tank reactor 3, while the filtrate 13 is carried forward to concentrate and purify the N-(phosphonomethyl)glycine product.

The temperature within the oxidation reaction zone is preferably maintained sufficiently high with respect to the N-(phosphonomethyl)glycine product concentration such that essentially all the N-(phosphonomethyl)glycine product in the reaction mixture effluent 7 withdrawn from the stirred tank reactor 3 is dissolved. Thus, for example, when the N-(phosphonomethyl)glycine product is the N-(phosphonomethyl)glycine free acid at a concentration of from about 7 to about 15% by weight, the temperature of the reaction mixture effluent withdrawn from the stirred tank reactor 3 is preferably maintained at from about 80° C. to about 180° C., more preferably from about 90° C. to about 150° C., more preferably from about 90° C. to about 135° C., even more preferably from about 95° C. to about 125° C., and still more preferably from about 95° C. to about 105° C. However, it should be understood that precipitation of the N-(phosphonomethyl)glycine product in the reaction mixture effluent 7 can be tolerated and satisfactory results still obtained. The precipitated N-(phosphonomethyl)glycine product may be separated with the particulate catalyst (e.g., co-filtered) from the remainder of the reaction mixture effluent 7.

At startup, the reaction mixture in the oxidation reaction zone 3 and/or the aqueous feed stream 1 may be heated to obtain the desired temperature for the oxidation reaction. If heat addition is required, all or at least a portion of the heat energy may be provided in pumping the various feed streams into the stirred tank reactor 3 and through the remainder of the reactor system such that a separate conventional feed preheater may not be necessary. Because the oxidation reaction is exothermic, it will normally be necessary to remove heat energy from the reaction mixture once the oxidation reaction begins to evolve significant amounts of heat in order to maintain the desired temperature within the oxidation zone. As shown in FIG. 2, excess reaction heat may be extracted from the reaction mixture within the stirred tank reactor 3 by passing the reaction mixture through an external heat transfer recirculation loop 15 containing a heat exchanger 16 wherein heat is transferred indirectly from the reaction mixture to a cooling medium (e.g., cooling water). The reaction temperature is controlled by, for example, controlling the supply of cooling water to heat exchanger 16 in response to the signal from a temperature controller. Reaction heat can be removed from the oxidation reaction zone by other conventional means as well, such as with cooling coils immersed within the reaction mixture or a reactor vessel jacket through which a cooling medium is circulated.

The total pressure in the stirred tank reactor 3 is generally from about 0 to about 500 psig and is preferably maintained sufficiently high to prevent the liquid reaction medium therein from boiling. Typically, the total pressure in the stirred tank reactor 3 is from about 30 to about 500 psig. When operating the oxidation reaction zone within the especially preferred temperature range of from about 95° C. to about 105° C., the total pressure maintained within the stirred tank reactor 3 is preferably from about 30 to about 130 psig and more preferably from about 90 to about 110 psig.

A wide range of N-(phosphonomethyl)iminodiacetic acid substrate concentrations may be used in the aqueous feed stream 1. The aqueous feed stream 1 includes the catalyst recycle stream 11 and any other recycle streams from other parts of the process introduced into stirred tank reactor 3. In slurry reactors, such as the stirred tank reactor shown in FIG. 2, the substrate concentration in the aqueous feed stream 1 is preferably selected with respect to the temperature of the reaction mixture effluent 7 such that essentially all of the desired N-(phosphonomethyl)glycine product is dissolved. As noted above, substrate concentrations which form reaction mixtures containing N-(phosphonomethyl)glycine product at a concentration exceeding the solubility limit of the product may also be employed, but are generally less preferred. Relative to many commonly-practiced commercial processes, this invention allows for greater temperatures and N-(phosphonomethyl)iminodiacetic acid substrate concentrations to be used to prepare N-(phosphonomethyl) glycine while minimizing by-product formation. In the commonly practiced commercial processes using a carbon-only catalyst, it has often been economically preferable to operate at low substrate concentrations and temperatures to minimize the formation of the N-methyl-N-(phosphonomethyl)glycine by-product. With those processes and catalysts, temperatures of from about 60° C. to 90° C. are typically used to achieve cost effective yields and to minimize the generation of waste. At such temperatures, the maximum N-(phosphonomethyl)glycine solubility typically is less than 6.5% ([mass of N-(phosphonomethyl)iminodiacetic acid substrate÷total reaction mass]×100%). But, with the preferred oxidation catalyst and reaction process of this invention, the loss of noble metal from the catalyst and catalyst deactivation is minimized and the formaldehyde is more effectively oxidized, thereby allowing for reaction temperatures as great as 180° C. (or greater). The use of higher oxidation reaction temperatures and reactor feed concentrations permits reactor throughput to be increased, reduces the amount of water that must be removed per pound of N-(phosphonomethyl)glycine product produced, and reduces the cost of manufacturing N-(phosphonomethyl) glycine. This invention thus provides economic benefits over many commonly-practiced commercial processes.

The preferred upper limit on the concentration of the N-(phosphonomethyl)iminodiacetic acid substrate is dependent on the specific substrate employed. For example, in the case of a salt of N-(phosphonomethyl)iminodiacetic acid (e.g., potassium salt) concentrations up to about 70 wt. % may be employed. Typically, however, an N-(phosphonomethyl)iminodiacetic acid substrate concentration of up to about 50 wt. % is preferred (especially at a reaction temperature of from about 20 to about 180° C.). More preferably, an N-(phosphonomethyl)iminodiacetic acid substrate concentration of up to about 25 wt. % is used (particularly at a reaction temperature of from about 60 to about 150° C.). Even more preferably, an N-(phosphonomethyl)iminodiacetic acid substrate concentration of from about 3 to about 20 wt. % is used (particularly at a reaction temperature of from about 100 to about 130° C.). At preferred reaction temperatures of from about 95 to about 105° C., the N-(phosphonomethyl)iminodiacetic acid substrate concentration preferably is from about 7 to about 15 wt. %, more preferably from about 7 to about 12% by weight, and even more preferably from about 9 to about 10 wt. %.

In some instances, the source of the N-(phosphonomethyl)iminodiacetic acid substrate fed to the process in the aqueous feed stream 1 contains chloride ions ($Cl^-$) which have been carried over from the synthesis of the substrate. Where the catalyst comprises a carbon-supported noble metal, chloride ions tend to interact with the catalyst to increase leaching of the noble metal and inhibit formic acid by-product oxidation. Moreover, chloride levels may tend to elevate in reactor systems in which streams (e.g., from the product concentrating and/or purifying steps of the process) are recycled and introduced into the oxidation reaction zone(s) as described below. Preferably, the chloride ion concentration in the liquid phase reaction medium in contact with the catalyst within the oxidation reaction zone(s) is maintained at no greater than about 500 ppm by weight, more preferably no greater than about 300 ppm by weight, and even more preferably no greater than 100 ppm by weight. Advantageously, control of chloride levels in the oxidation reaction zone(s) is established by using an N-(phosphonomethyl)iminodiacetic acid substrate source having a relatively low chloride content to form the aqueous feed stream 1. Preferably, the concentration of chloride ion in the source of the N-(phosphonomethyl)iminodiacetic acid substrate fed to the process in the aqueous feed stream is less than about 5000 ppm by weight, more preferably less than about 3000 ppm by weight, even more preferably less than about 2000 ppm by weight, and especially less than about 1000 ppm by weight on a dry basis. An N-(phosphonomethyl)iminodiacetic acid substrate source meeting such standards may be produced, for example, by the processes described in U.S. Pat. Nos. 4,724,103 and 4,775,498, which are expressly incorporated herein by reference. In addition, it may be advantageous to utilize a deeply reduced noble metal (e.g., platinum) on carbon catalyst modified with an addition of ruthenium as described above to catalyze the reactions in a continuous oxidation reactor system. Such ruthenium modified catalysts may provide increased resistance to chloride attack and noble metal leaching and may be particularly suited for use in a continuous oxidation reactor system where chloride levels in the oxidation reaction zone(s) are elevated due to various recycle streams.

The oxygen source may be introduced into the reaction mixture within the stirred tank reactor 3 by any conventional manner which maintains the dissolved oxygen concentration in the reaction mixture at the desired level. Preferably, the oxygen source is an $O_2$-containing gas such as air, pure $O_2$ or $O_2$ diluted with one or more non-oxidizing gases (e.g., He, Ar and $N_2$). More preferably, the oxygen source is an $O_2$-containing gas comprising at least about 95 mole % $O_2$, typically approximately 98 mole % $O_2$. The $O_2$-containing gas is introduced into the reaction mixture in a manner which provides intimate contact of the gas with the reaction mixture. For example, an $O_2$-containing gas may be introduced through a sparger conduit or similar distributor positioned in the bottom of the stirred tank reactor 3 below the impeller so that the turbulence induced by the rotating impeller intimately mixes and distributes the $O_2$-containing gas as it rises though the liquid reaction medium. Distribution of the $O_2$-containing gas within the reaction mixture may be further enhanced by passing the gas through a diffuser such as a porous frit or by other means well-known to those skilled in the art. Alternatively, the $O_2$-containing gas may be introduced into the headspace above the reaction mixture in the stirred tank reactor 3.

If the dissolved oxygen concentration in the reaction mixture is too great, the catalyst surface tends to become detrimentally oxidized, which, in turn, tends to lead to more leaching and decreased formaldehyde activity (which, in turn, leads to more N-methyl-N-(phosphonomethyl)glycine being produced). To avoid this problem, it is generally preferred to use an oxygen feed rate such that at least about 40%, more preferably at least about 60%, even more preferably at least about 80%, and still even more preferably at least about 90% of the oxygen is utilized. As used herein, the percentage of oxygen utilized equals: (the total oxygen consumption rate÷oxygen feed rate)×100%. The term total oxygen consumption rate means the sum of: (i) the oxygen consumption rate ($R_i$) of the oxidation reaction of the N-(phosphonomethyl)iminodiacetic acid substrate to form the N-(phosphonomethyl)glycine product and formaldehyde, (ii) the oxygen consumption rate ($R_{ii}$) of the oxidation reaction of formaldehyde to form formic acid, and (iii) the oxygen consumption rate ($R_{iii}$) of the oxidation reaction of formic acid to form carbon dioxide and water.

The oxygen partial pressure may vary in different regions of the oxidation reaction zone(s). Preferably, the oxygen partial pressure in the headspace above the liquid reaction mixture in a stirred tank reactor is from about 0.1 to about 35 psia, more preferably from about 1 to about 10 psia.

When the oxidation reaction is conducted in a single continuous stirred tank reactor system, the residence time in the reactor 3 can vary widely depending on the specific catalyst and oxidation reaction conditions employed. Typically, the residence time is from about 3 to about 120 minutes, more preferably from about 5 to about 90 minutes, still more preferably from about 5 to about 60 minutes, and still even more preferably from about 15 to about 60 minutes. The residence time is defined relative to the flowrate of filtrate 13 and the working volume of stirred tank reactor 3.

The particulate catalyst utilized in the continuous oxidation reaction system may comprise a support in the form of a powder exhibiting a particle size distribution as previously described. Preferably, the average particle size of the particulate catalyst is from about 15 to about 40 $\mu$m, more preferably about 25 $\mu$m. The concentration of the particulate catalyst in the reaction mixture within the stirred tank reactor 3 is preferably from about 0.1 to about 10 wt. % ([mass of catalyst÷total reaction mass]×100%). More preferably, the catalyst concentration is from about 0.5 to about 5 wt. %, even more preferably from about 1 to about 3 wt. %, and still even more preferably about 2 wt. %. Concentrations greater than about 10 wt. % are difficult to separate from the N-(phosphonomethyl)glycine product. On the other hand, concentrations less than about 0.1 wt. % tend to produce unacceptably low reaction rates.

The catalyst filter 9 used to separate the particulate catalyst from the reaction mixture 7 withdrawn from the stirred tank reactor 3 is preferably a filter adapted for continuous separation of catalyst from the reaction mixture. That is, the catalyst filter 9 is capable of receiving a continuous flow of reaction mixture 7 and continuously forming the filtrate 13 and the catalyst recycle stream 11 without having to interrupt the flow of reaction mixture introduced into the filter. In accordance with an especially preferred embodiment, catalyst filter 9 is a continuous cross-flow filter or a continuous back-pulse filter. In practicing the continuous oxidation process depicted in FIG. 2, a back-pulse filter is generally preferred over a cross-flow filter because the present commercially available back-pulse filters typically can form a catalyst recycle stream 11 containing a greater concentration of catalyst, often at least a 5-fold greater catalyst concentration, as compared to present commercially available cross-flow filters.

Figure 2A:
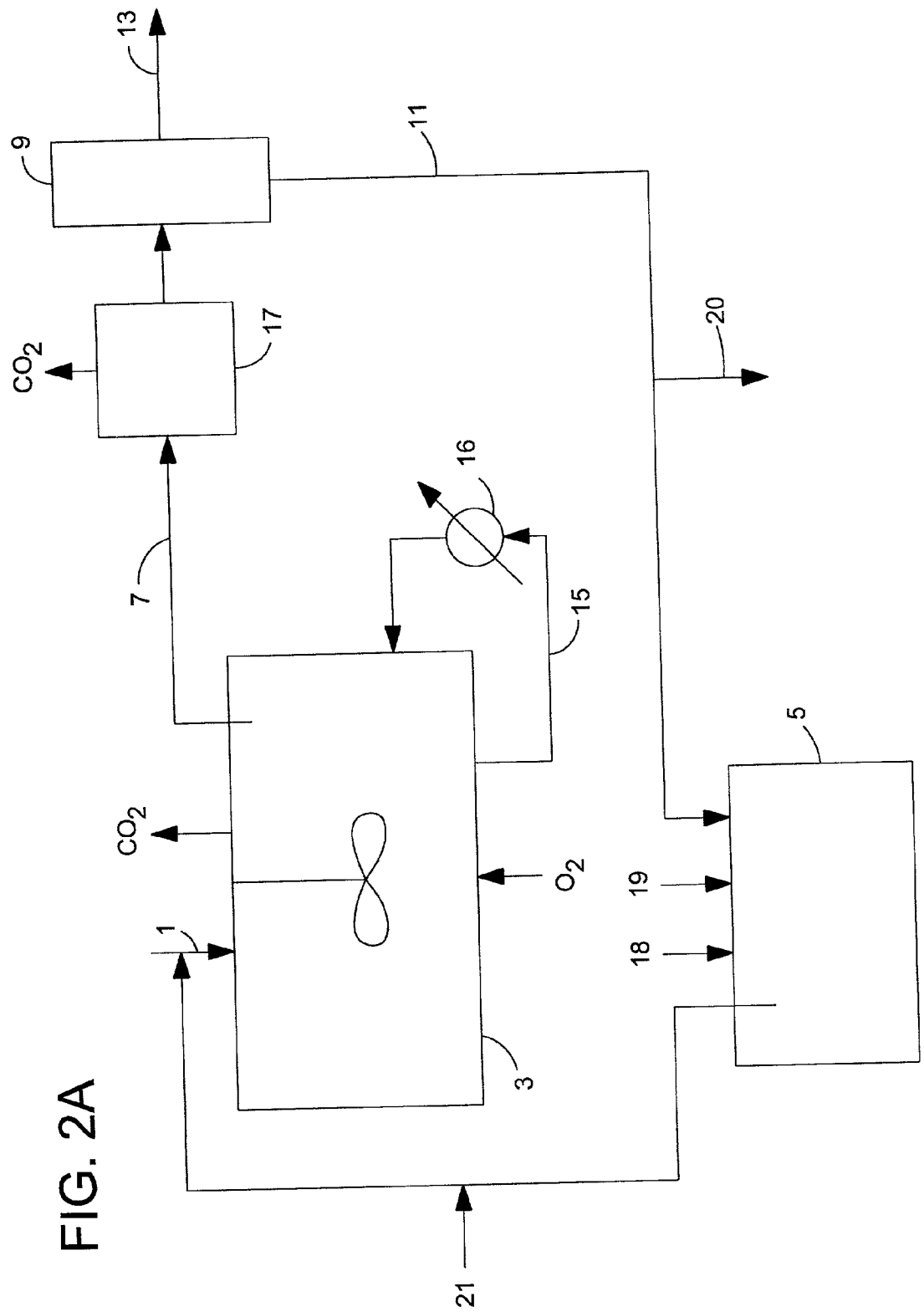
FIG. 2A is a schematic flow sheet of a continuous oxidation reactor system for oxidizing an N-(phosphonomethyl)iminodiacetic acid substrate to form an N-(phosphonomethyl)glycine product. The reactor system comprises a back-mixed oxidation reaction zone utilizing a heterogeneous particulate catalyst slurry recycled in a loop independent from a heat transfer recirculation loop and including a flash tank and catalyst recycle tank.

FIG. 2A is a schematic flow sheet of a continuous reactor system similar to that shown in FIG. 2 particularly adapted for use of a continuous back-pulse filter as catalyst filter 9. When the operating total pressure in the oxidation reaction zone(s) is much higher than atmospheric pressure, as is preferred, the pressure over the reaction mixture effluent 7 withdrawn from the stirred tank reactor 3 is typically reduced in connection with concentrating and purifying the N-(phosphonomethyl)glycine product. At least a portion of this pressure reduction may take place in a flash tank 17 upstream of catalyst filter 9. The flash tank 17 lowers the pressure on the reaction mixture 7 to some degree, causing dissolved $CO_2$ to be flashed out of the mixture and vented as vapor from the flash tank. Flash tank 17 reduces the pressure at which the continuous back-pulse catalyst filter 9 must operate, thereby reducing the capital costs and complexity of the filter system. An oxygen source (e.g., an $O_2$-containing gas) may be introduced (e.g., sparged) into the flash tank 17 to further oxidize N-(phosphonomethyl)iminodiacetic acid substrate in the reaction mixture 7 that did not oxidize in the stirred tank reactor 3, as well as to further oxidize formaldehyde and formic acid by-products present in the reaction mixture. In this manner, the flash tank may 17 act as an additional oxidation reaction zone in series with the stirred tank reactor 3.

The continuous back-pulse filter system comprises a filter element and is preferably operated adiabatically, but may be provided with heating or cooling capability. Preferably, the liquid used to back-pulse the filter element and remove separated catalyst is a portion of the filtrate 13. The filtrate 13 is carried forward to concentrate and purify the N-(phosphonomethyl)glycine product, while the recycle catalyst stream 11 is continuously withdrawn from the catalyst filter 9 and transferred to an optional catalyst holding tank 5 (also called a catalyst recycle tank or catalyst slurry tank) before the catalyst is reintroduced into stirred tank reactor 3.

Figure 2B:
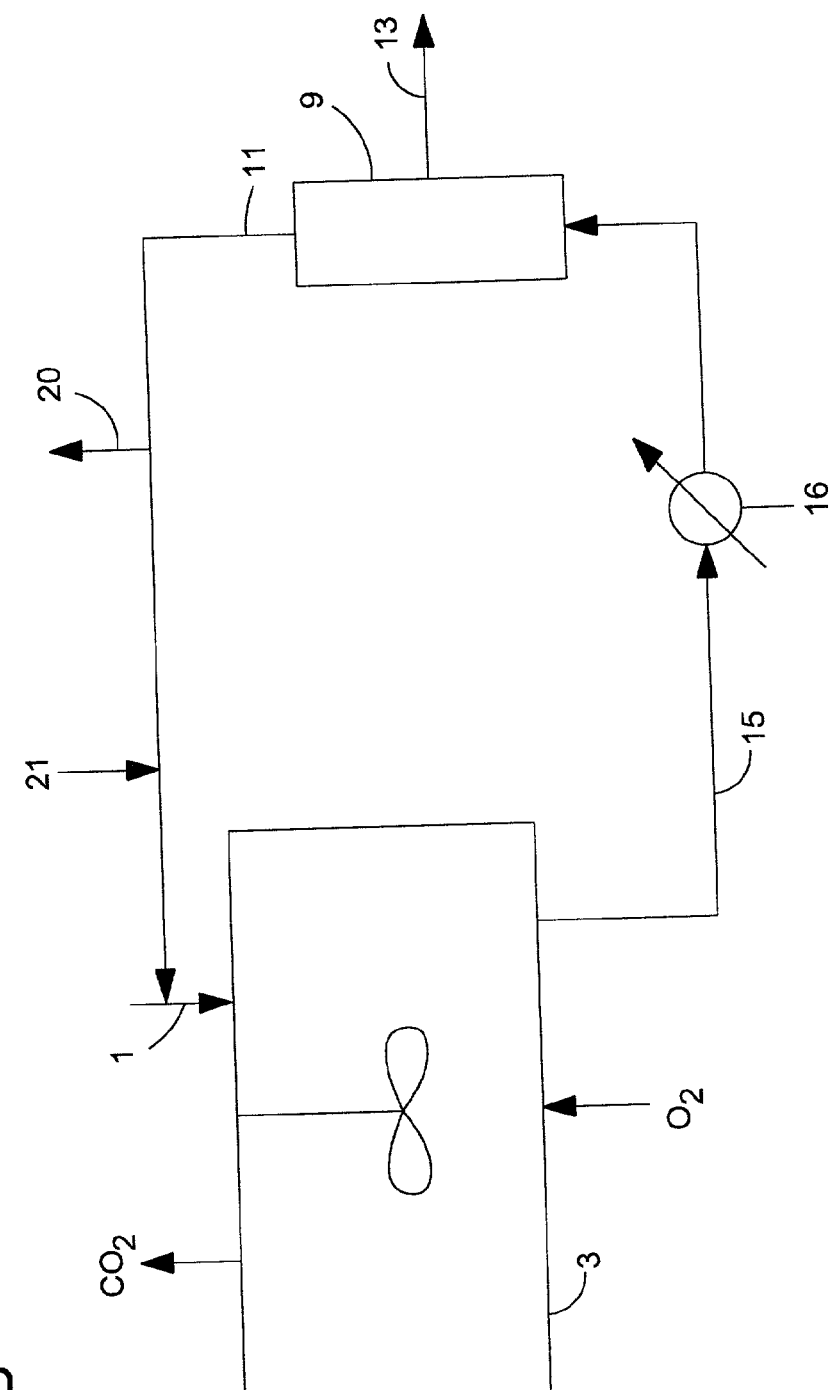
FIG. 2B is a schematic flow sheet of a continuous oxidation reactor system for oxidizing an N-(phosphonomethyl)iminodiacetic acid substrate to form an N-(phosphonomethyl)glycine product. The reactor system comprises a back-mixed oxidation reaction zone utilizing a heterogeneous particulate catalyst slurry recycled through a heat transfer recirculation loop.

Although the catalyst filter 9 in the oxidation reactor system shown in FIGS. 2 and 2A is preferably a continuous back-pulse filter, it should be recognized that continuous cross-flow filters are in some instances more preferred. The system depicted in FIG. 2B is similar to that shown in FIGS. 2 and 2A except that the catalyst filter 9 is placed within the external heat transfer recirculation loop 15 rather than in a separate catalyst recycle loop. In such an embodiment, catalyst filter 9 is preferably a continuous cross-flow filter. Typically, a pre-filter flash tank is not employed in conjunction with a cross-flow filter. Furthermore, due to the relatively large volume of the catalyst recycle stream 11 issuing from a continuous cross-flow filter, a catalyst holding tank is likewise typically omitted.

Aside from cross-flow and back-pulse filters, the catalyst filter 9 used in a continuous oxidation reactor system may alternatively be a vacuum filter or may comprise a bank of leaf filters used to treat a continuous flow of reaction mixture effluent 7 in staggered filtration cycles. As a further alternative, stirred tank reactor 3 may include an internal catalyst filter (e.g., a porous frit) which blocks the particulate catalyst from being withdrawn with the reaction mixture effluent 7 such that the catalyst is substantially retained within the oxidation reaction zone and the reaction mixture effluent is substantially free of the particulate catalyst. Moreover, it should be recognized that other means of catalyst separation may be used instead of (or in addition to) the catalyst filter 9. For example, the catalyst could be separated from the oxidation reaction mixture effluent using a centrifuge.

As the catalyst deactivates with use, it may be at least partially reactivated either continuously or intermittently. Reactivation may comprise reducing the surface of the catalyst after it has become heavily oxidized. In such an instance, the surface may, for example, be washed to remove the organics, and then reduced using the reduction treatments described above. Such a reducing treatment may comprise, for example, continuous or intermittent introduction of a reducing agent into the reactor system. For example, the reducing agent may comprise formaldehyde and/or formic acid and may often advantageously be obtained from various recycle streams described herein. Reactivation may also be achieved by, for example, introducing a supplemental promoter, especially bismuth oxide into the reactor system as described above. In accordance with a preferred embodiment of the present invention, a supplemental promoter (e.g., $Bi_2O_3$) is introduced continuously or intermittently into the continuous reactor system such that the concentration of formic acid in the reaction mixture effluent withdrawn from the last oxidation reaction zone is maintained at less than about 6000 ppm, more preferably from about 1000 ppm to about 3000 ppm. In accordance with an especially preferred practice of the present invention, the concentration of formic acid in the reaction mixture effluent withdrawn from the last oxidation reaction zone is monitored. Once the measured concentration exceeds about 6000 ppm, more preferably about 3000 ppm, even more preferably about 2000 ppm, continuous or intermittent introduction of a supplemental promoter into to the reactor system is initiated and continued until the concentration of formic acid in the reaction mixture effluent withdrawn from the last oxidation reaction zone begins to decline. Preferably, the rate of addition of the supplemental promoter to the reactor system is such that the concentration of formic acid in the reaction mixture effluent withdrawn from the last oxidation reaction zone continues to rise for a period of time after addition of a supplemental promoter to the system has commenced. In the case of $Bi_2O_3$ added to the reactor system as a supplemental promoter, the weight ratio of $Bi_2O_3$ to the N-(phosphonomethyl)iminodiacetic acid substrate fed to the system is from about 1:20,000,000 to about 1:200,000.

Although optional in the continuous oxidation reactor system shown in FIG. 2A, the catalyst holding tank 5 may be advantageous when a deeply reduced particulate catalyst is used because it provides a place for the catalyst mass to be uniformly reactivated. As shown in FIG. 2A, a reducing agent 18 and/or a supplemental promoter 19 may be introduced into the catalyst holding tank 5 containing recycled catalyst. The reducing agent and/or supplemental promoter may alternatively be added directly to the oxidation reaction zone(s) or introduced elsewhere into the reactor system. It should be further recognized that merely allowing the recycled catalyst to sit in the catalyst holding tank 5 with the residual reaction mixture may also beneficially reduce the catalyst surface particularly a catalyst comprising carbon-supported noble metal). Preferably, the catalyst holding tank is substantially free of $O_2$ and other oxidizing gases. Accordingly, it may be advantageous to introduce (e.g., sparge) nitrogen or other non-oxidizing gas into the tank 5 to help remove $O_2$. Allowing the slurry of particulate catalyst and residual slurry to remain outside the oxidation reaction zone(s) in an environment substantially free of $O_2$ for a period of time before being reintroduced into the oxidation reaction zone(s) is believed to reduce the surface of the catalyst and achieve a degree of reactivation and extend the useful life of the catalyst. The catalyst holding tank or catalyst slurry tank 5 may have various configurations, but is typically a stirred tank in which the catalyst slurry comprising the particulate catalyst and residual reaction mixture is agitated with a rotating impeller to improve uniformity in the catalyst slurry by preventing the catalyst from settling to the bottom of the tank 5 and promote uniform reactivation of the catalyst as well. The residence time of the catalyst in the catalyst holding tank 5 may be adjusted by adjusting the catalyst slurry volume in the catalyst holding tank relative to the working volume of reaction medium within the oxidation reaction zone(s). Longer catalyst residence times in the catalyst holding tank 5 are generally beneficial to catalyst performance. However, since longer residence times require a larger catalyst inventory in the reactor system, the benefits of longer residence times must be weighed against the increased catalyst costs, which may become significant, especially in the case of a catalyst comprising a carbon-supported noble metal. Preferably, the residence time of the recycled catalyst in the catalyst holding tank is at least about 2 minutes, more preferably at least about 5 minutes, even more preferably from about 5 to about 40 minutes.

Reduced losses of noble metal may be observed with this invention if a sacrificial reducing agent is maintained or introduced into the reaction solution. Suitable reducing agents include formaldehyde, formic acid, and acetaldehyde. Most preferably, formic acid, formaldehyde, or mixtures thereof (e.g., obtained from the various recycle streams described herein) are used.

Catalyst (e.g., catalyst having diminished activity and/or selectivity) may also be continuously or intermittently purged from the continuous oxidation reactor system via catalyst purge stream 20, and replaced with fresh catalyst via the fresh catalyst feed stream 21. When intermittently purging the catalyst, the entire catalyst mass may be purged from the process at the same time (which is typically the more preferred method), or a fraction of the catalyst mass may be purged at various time increments. In other words, intermittent purging includes any repeated purging of catalyst that is not continuous.

In accordance with a more preferred embodiment of the present invention, the continuous oxidation of an N-(phosphonomethyl)iminodiacetic acid substrate in the presence of a particulate heterogenous catalyst slurry is staged in two or more substantially back-mixed oxidation reaction zones (i.e., back-mixed in at least the liquid phase) operated in series. A combination of two or more back-mixed oxidation reaction zones in series is advantageous because such a reactor system tends to behave more like a plug flow reactor, producing fewer by-products and improving the yield of the N-(phosphonomethyl)glycine product. Moreover, the combination of two or more reaction zones provides the ability to vary reaction conditions in accord with the prevailing reaction kinetics at different stages of the oxidation reaction. The second and subsequent oxidation reaction zone(s) may provide further conversion of N-(phosphonomethyl)iminodiacetic acid substrate and/or oxidation of $C_1$ by-products (e.g., formaldehyde and formic acid).

The oxidation of an N-(phosphonomethyl)iminodiacetic acid substrate behaves approximately as a zero order reaction with respect to the substrate concentration until the N-(phosphonomethyl)iminodiacetic acid substrate concentration decreases to no greater than about 4.5% by weight, more typically to no greater than about 2.7% by weight, even more typically from about 0.4% to about 1.8% by weight, still even more typically from about 0.4% to about 1.3% by weight, and still yet even more typically no greater than about 1% by weight. Where, for example, the substrate concentration in the aqueous feed to the first reaction zone is about 9% by weight, the reaction will tend to behave approximately as a zero order reaction with respect to the substrate until at least about 50%, more typically at least about 70%, even more typically from about 80% to about 95%, and still even more typically from about 85% to about 95% of the substrate has been consumed. At that point, the oxidation rate becomes a stronger function of the substrate concentration (i.e., the oxidation approaches first order behavior with respect to the substrate concentration), and consequently tends to decrease as the substrate concentration further decreases. As the oxidation rate becomes a stronger function of the N-(phosphonomethyl)iminodiacetic acid substrate concentration, the oxidation of the substrate tends to be slower than the simultaneous oxidation reactions of the formaldehyde and formic acid by-products.

By utilizing a continuous oxidation reactor system comprising two or more oxidation reaction zones in series, the residence time and/or oxygen feed in the first reaction zone may be controlled so that the reaction in the first reaction zone substantially behaves as a zero-order reaction with respect to the substrate concentration (i.e., the residence time in the first reactor may be controlled so that the conversion of substrate in the first reactor is sufficient to form a reaction mixture having a substrate concentration of no greater than about 4.5% by weight, more preferably no greater than about 2.7% by weight, even more preferably from about 0.4% to about 1.8% by weight, still even more preferably from about 0.4% to about 1.3% by weight, and still yet even more preferably about 1% by weight). This reaction mixture may then be transferred to the second and any subsequent reaction zones, wherein the reaction behaves substantially as a first-order reaction with respect to the substrate concentration. In this manner, the reactor configuration and/or reaction conditions (e.g., catalyst type, average catalyst age, catalyst concentration, oxygen concentration, temperature, pressure, etc.) can be precisely controlled independently in each reaction zone to optimize the stages of the reaction and the oxidation of the formaldehyde and formic acid by-products.

Figure 3:
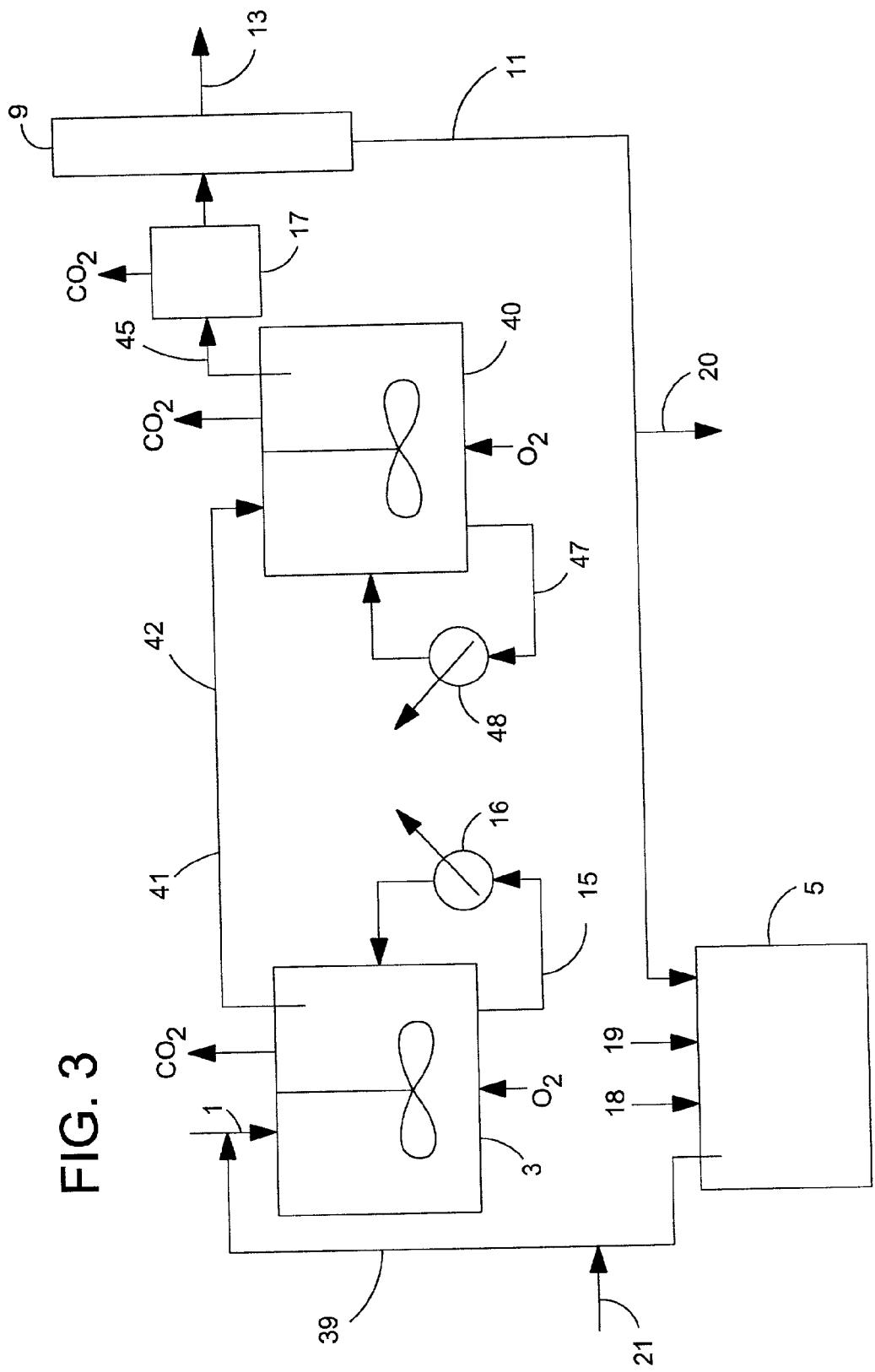
FIG. 3 is a schematic flow sheet of a continuous oxidation reactor system for oxidizing an N-(phosphonomethyl)iminodiacetic acid substrate to form an N-(phosphonomethyl)glycine product. The reactor system comprises two back-mixed oxidation reaction zones staged in series utilizing a heterogeneous particulate catalyst slurry which flows from the first reaction zone to the second reaction zone and is recycled to the first reaction zone.

FIG. 3 shows a preferred continuous oxidation reactor system in accordance with the present invention comprising two back-mixed oxidation reaction zones staged in series. The back-mixed oxidation reaction zones are preferably provided by two continuous stirred tank reactors 3 and 40. An aqueous feed stream 1 containing an N-(phosphonomethyl)iminodiacetic acid substrate is continuously or intermittently introduced into the first stirred tank reactor 3 along with an oxygen source, preferably an $O_2$-containing gas. The N-(phosphonomethyl)iminodiacetic acid substrate is continuously oxidized in the first stirred tank reactor 3 in the presence of the heterogeneous particulate catalyst to form an intermediate aqueous reaction mixture 41 comprising an N-(phosphonomethyl)glycine product and unreacted N-(phosphonomethyl)iminodiacetic acid substrate which is continuously or intermittently withdrawn from the first stirred tank reactor 3. An intermediate aqueous feed stream 42 comprising (a) N-(phosphonomethyl)glycine product from the intermediate aqueous reaction mixture 41; and (b) unreacted N-(phosphonomethyl)iminodiacetic acid substrate, which is also, at least in part, from the intermediate aqueous reaction mixture 41, is then introduced into the second stirred tank reactor 40. Typically, additional oxygen is also introduced into the second stirred tank reactor 40, preferably also in the form of an $O_2$-containing gas. In the second stirred tank reactor 40, additional N-(phosphonomethyl)iminodiacetic acid substrate is continuously oxidized in the presence of the heterogeneous particulate catalyst to form a final reaction mixture effluent 45 comprising N-(phosphonomethyl)glycine product. The headspace above the reaction mixture within the stirred tank reactors 3 and 40 is vented to remove vapor comprising $CO_2$ from the oxidation reaction zones as the oxidation reaction proceeds.

Figure 5:
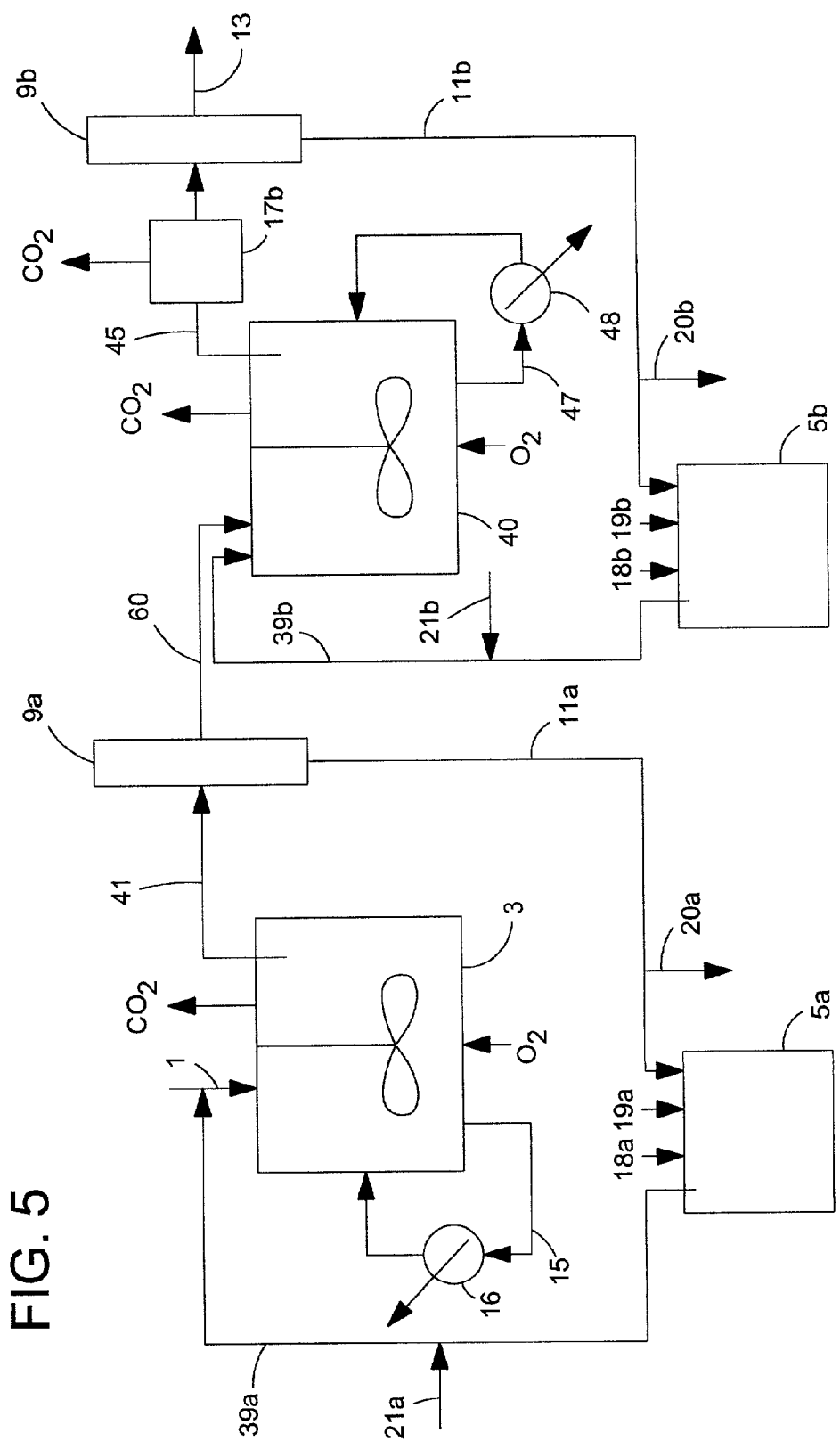
FIG. 5 is a schematic flow sheet of a continuous oxidation reactor system for oxidizing an N-(phosphonomethyl)iminodiacetic acid substrate to form an N-(phosphonomethyl)glycine product. The reactor system comprises two back-mixed oxidation reaction zones staged in series utilizing two independent heterogeneous particulate catalyst slurry masses such that catalyst from the first reaction zone is recycled to the first reaction zone and catalyst from the second reaction zone is recycled to the second reaction zone.
Figure 6:
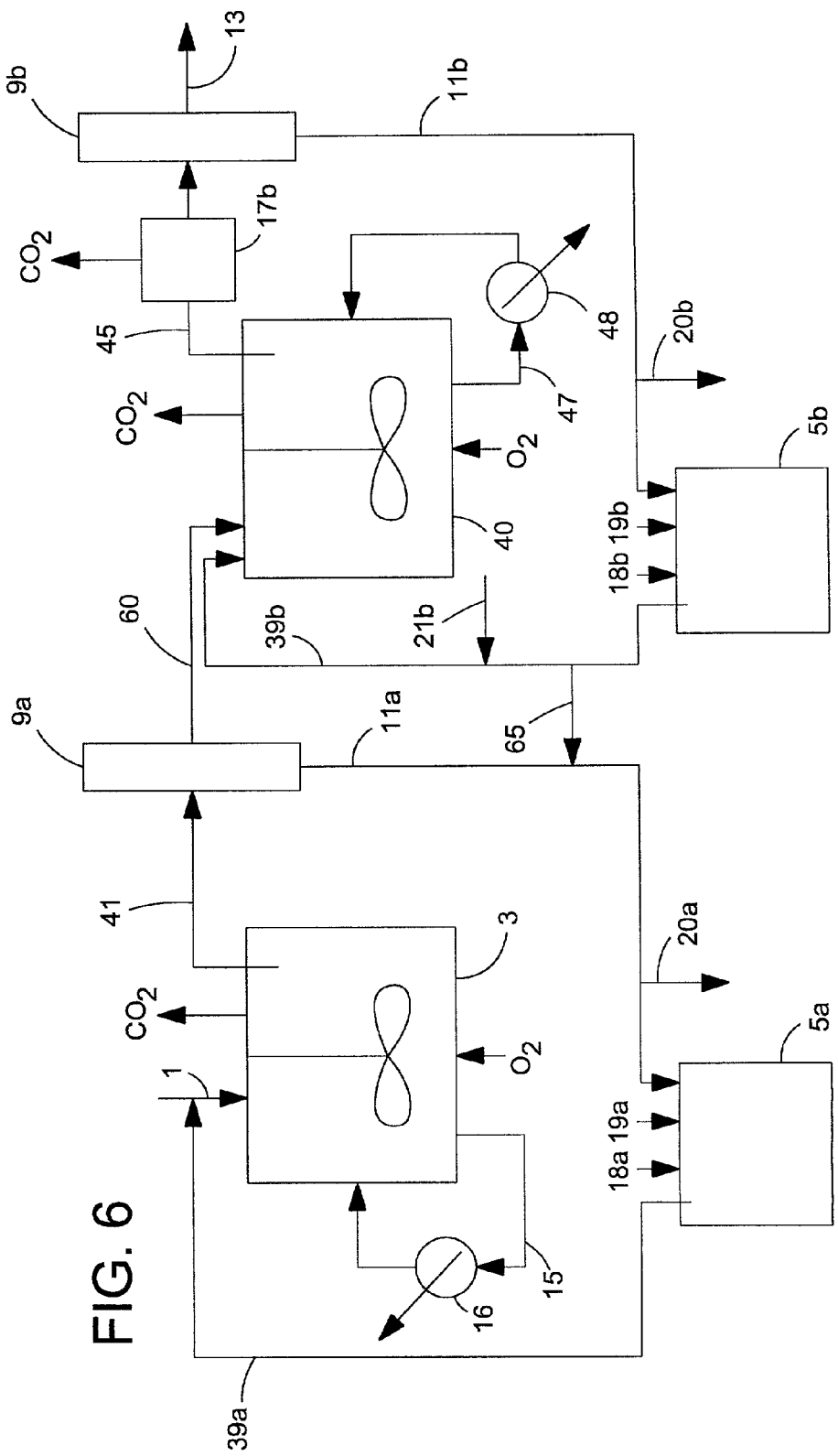
FIG. 6 is a schematic flow sheet of a continuous oxidation reactor system for oxidizing an N-(phosphonomethyl)iminodiacetic acid substrate to form an N-(phosphonomethyl)glycine product. The reactor system comprises two back-mixed oxidation reaction zones staged in series utilizing a heterogeneous particulate catalyst slurry which is recycled from the first reaction zone to the first reaction zone and from the second reaction zone to both reaction zones.

Although the intermediate aqueous feed stream 42 is shown in FIG. 3 as comprising the entire intermediate aqueous reaction mixture 41, it should be recognized that in some embodiments of the present invention, the intermediate aqueous feed stream 42 will contain less than the entire intermediate aqueous reaction mixture 41. For example, the particulate heterogenous catalyst may be partially or entirely removed from the intermediate aqueous reaction mixture 41, as described below (FIGS. 5 and 6). Furthermore, it should be understood that the first and second oxidation reaction zones do not have to be contained within separate stirred tank reactor vessels 3 and 40 as shown in FIG. 3. Multiple oxidation reaction zones may be staged in series and contained within a single reactor vessel divided into compartments or provided with baffles or other means for separating one reaction zone from another.

In the embodiment shown in FIG. 3, the particulate catalyst flows from the reaction zone in the first stirred tank reactor 3 to the reaction zone in the second stirred tank reactor 40. Preferably, the particulate catalyst is the above-described deeply reduced oxidation catalyst. The catalyst is continuously or intermittently introduced into the first stirred tank reactor 3 via catalyst feed stream 39. As shown in FIG. 3, the catalyst feed stream 39 is part of the aqueous feed stream 1 containing an N-(phosphonomethyl)iminodiacetic acid substrate. Catalyst is continuously or intermittently withdrawn from the first stirred tank reactor 3 as part of the intermediate aqueous reaction mixture 41, continuously or intermittently introduced into the second stirred tank reactor 40 as part of the intermediate aqueous feed stream 42 and finally continuously or intermittently withdrawn from the second stirred tank reactor 40 as part of the final reaction mixture effluent 45. The final reaction mixture effluent 45 is optionally depressurized in flash tank 17 and transferred to catalyst filter 9. In the catalyst filter 9, substantially all of the particulate catalyst is separated from the final reaction mixture effluent 45 to form (1) a catalyst recycle stream 11 comprising essentially all the catalyst and a residual amount of N-(phosphonomethyl)glycine product from the final reaction mixture 45; and (2) a filtrate 13 comprising the bulk of N-(phosphonomethyl)glycine product from the final reaction mixture 45. In the embodiment shown in FIG. 3, the catalyst filter 9 is preferably a continuous back-pulse filter system in order to minimize the volume of the catalyst recycle stream and preserve the staging effect in the reactor system. The catalyst recycle stream 11 is directed to the catalyst holding tank 5 and reintroduced into the first stirred tank reactor 3 via catalyst feed stream 39, while the filtrate 13 is carried forward to concentrate and purify the N-(phosphonomethyl)glycine product. As the catalyst deactivates with use, it may be at least partially reactivated as described above by continuously or intermittently contacting the particulate catalyst with a reducing agent 18 (e.g., in the catalyst holding tank 5) and/or introducing a supplemental promoter 19 into the process (e.g., into the catalyst holding tank 5 and/or directly into the first and/or second stirred tank reactors 3 and 40). Catalyst may be continuously or intermittently purged from the system through the catalyst purge stream 20 and replenished with fresh catalyst through catalyst feed stream 21.

During startup the reactor system in FIG. 3, the catalyst feed stream 39 and/or the aqueous feed stream 1 introduced to the first stirred tank reactor 3 may be heated to obtain the desired temperature in the oxidation reaction zones. During steady state or quasi-steady state operations, exothermic reaction heat is ordinarily sufficient to bring feed materials to the desired reaction temperature, and excess reaction heat is removed from the liquid reaction medium in the first reactor 3 via a heat exchanger 16 in external heat transfer recirculation loop 15. The reaction temperature is controlled by, for example, controlling the supply of cooling water to heat exchanger 15 in response to the signal from a temperature controller. Similarly, the temperature of the liquid reaction medium in the second oxidation reaction zone in reactor 40 may be controlled by the rate of heat removal via heat exchanger 48 in the external heat transfer recirculation loop 47 associated with the second reactor. However, the second oxidation reaction zone may be operated without the heat transfer loop 47 or other means for removing reaction heat (i.e., operated adiabatically). For example, in some instances, the incremental conversion of the N-(phosphonomethyl)iminodiacetic acid substrate and the extant oxidation of formaldehyde and formic acid are so limited in the second stirred tank reactor 40 that the heat evolved from the oxidation reactions does not necessitate cooling of the reaction mixture. Where it is desired to complete the reaction in the second reactor 40 at a temperature higher than the temperature prevailing in the first reactor 3, the autogenous heat of reaction in the second reactor may contribute all or part of the heat necessary to raise the temperature of the aqueous feed stream 42 and maintain the desired difference in temperature between the first reactor and the second reactor.

The temperature of the reaction medium within the second stirred tank reactor 40 is preferably maintained high enough with respect to the N-(phosphonomethyl)glycine product concentration such that essentially all of the N-(phosphonomethyl)glycine product in the final reaction mixture effluent 45 withdrawn from the second reactor remains dissolved. Optionally, N-(phosphonomethyl)glycine product precipitated in the final reaction mixture effluent 45 may be separated with the particulate catalyst as part of the catalyst recycle stream 11. It should be recognized that the temperature of the reaction mixture within the stirred tank reactors 3 and 40 can vary from reactor to reactor. For example, since the intermediate aqueous reaction mixture 41 is not filtered and also contains a lower concentration of N-(phosphonomethyl)glycine product than does the final reaction mixture effluent 45, the temperature of the reaction mixture within the first stirred tank reactor 3 can typically be somewhat lower than the preferred operating temperature of the reaction mixture in the second stirred tank reactor 40. Preferably, the first stirred tank reactor 3 is operated at a temperature of from about 80° C. to about 120° C., more preferably from about 85° C. to about 110° C. and still even more preferably from about 95° C. to about 100° C., while the second stirred tank reactor 40 is preferably operated at a temperature of from about 80° C. to about 120° C., more preferably from about 85° C. to about 110° C. and even more preferably from about 100° C. to about 105° C. Operating the first stirred tank reactor 3 at a lower temperature is often advantageous to reduce the rate of formation of N-methyl-N-(phosphonomethyl)glycine which increases at higher temperatures.

The total pressure in the first and second stirred tank reactors 3 and 40 is preferably maintained high enough to prevent the liquid reaction medium in the oxidation reaction zones from boiling and is generally from about 0 to about 500 psig. Typically, the total pressure in the stirred tank reactors 3 and 40 is from about 30 to about 500 psig. When maintaining the temperature of the reaction mixture in the first and second oxidation reaction zones within the preferred temperature ranges disclosed above, the total pressure maintained within the first and second stirred tank reactors 3 and 40 is preferably from about 30 to about 130 psig and more preferably from about 90 to about 110 psig.

The oxygen partial pressure may vary in different regions of the oxidation reaction zones. Preferably, the oxygen partial pressure in the headspace above the liquid reaction medium in stirred tank reactors 3 and 40 is from about 0.1 to about 35 psia, more preferably from about 1 to about 10 psia.

Particularly where the concentration of the N-(phosphonomethyl) iminodiacetic acid substrate in the aqueous feed stream 1 (which includes the catalyst recycle stream 11 and any other recycle streams from other parts of the process) is from about 7 to about 12% by weight, and even more particularly is about 9% by weight, it is typically preferred for the residence time in the first stirred tank reactor 3 to be such that the N-(phosphonomethyl)iminodiacetic acid substrate conversion to the N-(phosphonomethyl)glycine product in the first oxidation reaction zone is at least about 50%, more preferably at least about 70%, even more preferably from about 80% to about 95%, still even more preferably from about 85% to about 95%, and most preferably about 90%. The residence time necessary to achieve the desired degree of conversion will vary with the oxidation reaction conditions employed in the first stirred tank reactor 3. Typically, the residence time in the first stirred tank reactor 3 is from about 5 to about 50 minutes, preferably from about 10 to about 30 minutes, even more preferably from about 14 to about 24 minutes and still even more preferably about 20 minutes. The residence time in the second stirred tank reactor 40 is typically from about 1 to about 50 minutes, more preferably from about 1 to about 30 minutes, more preferably from about 3 to about 20 minutes, more preferably from about 6 to about 20 minutes, still even more preferably from about 6 to about 12 minutes and still yet even more preferably about 8 minutes. The residence time in the first stirred tank reactor 3 is defined relative to the flowrate of the intermediate reaction mixture 41 and the working volume of the reactor. The residence time in the second stirred tank reactor 40 is defined relative to the flowrate of the final reaction mixture effluent 45 and the working volume of the reactor Conversion achieved at a given residence time tends to decrease as the catalyst activity decreases with use, requiring fortification of catalyst activity by reactivation or charging the system with fresh catalyst or an increasing the $O_2$ feed rate.

Preferably, the ratio of the working volume of liquid reaction medium in the first stirred tank reactor 3 to the working volume of the liquid reaction medium in the second stirred tank reactor 40 is greater than 1, more preferably greater than 1 and up to about 10, even more preferably from about 1.1 to about 5, and still even more preferably from about 1.1 to about 2.5.

Normally, when the continuous reactor system comprises two stirred tank reactors in series, the total oxygen feed introduced to the continuous reactor system (i.e., the combined oxygen feed to both stirred tank reactors 3 and 40) and the amount of the total oxygen feed apportioned to each of the stirred tank reactors are adjusted to affect the yield and quality of the N-(phosphonomethyl)glycine product. In one embodiment, the total oxygen introduced to the continuous reactor system per mole of N-(phosphonomethyl)iminodiacetic acid substrate in the aqueous feed stream 1 introduced to the first stirred tank reactor 3 is varied to control the concentration of N-(phosphonomethyl)iminodiacetic acid substrate in the final reaction mixture effluent 45 withdrawn from the second stirred tank reactor 40. The concentration of unreacted N-(phosphonomethyl)iminodiacetic acid substrate in the final reaction mixture 45 is generally minimized to avoid excessive yield losses. Preferably, the concentration of unreacted N-(phosphonomethyl)iminodiacetic acid substrate is no greater than about 2000 ppm in the final reaction mixture effluent. However, the concentration of N-(phosphonomethyl)iminodiacetic acid substrate in the final reaction mixture effluent 45 should remain sufficiently high to inhibit the rate at which the N-(phosphonomethyl) glycine product oxidizes to form aminomethylphosphonic acid. The rate of aminomethylphosphonic acid formation is apparently inversely proportional to the N-(phosphonomethyl)iminodiacetic acid substrate concentration. Moreover, it is believed that the presence of N-(phosphonomethyl) iminodiacetic acid substrate may inhibit over-oxidation of the catalyst and extend the catalyst life. Accordingly, it is preferred that the concentration of the N-(phosphonomethyl) iminodiacetic acid substrate in the final reaction mixture effluent 45 be maintained within a range of from about 200 to about 2000 ppm, more preferably from about 500 to about 1500 ppm, and most preferably about 500 to about 700 ppm by weight. Typically, a suitable concentration of the N-(phosphonomethyl)iminodiacetic acid substrate in the final reaction mixture 45 is obtained when the total oxygen introduced to the continuous reactor system is from about 0.5 to about 5, more preferably from about 1 to about 3, still more preferably from about 1.5 to about 2.5 moles of $O_2$ per mole of N-(phosphonomethyl)iminodiacetic acid substrate in the aqueous feed stream 1 introduced to the first stirred tank reactor 3.

In addition, the apportionment of the total oxygen feed to the continuous reactor system between stirred tank reactors 3 and 40 is selected to reduce the quantity of by-products in the final reaction mixture effluent 45. The proportion of the total oxygen feed to the continuous reactor system introduced into the first stirred tank reactor 3 is from about 10% to about 95%, more preferably from about 30% to about 95%, still more preferably from 50% to about 95% and most preferably from about 70% to about 90% with the remaining portion of the total oxygen feed being introduced into the second stirred tank reactor 40.

In the practice of the present invention, the concentration of unreacted N-(phosphonomethyl)iminodiacetic acid substrate, N-(phosphonomethyl)glycine product and/or oxidation by-products in the intermediate aqueous reaction mixture 41 withdrawn from the first stirred tank reactor 3 and/or in the final reaction mixture effluent 45 withdrawn from the second stirred tank reactor 40 may be measured. Based on these measurements, the total oxygen feed to the continuous reactor system and/or the apportionment of the total oxygen feed between the first and second stirred tank reactors 3 and 40 may be adjusted to beneficially affect the yield and quality of the N-(phosphonomethyl)glycine product. The concentration of unreacted N-(phosphonomethyl)iminodiacetic acid substrate, N-(phosphonomethyl)glycine product and/or oxidation by-products can be measured using high pressure liquid chromatography (HPLC) or Fourier transform infrared spectroscopy (FTIR) analysis of stream samples. In addition, an in-line FTIR spectrometer may be used to provide real time compositional analysis of the reactor effluent streams and this data used in adjusting the oxygen feed practice in the continuous reactor system. In-line use of infrared spectroscopy to measure concentrations of analytes in oxidation reaction mixtures such as those prepared in accordance with the present invention for use in process control and endpoint detection are described in a U.S. provisional Patent application Ser. No. 60/292,659 entitled "Use of Infrared Spectroscopy for On-Line Process Control and Endpoint Detection", filed on May 22, 2001, the entire disclosure of which is expressly incorporated herein by reference.

Normally, when the continuous reactor system comprises two continuous stirred tank reactors 3 and 40 in series, the oxygen feed rate to the first reaction zone is preferably from about 0.5 to about 10, more preferably from about 0.5 to about 5, still more preferably from about 1.0 to about 4.0 moles of $O_2$ per mole of N-(phosphonomethyl)iminodiacetic acid substrate contained in the aqueous feed stream 1 introduced into the first reactor 3. The oxygen feed rate into the second reaction zone is preferably from about 0.5 to about 10, more preferably from about 0.5 to about 5, still more preferably from about 2 to about 4 moles of $O_2$ per mole of N-(phosphonomethyl)iminodiacetic acid substrate contained in the feed stream to the second reaction zone.

Where the process uses two stirred tank reactors in series, the molar ratio of N-(phosphonomethyl)iminodiacetic acid substrate to N-(phosphonomethyl)glycine product in the first reactor is preferably maintained such that the molar rate of oxidation of the N-(phosphonomethyl)iminodiacetic acid substrate is at least about 10, more preferably at least about 20, even more preferably at least about 100, still even more preferably at least about 150, and most preferably at least about 200 times as fast as the molar rate of oxidation of the N-(phosphonomethyl)glycine product.

Figure 4:
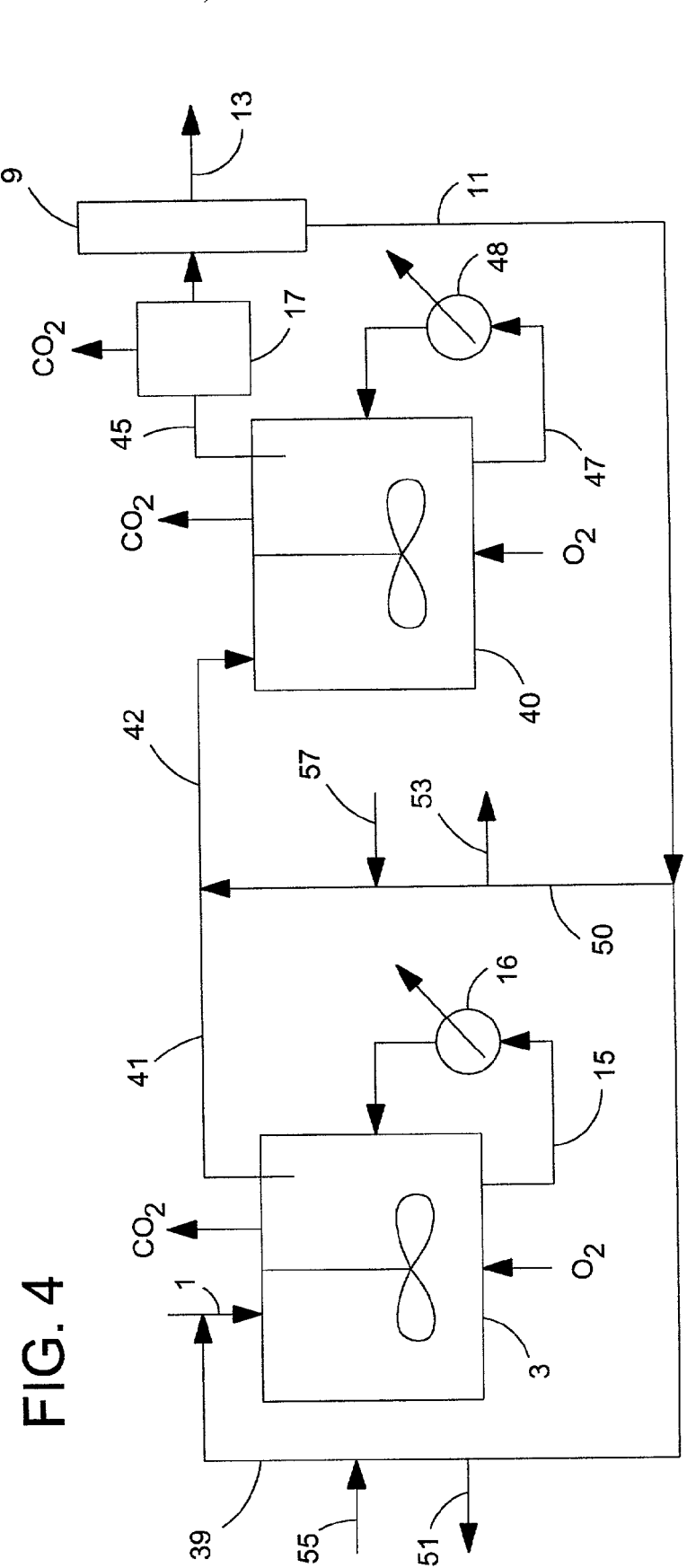
FIG. 4 is a schematic flow sheet of a continuous oxidation reactor system for oxidizing an N-(phosphonomethyl)iminodiacetic acid substrate to form an N-(phosphonomethyl)glycine product. The reactor system comprises two back-mixed oxidation reaction zones staged in series utilizing a heterogeneous particulate catalyst slurry which flows from the first reaction zone to the second reaction zone and is recycled to both reaction zones.

Various alternatives to the flow scheme shown in FIG. 3 may be used to circulate the particulate heterogenous catalyst through the back-mixed oxidation reaction zones within the continuous reactor system. Examples of such alternative flow schemes are shown in FIGS. 4–6. In each of the flow schemes shown in FIGS. 3–7, the catalyst age may be maintained within a desirable range or controlled near a specific level by continuously or intermittently adding fresh catalyst into the catalyst recycle stream(s) or directly into either of the reaction zones. Such catalyst age may optionally be further controlled by also continuously or intermittently purging a portion of the catalyst from the catalyst recycle stream(s). Often, the amount of purged catalyst is equal to the amount of fresh catalyst added to the system. Intermittent purging and adding of catalyst includes any repeated purging and adding of catalyst which is not continuous. For example, intermittent purging and adding includes periodic withdrawal of catalyst from a catalyst recycle stream, with addition of fresh catalyst at a point downstream of the withdrawal point within a catalyst recirculation loop. Intermittent purging and adding also includes, for example, withdrawing all the catalyst from fewer than all the reaction zones at one time, and then adding an entirely fresh batch of catalyst to fewer than all the reaction zones. Intermittent purging and adding further includes, for example, withdrawing all the catalyst from the continuous reactor system at the same time and then adding an entirely fresh batch of catalyst (e.g., once the production of N-(phosphonomethyl)glycine product from the reactor system has reached a predetermined target value based on the calculated useful life of the catalyst load or once the catalyst activity has declined to an extent that economical operation is impaired). The latter method is typically more preferred. This stems from, for example, the fact that it is often difficult to stabilize the system when only portions of the catalyst load are purged and added at a given time. It is also, for example, difficult to analyze any modification (e.g., new improvements) to a catalyst without first removing all the unmodified catalyst. It should be further noted that at startup of the continuous oxidation reactor system, it may be advantageous to operate the system for a time with significantly less than the design catalyst loading (e.g., 75% of the design catalyst loading) and then to incrementally charge additional catalyst to the system to arrive at an optimal catalyst loading at the prevailing operating conditions.

FIG. 4 shows an embodiment which provides more flexibility by allowing the catalyst loading into the first and second stirred tank reactors 3 and 40 to be manipulated so that a desired greater catalyst loading may be maintained in the second stirred tank reactor 40 to at least partially compensate for the reduced N-(phosphonomethyl)iminodiacetic acid substrate concentration driving force that is typically present due to the lower substrate concentration in the second reaction zone. Catalyst is continuously or intermittently introduced into the first stirred tank reactor 3 via catalyst feed stream 39. The catalyst is then continuously or intermittently withdrawn from the first stirred tank reactor 3 as part of the intermediate aqueous reaction mixture 41, continuously or intermittently introduced into the second stirred tank reactor 40 as part of the intermediate aqueous feed stream 42, and finally intermittently or continuously withdrawn from the second stirred tank reactor 40 as part of the final aqueous reaction mixture 45. The catalyst is then essentially removed from the final aqueous reaction mixture 45 by catalyst filter 9 to form (1) a catalyst recycle stream 11 comprising essentially all the catalyst and a residual amount of N-(phosphonomethyl)glycine product from the final aqueous reaction mixture 45; and (2) a filtrate 13 comprising the bulk of N-(phosphonomethyl)glycine product from the final aqueous reaction mixture 45. The catalyst recycle stream 11 is divided into the catalyst feed stream 39 and an intermediate catalyst feed stream 50. The catalyst feed stream 39 is recycled back to the first stirred tank reactor 3, while the intermediate catalyst feed stream 50 is recycled back to the second stirred tank reactor 40. Preferably, the catalyst is continuously or intermittently purged from the continuous reactor system through, for example, the catalyst purge stream 51 and/or catalyst purge stream 53, and replenished through, for example, catalyst feed stream 55 and/or catalyst feed stream 57. Catalyst could alternatively or additionally be purged from catalyst recycle stream 11, and likewise fresh catalyst could alternatively or additionally be added to catalyst recycle stream 11 prior to dividing recycle stream 11 into recycle catalyst streams 39 and 50. The catalyst may also be at least partially reactivated as described above by intermittently or continuously introducing a reducing agent and/or a supplemental promoter into the continuous reactor system, particularly where the catalyst comprises the deeply reduced catalyst described above. The reducing agent and/or supplemental promoter may be introduced, for example, in the catalyst recycle streams 11, 39 and/or 50. Such reactivation may optionally be conducted in one or more catalyst holding tanks (not shown).

FIG. 5 shows an embodiment wherein each oxidation reaction zone utilizes its own independent particulate catalyst mass. In such an embodiment, an aqueous feed stream 1 comprising the N-(phosphonomethyl)iminodiacetic acid substrate is fed into the first stirred tank reactor 3, wherein it is continuously oxidized in the presence of the first catalyst mass to form an intermediate aqueous reaction mixture 41. This intermediate aqueous reaction mixture 41 is filtered in catalyst filter 9a to separate essentially all the first catalyst mass from the intermediate aqueous reaction mixture 41 and form (1) a first catalyst recycle stream 11a comprising essentially all the catalyst from the intermediate aqueous reaction mixture 41; and (2) an intermediate aqueous feed stream 60, the filtrate from the filter 9a, comprising the bulk of N-(phosphonomethyl)glycine product and unreacted N-(phosphonomethyl)iminodiacetic acid from the intermediate aqueous reaction mixture 41. The first catalyst recycle stream 11a is fed back into the first stirred tank reactor 3 via catalyst feed stream 39a, while the intermediate aqueous feed stream 60 is introduced into the second stirred tank reactor 40, wherein further continuous oxidation of N-(phosphonomethyl)iminodiacetic acid substrate (and $C_1$ molecules, such as formaldehyde and formic acid) takes place in the presence of a second particulate catalyst mass to form the final reaction mixture effluent 45. The final reaction mixture 45, after optional depressurization in a flash tank 17b, is filtered in catalyst filter 9b to separate the second catalyst mass from the final aqueous reaction mixture 45 and form (1) a catalyst recycle stream 11b comprising essentially all the catalyst from the final aqueous reaction mixture 45; and (2) a filtrate 13 comprising the bulk of N-(phosphonomethyl)glycine product from the final aqueous reaction mixture 45. The catalyst recycle stream 11b is then fed back into the second stirred tank reactor 40 via catalyst feed stream 39b. Preferably, the catalyst mass utilized in the first stirred tank reactor 3 is continuously or intermittently purged through the catalyst purge stream 20a, and replenished through catalyst feed stream 21 a. Likewise, the catalyst mass utilized in the second stirred tank reactor 40 is preferably continuously or intermittently purged through the catalyst purge stream 20b, and replenished through catalyst feed stream 21b. The particulate catalyst masses for the first and second stirred tank reactors 3 and 40 may also be at least partially reactivated, as described above, by continuously or intermittently introducing a reducing agent 18a and 18b and/or a supplemental promoter 19a and 19b into the respective catalyst holding tanks 5a and 5b or at other locations in the continuous reactor system. For example, the supplemental promoter may also be added directly to one or both of the stirred tank reactors 3 and 40.

The catalyst recycle scheme shown in FIG. 5 is advantageous because it provides flexibility for independently manipulating the catalyst type, age, and loading in each reaction zone. For example, the catalyst employed in the first stirred tank reactor 3 may be tailored to obtain high conversion of N-(phosphonomethyl)iminodiacetic acid substrate under the selected operating conditions in the first oxidation reaction zone, while the catalyst employed in the second stirred tank reactor 40 may be optimized for improved oxidation of formaldehyde and formic acid by-products and minimal over-oxidation of the N-(phosphonomethyl)glycine product. Also, two filter reactor systems, such as the one shown in FIG. 5, can tolerate a filter that generates a catalyst recycle stream that is less concentrated than the desired concentration in a single filter reactor system, such as the system shown in FIG. 3.

In some embodiments, the benefits of a younger catalyst can be greater in one reaction zone versus another. For example, the effects of an aging catalyst in the first reaction zone (where the bulk of N-(phosphonomethyl)iminodiacetic acid substrate normally is oxidized) may, in some embodiments, not be as detrimental as the effects of an aging catalyst in the second reaction zone, and the effects of fresh catalyst may likewise be greater in the second reaction zone than in the first reaction zone. This may be true, for example, in embodiments where the bulk of N-(phosphonomethyl) iminodiacetic acid substrate is oxidized in the first reaction zone, and the resulting low substrate concentration in the second reaction zone causes a slower reaction rate. In such an instance, it may be sometimes preferable to use a reactor system having a flow scheme like the one shown in FIG. 6. In this embodiment, catalyst from the particulate catalyst mass utilized in the second stirred tank reactor 40 may be continuously or intermittently purged from the catalyst recycle stream 11b via stream 65 and introduced into the first stirred tank reactor 3 via the catalyst recycle stream 11a, thereby extending the useful life of the catalyst in the overall process. Such a scheme is particularly advantageous where the catalyst comprises a costly material, such as a noble metal. Normally, in this embodiment, fresh catalyst is introduced only into the second reaction zone via catalyst feed stream 21b, while catalyst is purged from the process only from the first reaction zone via catalyst purge stream 20a. The average catalyst age (i.e., cumulative time that the catalyst has been used to catalyze the oxidation reaction) in the second stirred tank reactor 40 is preferably from about 20 to about 65% of the average age of the catalyst utilized in the first stirred tank reactor 3. The average amount of N-(phosphonomethyl)glycine product produced per pound of catalyst in the second stirred tank reactor 40 preferably is from about 5 to about 30% the average amount of N-(phosphonomethyl)glycine product produced per pound of catalyst in the first stirred tank reactor 3.

It should be recognized that in some embodiments, it is more preferable to recycle the catalyst in the opposite direction as that shown in FIG. 6 (i.e., the catalyst flows co-currently with the substrate). In those instances, fresh catalyst is continuously or intermittently introduced into the first reaction zone, catalyst from the particulate catalyst mass utilized in the first stirred tank reactor 40 is continuously or intermittently purged from the catalyst recycle stream 11a and continuously or intermittently transferred to the second reaction zone and catalyst in the second reaction zone is continuously or intermittently purged from the reactor system. In such an embodiment, the average catalyst age in the first stirred tank reactor 3 is preferably from about 33 to about 80% of the average age of the catalyst in the second stirred tank reactor 40. The average amount of N-(phosphonomethyl)glycine product produced per pound of catalyst consumed in the first stirred tank reactor 3 preferably is from about 75 to about 90% the average amount of N-(phosphonomethyl)glycine product produced per pound of catalyst consumed in the second stirred tank reactor 40.

In the embodiments shown in FIGS. 5 and 6, either external heat transfer recirculation loop 15 or 47 may also be a catalyst recycle loop in the same manner as shown in FIG. 2B, rather than being independent of the catalyst recycle streams 11a or 11b, respectively. For such a combined loop, the catalyst filters 9a and 9b are preferably continuous cross-flow filters.

In processes including operating two oxidation reaction zones in series, particularly two stirred tank reactors 3 and 40 in series, it is desirable to achieve a high rate of mass transfer in the first oxidation reaction zone. Therefore, it is preferred to introduce the $O_2$-containing gas, preferably a gas containing at least about 95 mole % $O_2$, typically about 98 mole % $O_2$, directly into the reaction mixture in the first stirred tank reactor 3 through a sparger located just below or near the impeller and also to minimize the back-mixing of gases to maximize the oxygen concentration driving force for high mass transfer in the first oxidation reaction zone. For equivalent pressures and oxygen conversion, the average oxygen spatial concentration is expected to be higher in reaction environments with minimal gas phase back-mixing. Near the sparger, for example, the oxygen partial pressure in the undissolved gases is normally greater than in other regions in the reactor, such as near the interface between the liquid reaction medium and the headspace. However, in the second reaction zone, where the N-(phosphonomethyl)iminodiacetic acid substrate concentration is typically much lower, mass transfer demands and the need for a high oxygen concentration driving force are considerably less. Thus, back-mixing of gases is more easily tolerated in the second oxidation reaction zone and, in some instances, is preferred. The deeply reduced noble-metal-on-carbon catalyst preferred in the practice of the present invention is more susceptible to over-oxidation in reaction environments having pockets of high oxygen partial pressures in the undissolved gases, especially at low concentrations of N-(phosphonomethyl)iminodiacetic acid substrate such as those encountered in the second oxidation reaction zone. By back-mixing the gas phase in the liquid reaction medium within the second reaction zone, average oxygen spatial concentration is decreased and the stability of such a catalyst is enhanced.

Various reactor modifications may be employed to maintain a more uniform low oxygen partial pressure in the undissolved gases in the reaction mixture contained in the second reaction zone. One preferred alternative is to select an impeller system for the second stirred tank reactor 40 that is adapted to provide a high rate of gas induction from the headspace interface into the reaction mixture such as A340 up-pumping axial flow impeller system available from Lightnin (Rochester, N.Y., U.S.A.). Such an impeller system draws gas from the headspace into the liquid reaction mixture so that the difference between the oxygen partial pressure of the gas being drawn into the liquid reacting medium and the oxygen partial pressure of the headspace gas is reduced, thereby lowering the average oxygen spatial concentration in the undissolved gases in the reaction mixture. In addition, the second stirred tank reactor 40 may be modified so that the $O_2$-containing gas is fed into the headspace above the reaction mixture rather than being sparged directly into the liquid reaction mixture. This will even further reduce the occurrence of pockets of high oxygen concentration. Alternatively, the average oxygen spatial concentration may be reduced, by introducing the headspace gas within the second stirred tank reactor 40 into the liquid reaction mixture through the impeller. A commercially available example of such an impeller system including a hollow shaft for gas transport is the DISPERSIMAX system, sold by Autoclave France (Nogent-sur-Oise Cedex, France). Another possibility is to decrease the $O_2$ concentration in the $O_2$-containing gas introduced into the second stirred tank reactor 40 (e.g., air may be used as the oxygen source supplied to the second oxidation reaction zone).

Figure 7:
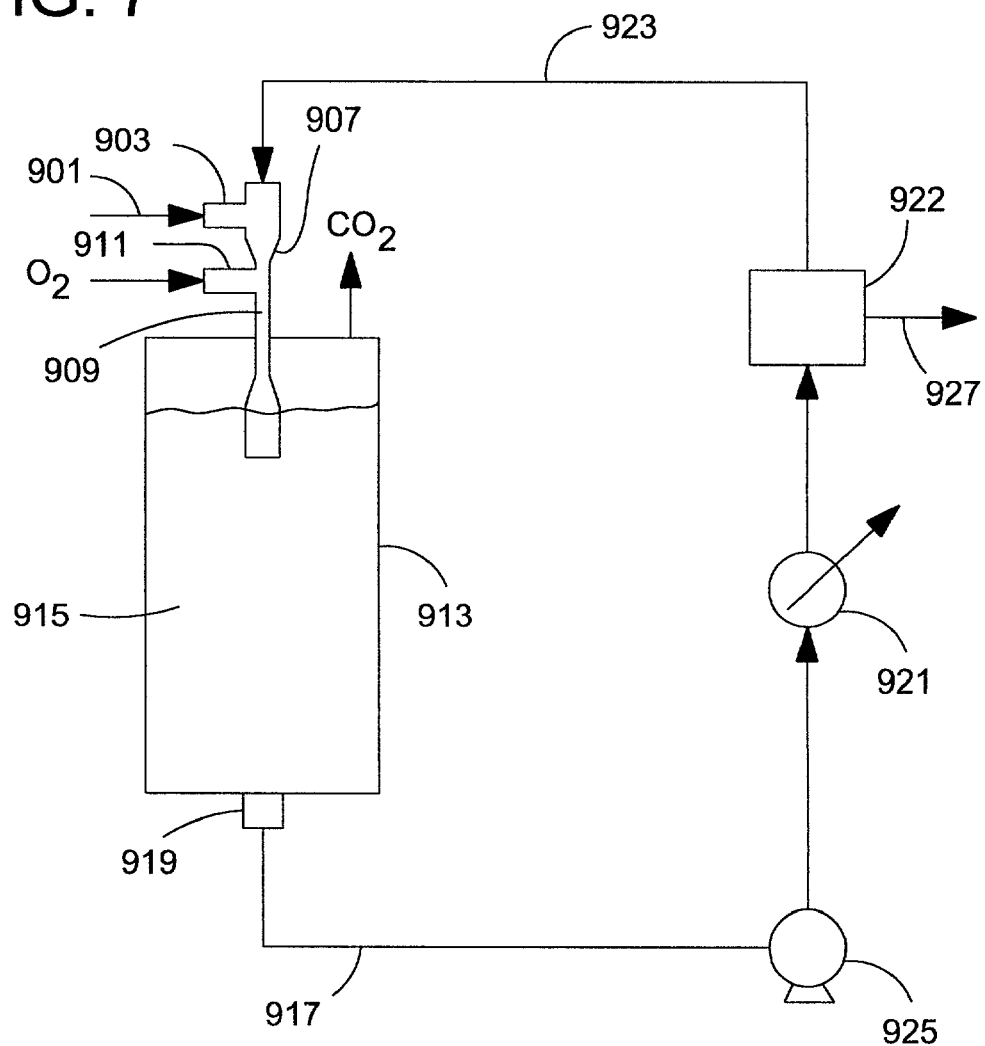
FIG. 7 is a schematic of an ejector nozzle loop reactor which may be used in the continuous oxidation reactor system of the present invention for oxidizing an N-(phosphonomethyl)iminodiacetic acid substrate to form an N-(phosphonomethyl)glycine product.

In a further modification, the second continuous stirred tank reactor 40 is replaced by an ejector nozzle loop reactor. A schematic diagram of such a reactor is shown in FIG. 7. Here, an aqueous feed stream 901 comprising at least a portion of the intermediate aqueous reaction mixture 41 withdrawn from the first oxidation reaction zone is pumped into inlet 903 and ejected through a nozzle 907 into a mixing chamber 909 into which an $O_2$-containing gas is also introduced via inlet 911 (i.e., the $O_2$-containing gas is introduced into the throat of the venturi nozzle 907). This creates a high mass transfer coefficient for oxygen transfer into the aqueous feed 901. Because of this high oxygen mass transfer coefficient and the high agitation within the reactor vessel 913 caused by the nozzle 907, the average oxygen spatial concentration in the undissolved gases in the liquid reaction mixture 915 is low. The reaction mixture effluent 917 is withdrawn from an outlet 919 near the bottom of the reactor vessel 913, cooled in a heat exchanger 921, and filtered by catalyst filter 922, preferably a cross-flow filter. Catalyst separated from the reaction mixture effluent 917 is recirculated back to the reactor 913 via catalyst recycle stream 923 using a pump 925. The filtrate 927, which contains the bulk of the N-(phosphonomethyl)glycine product, is forwarded to be purified and/or concentrated in additional steps. Operation and design of ejector nozzle loop reactors is described by van Dierendonck, et al. in "Loop Venturi Reactor-A Feasible Alternative to Stirred Tank Reactors?", *Ind. Eng. Chem. Res.* 37, 734–738 (1998), the entire disclosure of which is incorporated herein by reference. A commercially available example of an ejector nozzle loop reactor is the BUSS loop reactor sold by Kvaerner Buss CPS (Pratteln, Switzerland). It should be understood that in addition to providing a second or subsequent oxidation reaction zone in a continuous reactor system comprising multiple oxidation reaction zones in series, an ejector nozzle loop reactor could likewise suitably provide the first oxidation reaction zone. The oxidation reaction conditions and operating parameters for an ejector nozzle loop reactor are similar to those described above for oxidation reaction zones provided by stirred tank reactors.

Much of the preceding discussion has focused on continuous reactor systems utilizing a heterogeneous particulate catalyst slurry and comprising at least two stirred tank reactors in series providing oxidation reaction zones substantially back-mixed in at least the liquid phase. However, it should be recognized that reactor configurations other than stirred tank reactors may be equally or more suitable than stirred tank reactors for one or more of the oxidation reaction zones or could be used in combination with multiple stirred tank reactor stages. Furthermore, many such alternative reactor configurations are likewise suitable for use in continuous reactor systems including a single oxidation reaction zone. One of the disadvantages of a continuous reactor system including one or more stirred tank reactors utilizing a particulate catalyst slurry is the capital and operating cost associated with a catalyst recycle mechanism including a catalyst filter or other catalyst separation means necessary to recover the N-(phosphonomethyl)glycine product. Accordingly, reactor configurations in which the catalyst can remain in the oxidation reaction zone may provide an economic advantage in some applications. Two examples of such reactor configurations are fixed catalyst bed reactors and fluidized bed reactors. A further advantage of fixed bed reactors and fluidized bed reactors is that they can be operated in a manner to exhibit plug flow characteristics which tends to produce lower concentrations of undesirable byproducts (e.g., N-methyl-N-(phosphonomethyl)glycine), and, consequently, a greater N-(phosphonomethyl)glycine product yield.

Figure 8:
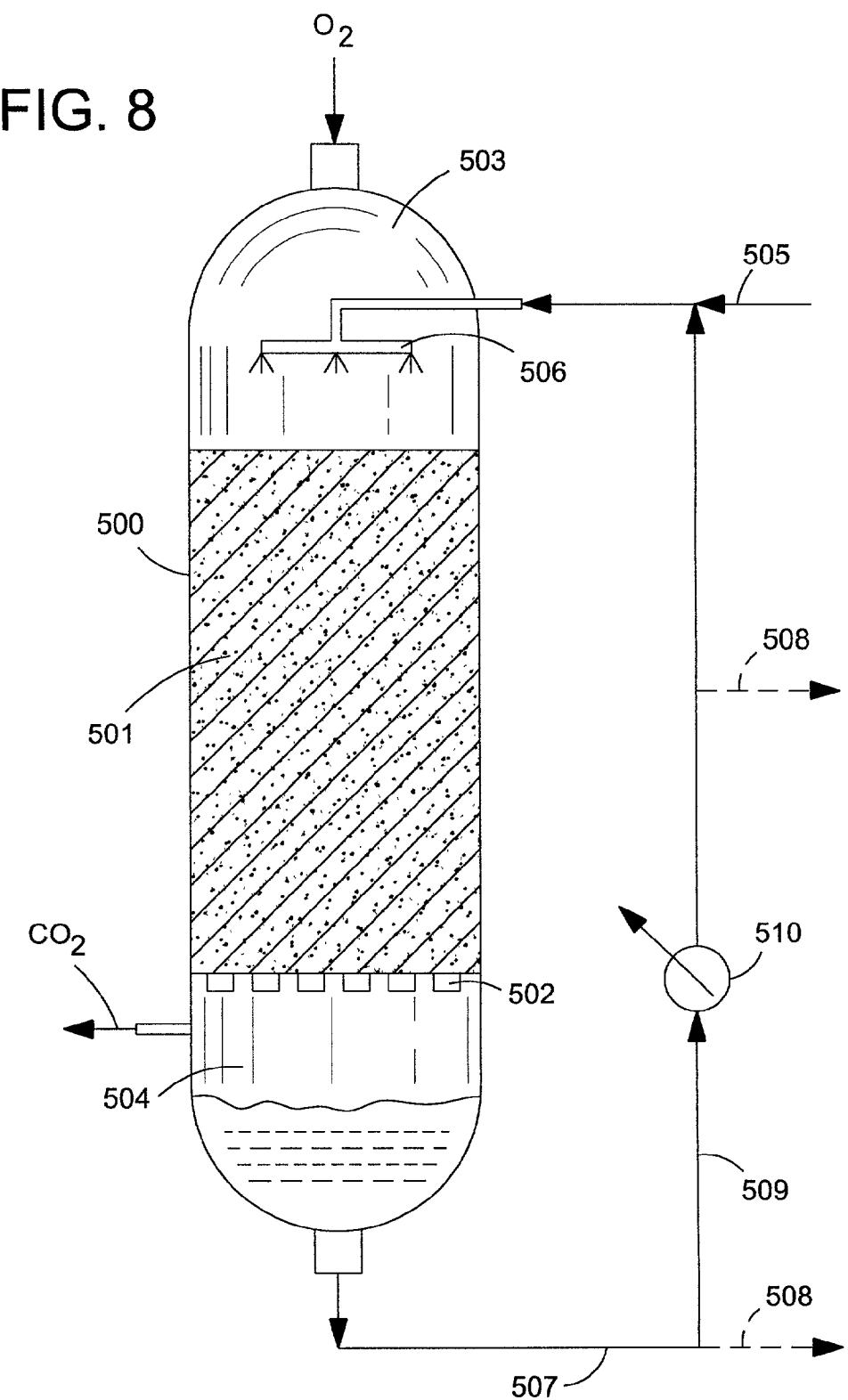
FIG. 8 is a schematic of a fixed bed reactor which may be used in the continuous oxidation reactor system of the present invention for oxidizing an N-(phosphonomethyl) iminodiacetic acid substrate to form an N-(phosphonomethyl)glycine product.

FIG. 8 shows an example of a fixed bed reactor 500 in accord with one embodiment of the present invention. Disposed within the reactor 500 is a primary oxidation reaction zone comprising a primary fixed bed 501 containing an oxidation catalyst, preferably the deeply reduced catalyst described above. A fixed bed support 502 is preferably positioned within the reactor 500 to provide an upper chamber 503 and a lower chamber 504 above and below the fixed bed 501, respectively. An aqueous feed stream 505 comprising the N-(phosphonomethyl)iminodiacetic acid substrate is continuously or intermittently introduced into the upper chamber 503 and distributed over the fixed bed 501 by spray nozzles 506 or other conventional liquid distribution system. An $O_2$-containing gas is likewise introduced into the upper chamber 503. As the $O_2$-containing gas flows cocurrently through the fixed bed 501 with the descending flow of liquid reaction mixture, the N-(phosphonomethyl)iminodiacetic acid substrate is continuously oxidized. A primary reactor effluent 507 comprising N-(phosphonomethyl)glycine product is withdrawn from the lower chamber 504 along with a vapor stream comprising $CO_2$.

Although downward, cocurrent flow of the liquid reaction mixture and the $O_2$-containing gas through the fixed bed 501 is shown in FIG. 8, it should be understood that various flow combinations are possible. For example, the aqueous feed stream 505 and the $O_2$-containing gas could be introduced into the lower chamber 504 of the reactor 500 and flow cocurrently, upward through the fixed bed 501. Alternatively, the liquid reaction mixture and the $O_2$-containing gas can flow countercurrently through the fixed bed 501, the $O_2$-containing gas being introduced into the lower chamber 504 and the aqueous feed stream 505 being introduced into the upper chamber 503 or vice versa.

The temperature within the oxidation reaction zone of the fixed bed reactor 500 is preferably in the range of from about 20° C. to about 180° C., more preferably from about 60° C. to about 140° C., still more preferably from about 80° C. to about 130° C., and yet still more preferably from about 90° C. to about 120° C. Although the reaction system may optionally be operated adiabatically, adverse effects on the catalyst or undue formation of by-products may result from excessive temperatures encountered in adiabatic operation within a primary oxidation reaction zone (i.e., a reaction zone into which a substantial fraction of unconverted substrate is introduced). Where the substrate is of limited solubility (e.g., N-(phosphonomethyl)iminodiacetic acid), a temperature of at least the saturation temperature is preferably maintained at the reactor inlet in order to prevent substrate solids from being deposited in the bed. However, effect on by-product formation and catalyst deterioration require that the maximum temperature be maintained within the ranges outlined above. As a practical matter, this limits the extent of conversion of substrate that may be achieved in an adiabatic fixed bed to not greater than about 10% by weight on a total reaction mixture basis, preferably not greater than about 7%, more typically in the range of about 3% to about 5%. Where the substrate is a salt, the conversion is not constrained by solubility of substrate, but is still limited in the aforementioned range by effects on catalyst and by-product formation.

To achieve a more substantial conversion in a single fixed bed, exothermic reaction heat must be removed from the reaction system. Although the reaction zone as such may be operated adiabatically, heat must be removed from somewhere in the reaction system so that the difference in unit weight sensible heat content between the reaction mixture and the aqueous feed stream is maintained at a value less than the exothermic reaction heat generated in the reaction zone per unit weight of the aqueous feed stream. As described below, measures to remove reaction heat may include cooling the reaction zone, or introducing a cooled recirculation stream with the aqueous feed mixture. By applying cooling in such manner, the conversion expressed as the difference between reaction mixture composition and feed composition may be increased to above 10% or even above 15%. Where the substrate and products are water-soluble salts, the conversion can be increased to 20%, 30%, or even 50%.

Controlling the temperature within the oxidation reaction zone of a fixed bed reactor is typically more difficult as compared to temperature control in a back-mixed reactor system. As shown in FIG. 8, primary reactor effluent 507 may be divided into a primary product fraction 508 and a recirculation fraction 509 which is cooled externally of the reaction zone and returned to the inlet of reactor. Typically at least about 5%, preferably at least about 33%, more preferably from about 50% to about 90%, and even more preferably from about 60% to about 80% of the primary reactor effluent 507 exiting the reactor is diverted to recirculation fraction. Expressed another way, the ratio of the volumetric flow rate of the recirculation fraction 509 to the volumetric flow rate of the primary reaction product fraction 508 is typically at least about 0.05:1, preferably at least about 0.5:1, more preferably from about 1:1 to about 10:1, and most preferably from about 1.5:1 to about 5:1. The recirculation fraction is cooled externally of the fixed bed before it is returned to the reactor, cooling being effected in a heat exchanger 510. In one embodiment shown in FIG. 8, the primary reaction mixture exiting the reactor is divided into a primary product fraction and recirculation fraction and the product fraction removed before the recirculation fraction is passed through the heat exchanger. This alternative may be advantageous in certain embodiments, for example, where the primary product fraction contains unreacted N-(phosphonomethyl)iminodiacetic acid substrate or by-product $C_1$ compounds which are to be oxidized in a further reaction zone. In addition this flow scheme may be advantageous if the primary product fraction is evaporated (e.g., to concentrate and recover the N-(phosphonomethyl)glycine product). In an alternative shown in FIG. 8, it may be preferable to produce a cooled product fraction by passing the entire primary reaction mixture, or substantially the entire primary reaction mixture through an external heat exchanger such as that illustrated at 510, and thereafter dividing the cooled primary reaction mixture stream into a recirculation stream and a cooled primary fraction. Throughout the Figures, dashed lines with directional arrowheads indicate optional, alternative or additional streams.

The cooled recirculation fraction 509 and the aqueous feed stream 505 are mixed to produce a combined inlet stream for the primary reaction zone. Due to the reaction, the recirculation fraction is relatively depleted in N-(phosphonomethyl)iminodiacetic acid substrate, a factor which can be exploited to maximize productivity by introducing an aqueous feed mixture having a high substrate content, including substrate concentrations in excess of the solubility limit of the substrate in the aqueous phase of the feed mixture. Because the recirculation fraction is relatively depleted in substrate, the effect of mixing is to produce a combined inlet stream which has a significantly lower substrate content than the aqueous feed mixture. This dilution effect allows the feed mixture to be much more concentrated than would otherwise be possible. For example, the feed mixture may comprise a slurry of N-(phosphonomethyl)iminodiacetic acid in a saturated, or substantially saturated aqueous solution thereof, which might otherwise tend to cause plugging of the fixed catalyst bed. Mixing with the recirculation fraction reduces the N-(phosphonomethyl)iminodiacetic acid content sufficiently to dissolve the slurry solids and provide a combined inlet stream that is substantially free of solid substrate. Typically, heat from the recirculation fraction also causes the temperature of the combined stream to exceed that of the aqueous feed mixture, further contributing to dissolution of the substrate solids. Moreover, because the oxidation of N-(phosphonomethyl)iminodiacetic acid to N-(phosphonomethyl)glycine is substantially zero order until a high conversion has been attained, the dilution effect does not adversely affect the reaction rate. Optionally, the aqueous feed mixture and recirculation fraction can be directed to a mixing tank to assure that solids have been dissolved before the combined inlet stream is introduced into the fixed catalyst bed. In this manner it is feasible to introduce an aqueous feed stream comprising between about 8% and about 15% by weight N-(phosphonomethyl)iminodiacetic acid, and to produce a combined inlet stream by mixing this aqueous feed stream with a primary reactor recirculation fraction comprising between about 0.5% and about 5% by weight N-(phosphonomethyl)glycine. As described hereinbelow, significantly higher concentrations can be processed where the substrate is a water-soluble salt of N-(phosphonomethyl)iminodiacetic acid and the product is a water-soluble salt of N-(phosphonomethyl)glycine.

It should be understood that, in reducing the substrate content of the combined inlet stream, dilution of the aqueous feed stream with the recirculation stream further serves to reduce the difference in substrate content between the combined catalyst bed liquid phase inlet stream and the catalyst bed liquid exit stream, allowing this difference to be maintained in the ranges which can be tolerated in an adiabatic reaction zone, as described above. Maintaining such limitation on proportional conversion of substrate within the reaction zone remains important in the system of FIG. 8 inasmuch as the catalyst bed itself may still be operated substantially adiabatically, though the overall reaction system, including the recirculation loop, is not.

In an alternative embodiment of the invention (not shown), a continuous reactor system may comprise a second oxidation reaction zone into which part or all of the primary reaction product fraction 508 may be continuously introduced for further conversion of N-(phosphonomethyl)iminodiacetic acid substrate and oxidation of $C_1$ by-products. In such an embodiment, all of the primary reactor effluent 507 may be diverted into the heat exchanger recycle loop and the primary product fraction 508 removed from the recirculation fraction 509 downstream of the heat exchanger 510. In this manner, some of the exothermic heat of reaction would be removed from the primary product fraction 508 before introduction into the second oxidation reaction zone. The second reaction zone contains an oxidation catalyst and may be back-mixed, as provided within a continuous stirred tank reactor, or may comprise a second fixed catalyst bed. Residual N-(phosphonomethyl)iminodiacetic acid substrate in the primary reaction product fraction is continuously oxidized to N-(phosphonomethyl)glycine product in the second reaction zone. In a preferred embodiment comprising two or more fixed bed reactors in series, the reaction is carried to a high conversion of N-(phosphonomethyl)iminodiacetic acid substrate to N-(phosphonomethyl)glycine product in the primary oxidation reaction zone (e.g., at least about 95%, preferably at least about 98%) which is quite feasible because the oxidation proceeds as an apparent zero order reaction until only a small fraction of the original N-(phosphonomethyl)iminodiacetic acid substrate, e.g., as low as about 0.2 ppm or lower, remains in the liquid phase. By operation in this manner, the heat load of the reaction is very predominantly dissipated via the heat exchanger 510 in the recirculation loop of the primary reactor, and the second oxidation reaction zone can be operated essentially adiabatically with only modest temperature increase. Optionally, the reaction heat can be removed to a cooling fluid in an internal heat exchanger (e.g., cooling coils) positioned within the second oxidation reaction zone. Such an arrangement without recirculation allows the liquid phase reaction mixture to be passed through the second fixed bed without undermining the plug flow characteristic (i.e., substantially without backmixing of the liquid phase via recycle). Plug flow operation is desirable in the second reaction zone since the oxidation of substrate to N-(phosphonomethyl)glycine product becomes essentially first order at high conversions. Plug flow operation maximizes the kinetic driving force for extinguishing the residual N-(phosphonomethyl)iminodiacetic acid substrate and reduces the amount of by-products from over-oxidation.

Preferably, both the primary and second catalyst beds contain a noble metal on carbon catalyst which is effective for oxidation of both the N-(phosphonomethyl)iminodiacetic acid substrate and the $C_1$ by-products, formaldehyde and formic acid. Since the noble metal functions primarily to catalyze the oxidation of the $C_1$ by-products, while the oxidation of the N-(phosphonomethyl)iminodiacetic acid substrate is primarily catalyzed by the carbon, an alternative embodiment of the invention comprises the use of a primary fixed bed that consists essentially of carbon catalyst, or has a significantly lower noble metal content than the catalyst deployed in a second fixed bed. The second reactor comprises a noble metal on carbon catalyst to assure oxidation of the $C_1$ by-products. Inasmuch as the $C_1$ oxidation is substantially first order in any case, it proceeds more effectively under the essentially plug flow conditions that are conveniently maintained in the second reactor. The heat load may be sufficiently modest in the second reactor that it can be operated without an external heat exchanger and without back mixing or recirculation. In a fixed bed system, it may be feasible to use a catalyst having a lower noble metal loading per unit weight of catalyst than may be optimal for a continuous back-mixed reaction system.

In a still further embodiment, a third fixed bed reaction zone can be provided, which also preferably comprises a fixed bed containing a noble metal on carbon catalyst, and which can be operated substantially in plug flow and optionally, in fact preferably, under adiabatic conditions. This option may be of particular value where the first reactor uses only a carbon catalyst. Thus, the oxidation of N-(phosphonomethyl)iminodiacetic acid substrate to N-(phosphonomethyl)glycine product proceeds well in the presence of the carbon catalyst in the primary oxidation reaction zone, but $C_1$ by-products tend to accumulate in the primary reactor effluent. The second reaction zone promotes both extinction of the substrate and oxidation of $C_1$ by-products, both of which are essentially first order reactions that are promoted by the essentially plug flow operation of the second fixed bed. Residual $C_1$ compounds are effectively extinguished in the third fixed bed oxidation reaction zone.

In a still further embodiment, the continuous reactor system may comprise a plurality of shorter (or shallower) fixed bed reactors in series such that the intermediate reaction mixture effluent exiting one stage is passed through the following stage. This embodiment varies from the two or three reactor system described above in that only modest conversion would be achieved in any of the series of relatively shallow fixed bed reactor stages. Since substrate conversion in any one bed is relatively limited, each bed can be operated substantially adiabatically with a heat exchanger being placed between each successive shorter fixed bed reactor and the immediately succeeding reactor to cool the reaction mixture so that the temperatures of the reaction mixture do not exceed the desired operating temperature in any of the fixed bed reactors. Where the series comprises more than two reactors, it may be necessary to cool only the intermediate reaction mixture exiting the first one, two or three fixed bed reaction zones, after which it may be feasible for the remainder to operate adiabatically. The reaction temperature in a fixed bed reactor may also be controlled by, for example, incorporating separate channels or conduits within the fixed bed through which a cooling medium may be passed. It may be noted that, in this embodiment, not all the reactors of the series need necessarily be fixed bed reactors. For example, the first reactor of the series could be a continuous stirred tank reactor within which a substantially zero order oxidation of N-(phosphonomethyl)iminodiacetic acid substrate to N-(phosphonomethyl)glycine product may be carried to a substantial conversion to produce an intermediate reaction mixture, and the intermediate reaction mixture may be transferred to a fixed bed reactor, or a series of fixed bed reactors for completing the conversion and oxidizing residual $C_1$ by-products.

As described above, catalyst utilized in fixed bed reactors may take a variety of forms and comprise different types of supports including both pellet supports and monolithic supports. As shown in FIG. 8, it is generally preferred that the oxidation catalyst contained within the fixed bed 501 be in the form of a pellet (e.g., the deeply reduced catalyst described above comprising a carbon pellet support having a noble metal deposited thereon). Such pellet catalysts typically have a particle size of from about 1 mm to about 10 mm, more preferably from about 1.5 mm to 5 mm. A typical packing density for noble metal on carbon catalyst particles in this preferred size range is from about 0.1 to about 1.4 g/l, more preferably 0.25 to about 0.6 g/l, even more preferably from about 0.3 to about 0.4 g/ml. It has further been determined that the noble metal loading in a noble metal on carbon catalyst that is used in a fixed bed may be lower relative to the loading on a comparable catalyst for use in a slurry reactor. For example, effective operation of a fixed bed has been demonstrated using only a 2 wt. % Pt on carbon catalyst within the 200 to 2000 $m^2/cm^3$ BET surface to liquid holdup volume ratio noted below. Generally, a loading lower than 3 wt. % Pt may be satisfactory. Where the catalyst comprises platinum on carbon, the platinum loading on the catalyst may be less than 70% of the loading required in a slurry reactor.

Another advantage of a fixed bed reactor is that by combining different catalysts, the catalyst activity can be selectively varied over the length of fixed bed reactor stage or from one stage to the next in the direction of reaction mixture flow. For example, a less active catalyst (e.g., a carbon only catalyst) may be deployed in the upstream portion of a fixed bed reactor stage or in earlier stages of a multi-stage fixed bed reactor system and a more active catalyst (e.g., a deeply reduced noble metal on carbon catalyst) may be deployed in the downstream portion of a fixed bed reactor stage or in later stages of a multi-stage system. Alternatively, the fixed bed may comprise a combination of oxidation catalyst bodies and other means for promoting gas/liquid mass transfer such as rings, saddles, or structured packing. The rings, saddles, or other inert packing functions as a diluent for the catalyst, thereby modulating the activity of the catalyst bed. In this manner, the activity of the catalyst bed may be varied in the direction of fluid flow as a function of variation of the surface area of the catalyst bodies relative to the surface area of the inert packing. Such a variation in catalyst activity acts to offset the declining concentration of the N-(phosphonomethyl)

iminodiacetic acid substrate in the reaction mixture while reducing catalyst costs and noble metal losses from the process.

The tendency of fixed bed reactors to produce lower concentrations of undesirable byproducts due to plug flow characteristics may be enhanced by using a ratio of effective catalyst surface area to liquid in the working volume which is significantly greater than the ratio used in typical backmixed (i.e., well-mixed) reactors. In fact, the need to cool the reaction mixture to reduce impurity formation may be reduced or entirely eliminated by using such a ratio. This is due to the fact that the large effective catalyst surface area increases the reaction rate and consequently reduces the liquid residence time. The reduced residence time, in turn, tends to reduce the formation of impurities that are formed by homogeneous reactions, particularly N-methyl-N-(phosphonomethyl)glycine. In this embodiment, the ratio of catalyst BET surface area to volume of liquid (liquid holdup) in the working volume of the fixed bed reactor preferably is at least about 3 $m^2/cm^3$, more preferably from about 100 to about 6000 $m^2/cm^3$, and even more preferably from about 200 to about 2000 $m^2/cm^3$. In some applications a catalyst BET surface area to liquid holdup in the reactor may most preferably be in the range of about 400 to about 1500 $m^2/cm^3$. The volumetric ratio of liquid holdup to total bed volume in the fixed bed is preferably in the range of between about 0.1 and about 0.7. In certain embodiments the low liquid residence time and high surface to volume ratio may make it advantageous to operate a fixed bed reactor in a relatively high temperature range of, e.g. 150° C., wherein the integrated average temperature of the liquid phase across the liquid phase flow path in the primary fixed bed is between about 80° C. and about 130° C., preferably 105° C. to 120° C.

Fixed bed reactors containing a catalyst in monolith form (e.g., comprising a honeycomb support such as that shown in FIG. 1) are sometimes more preferred than reactors containing a fixed bed of discrete catalyst particles. This is due to the fact that a fixed bed of catalyst particles may be subject to clogging if the N-(phosphonomethyl)iminodiacetic acid substrate contained in the aqueous feed stream 505 precipitates to any significant degree in the oxidation reaction zone. Accordingly, it is typically required that the concentration of the N-phosphonomethyl)iminodiacetic acid substrate in the aqueous feed stream 505 not exceed the saturation concentration at the reactor feed temperature, which may significantly limit throughput. However, if the fixed bed 501 comprises a catalyst in the form of a honeycomb or similar monolith, the channels therein can be made substantially straight and with a large enough cross-section so that they will not be clogged by a reaction mixture containing a slurry of solid N-(phosphonomethyl)iminodiacetic acid substrate. Even if a packed bed reactor is not subject to plugging, the monolith can be operated with substantially lower pressure drop. This potential advantage of utilizing a monolithic catalyst in a fixed bed reactor must be weighed against the increased costs associated with production of the monolith supports as compared to the often significantly cheaper pellet or particulate supports generally preferred in the practice of the present invention. This is particularly true where multiple fixed bed stages are employed with separate N-(phosphonomethyl)iminodiacetic acid substrate feed streams to each stage, thereby avoiding the need for a high substrate concentration in the feed stream to the first fixed bed stage to obtain the desired throughput.

The amount and pressure of oxygen within the oxidation reaction zone may very significantly depending upon a variety of considerations, including total pressure, bed temperature profile, superficial gas velocity, catalyst bed volume, specific catalyst type and geometry, feed concentrations, number of oxidation reaction zones, productivity as well as other factors.

To achieve high conversion in a packed bed reactor system, each of the fixed bed reaction zones, especially the primary reaction zone, is preferably operated under relatively high oxygen partial pressure to promote oxygen transfer to the liquid phase. Preferably, the integrated average oxygen partial pressure over the liquid phase flow path in the primary oxidation reaction zone is at least about 50 psia, more preferably at least about 100 psia, even more preferably at least about 200 psia. In some embodiments, integrated average oxygen partial pressures in the range of about 300 psia to about 500 psia may be appropriate. Oxygen content of the gas phase at the gas exit of the reactor may be in the range of 20% to 30% or even lower. Oxygen transfer may also be promoted by the high ratio of catalyst surface area to volume ratio of liquid phase reacting mixture in a fixed bed reactor as described above. Oxygen utilization in the primary reaction zone is preferably between about 50% and about 95%. Typically, oxygen is fed to the reactor in a quantity of from about 1.5 to about 10 mole $O_2$/mole N-(phosphonomethyl)iminodiacetic acid substrate introduced to the reactor.

The total operating pressure in the fixed bed reactor 500 may typically be higher than that in a stirred tank reactor and is preferably from about 0 to about 1000 psig, more preferably from about 300 to about 1000 psig, and even more preferably from about 100 to about 300 psig.

Generally, a somewhat lower oxygen partial pressure may be preferred in a second and/or third fixed bed oxidation reaction zone(s) in order to avoid over-oxidation of the catalyst and compromising its effectiveness in oxidation of $C_1$ by-products. Thus, in the second or third reaction zone, the integrated average oxygen partial pressure along the liquid flow path is preferably between about 30 psia and about 300 psia, more preferably between about 30 psia and about 100 psia. Alternatively, the primary fixed bed reactor of FIG. 8 and/or the second or third fixed bed reactor(s) in the series may be operated using an oxidant other than molecular oxygen, for example, $H_2O_2$, in which case the total reaction pressure and partial pressure of oxygen may be substantially lower than as described above.

To protect the catalyst against over-oxidation, it is generally preferred that oxygen partial pressure at the liquid exit of any fixed bed reactor be not greater than about 100 psia, and is preferably between about 10 psia and about 50 psia. It is also preferred that the oxygen partial pressure not exceed about 50 psia at any location in the fixed bed wherein the N-(phosphonomethyl)iminodiacetic acid substrate content of the liquid phase is less than 0.2 ppm; more preferably, the oxygen partial pressure is maintained below about 50 psia at any location in the bed wherein the substrate content of the liquid phase is less than greater than about 0.1 ppm.

By observing the operational guidelines set forth above and particularly in connection with fixed bed reactors comprising a deeply reduced noble metal on carbon catalyst as described above, N-(phosphonomethyl)iminodiacetic acid substrate may be converted to N-(phosphonomethyl)glycine product in a single fixed bed reactor at productivities on a reactor volume basis in the range of from about 0.05 to about 4 gmole/l/hr, more typically from about 0.2 to about 2 gmole/l/hr.

In accordance with the invention, a fixed bed reactor may be operated at a substantial throughput, provided that adequate heat transfer capacity is provided, as depicted, for example, in FIG. 8. Generally, the relative liquid feed rate to the reactor and the reactor volume are such that a fixed bed reactor may be operated at a liquid hourly space velocity between about 0.5 hr$^{-1}$ and about 20 hr$^{-1}$, as computed on the basis of total catalyst bed volume, at N-(phosphonomethyl)iminodiacetic acid substrate conversions in excess of about 50%. Higher conversions, in excess of 95% or 98% can be achieved at liquid hourly space velocities in the range of from about 0.5 to about 5 hr$^{-1}$. It will be understood that the liquid hourly space velocity is based on the total liquid phase feed stream. Thus, in the reaction system depicted in FIG. 8, the liquid phase feed stream comprises the combined inlet stream produced by mixing the aqueous feed mixture stream and the recirculation stream, as well as any other recycle or cross-flow streams that might be introduced into a fixed bed reactor in accordance with a particular process flow sheet. Typically, the fixed be is cylindrical and of circular cross-section and the height to diameter ratio is selected so as to provide adequate liquid distribution over the bed and appropriate gas superficial velocity for mass transfer characteristics. Typically, the height to diameter ration for a fixed bed used in the continuous oxidation reactor systems of the present invention is greater than one, more preferably from about 3 to about 40.

It is difficult to maintain a constant catalyst activity and selectivity over time in a fixed bed reactor. Eventually the activity and selectivity of the catalyst decreases to an unacceptable level such that the reactor system may have to be shut down to allow replacement and/or reactivation of the catalyst. This is a disadvantage as compared to the continuous reactor systems including one or more stirred tank reactors described above where catalyst replacement and/or reactivation can occur while the reactor system remains online. The problem of catalyst removal and reclamation can be resolved by providing duplicate fixed bed reactors that are valved in parallel to the remainder of the reaction system, and operating them on an alternating basis. Catalyst can be removed from the reactor that is out of service and replaced with fresh catalyst; or catalyst reactivation can be conducted in situ in the reactor that is off line.

Figure 9:
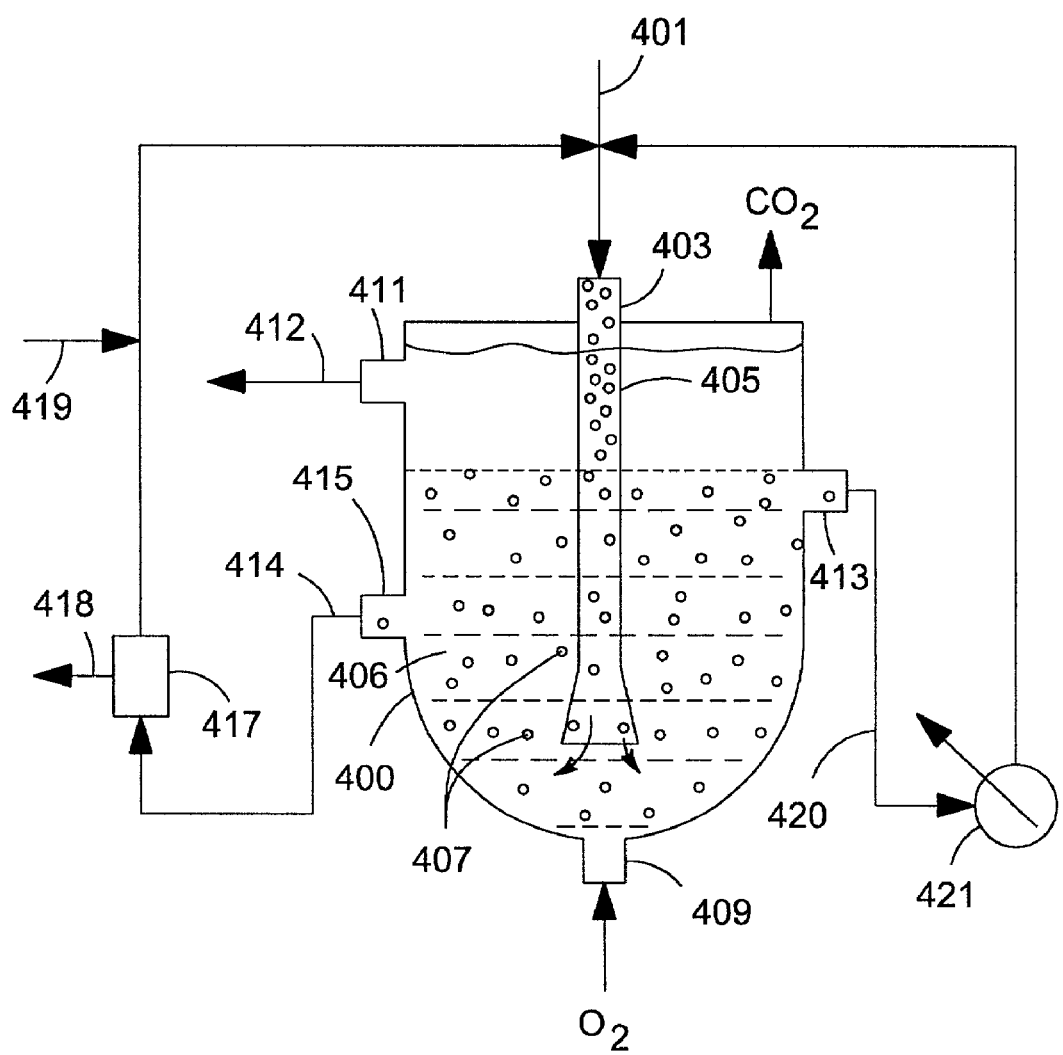
FIG. 9 is a schematic of a circulating fluidized bed reactor which may be used in the continuous oxidation reactor system of the present invention for oxidizing an N-(phosphonomethyl)iminodiacetic acid substrate to form an N-(phosphonomethyl)glycine product.

In accordance with another embodiment of the present invention, the oxidation of the N-(phosphonomethyl)iminodiacetic acid substrate is carried out in a circulating fluidized bed reactor utilizing a particulate heterogenous catalyst, preferably the deeply reduced particulate catalyst described above. A circulating fluidized bed reactor typically provides a greater mass transfer coefficient than a stirred tank reactor and may be operated in a manner to substantially retain the particulate catalyst within the oxidation reaction zone such that a catalyst filter or other catalyst separation means may not be required at all or at least substantially reduced in size and pressure drop requirements. FIG. 9 shows an example of a circulating fluidized bed reactor 400 defining an oxidation reaction zone therein. An aqueous feed stream 401 comprising the N-(phosphonomethyl)iminodiacetic acid substrate is pumped into the top of the reactor 400 through an inlet 403 of draft tube 405 and discharged near the bottom of the reactor 400 into liquid reaction medium 406 in contact with the catalyst particles 407. An O$_2$-containing gas may be sparged into the reaction mixture through a nozzle 409 at the bottom of the reactor 400. Reaction solution 412 is withdrawn from the reaction zone at an overflow port 411 and vapor comprising CO$_2$ is vented through the top of the reactor. The reactor has a reacting mixture circulation withdrawal port 413 located well above the discharge mouth of draft tube 405 but below the overflow port 411. Reacting mixture having particulate catalyst suspended therein is withdrawn at port 413, circulated via an external loop 420 through a heat exchanger 421 for removal of reaction heat, and then combined with feed stream 401 for reintroduction into the reactor via draft tube 405. By maintaining a high rate of circulation in loop 420 relative to the rate of supply of feed 401 and withdrawal of reaction solution 412, an upward flow velocity is established in a lower slurry region of the oxidation reaction zone generally below port 413 that is much higher than the upward flow velocity in a upper decantation region of the oxidation reaction zone generally above port 413. The equipment is sized and the recirculation flow controlled so that upward velocity in the lower slurry region is well above the sedimentation velocity of the catalyst particles 407 and therefore effective to maintain the catalyst in suspension (i.e., entrained) in the reaction medium within the slurry region. However, the upward velocity in the decantation region above port 413 is well below the sedimentation velocity of the catalyst particles 407, allowing separation of a relatively clear reaction solution decantate 412 which exits through port 411. Typically, the size of the catalyst particles 407 utilized in a reactor such as that shown in FIG. 9 is from about 200 $\mu$m to about 1000 $\mu$m. Smaller catalyst particles that might be entrained in the decantate 412, for example at startup, may be removed with a polish filter (not shown). Thus, the slurry catalyst is maintained within the reactor obviating the need for filtration, or at least for a filter having the capacity to remove catalyst at the rate that would be required if the concentration of catalyst in the forward flowing reaction solution 412 were comparable to the concentration of catalyst in the slurry region.

For removal of catalyst, the circulating fluidized bed reactor may also include a catalyst separation loop 414, as is also shown in FIG. 9. In this loop, a sidestream of slurry is removed from port 415 in the slurry region of the reaction zone and passed through a catalyst filter 417 for removal of catalyst 418. Fresh catalyst 419 may be added to the filtered reacting solution that is conveniently recycled to the reactor by mixing it with fresh feed stream 401 and recirculation stream 420 for introduction into draft tube 403. The catalyst separation loop 414 may be operated continuously or intermittently as needed (e.g., to purge catalyst having diminished activity and/or selectivity) and obviates the need to periodically shut down the reactor for replacement of particulate catalyst. However, the capacity of catalyst filter 417 need not be nearly as great as the filters used for separation of catalyst from the reaction slurry exiting a continuous stirred tank reactor as described above. Thus, significant savings in capital, operating, and maintenance expense can be realized.

Various modifications may be made to the fluidized bed reactor 400 shown in FIG. 9. For example, rather than sparging the O$_2$-containing gas into the reaction mixture 406 at the bottom of the reactor 400, an ejector nozzle similar to that shown in FIG. 7 may be provided at the top of the reactor through which both the aqueous feed stream 401 and the O$_2$-containing gas are combined and discharged into the reaction mixture 406. Alternatively, circulation of the reacting mixture containing the particulate catalyst may be provided by an impeller rotated within the draft tube 405 in a manner to draw the reacting mixture downward through the draft tube and into the lower region of the oxidation reaction zone. Moreover, the catalyst separation loop 414 may optionally be integrated into the heat transfer recirculation loop 420. The oxidation reaction conditions and operating parameters for a circulating fluidized bed reactor are similar to those described above for oxidation reaction zones provided by stirred tank reactors.

Figure 10:
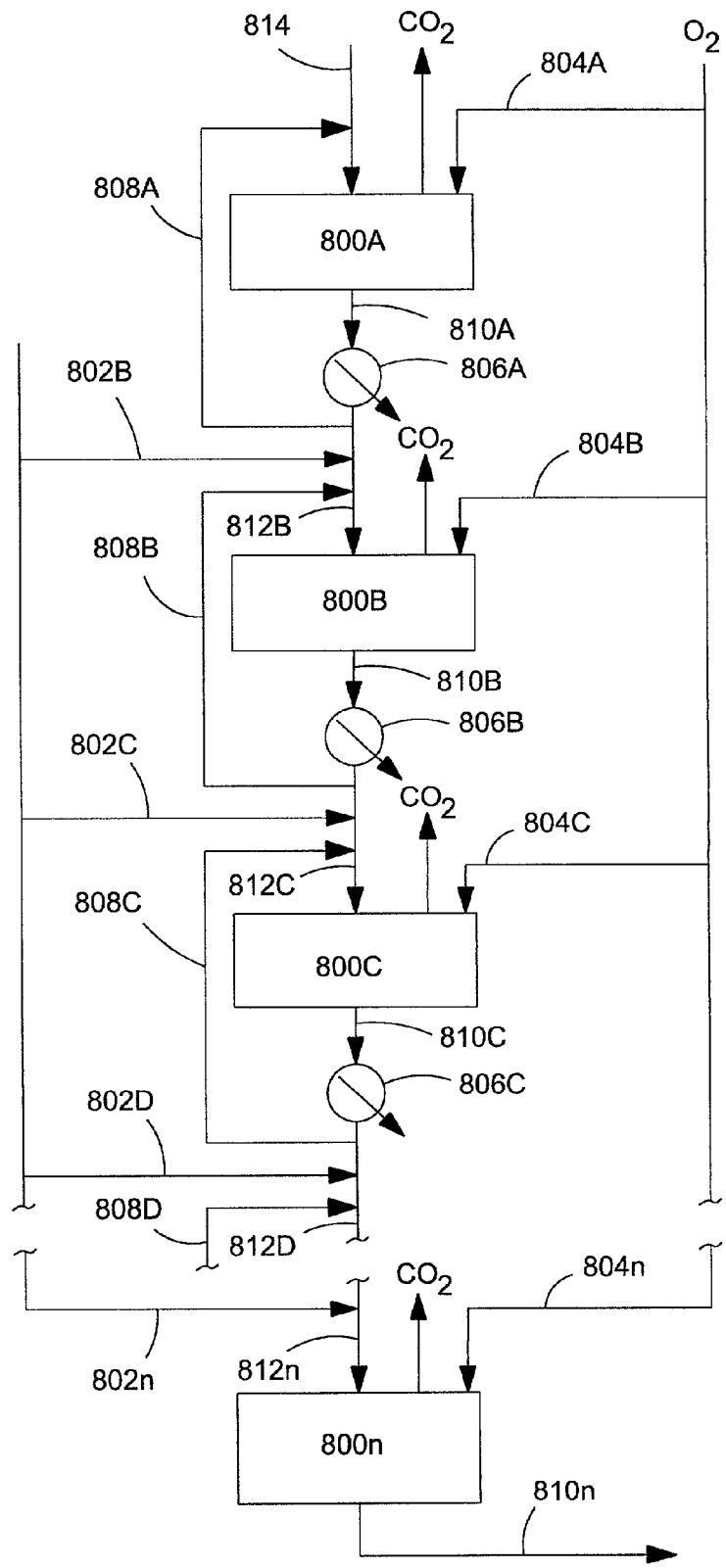
FIG. 10 is a schematic flow sheet of a continuous distributed reactor system for oxidizing an N-(phosphonomethyl)iminodiacetic acid substrate to form an N-(phosphonomethyl)glycine product. The reactor system comprises a plurality of reactors in which reacting mixture progresses in series from each reactor to the succeeding reactor in the series.

A still further alternative embodiment of the invention is illustrated in FIG. 10 wherein the oxidation of N-(phosphonomethyl)iminodiacetic acid substrate to N-(phosphonomethyl)glycine product is conducted in a distributed reactor system comprising a plurality of reactors 800A, 800B, 800C, . . . 800n in which reacting mixture progresses in series from each reactor to the succeeding reactor in the series. Primary feed mixture 814 comprising N-(phosphonomethyl)iminodiacetic acid substrate is introduced into reactor 800A and supplemental feed mixture is divided into parallel component feed streams 802B, 802C, 802D, . . . 802n that are distributed among the series of reactors. Each reactor receives a component of distributed supply of oxygen or other oxidizing agent via feed lines 804A, 804B, 804C, . . . 804n. Optionally, a heat exchanger 806A, 806B, 806C, etc. is interposed between each succeeding reactor and the immediately preceding reactor to remove heat of reaction from the intermediate reaction mixture 810A, 810B, 810C, etc. exiting the immediately preceding reactor 800A, 800B, 800C, etc. and allow each reactor to operate adiabatically if desired. Alternatively, a cooled recirculation stream 808A, 808B, 808C, 808D, etc. can be returned to each reactor to remove exothermic heat of reaction and provide cooling of the reacting mixture in the reactor. In each of the series of reactors subsequent to the first reactor 800A, a combined inlet stream 812B, 812C, 812D, . . . 812n is the combination of the component feed stream 802B, 802C, 802D, etc., the intermediate reaction mixture exiting the immediately preceding reactor 810A, 810B, 810C, etc., minus any recirculation 808A, 808B, 808C, 808D, etc. and any recirculation stream 808B, 808C, 808D, etc. Each of reactors 800A, 800B, etc. can assume any of the configurations described herein, but is preferably in the form of a reactor in which catalyst is retained (e.g., a fixed bed or fluidized bed reactor). A final reaction product 810n is withdrawn from the last reaction zone 800n of the reaction zone series.

Each component feed stream 802B, 802C, etc. of a distributed reactor system may be highly concentrated, thereby contributing to high productivity of the process. In fact, component feed streams comprising a dense N-(phosphonomethyl)iminodiacetic acid substrate slurry or paste component feed streams can be used. In each succeeding reactor following the first reactor 800A, (e.g., reactor 800B) a slurry or paste component feed mixture can be introduced, though it is preferred, especially in the case of fixed bed reactors, that the combination of component 802B feed composition, component 802B feed rate, composition and flow rate of intermediate reaction mixture 810A exiting the immediately preceding reactor 800A (minus any recirculation 808A), any recirculation 808B of intermediate reaction mixture from reactor 800B are such that the combined inlet stream 812B is substantially free of substrate solids or N-(phosphonomethyl)glycine product solids. However, it will be understood by those skilled in the art that, in certain embodiments of the invention, the component feed and intermediate reaction mixtures can be in slurry form throughout, for example, where the oxidation catalyst is a homogeneous catalyst, or where a monolithic catalyst such as fixed bed in honeycomb form is utilized.

Although both an additional component feed stream 802B, 802C, etc. and oxidant are preferably introduced into each of the series of reaction zones 800B, 800C, etc. following the first reaction zone, it will be understood that in a particular application, it may be necessary or desirable to supply a component reaction mixture only to some but not all of the successive reaction zones. In some instances, it may not be necessary to supply oxidant to all reaction zones, though in most cases, supply of oxidant to each zone is preferred.

The fixed bed and distributed feed embodiments of the invention are uniquely suited for conversion of water-soluble salts of N-(phosphonomethyl)iminodiacetic acid to water-soluble salts of N-(phosphonomethyl)glycine. Because of the generally high solubility of alkali metal and amine salts, e.g., potassium, ammonium, isopropylamine, and alkanolamine salts, of both the substrate acid and the product acid, either a fixed bed or stirred tank reactor may be operated at much higher substrate and product concentrations than is feasible in the acid process wherein productivity is limited by relatively low solubility. In fact, in the case of the salts, a fixed bed process may be particularly advantageous because it can be operated without need for any filtration or centrifugation operation, either for removal of crystalline product or for removal of catalyst. An N-(phosphonomethyl)glycine salt solution can be formulated with various excipients commonly used in the commercial application of N-(phosphonomethyl)glycine and soluble with minimal further processing. To produce the desirable concentrates of commerce, only modest concentrating steps are required. Extensive impurity separation may not be required.

A stirred tank reaction system, especially a continuous stirred tank reaction system may be advantageous for synthesis of salts because of the more substantial reaction heat load associated with the oxidation of high concentration of substrate, and the accompanying exothermic oxidation of relatively large proportions of $C_1$ by products such as formaldehyde and formic acid. A continuous stirred tank reactor offers a significant advantage over a batch reactor in the utilization of reaction heat to preheat aqueous feed to the reactor. Combinations of a primary continuous stirred tank for initial conversion with a fixed bed finishing reactor may also be advantageous.

A fixed bed substantially plug flow reactor nonetheless offers particular advantages, especially where the catalyst bed comprises noble metal on carbon, because the plug flow operation serves to promote oxidation of $C_1$ by-products, a reaction which is essentially first order in $C_1$ substrate. However, for the same reason, plug flow exacerbates the heavy heat load associated with oxidation of an aqueous feed mixture containing a high concentration of substrate salt. Although the recirculation reaction system of FIG. 8 may be used to establish adequate heat transfer, it has an unfavorable effect on the kinetics of destruction of formaldehyde and formic acid, though depending on the recirculation rate the effect on $C_1$ destruction may remain marginally superior to a fully back-mixed reactor.

Accordingly, in some instances it may be advantageous to conduct the oxidation reaction in a reaction system wherein the fixed bed is cooled by indirect transfer of heat to a cooling fluid comprising a heat transfer or process fluid flowing through a conduit within or in contact with the catalyst bed. For example, the fixed bed may be disposed within the shell or tube side of a shell and tube heat exchanger, with the cooling fluid being passed through the other side of the exchanger. In one such embodiment, the fixed bed may comprise multiple component beds separately disposed in the tubes of the heat exchanger, with the aqueous feed mixture and oxidant being distributed among the component beds and the cooling fluid flowing through the shell side of said heat exchanger. In an alternative embodiment, the fixed bed may be contained within the shell of the heat exchanger, baffles on the shell side optionally being used to assure substantially plug flow of the liquid phase through the bed.

Alternatively, salts of N-(phosphonomethyl)glycine may be prepared in a series of reactors separated by heat exchangers for cooling the intermediate reaction solution as described above. The distributed feed reaction system of FIG. 10 may be especially advantageous in dealing with the heat load generated in the oxidation of N-(phosphonomethyl)iminodiacetic acid salts to N-(phosphonomethyl)glycine salts. As noted, especially high productivities may be achieved where the substrate and product are both water-soluble salts. For example, where the aqueous feed mixture may contains at least about 15% by weight of the substrate salt, the final reaction mixture may contain at least about 12% by weight of a water-soluble product salt; where the aqueous feed mixture contains at least about 25% by weight of a water-soluble substrate salt, the final oxidation reaction mixture may contain at least about 20% by weight of a water-soluble product salt; and where the aqueous feed mixture contains at least about 35% by weight of a water-soluble substrate salt, the final oxidation reaction mixture may contain at least about 28% by weight of a water-soluble product salt; all on an acid equivalent basis. In fact, even high product salt concentrations can be realized, in excess of 35%, preferably in excess of 40% or even 50% by weight. As described above, the final reaction product may be the primary reaction mixture obtained in a single reactor, the primary product fraction of a single recirculating fixed bed system as depicted in FIG. 8 or the effluent of the last of a series of reactors as is further described above.

The final reaction product is preferably further concentrated by removal of water therefrom. For example, the final reaction mixture may be introduced into a flash evaporation zone wherein the pressure is lower than the vapor pressure of the final oxidation mixture at the temperature at which it exits the reactor, or the last of a series of reactors. With relatively low expenditure of energy, sufficient water may be removed from the final oxidation reaction product to produce a concentrated solution containing at least about 40% by weight of a water-soluble salt of N-(phosphonomethyl) glycine on an acid equivalent.

Typically, the concentration of N-(phosphonomethyl)glycine product in the oxidation reaction mixture effluent exiting the reactor systems of the present invention may be as great as 40% by weight, or greater. Preferably, the N-(phosphonomethyl)glycine product concentration is from about 5 to about 40%, more preferably from about 8 to about 30%, and still more preferably from about 9 to about 15%. The concentration of formaldehyde in the product mixture is preferably less than about 5000 ppm, more preferably less than about 4000 ppm, still more preferably less than about 2800 ppm by weight, and still even more preferably less than about 1500 ppm. The concentration of formic acid in the product mixture is preferably less than about 12,000 ppm, more preferably less than about 4000 ppm, still more preferably less than about 2000 ppm by weight, and still even more preferably less than about 1500 ppm. The concentrations of aminomethylphosphonic acid (AMPA), N-methyl-aminomethylphosphonic acid (MAMPA), N-methyl-N-(phosphonomethyl)glycine (NMG) in the product mixture are readily controlled at each less than 9000 ppm, can usually be controlled at less than 4500 ppm, and often be maintained below 1500 ppm. It will be understood that these concentrations of by-products are based on a single pass operation in which the only feed to the reactor system is an aqueous mixture containing N-(phosphonomethyl)iminodiacetic acid or salt thereof as obtained from the phosphonomethylation of iminodiacetic acid. Where any recycle stream such as the decantate from an adiabatic crystallizer as described below is introduced into the reactor system, the attendant recycle of by-products tends to increase the by-product content of the reaction product mixture.

Purifying and/or Concentrating the N-(phosphonomethyl) glycine Product

Another aspect of this invention relates to purifying and/or concentrating the N-(phosphonomethyl)glycine product obtained in the oxidation reaction mixture effluent. The various improvements in N-(phosphonomethyl)glycine product recovery provided by the present invention have wide application and, for example, may be used to recover N-(phosphonomethyl)glycine product from the oxidation reaction mixture produced by the various continuous oxidation reactor systems described herein. However, this further aspect of the present invention is not limited to such application or to use in conjunction with continuous oxidation reactor systems generally. As will be apparent to those skilled in the art, the strategies set forth herein may be advantageously applied in recovering N-(phosphonomethyl) glycine product from oxidation reaction mixture effluents produced by other reactor systems as well, including batch reactor systems.

The reaction mixture normally contains water and various impurities besides the desired N-(phosphonomethyl)glycine product. These impurities may include, for example, various by-products and unreacted starting materials such as unreacted N-(phosphonomethyl)iminodiacetic acid substrate, N-formyl-N-(phosphonomethyl)glycine, phosphoric acid, phosphorous acid, hexamethylenetetraamine, aminomethylphosphonic acid, N-methyl-aminomethylphosphonic acid, iminodiacetic acid, formaldehyde, formic acid, and the like. The value of the N-(phosphonomethyl)glycine product normally dictates maximal recovery of the product from the reaction mixture and also often provides incentive for recycling at least a portion of the depleted reaction mixture to the oxidation reaction zone(s) for further conversion of unreacted substrate and recovery of unrecovered product.

Commercial considerations also sometimes dictate that the concentration of the N-(phosphonomethyl)glycine product in the commercially sold mixtures be significantly greater than the concentrations in the reaction mixtures that are typically formed using the above described oxidation reaction systems, particularly where the N-(phosphonomethyl)glycine product is being used for agricultural purposes. For example, when using a heterogenous catalyst to make the N-(phosphonomethyl)glycine free acid at the more preferred operating temperatures (i.e., from about 95 to about 105° C.), the maximum concentration of the N-(phosphonomethyl)glycine product in the reaction mixture is preferably no greater than about 9% by weight so that it will remain solubilized. Sometimes, however, it is desirable for the commercially sold mixtures to have an N-(phosphonomethyl)glycine concentration which is significantly greater.

Thus, after the N-(phosphonomethyl)glycine product has been formed and, if necessary, separated from the catalyst, it is typically preferable to concentrate the product and separate the product from the various impurities in the oxidation reaction mixture.

Smith (in U.S. Pat. No. 5,087,740) describes one process for purifying and concentrating an N-(phosphonomethyl) glycine product. Smith discloses passing a reaction mixture containing N-(phosphonomethyl)glycine through a first ion exchange resin column to remove impurities that are more acidic than the N-(phosphonomethyl)glycine, passing the effluent from the first ion exchange resin column through a second ion exchange resin column which adsorbs the N-(phosphonomethyl)glycine, and recovering the N-(phosphonomethyl)glycine by passing a base or strong mineral acid through the second ion exchange resin column.

Many other techniques for purifying and concentrating an N-(phosphonomethyl)glycine product include a crystallization step, wherein the N-(phosphonomethyl)glycine product is crystallized to separate it from at least a portion of the remaining reaction mixture.

The product recovery processes illustrated in FIGS. 11–14A and described below have particular application in the concentration and recovery of product from oxidation reaction mixtures containing N-(phosphonomethyl)glycine product susceptible to crystallization, and especially those containing N-(phosphonomethyl)glycine free acid. The concentrated N-(phosphonomethyl)glycine free acid is typically used in the preparation of the other N-(phosphonomethyl) glycine products such as those described above.

In a particularly preferred embodiment, at least a portion of the final reaction mixture (preferably absent any catalyst, and particularly absent any heterogeneous catalyst or homogeneous catalyst that co-crystallizes with the N-(phosphonomethyl)glycine product) is introduced into a non-adiabatic heat-driven evaporative crystallizer, where heat is added to the oxidation reaction mixture to evaporate off water from the reaction mixture and thereby concentrate and crystallize the N-(phosphonomethyl)glycine product. The heat used in the non-adiabatic crystallizer is normally derived from steam. Preferably, at least about 30%, more preferably at least about 50%, even more preferably from about 80% to about 100%, still even more preferably from about 90% to nearly 100% of the water in the reaction mixture is evaporated in the non-adiabatic crystallizer system. Evaporative crystallization is particularly advantageous because it also separates the product from small molecule impurities, most notably formaldehyde and formic acid, which tend to evaporate from the reaction mixture along with the water.

The pressure in the heat-driven evaporative crystallizer preferably is no greater than about 10 psia, more preferably from about 1 to about 10 psia, even more preferably from about 1 to about 5 psia, still more preferably from about 2 to about 3 psia, and still yet even more preferably about 2.8 psia. The operating temperature of the heat-driven evaporative crystallizer preferably is no greater than about 80° C., more preferably from about 40° C. to about 80° C., even more preferably from about 50° C. to about 70° C., and still even more preferably about 60° C.

Figure 11:
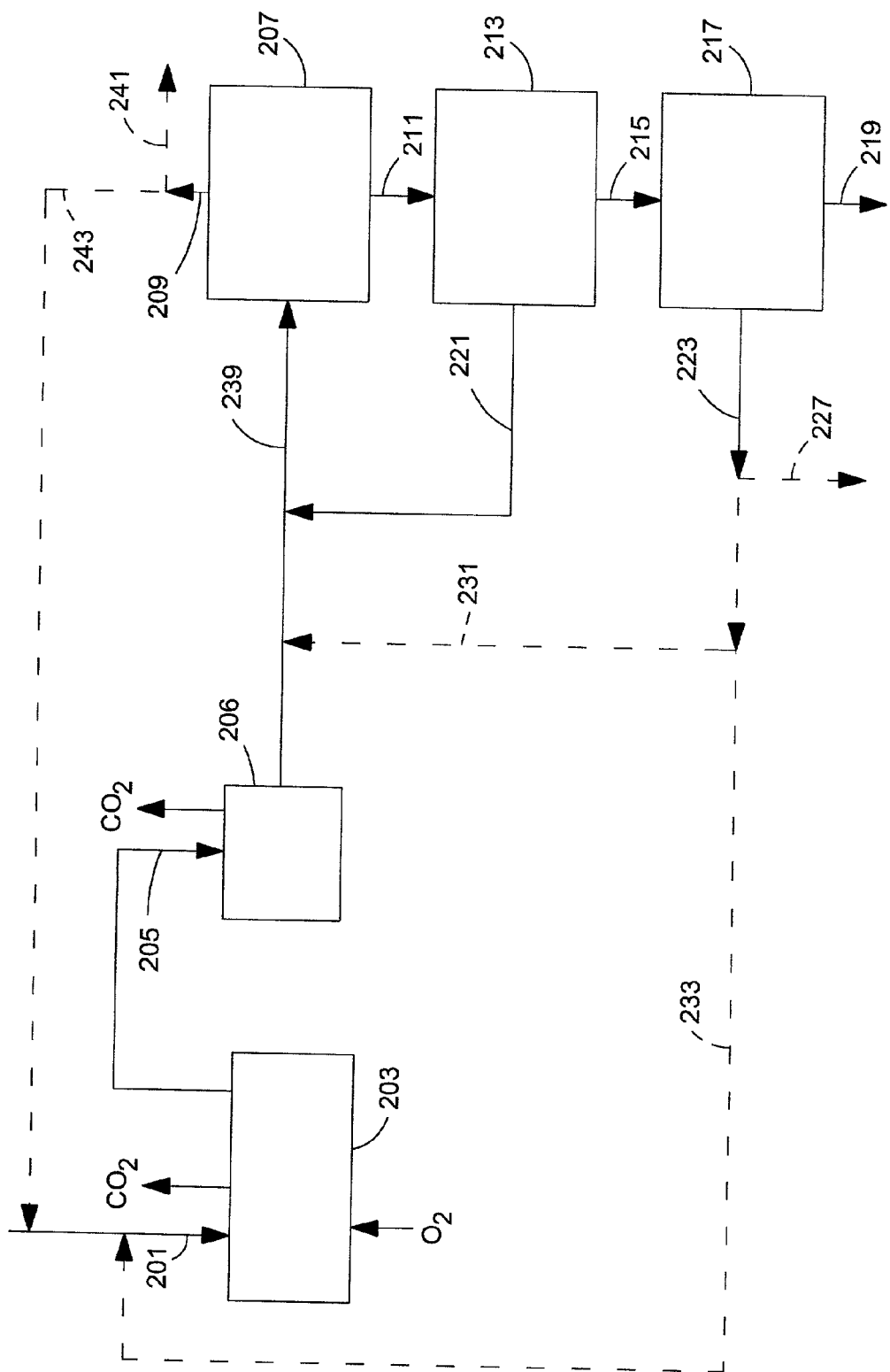
FIG. 11 is a schematic flow sheet of an integrated process for oxidizing an N-(phosphonomethyl)iminodiacetic acid substrate in a reactor system to form an oxidation reaction mixture comprising an N-(phosphonomethyl)glycine product and for recovering the N-(phosphonomethyl)glycine product from the oxidation reaction mixture using a non-adiabatic heat-driven evaporative crystallizer.

FIG. 11 shows an example of one system which employs an evaporative crystallizer. An aqueous feed 201 comprising an N-(phosphonomethyl)iminodiacetic acid substrate is introduced into an oxidation reactor system 203 comprising one or more oxidation reaction zone(s) wherein the substrate is oxidized to form an oxidation reaction mixture 205 comprising N-(phosphonomethyl)glycine product. In FIGS. 11, 12, 13 and 14A, details of the oxidation reactor system, including catalyst separation and recycle mechanisms (e.g., catalyst filters, catalyst holding tanks, pre-filter flash tanks and the like) that may be present have been omitted, it being understood that the oxidation reaction mixture withdrawn from the reactor system has been substantially freed of catalyst, as necessary, depending on the specific reactor configuration(s) employed. The oxidation reaction mixture 205 may optionally be passed through a pre-crystallizer flash tank 206. The pre-crystallizer flash tank 206 lowers the pressure on the reaction mixture 205 to some degree causing dissolved $CO_2$ to be flashed out of the mixture and vented from the flash tank. An oxygen source (e.g., an $O_2$-containing gas) may be introduced into the pre-crystallizer flash tank 206 to further oxidize N-(phosphonomethyl)iminodiacetic acid substrate in the reaction mixture 205 that did not oxidize in the oxidation reaction zone(s) of the reactor system 203, as well as to further oxidize formaldehyde and formic acid by-products present in the reaction mixture 205. In this manner, the pre-crystallizer flash tank 206 acts as an oxidation reaction zone in series with the reactor system 203.

An evaporative crystallizer feed stream 239 is then introduced into the heat-driven evaporative crystallizer 207 in which heat is transferred to the evaporative crystallizer feed stream 239 to vaporize water (and small molecule impurities, such as formaldehyde and formic acid) to form the non-adiabatic crystallizer overhead vapor stream 209. A large portion of the N-(phosphonomethyl)glycine product precipitates (typically from about 50% to about 60% on a per pass basis) to produce an evaporative crystallization slurry 211. Slurry 211 is withdrawn from the non-adiabatic evaporative crystallizer 207, and can be introduced into a hydroclone (or bank of hydroclones) 213, which forms a concentrated slurry 215 enriched in precipitated N-(phosphonomethyl)glycine product and a solids-depleted stream 221. The concentrated slurry 215 is introduced into a solids separation device, preferably a centrifuge, which forms a centrate 223 (which is further depleted in precipitated N-(phosphonomethyl)glycine product) and an N-(phosphonomethyl)glycine product wet cake 219.

Normally, the concentration of the N-(phosphonomethyl) glycine product in the wet cake 219 is at least about 95% (by weight of all compounds besides water). A lower product concentration may be tolerated if the wet cake 219 is subsequently washed with water or blended with higher purity product as described below.

At least a portion of the heat-driven crystallizer overhead 209 may be recycled back to the oxidation reaction zone(s) of the reactor system 203. In the embodiment shown in FIG. 11, a portion 243 is condensed and recycled back for use as a source of water for dissolving the N-(phosphonomethyl) iminodiacetic acid substrate to form the feed stream 201 for the reactor system 203. Preferably, condensate 243 is introduced into the most upstream oxidation reaction zone where the reactor system 203 comprises two or more oxidation reaction zones in series. Stream 243, as with nearly all recycle streams of this invention, may alternatively (or additionally) be introduced directly into the oxidation reaction zone(s) rather than combined with other ingredients (e.g., in aqueous feed stream 201) before being introduced into the oxidation reaction zone(s). Particularly where the catalyst is a carbon-containing catalyst and more particularly where the catalyst comprises carbon-supported noble metal, a portion of the non-adiabatic crystallizer overhead 209, may also advantageously be used to reduce the catalyst surface. This is due to the fact that the heat-driven evaporative crystallizer overhead 209 typically contains formaldehyde and/or formic acid, which both act as reducing agents, particularly toward carbon-containing catalysts and more particularly toward catalysts comprising carbon-supported noble metal. Typically, the portion of the non-adiabatic crystallizer overhead 209 used in such a reduction treatment is first condensed and the condensate may be introduced into one or more catalyst holding tank(s) within reactor system 203 where the reduction treatment takes place. In addition to reducing the catalyst, such treatment may act to wash the catalyst and takes advantage of the residence time of the catalyst in the catalyst holding tank(s). In one particularly preferred embodiment, a portion of the non-adiabatic crystallizer overhead 209 is further rectified or distilled to obtain a vapor stream containing an enriched concentration of formaldehyde and/or formic acid. This enriched vapor stream, in turn, may be condensed and contacted with the carbon-containing catalyst.

At least another portion 241 of the heat-driven evaporative crystallizer overhead 209 is typically purged (i.e., discharged) from the system as purge stream 241. In a continuous system, this purge 241 helps to reduce the amount of waste buildup (particularly small molecule impurity buildup) in the system and helps manage the water balance of the system. The purged waste 241 may, in turn, be further treated to remove impurities. Such a treatment may include, for example, contacting the purge stream 241 with an $O_2$-containing gas and a catalyst comprising a Group VIII metal (particularly platinum, palladium, and/or rhodium) and, optionally, a carbon support, thereby oxidizing formaldehyde and formic acid to form environmentally benign $CO_2$ and water. The reaction is preferably conducted at a temperature of from about room temperature to about 90° C. (more preferably from about 50° C. to about 90° C.), a pressure of from about atmospheric to about 200 psi, a dissolved oxygen concentration of from about 1 to about 7 ppm, and a Group VIII metal to working reactor volume ratio of from about 0.00015:1 to about 0.00040:1. This process is described in detail by Smith in U.S. Pat. No. 5,606,107. The product resulting from oxidation of the heat-driven evaporative crystallizer overhead 209 may be recycled to the oxidation reaction zone(s) of reactor system 203 and used as a source of makeup water.

The hydroclone solids-depleted stream 221 is preferably recycled back to the heat-driven evaporative crystallizer 207 for further recovery of the N-(phosphonomethyl)glycine product.

At least a portion 231 of the centrate 223 from the centrifuge 217 is preferably recycled back to the heat-driven crystallizer 207 for further recovery of the N-(phosphonomethyl)glycine product. Alternatively (or in addition), a portion 233 of the centrate 223 can be recycled back to the oxidation reaction zone(s) of the reactor system 203 to convert unreacted N-(phosphonomethyl)iminodiacetic acid substrate in the centrate 223 to N-(phosphonomethyl)glycine product. Alternatively (or in addition), a portion 227 of the centrate 223 can be purged from the system.

Purging a portion 227 of the centrate 223 from the centrifuge 217 in a continuous system helps to reduce the amount of impurity buildup (particularly larger molecule impurity buildup) in the system and thus in wet cake 219. Such a treatment may include, for example:

1. The purge stream 227 may be contacted with $O_2$ and a Group VIII metal catalyst to oxidize formaldehyde and formic acid in the purge stream 227, as described above for the non-adiabatic crystallizer overhead purge 241.
2. The purged waste 227 may be contacted with $O_2$ and a noble-metal-containing catalyst to oxidatively cleave any N-substituted-N-(phosphonomethyl)glycine (often most notably N-methyl-N-(phosphonomethyl)glycine) to form additional N-(phosphonomethyl)glycine product, which, in turn, may be collected in a crystallizer, such as by recycling it back to the non-adiabatic crystallizer 207. Preferably, this reaction is conducted at a pressure of at least atmospheric pressure (more preferably from about 30 to about 200 psig), a temperature of from about 50° C. to about 200° C. (more preferably from about 70° C. to about 150° C., and even more preferably from about 125° C. to about 150° C.), a dissolved oxygen concentration of no greater than about 2 ppm, and a weight ratio of the noble metal to the N-substituted-N-(phosphonomethyl)glycine by-product(s) of from about 1:500 to about 1:5 (more preferably from about 1:200 to about 1:10, and even more preferably from about 1:50 to about 1:10). This method of treatment is described in detail by Morgenstern et al. in U.S. Pat. No. 6,005,140.
3. The purged waste 227 may be combined with formaldehyde in stoichiometric excess relative to the N-(phosphonomethyl)glycine compounds and derivatives thereof, and then heated in the presence of a transition metal catalyst (e.g., manganese, cobalt, iron, nickel, chromium, ruthenium, aluminum, aluminum, molybdenum, vanadium, copper, zinc, or cerium) to form more environmentally benign compounds. This process is described in detail by Grabiak et al. in U.S. Pat. No. 4,851,131.
4. The purged waste 227 may be passed through another crystallizer for further recovery of N-(phosphonomethyl)glycine product.

In another particularly preferred embodiment, at least a portion of the oxidation reaction mixture effluent (preferably absent any catalyst, particularly absent any heterogeneous catalyst or a homogeneous catalyst that co-precipitates with the N-(phosphonomethyl)glycine product) is introduced into a crystallizer which operates substantially adiabatically (i.e., any heat input or removal to the crystallizer is no greater than about 200 kcal. per kg of oxidation reaction mixture fed to the crystallizer), and more preferably fully adiabatically. Unlike the process as conducted in a non-adiabatic crystallizer as described above, the separation process in an adiabatic crystallizer results primarily from reduction in solubility due to cooling rather than to the concentrating effect of removal of water. In a preferred embodiment, separation of mother liquor from precipitated crystallization solids is accomplished in part by decantation. Because the amount of water removed in adiabatic crystallization is relatively small, the mother liquor has a relatively low impurities content. In accordance with the invention, it has been discovered that this mother liquor may be directly recycled to the oxidation reactor system as a source of process water. Adiabatic crystallization is advantageous because it does not require the energy (typically in the form of steam) that is required for the evaporation in a non-adiabatic crystallizer.

In an especially preferred adiabatic crystallizer system, the final reaction mixture is subjected to a sudden drop in pressure in a flash section, which causes part of the water in the reaction mixture to evaporate. This evaporation, in turn, causes the remaining reaction mixture to cool. Cooling results in the precipitation of N-(phosphonomethyl)glycine product. Mother liquor may then be decanted to concentrate the slurry of the N-(phosphonomethyl)glycine product. Adiabatic crystallization is advantageous because it does not require the energy (typically in the form of steam) that is required for the evaporation in a non-adiabatic crystallizer.

Figure 12:
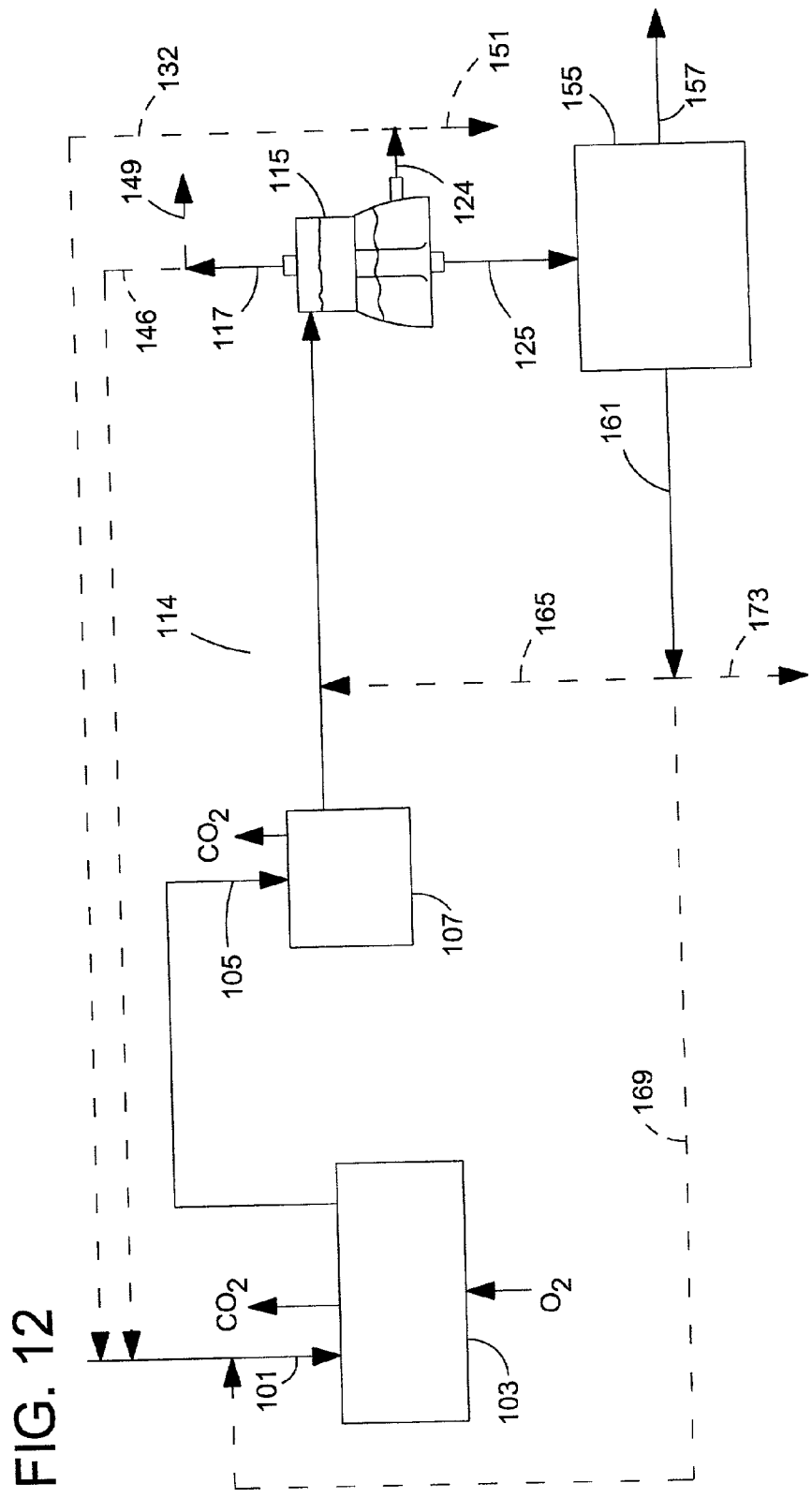
FIG. 12 is a schematic flow sheet of an integrated process for oxidizing an N-(phosphonomethyl)iminodiacetic acid substrate in a reactor system to form an oxidation reaction mixture comprising an N-(phosphonomethyl)glycine product and for recovering the N-(phosphonomethyl)glycine product from the oxidation reaction mixture using an adiabatic crystallizer.

FIG. 12 shows one embodiment of a system comprising an adiabatic crystallizer 115. An aqueous feed 101 comprising an N-(phosphonomethyl)iminodiacetic acid substrate is introduced into an oxidation reactor system 103 comprising one or more oxidation reaction zone(s) wherein the substrate is oxidized to form an oxidation reaction mixture 105 comprising N-(phosphonomethyl)glycine product. The oxidation reaction mixture 105 withdrawn from the reactor system 103 may optionally be passed through a pre-crystallizer flash tank 107. The pre-crystallizer flash tank 107 lowers the pressure on the reaction mixture 105 to some degree causing dissolved $CO_2$ to be flashed out of the mixture and vented from the flash tank. The preferred pressure drop depends on the pressure at which the oxidation reaction is conducted in the reactor system 103. Normally, for example, where the oxidation reaction zone(s) pressure is 115 psia, the pressure drop in the pre-crystallizer flash tank 107 is no greater than about 100 psig, more preferably from about 20 to about 80 psig, even more preferably from about 60 to about 80 psig, and still even more preferably about 75 psig; while the preferred pressure drop where the reaction zone(s) pressure is 215 psia is no greater than about 200 psig, more preferably from about 120 to about 180 psig, even more preferably from about 160 to about 180 psig, and still even more preferably about 175 psig. This typically causes up to about 1.5% (more typically from about 0.2 to about 1%, even more typically from about 0.2 to about 0.5%, and still even more typically about 0.25%) by weight of the final reaction mixture 105 to go into the vapor phase. Typically, the pressure over the resulting crystallizer feed steam 114 leaving the pre-crystallizer flash tank 107 is at least about 15 psia, more preferably from about 25 to about 100 psia, even more preferably from about 30 to about 60 psia, and still even more preferably about 40 psia.

An oxygen source (e.g., an O2-containing gas) may be introduced into the pre-crystallizer flash tank 107 to further oxidize N-(phosphonomethyl)iminodiacetic acid substrate in the reaction mixture 105 that did not oxidize in the oxidation reactor system 103, as well as to further oxidize formaldehyde and formic acid by-products present in the reaction mixture 105. In this manner, the pre-crystallizer flash tank 107 acts as an oxidation reaction zone in series with the reactor system 103.

The crystallizer feed stream 114 is introduced into the adiabatic crystallizer 115. A detailed description of the operation of an adiabatic crystallizer system in accordance with the present invention is set forth below in connection with FIG. 12A. Operation of the adiabatic crystallizer 115 produces vapor 117 (i.e., the adiabatic crystallizer overhead) discharged from the top of the crystallizer, a decantate (i.e., mother liquor) stream 124 withdrawn from the crystallizer and a crystallization product slurry 125 comprising precipitated crystalline N-(phosphonomethyl)glycine product removed from the bottom of the crystallizer.

At least a portion 146 of the adiabatic crystallizer overhead 117 and/or and at least a portion 132 of the withdrawn decantate 124 may be recycled back to the oxidation reaction zone(s) of the reactor system 103. Typically, the recycled adiabatic crystallizer overhead 117 and/or withdrawn decantate 124 is/are recycled back to the oxidation reaction zone(s) and used as a source of water for dissolving the N-(phosphonomethyl)iminodiacetic acid substrate to form the feed stream 101 for the reactor system 103. Preferably, the recycled adiabatic crystallizer overhead 117 and/or withdrawn decantate 124 is/are introduced into the most upstream oxidation reaction zone where the reactor system 103 comprises two or more oxidation reaction zones in series. Recycling at least a portion 132 of the decantate 124 back to the reactor system is advantageous because it reduces the water requirements and the volume of waste from the system. It also often allows recovery of additional N-(phosphonomethyl)glycine product from the unreacted N-(phosphonomethyl)iminodiacetic acid substrate in the decantate 124. This recycle is additionally advantageous because it often allows for additional by-products, such as formaldehyde and formic acid, to be oxidized. The recycle of stream 132 is further advantageous because it allows water to be recycled directly back to the oxidation reaction zone(s) from the crystallizer 115 without having to expend energy to evaporate the water (as is the case with the recycle of the overheads from the heat-driven evaporative crystallizer discussed above). Because the recycled decantate 132 also remains at a relatively elevated temperature (most preferably 60° C.), the recycled decantate 132 can be used to preheat the aqueous feed stream 101. When a noble metal on carbon catalyst is utilized in the reactor system 103, a still further benefit of decantate recycle stream 132 may be realized in that noble metal leached from the catalyst is returned to the reactor system. It is believed that recycling noble metal-containing streams such as stream 132 to the reactor system 103 reduces the net loss of noble metal from the system. A portion of the leached noble metal contained in such a recycle stream may redeposit on the surface of the heterogeneous catalyst in the catalytic reactor system.

Particularly where the catalyst is a carbon-containing catalyst (and even more particularly where the catalyst comprises a carbon-supported noble metal), it is preferable to recycle at least a portion of the adiabatic crystallizer overhead 117 indirectly by condensing it and then mixing the condensate with the catalyst. This is often advantageous because the adiabatic crystallizer overhead 117 often contains formaldehyde and/or formic acid, which, as noted above, both act as reducing agents. In one particularly preferred embodiment, a portion of the adiabatic crystallizer overhead 117 is rectified or condensed and further distilled to obtain a condensate enriched in formaldehyde and/or formic acid. This enriched solution, in turn, is the portion of the adiabatic crystallizer overhead that is contacted with the carbon-containing catalyst. As noted above, this reduction treatment can occur in one or more catalyst holding tank(s) within the reactor system 103.

At least another portion 149 of the adiabatic crystallizer overhead 117 and/or at least a portion 151 of the withdrawn decantate 124 may be purged (i.e., discharged) from the system as waste. In a continuous system, this purge helps to reduce the amount of impurity buildup in the system. This purged waste may, in turn, be further treated to remove impurities by techniques known in the art, such as those described above for the purged waste stream of the centrifuge downstream of a non-adiabatic crystallizer. For example, the purged waste may be contacted with an $O_2$-containing gas and Group VIII metal catalyst to oxidize formaldehyde and formic acid to $CO_2$ and water. The product of such oxidation treatment may be recycled to the oxidation reaction zone(s) of the reactor system 103 and used as a source of makeup water.

The N-(phosphonomethyl)glycine product slurry 125 withdrawn from the bottom of the adiabatic crystallizer 115 contains the bulk of the N-(phosphonomethyl)glycine product. The slurry 125 is typically passed through a centrifuge 155 to further concentrate the slurry 125 and form a wet cake 157 containing the N-(phosphonomethyl)glycine product. Normally, the concentration of the N-(phosphonomethyl)glycine product in the wet cake 157 is at least about 95% (by weight of all compounds besides water). The solids-depleted stream 161 (i.e., the centrate) from the centrifuge 155 may, for example, be recycled back to the adiabatic crystallizer 115 via stream 165 or recycled back to the oxidation reaction zone(s) of the reactor system 103 via stream 169 to be used as a source of water in the aqueous feed stream 101. In order to maintain impurity concentrations at acceptable levels and enable the advantageous use of recycled decantate stream 132, at least a portion of the solids-depleted stream 161 may be removed via stream 173. Stream 173 may be subsequently treated by, for example, the waste treatment processes described above for the purge stream of the centrifuge downstream of a non-adiabatic heat-driven crystallizer. In a further embodiment, stream 173 is sent to a heat-driven evaporative crystallizer for additional product recovery in manner similar to that shown in FIG. 13.

Figure 12A:
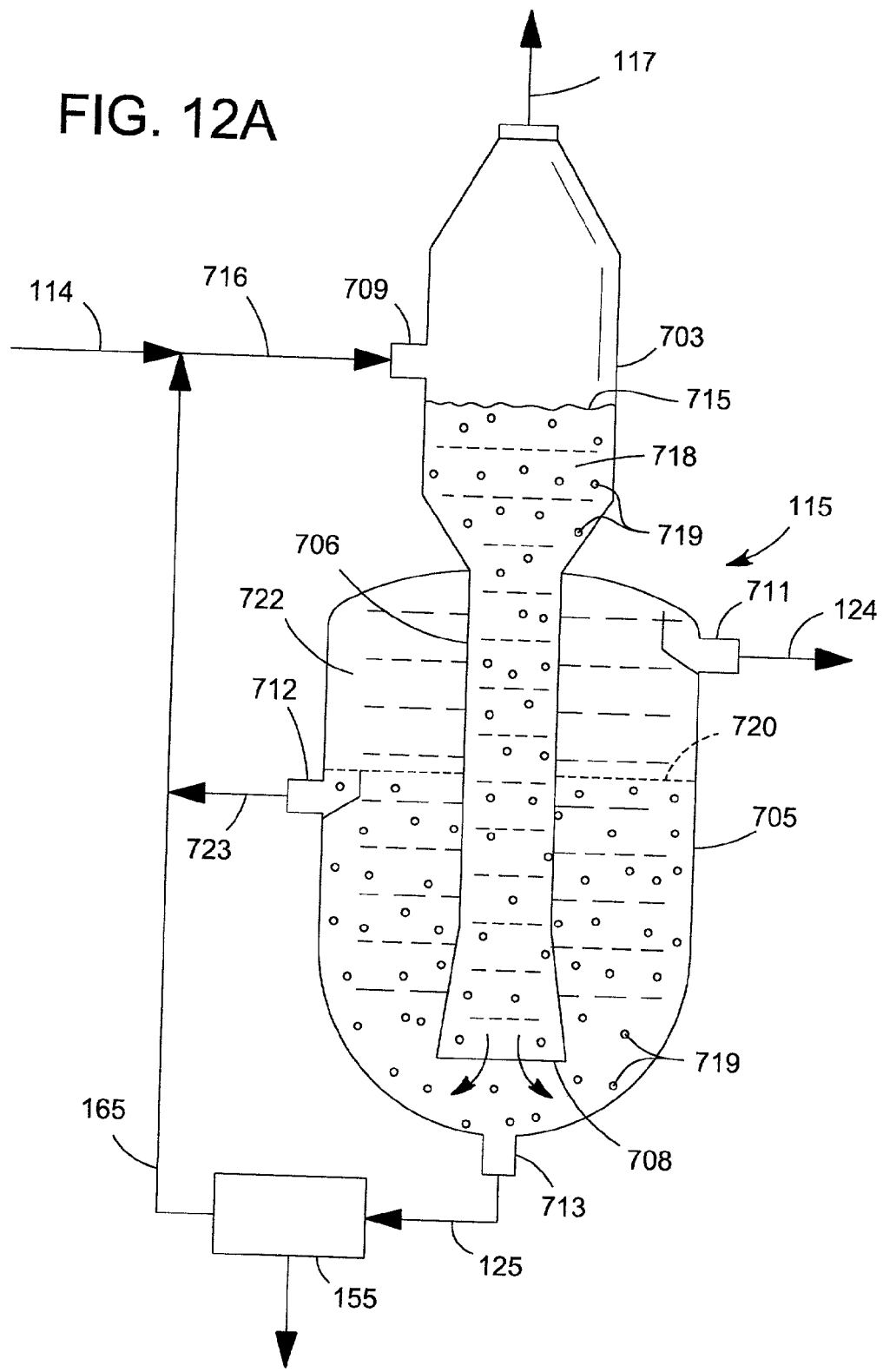
FIG. 12A is a schematic flow sheet of an adiabatic crystallizer system used to recover an N-(phosphonomethyl)glycine product from an oxidation reaction mixture.

FIG. 12A is a schematic of a preferred adiabatic crystallization system for use in the practice of the present invention. As shown, the system 115 comprises vapor/liquid separator 703 defining a vapor/liquid separation zone positioned generally above and in fluid flow communication with a retention chamber 705. Vapor/liquid separator 703 is segregated from direct communication with the upper region of retention chamber 705, but is in fluid flow communication with the lower region of the retention chamber via a draft tube 706, the mouth 708 of draft tube 706 being separated by only a relatively short distance from the bottom of the retention chamber. Crystallizer apparatus of this general configuration are available from HPD Products Division of U.S. Filter (Plainfield, Ill., U.S.A.). A crystallizer recirculation inlet 709 is located on vapor/liquid separator 703, while retention chamber 705 is provided with a decantation liquid exit 711 for crystallization mother liquor located above mouth 708 of draft tube 706, an intermediate recirculation slurry exit 712 located above the mouth of the draft tube and below decantation liquid exit 711 and a lower product slurry exit 713 located at the bottom of chamber 705. During operation, retention chamber 705 is essentially filled with liquid while the liquid level 715 in vapor/liquid separator 703 is maintained somewhat below crystallizer recirculation inlet 709.

An aqueous crystallizer feed mixture 716 comprising N-(phosphonomethyl)glycine product obtained from the reaction mixture effluent 114 withdrawn from the oxidation reaction zone(s) of the oxidation reactor system (along with various recycle streams as will be described below) is introduced through recirculation inlet 709 into vapor/liquid separator 703. The vapor/liquid separator defines an evaporation zone maintained by a vacuum system (not shown) at sub-atmospheric pressure and below the vapor pressure of the crystallizer feed mixture 716. The liquid level 715 in the vapor/liquid separator 703 is maintained by pressure equilibration through holes provided in the upper section of the draft tube 708 communicating with the retention chamber 705. The crystallizer feed mixture 716 comprises: (a) the oxidation reaction mixture effluent 114 withdrawn from the oxidation reaction zone(s) of the reactor system (i.e., starting solution) which may have been filtered to remove catalyst; (b) a recycle slurry stream 723 comprising at least a portion of the slurry exiting the intermediate recirculation slurry exit 712 as described below; and typically also (c) a centrate 165 comprising crystallization mother liquor recycled from a centrifuge system 155 to which a crystallization product slurry 125 from exit 713 is directed for recovery of solid N-(phosphonomethyl)glycine product, as further described below. The pressure maintained in vapor/liquid separator 703 is generally no greater than about 8 psia, preferably from about 1.5 to about 4 psia, even more preferably from about 2.5 to about 3.5 psia, and still even more preferably about 3 psia. Typically, the pressure of the crystallizer feed mixture 716 immediately upstream of the vapor/liquid separator is such that the feed mixture is subjected to a pressure reduction of at least about 100 psig, preferably from about 10 to about 80 psig, more preferably from about 30 about 60 psig, and even more preferably of about 38 psig, upon entry into the vapor/liquid separator. The sudden decrease in pressure causes water and small molecule impurities (e.g., formaldehyde and formic acid) to flash (i.e., evaporate) from the feed mixture 716 in the vapor/liquid separator 703. The vapor 117 (i.e., overhead) produced is separated and discharged from the top of separator 703 and directed to a condensing unit (not shown). Normally, no greater than about 30% by weight, more preferably from about 5% to about 30% by weight, and even more preferably from about 5% to about 10% by weight of the oxidation reaction mixture 114 is discharged as vapor 117. As a result of evaporation, the remaining condensed phase portion of the crystallizer feed mixture 716 is cooled considerably, thereby resulting in precipitation of N-(phosphonomethyl)glycine product and producing an evaporation product slurry 718 comprising crystalline N-(phosphonomethyl)glycine product solids 719 suspended in mother liquor that is substantially saturated or supersaturated in N-(phosphonomethyl)glycine product. Preferably, the cooling effect resulting from the pressure reduction entering vapor/liquid separator 703 is sufficient that the temperature of the evaporation product slurry 718 is from about 30° C. to about 40° C. lower than the temperature of the oxidation reaction mixture 114 introduced into the adiabatic crystallization system. The temperature of the evaporation product slurry 718 is no greater than about 80° C., more preferably from about 45° C. to about 80° C., even more preferably from about 55° C. to about 70° C., and especially from about 60° C. to about 70° C.

The evaporation product slurry 718 exits separator 703 by descending draft tube 706 and is introduced into the lower region of a retention zone within retention chamber 705. The retention zone is divided into a lower crystallization region, generally below level 720, and an upper decantation region, generally above level 720. In the retention zone, the evaporation product slurry 718 is separated into a supernatant liquid 722 comprising a fraction of the mother liquor (typically the net production thereof) and second slurry stream 723 comprising precipitated N-(phosphonomethyl)glycine product crystals and mother liquor which is withdrawn from the retention chamber 705 through intermediate slurry exit 712. A decantate stream 124 comprising supernatant liquid 722 is withdrawn from retention chamber 705 through decantation exit 711 near the top of the retention chamber in the decantation region.

Crystallization product slurry 125 comprising N-(phosphonomethyl)glycine product slurry is withdrawn from the bottom of retention chamber 705 through exit 713 in the crystallization region. The crystallization product slurry is forwarded to centrifuge system 155 wherein N-(phosphonomethyl)glycine product crystals are separated as wet cake. Normally N-(phosphonomethyl)glycine product in the wet cake is at least about 95% (by weight of all compounds besides water). The resulting centrate 165 is recycled and combined with a second portion of product slurry in slurry steam 723 withdrawn from retention chamber 705 at the interface (i.e., cloud zone) between the decantation region and the crystallization region of the retention zone. The combined flow is introduced into vapor/liquid separator 703 along with the oxidation reaction mixture 114 as the crystallizer feed mixture 716.

At least a major portion, preferably substantially all of the second slurry stream 723 withdrawn from exit 712 is recirculated to the vapor/liquid separator 703, being mixed with the reaction mixture stream 114 and the centrate 165 from centrifuge 155 to form the feed mixture 716 to the vapor/liquid separator. Mother liquor 722 is separated (i.e., decanted) from the evaporation product slurry 718 in the decantation region. Decantation is accomplished by maintaining the relative rates at which reaction mixture 114 is introduced through inlet 709, decantate 124 is withdrawn from exit 711, and all or a portion of the second slurry 723 is recirculated from intermediate slurry exit 712 via crystallizer feed stream 716 (thereby controlling the rate at which evaporation product slurry 718 is introduced into the retention zone) such that the upward flow velocity in the lower crystallization region of the retention zone below the intermediate slurry exit 712 is sufficient to maintain precipitated N-(phosphonomethyl)glycine product crystals 719 in suspension (i.e., entrained) in the liquid phase, while the upward flow velocity in the upper decantation region of the retention zone above the intermediate slurry exit 712, is below the settling velocity of at least about 80% by weight, preferably below the settling velocity of at least about 95% by weight, most preferably below the settling velocity of at least about 98% by weight, of the N-(phosphonomethyl) glycine product crystals 719 in the crystallization region. Thus, an interface is established, at approximately the level of intermediate slurry exit 712, between the upper decantation region of the retention zone which contains substantially clear mother liquor, and the lower crystallization region of the retention zone which contains a crystallization slurry.

Preferably, the relative rates at which oxidation reaction mixture 114 is introduced into the adiabatic crystallization system 115, decantate 124 is withdrawn from exit 711, product slurry 125 is withdrawn from exit 713, and centrate 165 is recycled from centrifuge 155 are controlled so that the ratio of N-(phosphonomethyl)glycine product solids to mother liquor in the lower crystallization region of the retention zone is higher than the incremental ratio of N-(phosphonomethyl)glycine product to mother liquor ratio resulting from the effects of the evaporation, such incremental ratio being the ratio of N-(phosphonomethyl)glycine product solids incrementally produced to the mother liquor incrementally produced thereby, i.e., the net production of crystalline N-(phosphonomethyl)glycine product. Expressed another way, the incremental ratio is the ratio that would be obtained if the oxidation reaction mixture were flashed in the absence of solids in the crystallizer feed mixture (i.e., in the absence of recirculated second slurry). It will be understood that the effects of evaporation include both the concentrating effects and cooling effects; but where operation of the crystallizer is substantially adiabatic, as is preferred, crystallization results primarily from cooling of the liquid phase to a temperature at which solubility of N-(phosphonomethyl)glycine product is substantially lower than it is at the temperature of the oxidation reaction mixture. Preferably, the solids/mother liquor ratio in the lower region of the retention zone is at least about twice the incremental ratio resulting from evaporation effects, and the concentration of product solids in the crystallization region is also at least twice the concentration incrementally produced. Expressed in another way, the N-(phosphonomethyl) glycine product solids concentration in the lower crystallization region of the retention zone is at least about 12% by weight, preferably at least about 15% by weight, more preferably in the range of between about 18% and about 25% by weight. In the system as illustrated, the rate of removal of solid product in the centrifuge 155 and of mother liquor as decantate 124 are ultimately fixed by the system material balance, but the solids inventory in the lower crystallization region of the retention zone may be adjusted by transient decrease or increase of the rate at which product slurry is removed from exit 713 relative to the decantation rate via exit 711. As is further discussed hereinbelow, control of the solids inventory in the crystallization region of the retention zone has been found to provide control of the average particle size of the N-(phosphonomethyl)glycine product of the crystallization process.

The steady state upward flow velocity in the upper decantation region of the retention zone is determined by sizing the cross section of retention chamber 705 based on the process material balance and the solids settling velocity. Preferably, a relatively high upward velocity in the lower crystallization region of the retention zone is established by maintaining a high rate of recirculation of the second slurry 723 between intermediate slurry exit 712 and the recirculation inlet 709 to the vapor/liquid separator 703 (e.g., in the range of 20:1 to 100:1 relative to the rate of oxidation reaction medium 114 introduced into the crystallization system or decantate 124 removed therefrom). The fraction of centrate 165 from centrifuge 155 that is recycled as part of crystallizer feed mixture 716 also augments the rate of recirculation and upward flow velocity, but otherwise tends to dilute the slurry in the crystallization region. By combining a high second slurry recirculation rate with proper sizing of retention chamber 705, the upward flow velocity in the lower crystallization region of the retention zone can be controlled at least four times the sedimentation velocity of at least 80% by weight of the solids contained therein while the upward flow velocity in the upper decantation region of the retention zone can be established at less than one fourth of the sedimentation velocity of at least 80% by weight of the solids contained in the second slurry stream.

Operating at a high solids content in the crystallization region, combined with a high rate of recirculation of second slurry 723 from intermediate slurry exit 712 to vapor/liquid separator 703 further provides a high solids concentration throughout the evaporation zone. This mode of operation has been found to have a significantly favorable effect on both productivity of the crystallization process and the particle size and drainage characteristics of the crystalline N-(phosphonomethyl)glycine product obtained. There is a trade off between particle size and productivity because productivity relates positively to the degree of supersaturation, but the degree of supersaturation generally correlates negatively with particle size. However, even at the relatively high average particle size, operation at high solids content effectively increases the surface of solid N-phosphonomethyl)glycine product crystals on which crystallization can occur, and thus allows the crystallization process to proceed at high productivity with relatively minimal supersaturation of the liquid phase required to provide a driving force for crystallization. Crystallization at low levels of supersaturation in turn promotes formation of relatively large crystals. Thus, for a given productivity of the evaporation zone, the crystallization process of the invention provides an average particle size substantially larger than the average particle size obtained in a reference evaporator that is fully back mixed and wherein the ratio of N-(phosphonomethyl)glycine product solids to mother liquor is equal to the ratio of N-(phosphonomethyl)glycine product solids incrementally produced by the effects of the evaporation to the mother liquor incrementally produced thereby. For example, the crystallization process of the invention can be operated at high productivity to obtain a product having (1) a median cube weighted particle size of at least about 200 $\mu$m, preferably at least about 225 $\mu$m, more preferably at least about 250 $\mu$m, even more preferably at least about 275 $\mu$m, still more preferably at least about 300 $\mu$m, and especially at least about 350 μm; (2) a median length weighted particle size of at least about 85 μm, preferably at least about 90 μm, more preferably at least about 95 μm, even more preferably at least about 100 μm, still more preferably at least about 105 μm, and especially at least about 110 μm; and (3) a BET (Brunauer-Emmett-Teller) surface area not greater than about 0.11 m$^2$/g, more preferably not greater than about 0.09 m$^2$/g, even more preferably not greater than about 0.07 m$^2$/g, and still even more preferably not greater than about 0.06 m$^2$/g. The median cube weighted and median length weighted particle sizes set forth above may be determined using a focused beam reflectance measurement (FBRM) device such as a LASENTEC Model M100F available from Laser Sensor Technology Inc. (Redmond, Wash., U.S.A.).

At the high flow rates prevailing along the recirculation path between intermediate slurry exit 712 and mouth 708 of draft tube 706, the crystallization system operates in an essentially plug flow manner (i.e., without substantial axial back-mixing). As a result, a descending gradient in the degree of supersaturation prevails along this path, thereby maximizing the integrated average driving force available for crystallization, and enabling a lower degree of supersaturation to be realized at the downstream end of the plug flow path (i.e., at the mouth of the draft tube) than could be realized in a back-mixed system. Compounding the effect of plug flow with the generally low degree of supersaturation made feasible by the high crystal surface area presented by the high solids content within the recirculating slurry, the net result at any given rate of production is to further reduce the degree of supersaturation in the liquid phase within the lower crystallization region of the retention zone, and therefore in the decantate mother liquor 124 that is removed from the system.

Plug flow operation in combination with high solids content can also be exploited with respect to productivity. It has been found that high productivity can be realized even where the maximum supersaturation, i.e., the driving force for crystallization, expressed as the difference between the N-(phosphonomethyl)glycine product concentration in the aqueous liquid phase at any location within the recirculation path and the saturation concentration of N-(phosphonomethyl)glycine product in the aqueous liquid phase at such location is not greater than about 0.7% by weight, basis the aqueous liquid phase; or where the integrated average extent of supersaturation over the recirculation path is not greater than 0.5%. Looking at the relationship between supersaturation and productivity in yet another way, the process as described can operate effectively at an integrated average supersaturation over the recirculation path that is at least 0.2% lower than the extent of supersaturation required to provide equivalent crystallization productivity per unit working volume of a reference evaporator consisting of a fully back mixed evaporation zone in which the ratio of N-(phosphonomethyl)glycine product solids to mother liquor is equal to the ratio of N-(phosphonomethyl)glycine product solids incrementally produced by the effects of the evaporation to mother liquor incrementally produced thereby.

Because of the coarse particle size of the crystals produced in accordance with the process illustrated in FIG. 12A, the capacity of a centrifuge or filter for dewatering product slurry 125 is substantially enhanced, with attendant savings in capital and maintenance expense. For example, by use of a vertical basket centrifuge system or other dewatering device, a crystalline N-(phosphonomethyl)glycine product is obtained having a relatively low water content, e.g., exhibiting a loss on drying of not greater than about 15% by weight, more preferably not greater than about 8% by weight. Lower centrifuge cake wetness translates directly into lesser contamination of the centrifuge cake with chlorides, NMG, unreacted N-(phosphonomethyl)iminodiacetic acid substrate, etc. Thus, the use of the adiabatic crystallization system affords the opportunity to produce an exceptionally pure grade of N-(phosphonomethyl)glycine product. So as to minimize attrition of the N-(phosphonomethyl)glycine product crystals, an axial flow pump is used to recirculate material in the adiabatic crystallizer system.

Advantageously, the crystallization operation of FIG. 12A is conducted adiabatically, i.e., there is no substantial transfer of heat to or from the system via heat transfer to or from the vapor/liquid separation zone, the retention zone, the feed mixture to the vapor/liquid separation zone, the second slurry that is recirculated to the vapor/liquid separation zone, or the centrate that is returned from the centrifuge system. By reduction in pressure of the feed mixture as described above, sufficient evaporation is achieved for cooling the liquid phase to the extent that substantial crystallization of N-(phosphonomethyl)glycine product is realized. Capital and energy savings are realized by obviating the need for evaporator heat exchangers, and process downtime required to periodically parboil fouled heat exchangers is also eliminated.

Moreover, without substantial expenditure of energy for the separation, a decantation stream 124 is provided which can readily serve as a source of process water for recycle to the oxidation reaction zone(s) of the oxidation reactor system. Because crystallization can be effected at high productivity at a relatively limited degree of supersaturation, the decantate recycled to the oxidation reaction zone(s) has nearly the minimum theoretical N-(phosphonomethyl)glycine product concentration. Since productivity of the oxidation reaction system may typically be limited by the solubility of N-(phosphonomethyl)glycine product in the reaction mixture effluent, especially where a particulate catalyst is utilized in the preparation of the free acid form of N-(phosphonomethyl)glycine, N-(phosphonomethyl)glycine product in the recycle decantate can at least marginally detract from the net productivity of the oxidation reactor system by limiting the rate at which N-(phosphonomethyl)iminodiacetic acid substrate can be converted to N-(phosphonomethyl)glycine product therein without exceeding N-(phosphonomethyl)glycine product solubility. This modest penalty associated with decantate recycle is minimized by recovering nearly the maximum theoretical proportion of N-(phosphonomethyl)glycine product in the crystallizer and thereby minimizing the N-(phosphonomethyl)glycine product content of the water stream that is recycled.

Although the system depicted in FIG. 12A is preferred, those skilled in the art will recognize that other options exist for establishing and maintaining the high N-(phosphonomethyl)glycine product to mother liquor ratios in the crystallization region of the retention zone that are effective to provide relatively coarse crystals. The process of FIG. 12A is effective to retain solids in the evaporation zone; the process could alternatively be operated to return solids to the evaporation zone. For example, if crystallization is conducted in a fully back mixed evaporative crystallizer, it is possible to establish and maintain a high and disproportionate inventory of solids in the crystallizer by recycling crystalline product from the filter or centrifuge used for N-(phosphonomethyl)glycine product solids recovery, while either not recycling filtrate/centrate or recycling a lesser proportion of filtrate/centrate relative to solids recycled.

However, as those skilled in the art will appreciate, the latter scheme of operation comes with a penalty in capital intensive filter or centrifuge capacity. A significant advantage of the preferred process of FIG. 12A is the achievement of high solids inventory by decantation rather than by expensive mechanical means for solid/liquid separation.

Surprisingly, it has been discovered that operation of the adiabatic crystallizer in the preferred, manner as described above, may obviate the need for concentrating the product slurry of the decantation (as by use of a hydroclone) prior to introduction of the slurry into a centrifuge.

Figure 13:
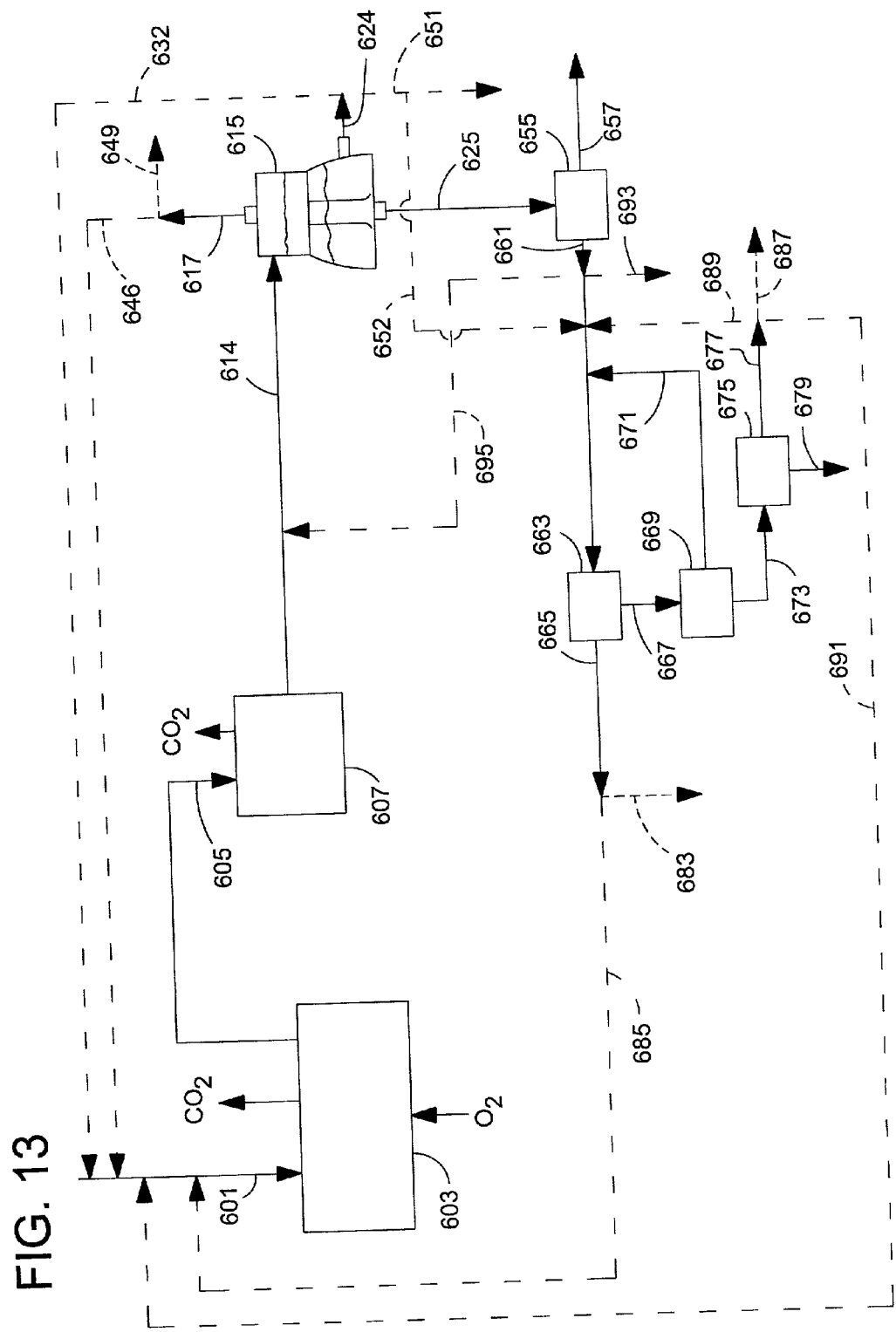
FIG. 13 is a schematic flow sheet of an integrated process for oxidizing an N-(phosphonomethyl)iminodiacetic acid substrate in a reactor system to form an oxidation reaction mixture comprising an N-(phosphonomethyl)glycine product and for recovering the N-(phosphonomethyl)glycine product from the oxidation reaction mixture using a combination of an adiabatic crystallizer and a non-adiabatic heat-driven evaporative crystallizer operated in series.

FIG. 13 shows an example of one preferred embodiment wherein the process comprises an adiabatic crystallizer operating in series with a non-adiabatic crystallizer.

Many of the various streams shown in FIG. 13 are analogous to those described above for non-adiabatic crystallizers and adiabatic crystallizers alone. An aqueous feed stream 601 comprising an N-(phosphonomethyl)iminodiacetic acid substrate is introduced into an oxidation reactor system 603 comprising one or more oxidation reaction zone(s) wherein the substrate is oxidized to form an oxidation reaction mixture 605 comprising N-(phosphonomethyl) glycine product. The oxidation reaction mixture 605 may optionally be passed through a pre-crystallizer flash tank 607. The pre-crystallizer flash tank 607 lowers the pressure on the reaction mixture 605 to some degree causing dissolved $CO_2$ to be flashed out of the mixture and vented from the flash tank. An oxygen source (e.g., an $O_2$-containing gas) may be introduced into the pre-crystallizer flash tank 607 to further oxidize N-(phosphonomethyl)iminodiacetic acid substrate in the reaction mixture 605 that did not oxidize in the oxidation reaction zone(s) of the reactor system 603, as well as to further oxidize formaldehyde and formic acid by-products present in the reaction mixture 605. In this manner, the pre-crystallizer flash tank 607 acts as an oxidation reaction zone in series with the reactor system 603.

A crystallizer feed stream 614 which comprises most of the N-(phosphonomethyl)glycine product is introduced into the adiabatic crystallizer 615. Operation of the adiabatic crystallizer 615 produces vapor 617 (i.e., the adiabatic crystallizer overhead) discharged from the top of the crystallizer, a decantate (i.e., primary mother liquor) stream 624 withdrawn from the crystallizer and a primary crystallization product slurry 625 comprising precipitated crystalline N-(phosphonomethyl)glycine product removed from the bottom of the crystallizer.

At least a portion 646 of the adiabatic crystallizer overhead 617 and/or and at least a portion 632 of the withdrawn decantate 624 may be recycled back to the oxidation reaction zone(s) of reactor system 603. Typically, the recycled adiabatic crystallizer overhead 617 and/or withdrawn decantate 624 is/are recycled back to the oxidation reaction zone(s) and used as a source of water for dissolving the N-(phosphonomethyl)iminodiacetic acid substrate to form the feed stream 601 for the reactor system 603. Preferably, the recycled adiabatic crystallizer overhead 617 and/or withdrawn decantate 624 is/are introduced into the most upstream oxidation reaction zone where the reactor system 603 comprises two or more oxidation reaction zones in series. Recycling at least a portion 632 of the decantate 624 back to the oxidation reactor system is advantageous because it reduces the water requirements and the volume of waste from the system. It also often allows recovery of additional N-(phosphonomethyl)glycine product from the unreacted N-(phosphonomethyl)iminodiacetic acid substrate in the decantate 624. This recycle is additionally advantageous because it often allows for additional by-products, such as formaldehyde and formic acid, to be oxidized. The recycle of stream 632 is further advantageous because it allows water to be recycled directly back to the oxidation reaction zone(s) from the crystallizer 615 without having to first expend energy to evaporate the water (as is the case with the non-adiabatic heat-driven crystallizer discussed above). Because the recycled decantate 632 also remains at a relatively elevated temperature (most preferably 60° C.), the recycled decantate 632 can be used to preheat the aqueous feed stream 601.

Particularly where the catalyst is a carbon-containing catalyst (and especially such a catalyst which also comprises a noble metal), it is preferable to recycle at least a portion of the adiabatic crystallizer overhead 617 indirectly by mixing it with the catalyst. This is advantageous because the adiabatic crystallizer overhead 617 often contains formaldehyde and/or formic acid, which, as noted above, both act as reducing agents. In one particularly preferred embodiment, a portion of the adiabatic crystallizer overhead 617 is further distilled to obtain a solution containing an enriched concentration of formaldehyde and/or formic acid. This enriched solution, in turn, is contacted with the carbon-containing catalyst. As noted above, this reduction treatment can occur in one or more catalyst holding tank(s) in reactor system 603.

At least another portion 649 of the adiabatic crystallizer overhead 617 and/or at least a portion 651 of the withdrawn decantate 624 may be purged (i.e., discharged) from the system as waste. In a continuous system, this purge helps to reduce the amount of impurity buildup in the system. This purged waste may, in turn, be further treated to remove impurities by techniques known in the art, such as those described above for the purged waste streams of the centrifuge downstream of a non-adiabatic crystallizer. At least a portion 652 of the withdrawn decantate 624 may alternatively be sent to the non-adiabatic evaporative crystallizer 663.

The primary N-(phosphonomethyl)glycine product slurry 625 withdrawn from the bottom of the adiabatic crystallizer 615 contains the bulk of the N-(phosphonomethyl)glycine product. The slurry 625 is typically passed through a centrifuge 655 to further concentrate the slurry 625 and form a wet cake 657 containing the N-(phosphonomethyl)glycine product. Normally, the concentration of the N-(phosphonomethyl)glycine product in the wet cake 657 is at least about 95% (by weight of all compounds besides water).

At least a portion (preferably at least about 1%, more preferably from about 1% to about 67%, even more preferably from about 20% to about 50%, still even more preferably from about 30% to about 40%, and still yet even more preferably about 33%) of the centrate 661 (i.e., primary mother liquor) from the centrifuge 655, on the other hand, is sent to a heat-driven evaporative crystallizer 663, which provides heat to the centrate 661 to vaporize water and small molecule impurities to form the evaporative crystallizer overhead vapor stream 665. Much of the N-(phosphonomethyl)glycine product precipitates in the liquid medium 667. This liquid medium 667 is withdrawn from the non-adiabatic evaporative crystallizer 663 and introduced into a hydroclone 669, which forms a product-rich stream 673 enriched in precipitated N-(phosphonomethyl)glycine product and a solids-depleted stream 671. The product-rich stream 673 is introduced into a centrifuge 675 which forms a centrate 677 (which is further depleted in precipitated N-(phosphonomethyl)glycine product) and an N-(phosphonomethyl)glycine product wet cake 679. In instances where the entire centrate 661 from the centrifuge 655 is not all introduced into the non-adiabatic crystallizer 663, a portion 695 of the centrate 661 may be recycled back to the adiabatic crystallizer 615 and/or purged from the system via purge stream 693 and treated using, for example, the various liquid waste treatments discussed above.

In the embodiment shown in FIG. 13, at least a portion of the heat-driven evaporative crystallizer overhead 665 may be recycled back to the reactor system 603. Often, a portion 685 is recycled back to the reactor system 603 and used as a source of water for dissolving the N-(phosphonomethyl) iminodiacetic acid substrate to form the feed stream 601 for the oxidation reaction zone(s). Particularly where the catalyst is a carbon-containing catalyst, a portion of the heat-driven evaporative crystallizer overhead 665 also may advantageously be used to reduce the catalyst surface. This is due to the fact that the evaporative crystallizer overhead 665 often contains formaldehyde and/or formic acid, which both act as reducing agents, particularly toward carbon-containing catalysts. The reduction treatment may occur in one or more catalyst holding tank(s) of the reactor system 603.

At least another portion of the heat driven evaporative crystallizer overhead 665 is normally purged from the system as purge stream 683. In a continuous system, this purge 683 helps to reduce the amount of impurity buildup (particularly small molecule impurity buildup) in the system. The purged waste 683 may, in turn, be further treated to remove impurities, as discussed above for the purged overhead streams for adiabatic crystallizers and non-adiabatic crystallizers discussed above.

At least a portion 689 of the centrate 677 from the centrifuge 675 is preferably recycled back to the heat-driven evaporative crystallizer 663 (and/or to the adiabatic crystallizer 615) for further recovery of the N-(phosphonomethyl) glycine product. Alternatively (or in addition), a portion 691 of the centrate 677 is recycled back to the oxidation reaction zone(s) of the reactor system 603 to convert unreacted N-(phosphonomethyl)iminodiacetic acid substrate in the centrate 677 into N-(phosphonomethyl)glycine product. A portion 687 of the centrate 677 is also normally purged from the system. In a continuous system, this purge 687 helps to reduce the amount of impurity buildup (particularly larger molecule impurity buildup) in the system. The purged waste 687 may be further treated to remove impurities by, for example, the same techniques described above for the liquid purged wastes discussed above for adiabatic and non-adiabatic crystallizers.

In an alternative embodiment, rather (or in addition to) feeding the centrate 661 from the centrifuge 655 to the non-adiabatic crystallizer 663, at least a portion 652 (preferably at least about 1%, more preferably from about 1 to about 67%, even more preferably from about 20 to about 50%, still even more preferably from about 30 to about 40%, and still yet even more preferably about 33%) of the withdrawn decantate 624 from the adiabatic crystallizer 615 is introduced into the non-adiabatic crystallizer 663. In that instance, the centrate 661 may be, for example, recycled to the adiabatic crystallizer 615 (via stream 695), recycled back to the reactor system 603, purged from the system (via stream 693), and/or introduced into the non-adiabatic crystallizer 663.

Figure 14:
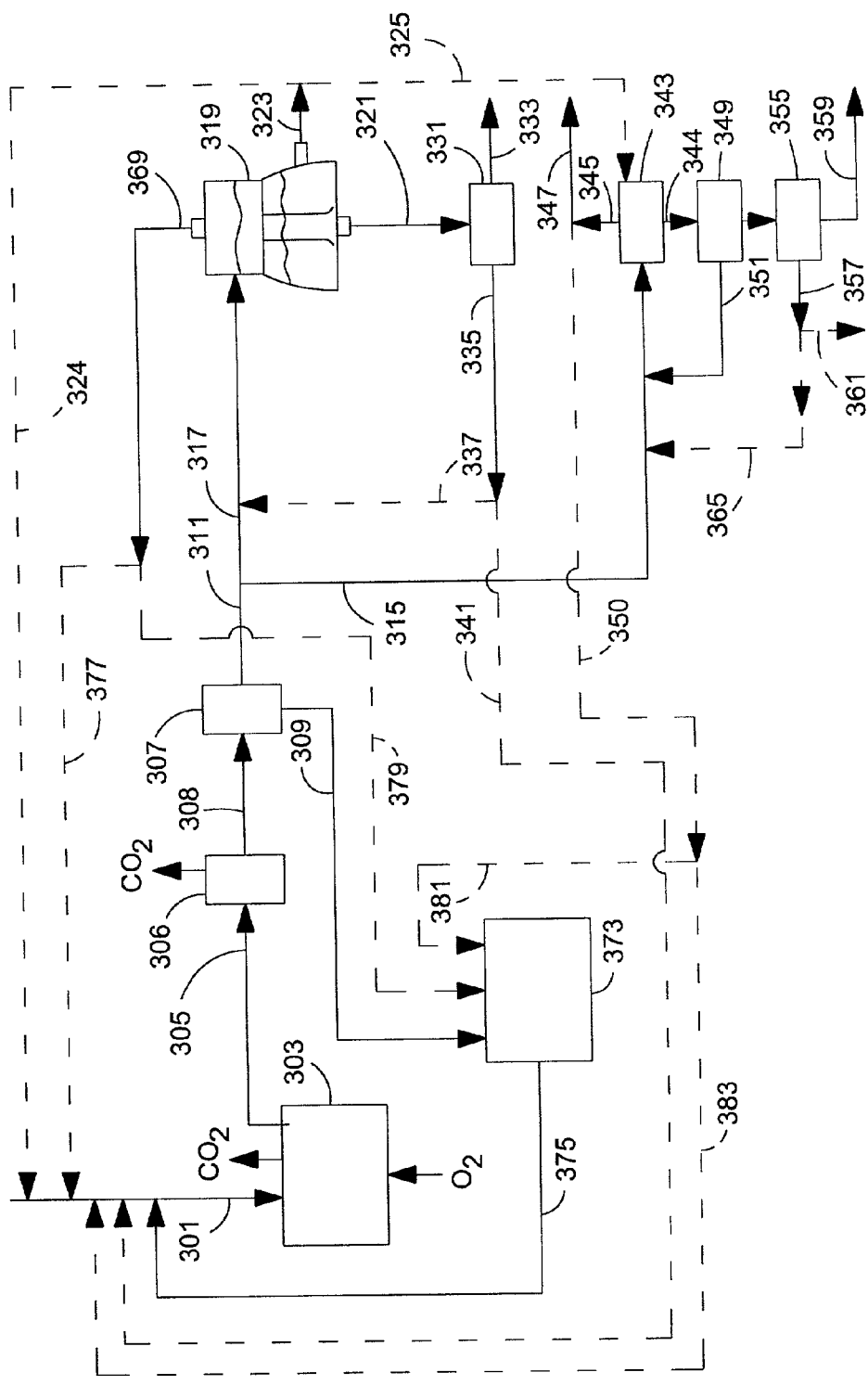
FIG. 14 is a schematic flow sheet of an integrated process for oxidizing an N-(phosphonomethyl)iminodiacetic acid substrate in a reactor system to form an oxidation reaction mixture comprising an N-(phosphonomethyl)glycine product and for recovering the N-(phosphonomethyl)glycine product from the oxidation reaction mixture using a combination of an adiabatic crystallizer and a non-adiabatic heat-driven evaporative crystallizer operated in semi-parallel.

FIG. 14 shows an example an especially preferred embodiment wherein the process comprises an adiabatic crystallizer 319 and a non-adiabatic crystallizer 343. Here, the adiabatic crystallizer 319 and non-adiabatic crystallizer 343 operate in a semi-parallel manner.

Many of the various streams shown in FIG. 14 are analogous to those described above for non-adiabatic crystallizers and adiabatic crystallizers alone. An aqueous feed stream 301 comprising an N-(phosphonomethyl)iminodiacetic acid substrate is introduced along with oxygen into an oxidation reactor system 303 comprising one or more oxidation reaction zone(s), wherein the N-(phosphonomethyl) iminodiacetic acid substrate is oxidatively cleaved in the presence of a catalyst to form an oxidation reaction product solution 305. The oxidation reaction product solution 305 withdrawn from the last oxidation reaction zone of reactor system 303 is then introduced into a pre-crystallizer flash tank 306 to reduce the pressure and flash out much of the dissolved $CO_2$. In the embodiment shown in FIG. 14, the resulting liquid stream 308 is filtered with a catalyst filter 307 to remove a heterogenous particulate catalyst suspended in liquid stream 308 and form a catalyst recycle stream 309 and filtrate 311. The filtrate 311 is divided into plural fractions and a portion 317 (i.e., a primary fraction of the reaction product solution) is introduced into the adiabatic crystallizer 319 to produce a primary product slurry comprising precipitated N-(phosphonomethyl)glycine product crystals and primary mother liquor, while another portion 315 (i.e., a secondary fraction of the reaction product solution) is introduced into the non-adiabatic heat-driven evaporative crystallizer 343 to produce an evaporative crystallization slurry 344 (i.e., a secondary product slurry) comprising precipitated N-(phosphonomethyl)glycine product crystals and secondary mother liquor. In such an embodiment, the portion 315 of the filtrate 311 which is introduced into the evaporative crystallizer 343 may first be introduced into a crystallizer feed tank (not shown), where it is mixed with the solids-depleted hydroclone stream 351 and/or recycled centrate 365. In addition to providing a location for mixing, such a feed tank also provides a timing buffer to hold materials during, for example, startup and shut down of the process.

Operation of the adiabatic crystallizer 319 produces vapor 369 (i.e., the adiabatic crystallizer overhead) discharged from the top of the crystallizer, a decantate (i.e., primary mother liquor) stream 323 withdrawn from the crystallizer and a primary crystallization product slurry 321 comprising precipitated crystalline N-(phosphonomethyl)glycine product and primary mother liquor removed from the bottom of the crystallizer. Preferably, at least a portion (and preferably all) of the adiabatic crystallizer overhead 369 and/or decantate 323 withdrawn from the adiabatic crystallizer 319 is/are recycled back to the oxidation reaction zone(s) of the reactor system 303. Typically, at least a portion 377 of the adiabatic crystallizer overhead 369 and/or a portion 324 of the withdrawn decantate 323 is/are recycled back to the reactor system 303 and used as a source of water for the oxidation reaction zone(s). At least a portion 325 of the withdrawn decantate 323 may alternatively be sent to the non-adiabatic evaporative crystallizer 343. At least a portion of the adiabatic crystallizer overhead 369 can be indirectly recycled (via stream 379) back to the reactor system 303 by being used to reduce the catalyst surface. As noted above, this reduction treatment often occurs in a catalyst holding tank(s) 373.

Because the solids-depleted liquid streams from the adiabatic crystallizer 319 (i.e., the decantate stream 323) and subsequent centrifuge 331 (i.e., the centrate stream 335) typically have a lower concentration of impurities (particularly of larger molecule impurities) than the solids-depleted stream (i.e., the centrate) 357 of the centrifuge 355 (e.g., a solid bowl centrifuge) downstream of the heat-driven evaporative crystallizer 343, it is normally more preferable to recycle back to the reactor system 303 the entire withdrawn decantate 323 from the adiabatic crystallizer 319, and optionally the entire solids-depleted stream 335 from the centrifuge 331 downstream of the adiabatic crystallizer 319, while using the solids-depleted stream (i.e., the centrate) 357 of the centrifuge 355 downstream of the heat-driven evaporative crystallizer 343 for purging larger molecule impurities from the system (via purge stream 361). Purging is advantageous for continuous systems because it reduces the rate of contaminant buildup in the system, thus making recycle of the solids-depleted streams (i.e., streams 323 and 335) from the adiabatic crystallizer 319 more feasible. Like the purged waste streams discussed above, this purged waste 361 may be treated by, for example, further crystallization. It may also be treated by the techniques described by Smith in U.S. Pat. No. 5,606,107. It may additionally be treated, for example, by the technique described in detail by Morgenstern et al. in U.S. Pat. No. 6,005,140. It may further be treated by the technique described in detail by Grabiak et al. in U.S. Pat. No. 4,851,131.

The solids-depleted stream 335 from the centrifuge 331 downstream of the adiabatic crystallizer 319, on the other hand, is typically entirely recycled, for example, back to the adiabatic crystallizer 319 (via stream 337) or to the reactor system 303 (via stream 341). The solids-depleted stream 351 from the hydroclone 349 downstream of the heat-driven evaporative crystallizer 343 can be recycled back to the evaporative crystallizer. Any non-purged portion 365 of the solids-depleted stream 357 from the centrifuge 355 downstream of the evaporative crystallizer 343 is typically recycled back to the evaporative crystallizer. At least a portion of the heat-driven evaporative crystallizer overhead 345 is typically purged from the system via stream 347, although a portion 350 optionally may be recycled back to the oxidation reactor system 303 directly via stream 383 or indirectly via stream 381 to be used as a reducing agent for the catalyst.

Preferably, from about 30% to about 85%, more preferably from about 50% to about 80%, and even more preferably from about 65% to about 75% of the oxidation reaction mixture absent the catalyst (i.e., stream 311) is introduced into the adiabatic crystallizer 319 via stream 317 as the primary fraction, while the remaining portion is introduced into the non-adiabatic heat-driven crystallizer 343 via stream 315 as the secondary fraction. The weight ratio of the secondary fraction 315 to the N-(phosphonomethyl)iminodiacetic acid substrate fed into the system is preferably from about 0.1 to about 9, more preferably from about 2 to about 7, even more preferably from about 2.5 to 4.

Embodiments operating an adiabatic crystallizer and a heat-driven evaporative crystallizer in a semi-parallel manner (such as the one shown in FIG. 14) are typically more preferred than embodiments operating an adiabatic crystallizer and an evaporative crystallizer in series. This stems, for example, from the fact that for a given evaporative crystallizer size, greater crystallization capacity generally may be obtained where the crystallizers are in parallel. This provides more flexibility in retrofitting existing plants.

The system in FIG. 14 produces two N-(phosphonomethyl)glycine product wet cake streams: a wet cake stream 333 from centrifuge 331 downstream of the adiabatic crystallizer 319, and a wet cake stream 359 from centrifuge 355 downstream of the heat-driven evaporative crystallizer 343. Normally, the wet cake stream 333 from the adiabatic crystallizer 319 preferably has an N-(phosphonomethyl) glycine product concentration of at least 90% (by weight of all compounds besides water), more preferably at least 95% (by weight of all compounds besides water), and even more preferably at least about 99% (by weight of all compounds besides water), while the wet cake stream 359 from the evaporative crystallizer 343 has an N-(phosphonomethyl) glycine product concentration of at least about 85% (by weight of all compounds besides water), more preferably at least about 90% (by weight of all compounds besides water), and even more preferably at least about 95% (by weight of all compounds besides water). Typically, the purity of the wet cake 333 from the adiabatic crystallizer 319 section is greater than the purity of the wet cake 359 from the heat-driven evaporative crystallizer 343.

It is often advantageous to combine these wet cakes 333 and 359. This combination allows lesser purity levels in the wet cake 359 from the evaporative crystallizer 343 to be tolerated due to the greater purity levels normally obtained in the wet cake 333 issuing from the adiabatic crystallizer 319. Thus, for example, if 45% of the combined wet cake is from the evaporative crystallizer 343 and 55% of the combined wet cake is from the adiabatic crystallizer 319, the purity level of the wet cake 359 from the evaporative crystallizer 343 may be as low as 90.2% by weight to achieve a combined purity level of at least 95% by weight where the wet cake 333 from the adiabatic crystallizer 319 is 99% by weight pure. Normally, it is desirable for the combined wet cake to have an N-(phosphonomethyl)glycine product concentration of at least about 95% (by weight of all compounds besides water), and more preferably about 96% (by weight of all compounds besides water).

Figure 14A:
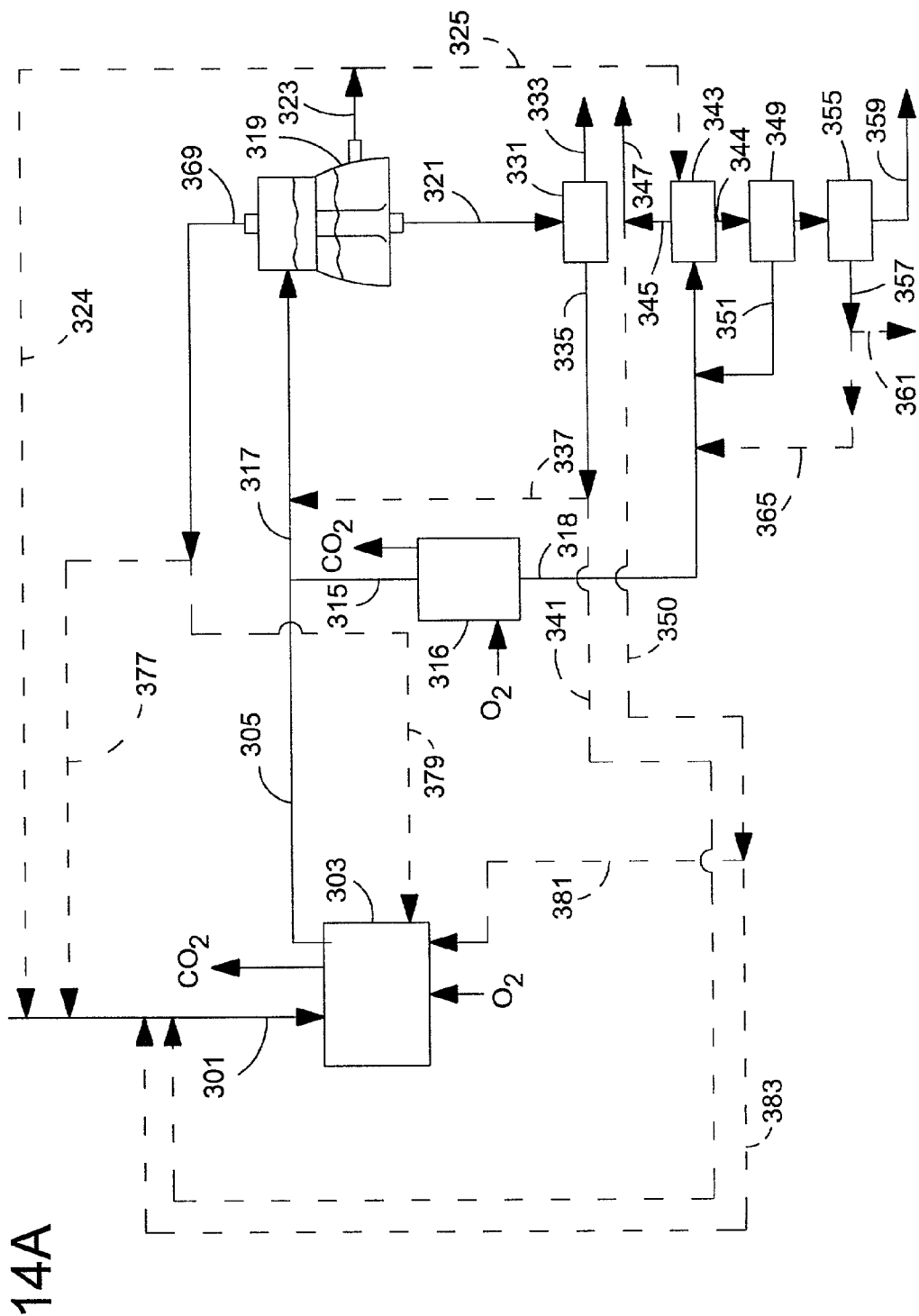
FIG. 14A is a schematic flow sheet of an integrated process for oxidizing an N-(phosphonomethyl)iminodiacetic acid substrate to form an N-(phosphonomethyl)glycine product and for recovering the N-(phosphonomethyl)glycine product using a combination of an adiabatic crystallizer and a non-adiabatic heat-driven evaporative crystallizer operated in semi-parallel. The N-phosphonomethyl)iminodiacetic acid substrate is oxidized in a primary reactor system to form an oxidation reaction mixture comprising the N-(phosphonomethyl)glycine product and unreacted N-(phosphonomethyl)iminodiacetic acid substrate. A primary fraction of the oxidation reaction mixture from the primary reactor system is introduced into the adiabatic crystallizer, while unreacted N-(phosphonomethyl)iminodiacetic acid substrate in a secondary oxidation reactor feed fraction of the oxidation reaction mixture is oxidized in a secondary reactor system to form additional N-(phosphonomethyl)glycine product before being passed to the non-adiabatic crystallizer.

FIG. 14A shows an example of another especially preferred embodiment wherein the process comprises an adiabatic crystallizer and a non-adiabatic heat-driven evaporative crystallizer operated in a semi-parallel manner as described above in FIG. 14. However, this reaction system further includes a secondary reactor system comprising one or more secondary oxidation reaction zone(s) used in conjunction with the fraction of the reaction product mixture from the primary oxidation reactor system sent to the heat-driven evaporative crystallizer.

Many of the various streams shown in FIG. 14A are analogous to those described above for the reaction system shown in FIG. 14 in which the adiabatic crystallizer 319 and the heat-driven evaporative crystallizer 343 are operated in a semi-parallel manner. An aqueous feed stream 301 comprising an N-(phosphonomethyl)iminodiacetic acid substrate is introduced along with oxygen into a primary oxidation reactor system 303 comprising one or more oxidation reaction zone(s), wherein the N-(phosphonomethyl) iminodiacetic acid substrate is oxidatively cleaved in the presence of a catalyst to form a reaction product solution 305 comprising N-(phosphonomethyl)glycine product and unreacted N-(phosphonomethyl)iminodiacetic acid substrate. The reaction product solution 305 from the primary reactor system 303, after catalyst separation (e.g., by filtration) if necessary, is divided into plural fractions comprising a primary fraction 317 and a secondary oxidation reactor feed fraction 315. The primary fraction 317 is introduced into the adiabatic crystallizer 319 and is cooled by flash evaporation of water therefrom under reduced pressure conditions to recover the N-(phosphonomethyl)glycine product as described above. The secondary oxidation reactor feed fraction 315 is introduced into a secondary oxidation reactor system 316 comprising one or more oxidation reaction zones in which unreacted N-(phosphonomethyl)iminodiacetic acid substrate is oxidized to produce a secondary oxidation reactor effluent 318 comprising N-(phosphonomethyl)glycine product. The secondary reactor feed fraction 315 may be cooled prior to introduction into the secondary oxidation reactor system 316 to remove exothermic heat generated in the primary oxidation reactor system 303 and reduce production of by-products. Reactor effluent 318 is introduced into the non-adiabatic heat-driven evaporative crystallizer wherein water is evaporated therefrom to precipitate and recover the N-(phosphonomethyl)glycine product as described above.

In the reaction system in FIG. 14A it should be understood that the primary and secondary reactor systems 303 and 316, respectively, may include one or more oxidation reaction zone(s) provided by various reactor configurations including, for example, the continuous reactor systems described hereinabove. For purposes of illustration, the primary reactor system 303 may comprise a single stirred tank reactor as shown in FIGS. 2, 2A and 2B, two stirred tank reactors in series as shown in FIGS. 3–6 or one or more fixed bed reactors as shown in FIG. 8. In one embodiment, the primary reactor system 303 comprises one or more oxidation reaction zone(s) in series and the reaction product solution 305 is withdrawn from the last oxidation reaction zone, in the series, and filtered as necessary. However, it should be understood that the reaction product solution 305 may be divided before the last oxidation reaction zone of the primary reactor system 303 such that the primary fraction 317 passes through the remaining oxidation reaction zone(s) of the primary reactor system before being introduced into the adiabatic crystallizer 319.

Preferably, the secondary reactor system 316 comprises one or more oxidation reaction zone(s) provided by one or more fixed bed reactors or stirred tank reactors utilizing a particulate catalyst slurry or combinations thereof. However, fixed bed reactors are generally more preferred since a catalyst recycle mechanism including a catalyst filter can be avoided in the secondary reactor system 316. Moreover, concerns regarding dissipation of exothermic reaction heat and temperature control that arise when a fixed bed reactor serves as the first oxidation reaction zone in the primary reactor system 303 are largely circumvented in the secondary reactor system 316 since the majority of the N-(phosphonomethyl)iminodiacetic acid substrate is preferably oxidized in the primary reactor system 303. Accordingly, the oxidation reaction zone(s) within the secondary reactor system may be operated adiabatically. In accordance with an especially preferred embodiment, the secondary reactor system 316 comprises a single oxidation reaction zone provided by a fixed bed reactor. Preferably, such a fixed bed reactor is operated with cocurrent gas and liquid flows through the oxidation reaction zone.

The presence of the secondary reactor system 316 in the reaction system shown in FIG. 14A permits the primary reactor system 303 to be configured and operated in a manner which allows a higher concentration of unreacted N-(phosphonomethyl)iminodiacetic acid substrate in the reaction mixture 305. For example, the second or subsequent oxidation reaction zone(s) of the primary reactor system 303 may be sized considerably smaller or eliminated completely (i.e., the primary reactor system 303 may comprise a single oxidation reaction zone). However, the concentration of unreacted N-(phosphonomethyl)iminodiacetic acid substrate in the reaction product solution 305, and thus in the primary fraction 317 sent to the adiabatic crystallizer 319, is nevertheless preferably maintained sufficiently low to avoid precipitation of unreacted N-(phosphonomethyl)iminodiacetic acid substrate at the prevailing stream temperature. For typical operating temperatures of the adiabatic crystallizer (e.g., 60° C.), the concentration of N-(phosphonomethyl)iminodiacetic acid substrate in the reaction product solution 305 is no greater than about 2% by weight. However, in order to take advantage of the presence of the secondary reactor system 316 which permits the primary reactor system 303 to be sized and operated more economically, the concentration of N-(phosphonomethyl)iminodiacetic acid substrate in the reaction product solution 305 is preferably at least about 0.2% by weight and more preferably at least about 0.5% by weight.

Unreacted N-(phosphonomethyl)iminodiacetic acid substrate in the primary fraction 317 introduced into the adiabatic crystallizer 319 is preferably recovered and returned to the primary reactor system 303 via the decantate 323 withdrawn from the adiabatic crystallizer 319, as well as by optionally recycling at least a portion of the solids-depleted stream 335 from the centrifuge 331 downstream of the adiabatic crystallizer 319 to the primary reactor system via stream 341. By employing a high dewatering centrifuge (e.g., a vertical basket centrifuge) as centrifuge 331, recovery of unreacted N-(phosphonomethyl)iminodiacetic acid substrate in the solids-depleted stream 335 is enhanced, while advantageously minimizing the fraction of unreacted N-(phosphonomethyl)iminodiacetic acid substrate contained in wet cake stream 333.

In a further embodiment of the present invention, the system shown in FIG. 13 may be modified by the addition of a secondary reactor system to further oxidize unreacted N-(phosphonomethyl)iminodiacetic acid substrate in the centrate 661 from the centrifuge 655 upstream of the non-adiabatic evaporative crystallizer 663.

Particularly where the N-(phosphonomethyl)glycine product is N-(phosphonomethyl)glycine itself, it has long been known that the product may be converted to various salts or esters to increase its solubility in water so that it is more readily amenable to commercial use. This is generally discussed, for example, by Franz in U.S. Pat. Nos. 3,977,860 and 4,405,531. Preferred salts of N-(phosphonomethyl)glycine include, for example, alkali metal salts (particularly the potassium salt), alkanolamine salts (particularly the monoethanolamine salt), alkyl amine salts (particularly the isopropylamine salt), and alkyl sulfonium salts (particularly the trimethyl sulfonium salt). The isopropylamine salt of N-(phosphonomethyl)glycine is particularly preferred. See, e.g., Bugg et al., U.S. Pat. No. 5,994,269. This salt typically has a significantly greater activity than the free acid, and is, for example, roughly 40 times as soluble as the free acid at 25° C.).

In some embodiments of this invention, the N-(phosphonomethyl)glycine product formed in the oxidation reaction zone(s) comprises an ester or salt which is sufficiently great to form a mixture having the desired commercial concentration. In those instances, the desirability for process steps (e.g., crystallization, hydrocycloning, centrifugation, and the like) for concentrating the product may be significantly reduced or entirely eliminated. This is especially true if the catalyst is the deeply reduced catalyst discussed above, which typically forms a reaction mixture having a low concentration of impurities and consequently requiring little or no purification.

In some embodiments, for example, the N-(phosphonomethyl)glycine product formed in the oxidation reaction zone(s) is the isopropylamine salt of N-(phosphonomethyl) glycine. At the more preferred oxidation operating temperatures (i.e., from about 95 to about 105° C.), such a product will remain soluble at concentrations of up to about 50% by weight or greater. The salt product may be formed in the oxidation reaction zone(s) by (a) using the isopropylamine salt of N-(phosphonomethyl)iminodiacetic acid as the substrate, (b) introducing isopropylamine into the oxidation reaction zone(s) to aminate the oxidation product while in the oxidation reaction zone(s), and/or (c) introducing isopropylamine into a vessel downstream of the oxidation reaction zone(s) and before catalyst filtration. Where there are more than one oxidation reaction zones in series, it is normally preferable (although not absolutely necessary) to use the isopropylamine salt of N-(phosphonomethyl)iminodiacetic acid as the substrate and/or introduce isopropylamine into the first of the oxidation reaction zones. Regardless, at least one equivalent (and more preferably slightly more than one equivalent) of isopropylamine cations are preferably present per mole of N-(phosphonomethyl)glycine product formed. It should be recognized these principles with respect to forming the isopropylamine salts also generally apply to forming other salts, e.g., alkali metal salts (particularly the potassium salt), alkanolamine salts (particularly the monoethanolamine salt), alkyl amine salts besides the isopropylamine salt, and alkyl sulfonium salts (particularly the trimethyl sulfonium salt).

EXAMPLES

The following examples are simply intended to further illustrate and explain the present invention. This invention, therefore, should not be limited to any of the details in these examples.

Example 1

Measuring Pore Volume of Carbon Support

A Micromeritics ASAP 2000 surface area and pore volume distribution instrument was used to acquire the data. Total surface area determination involves exposing a known weight of a solid to some definite pressure of a non-specific adsorbate gas at a constant temperature, e.g., at the temperature of liquid nitrogen, $-196°$ C. During equilibration, gas molecules leave the bulk gas to adsorb onto the surface which causes the average number of molecules in the bulk gas to decrease which, in turn, decreases the pressure. The relative pressure at equilibrium, p, as a fraction of the saturation vapor pressure, $p_o$, of the gas is recorded. By combining this decrease in pressure with the volumes of the vessel and of the sample, the amount (i.e., the number of molecules) of gas adsorbed may be calculated by application of the ideal gas laws. These data are measured at relative pressures $(p/p_o)$ of approximately 0.1 to 0.3 where the Brunauer, Emmett and Teller (BET) equation for multi-layer adsorption typically applies. With the number of adsorbed gas molecules known, it is possible to calculate the surface area using the "known" cross-sectional area of the adsorbate. For cases where only physical adsorption due to Van der Waals forces occurs (i.e., Type I Langmuir isotherms) the determination of surface area from the observed changes in pressure is accomplished using the BET equation. Pore size and pore size distributions are calculated by obtaining relative pressure data approaching $p/p_o=1$, i.e., in the regime where multi-layer adsorption and capillary condensation occur. By applying the Kelvin equation and methods developed by Barrett, Joyner and Halenda (BJH), the pore volume and area may be obtained.

Example 2

High-Temperature Deoxygenation of a Carbon Support

The high-temperature deoxygenation procedures described in the following examples may be used with any carbon support to produce a deoxygenated carbon support.

Single-Step High-Temperature Deoxygenation #1 Using $NH_3/H_2O$ Gas

An activated carbon support (2.5 g) was placed into a 1.9 cm I.D.×40.6 cm length quartz tube. The tube was connected to a gas stream resulting from sparging a 70 to 100 ml/min. $N_2$ stream through a 70° C., 10% $NH_4OH$ aqueous solution. The quartz tube then was placed into a preheated 30.5 cm tubular furnace and pyrolyzed at 930° C. for 60 min. and then cooled to room temperature under a dry $N_2$ atmosphere without contacting any air.

Single-Step High-Temperature Deoxygenation #2 Using $NH_3/H_2O$ Gas

An activated carbon support (3.55 g) was placed into a 1.9 cm I.D.×35.6 cm long quartz tube. The tube was connected to streams of 50 ml/min. of $NH_3$ gas and 89 ml/min. of steam and then placed into a preheated 30.5 cm tubular furnace and pyrolyzed at 930° C. for 30 minutes. The tube subsequently was cooled to room temperature under a dry $N_2$ atmosphere without any contact with air.

To show the advantages of deoxygenating the carbon support before dispersing the noble metal onto the surface of the support, the performances of the following two catalysts were compared: one having a carbon support, which was deoxygenated using the above treatment before platinum was dispersed onto its surface; and one having an SA-30 carbon support (Westvaco Corp. Carbon, Department Covington, Va.) which was used as received from Westvaco. Platinum was dispersed onto the surfaces of the carbon supports using the technique described in Example 3 below. The catalysts then were reduced. In one experiment, the catalysts were reduced using $NaBH_4$ (See Example 12 for protocol). In a second experiment, the catalysts were reduced by heating them in 20% $H_2$ and 80% argon for 8 hours at 640° C.

The reduced catalysts were used to catalyze the oxidation of N-(phosphonomethyl)iminodiacetic acid to N-(phosphonomethyl)glycine (i.e., "glyphosate") using the reaction conditions set forth in Example 5. Table 1 shows the results. Use of the deoxygenated carbon support resulted in smaller CO desorption values, less noble metal leaching, higher formaldehyde activity, and shorter reaction times.

TABLE 1

Effect of Deoxygenating the Carbon Support before Dispersing Noble Metal onto Its Surface

| Deoxygenation treatment | CO desorption from carbon support (mmole/g) | Reduction | Pt in soln. (µg/g glyph. prod.) | $CH_2O$ (mg/g glyph. prod.) | Reaction time[1] (min.) |
|---|---|---|---|---|---|
| Single-step high-temperature deoxygenation #2 | 0.23 | $NaBH_4$ Reduced (Ex. 12) | 8.6 | 28.5 | 35.1 |
| SA-30, used as received | 1.99 | $NaBH_4$ Reduced (Ex. 12) | 54.3 | 43.1 | 62.7 |
| Single-step | 0.23 | 8 hrs at | 4.8 | 15.6 | 29.8 |

TABLE 1-continued

Effect of Deoxygenating the Carbon Support before Dispersing Noble Metal onto Its Surface

| Deoxygenation treatment | CO desorption from carbon support (mmole/g) | Reduction | Pt in soln. (μg/g glyph. prod.) | $CH_2O$ (mg/g glyph. prod.) | Reaction time[1] (min.) |
|---|---|---|---|---|---|
| high-temperature deoxygenation #2 | | 640° C. in 20% H2, 80% Ar | | | |
| SA-30, used as received | 1.99 | 8 hrs at 640° C. in 20% H2, 80% Ar | 31 | 19.7 | 50.7 |

[1]When ≧98% of the N-(phosphonomethyl)iminodiacetic acid has been consumed.

Example 3

Depositing Platinum onto the Surface of a Carbon Support

Twenty grams of NUCHAR activated carbon SA-30 (Westvaco Corp., Carbon Department, Covington, Va.) was slurried in 2 L of water for 2 hours. Then, 2.81 grams of $H_2PtCl_6$ dissolved in about 900 ml of water was added dropwise over a period of 3 to 4 hours. After the $H_2PtCl_6$ solution was completely added, the slurry was stirred for 90 more minutes. The pH of the slurry then was readjusted to 10.5 using NaOH, and stirred for 10 to 14 more hours. The resulting slurry was filtered and washed with water until the filtrate reached a constant conductivity. The wet cake was dried at 125° C. under vacuum for 10 to 24 hours. This material produced 5% platinum on carbon upon reduction.

It should be recognized that the above procedure may be used to deposit platinum onto the surface of other carbon supports as well.

Example 4

High-Temperature Hydrogen Reduction of a Carbon Support

Approximately 5.8 g of a dried, unreduced catalyst consisting of 5% platinum on a NUCHAR SA-30 carbon support (Westvaco Corp., Carbon Department, Covington, Va.) was dehydrated in-situ at 135° C. in argon for one hour before being reduced at 640° C. with 20% $H_2$ in argon for 11 hours. Upon cooling to room temperature under 20% $H_2$ in argon, the catalyst was ready to use.

It should be recognized that the above procedure may be used to heat other carbon supports as well.

Example 5

Use of the Catalyst to Oxidize N-(phosphonomethyl)iminodiacetic acid to N-(Phosphonomethyl)glycine This example demonstrates the use of high-temperature gas-phase reduction to improve catalyst performance.

An Aldrich catalyst consisting of 5% platinum on an activated carbon support (catalog No. 20,593-1, Aldrich Chemical Co., Inc., Milwaukee, Wis.) was heated at 640° C. for 4–6 hours in the presence of 20% $H_2$ and 80% argon. Subsequently, it was used to catalyze the oxidation of N-(phosphonomethyl)iminodiacetic acid to Glyphosate. Its performance was compared to the performance of a sample of the Aldrich catalyst which was used as received from Aldrich.

The N-(phosphonomethyl)iminodiacetic acid oxidation reaction was conducted in a 200 ml glass reactor using 11.48 g of N-(phosphonomethyl)iminodiacetic acid, 0.5% catalyst (dry basis), a total reaction mass of 140 g, a temperature of 90° C., a pressure of 50 psig, a stir rate of 900 rpm, and an oxygen flow rate of 100 ml/min.

Table 2 shows the results. The high-temperature hydrogen-reduced catalyst had less leaching, better formaldehyde activity, and produced less N-methyl-N-(phosphonomethyl) glycine. Also, reaction time was shortened by 30% when the high-temperature hydrogen-reduced catalyst was used.

TABLE 2

N-(phosphonomethyl)iminodiacetic acid Oxidation Results for 5% Pt on Activated Carbon (Aldrich Cat. No. 20,593-1)

| Catalyst | As Received | High-Temp., $H_2$ Reduced |
|---|---|---|
| NPMIDA (%) | 0.4619 | 0.4430 |
| N-(phosphonomethyl)glycine (%) | 5.58 | 5.54 |
| $HCO_2H$ (mg/g glyph. prod.) | 46.99 | 35.87 |
| $CH_2O$ (mg/g glyph. prod.) | 32.96 | 14.60 |
| NMG (mg/g glyph. prod.) | 3.58 | 1.32 |
| AMPA (ppm) | 172.5 | 182.0 |
| End Point (min.) | 64.67 | 44.17 |
| Pt in soln. (μg/g glyph. prod.) | 32.26 | 10.50 |
| % of Pt Lost | 0.72 | 0.232 |

Example 6

Further Examples Showing Use of Catalyst to Oxidize N-(phosphonomethyl)iminodiacetic acid to N-(Phosphonomethyl)glycine This example demonstrates using the high-temperature, gas-phase reduction treatment and ammonia washing to improve catalyst performance.

The performances of six catalysts in catalyzing the N-(phosphonomethyl)iminodiacetic acid oxidation were compared. These catalysts were: (a) a catalyst consisting of 5% platinum on an activated carbon support (Catalog No. 33,015-9, Aldrich Chemical Co., Inc., Milwaukee, Wis.); (b) the catalyst after being washed with ammonia (ammonia washing was conducted using the same technique described in Example 10 except that the pH of the catalyst slurry was adjusted to and maintained at 11.0 rather than 9.5); (c) the catalyst after being heated at 75° C. in 20% $H_2$ and 80% argon for 4–6 hours (GPR@75° C.); (d) the catalyst after being heated at 640° C. for 4–6 hours in the presence of 20% $H_2$ and 80% argon (GPR@640° C.); and (e) two catalysts after being washed with ammonia and then heated at 640° C. for 4–6 hours in the presence of 20% $H_2$ and 80% argon. The N-(phosphonomethyl)imino acid oxidation reaction conditions were the same as in Example 5.

Table 3 shows the results. The untreated catalyst showed relatively high leaching and poor formaldehyde activity. High-temperature gas-phase reduction at 640° C. in the presence of $H_2$ leads to the greatest decrease in leaching and increase in formaldehyde activity. Heating the catalyst at 75° C. in 20% $H_2$ at 75° C. decreased leaching to a lesser extent, but did not enhance the formaldehyde activity.

TABLE 3

NPMIDA Oxidation Results for 5% Pt on Activated Carbon (Aldrich Cat. No. 33.015-9)

| Catalyst | As-received | $NH_3$ wash w/o GPR[1] | GPR @ 75° C. | GPR @ 640° C. | $NH_3$ wash + GPR @ 640° C. | $NH_3$ wash + GPR @ 640° C. |
|---|---|---|---|---|---|---|
| NPMIDA (%) | ND | ND | ND | 0.097 | 0.083 | ND |
| Glyphosate (%) | 5.87 | 5.65 | 5.81 | 5.89 | 5.85 | 5.91 |
| $HCO_2H$ (mg/g glyph. prod.) | 43.46 | 43.65 | 38.97 | 42.14 | 46.91 | 52.12 |
| $CH_2O$ (mg/g glyph. prod.) | 19.39 | 22.73 | 19.85 | 13.78 | 15.70 | 17.61 |
| NMG (mg/g glyph. prod.) | 1.27 | 0.89 | 0.89 | 1.00 | 1.31 | 1.68 |
| AMPA (ppm) | 149.4 | 147.6 | 134.6 | 349.8 | 324.8 | 283.8 |
| End Point (min.) | 39.33 | 44.33 | 38 | 31.42 | 34.33 | 33.33 |
| Pt in soln. (μg/g glyph. prod.) | 42.59 | 40.71 | 27.54 | 5.26 | 5.30 | 4.23 |
| % of Pt Lost | 1 | 0.92 | 0.64 | 0.12 | 0.12 | 0.1 |

[1]"GPR" means reduction in $H_2$
[2]"ND" means none detected.

In the next experiment, five catalysts were analyzed while catalyzing the N-(phosphonomethyl)iminodiacetic acid oxidation. These catalysts were: (a) a catalyst consisting of 5% platinum on NUCHAR SA-30 (Westvaco Corp., Carbon Department, Covington, Va.); (b) the catalyst after being treated with $NaBH_4$ (see Example 12 for protocol); (c) the catalyst after being heated at 75° C. in 20% $H_2$ and 80% argon for 4–6 hours (GPR@75° C.); (d) the catalyst after being heated at 640° C. in 20% $H_2$ and 80% argon for 4–6 hours (GPR@640° C.); (e) the catalyst after being washed with ammonia (using the same technique described in Example 10) and then heated at 640° C. in 20% $H_2$ and 80% argon for 4–6 hours. The reaction conditions were the same as those in Example 5.

Table 4 shows the results. The untreated catalyst showed relatively high platinum leaching and low formaldehyde activity. The catalyst also showed high leaching and low formaldehyde activity after being treated with $NaBH_4$, as did GPR@75° C. In contrast, GPR@640° C. showed a greater formaldehyde activity and less leaching.

TABLE 4

NPMIDA Oxidation Results Using 5% Pt on NUCHAR SA-30

| Catalyst | Unreduced | $NaBH_4$ red. | GPR @ 75° C. | GPR @ 640° C. | $NH_3$ wash + GPR @ 640° C. |
|---|---|---|---|---|---|
| Glyphosate (%) | 2.50 | 5.71 | 4.92 | 5.17 | 5.19 |
| $HCO_2H$ (mg/g glyph. prod.) | 59.56 | 51.14 | 57.85 | 30.85 | 38.21 |
| $CH_2O$ (mg/g glyph. prod.) | 115.28 | 43.13 | 48.52 | 19.67 | 20.79 |
| NMG (mg/g glyph. prod.) | 1.64 | 2.17 | 6.41 | 0.37 | 1.73 |
| AMPA (ppm) | 58.16 | 193.9 | 174.0 | 138.5 | 156.3 |
| End point (min.) | 62.67 | 62.67 | 70.67 | 50.67 | 59.33 |
| Pt in soln. (μg/g glyph. prod.) | 84.00 | 54.29 | 81.30 | 30.95 | 19.27 |
| % of Pt Lost | 0.84 | 1.24 | 1.6 | 0.64 | 0.4 |

Example 7

Effect of C/O and O/Pt Ratios at the Surface of the Catalyst

The carbon atom to oxygen atom ratio and the oxygen atom to platinum atom ratio at the surfaces of various fresh catalysts were analyzed using a PHI Quantum 2000 ESCA Microprobe Spectrometer (Physical Electronics, Eden Prairie, Minn.). The surface analysis was performed by electron spectroscopy for chemical analysis ("ESCA") with the instrument in a retardation mode with the analyzer at fixed band pass energy (constant resolution). The analysis entails irradiation of the sample with soft X-rays, e.g., Al $K_\alpha$ (1486.6 eV), whose energy is sufficient to ionize core and valence electrons. The ejected electrons leave the sample with a kinetic energy that equals the difference between the exciting radiation and the "binding energy" of the electron (ignoring work function effects). Because only the elastic electrons, i.e., those that have not undergone energy loss by any inelastic event, are measured in the photoelectron peak, and because the inelastic mean free path of electrons in solids is short, ESCA is inherently a surface sensitive technique. The kinetic energy of the electrons is measured using an electrostatic analyzer and the number of electrons are determined using an electron multiplier. The data are presented as the number of electrons detected versus the binding energy of the electrons. ESCA survey spectra were taken using monochromatic Al $K_\alpha$ x-rays for excitation of the photoelectrons with the analyzer set for a 117 eV band pass energy. The X-ray source was operated at 40 watts power and data were collected from the 200 μm spot on the sample being irradiated. These conditions give high sensitivity but low energy resolution. The spectra were accumulated taking a 1.0 eV step size across the region from 1100 eV to 0 eV and co-adding repetitive scans to achieve acceptable signal/noise in the data. The elements present were identified and quantified using the standard data processing and analysis procedures provided with the instrumentation by the vendor. From the relative intensities of the photoelectron peaks, the relative atomic concentrations of the elements Pt/C/O are obtained. ESCA analysis is generally cited as having a precision of ±20% using tabulated response factors for a particular instrument configuration.

Table 5 shows the C/O and O/Pt ratios at the surface of each fresh catalyst, and the amount of leaching for each of the catalysts during a single-cycle N-(phosphonomethyl)iminodiacetic acid oxidation reaction.

TABLE 5

Effects of C/O and O/Pt Ratios During NPMIDA Oxidation[1]

| Catalyst | Reduction Treatment After Depositing Noble Metal | C/O Ratio | O/Pt Ratio | Pt in Soln. (μg/g)[2] | $CH_2O$ (mg/g)[3] |
|---|---|---|---|---|---|
| 5% Pt on deoxygenated carbon[5] | $NaBH_4$ Reduced | 23.7 | 3 | ND[4] | |
| 5% Pt on deoxygenated carbon[5] | Pt(II)[6] 640° C./9 hr/10% $H_2$ | 35.3 | 17 | 1.2 | 24.44 |
| 5% Pt on deoxygenated carbon[5] | $NaBH_4$ Reduced | 21.1 | 3 | 6.9 | |
| Aldrich Cat. No. 33015-9 | 640° C./6 hr/20% $H_2$ | 67.9 | 3 | 5.2 | 13.78 |
| Aldrich cat. No. 33015-9 | 75° C./6 hr/20% $H_2$ | 13.4 | 10 | 27.5 | 19.85 |

TABLE 5-continued

Effects of C/O and O/Pt Ratios During NPMIDA Oxidation[1]

| Catalyst | Reduction Treatment After Depositing Noble Metal | C/O Ratio | O/Pt Ratio | Pt in Soln. (µg/g)[2] | $CH_2O$ (mg/g)[3] |
|---|---|---|---|---|---|
| Aldrich Cat. No. 33015-9 | Used as Received | 13.3 | 10 | 42.6 | 19.39 |
| Aldrich Cat. #20593-1 | 640° C./6 hr/20% $H_2$ $NH_3$ wash/ph = 11 | 45.2 | 7 | 10.5 | 21.90 |
| Aldrich Cat. #20593-1 | 640° C./6 hr/20% $H_2$ | 37.7 | 10 | 10.5 | 14.60 |
| Aldrich Cat. #20593-1 | Used as Received | 9.1 | 26 | 32.3 | 32.96 |
| 5% Pt on SA-30 Westvaco carbon | 640° C./7 hr/20% $H_2$ $NH_3$ wash/pH = 9.5 | 67.7 | 8 | 19.3 | 20.79 |
| 5% Pt on SA-30 Westvaco carbon | 640° C./8 hr/20% $H_2$ | 63.3 | 8 | 30.9 | 19.67 |
| 5% Pt on SA-30 Westvaco carbon | 75° C./7 hr/20% $H_2$ | 13.2 | 32 | 81.3 | 48.52 |

[1]The reaction conditions were the same as those used in Example 5.
[2]µg Pt which leached into solution per gram Glyphosate produced.
[3]mg formaldehyde per gram Glyphosate produced.
[4]"ND" means none detected.
[5]Carbon support deoxygenated with the single-step high-temperature technique #2 of Example 2.
[6]Pt deposited using diamminedinitrito P(II) as described in Example 11.

Example 8

Analysis of Catalyst Surface Using Thermogravimetric Analysis with In-Line Mass Spectroscopy (TGA-MS)

The concentration of oxygen-containing functional groups at the surfaces of various fresh catalysts was determined by thermogravimetric analysis with in-line mass spectroscopy (TGA-MS) under helium. To perform this analysis, a dried sample (100 mg) of fresh catalyst is placed into a ceramic cup on a Mettler balance. The atmosphere surrounding the sample then is purged with helium using a flow rate 150 ml/min. at room temperature for 10 minutes. The temperature subsequently is raised at 10° C. per minute from 20 to 900° C., and then held at 900° C. for 30 minutes. The desorptions of carbon monoxide and carbon dioxide are measured by an in-line mass spectrometer. The mass spectrometer is calibrated in a separate experiment using a sample of calcium oxalate monohydrate under the same conditions.

Table 6 shows the amount of carbon monoxide desorbed per gram of each catalyst using TGA-MS, and the amount of leaching for each of the catalysts during a single-cycle N-(phosphonomethyl)iminodiacetic acid oxidation reaction using the same reaction conditions as in Example 5. As Table 6 shows, leaching tends to decrease as the amount of CO desorption decreases, and is particularly low when the desorption is no greater than 1.2 mmole/g (mmole CO desorbed per gram of catalyst).

TABLE 6

Effects of Oxygen-Containing Functional Groups Which Desorb from Catalyst Surface as CO during TGA-MS

| Catalyst | Reduction Treatment | TGA-MS (mmole/g)[1] | Pt in Soln. (µg/g)[2] | $CH_2O$ (mg/g)[3] |
|---|---|---|---|---|
| Aldrich Cat. #33015-9 | 640° C./6 hr/20% $H_2$ | 0.41 | 5.2 | 13.78 |
| Aldrich Cat. #33015-9 | 640° C./6 hr/20% $H_2$ $NH_3$ wash/pH = 9.5 | 0.38 | 5.3 | 15.70 |
| Aldrich Cat. #33015-9 | 75° C./6 hr/20% $H_2$ | 1.87 | 27.5 | 19.85 |
| Aldrich Cat. #33015-9 | $NH_3$ wash/pH = 9.5 | 1.59 | 40.7 | 22.73 |
| Aldrich Cat. #33015-9 | Used as Received | 1.84 | 42.6 | 19.39 |

[1]mmole of CO per gram of catalyst
[2]µg of noble metal which leaches into solution per gram of Glyphosate produced
[3]mg of formaldehyde per gram of Glyphosate produced Example 9

Effect of Temperature During High-Temperature Gas-Phase Reduction

This example demonstrates the effects of using various temperatures when heating the catalyst in the presence of a reducing agent.

An unreduced catalyst having 5% platinum on an activated carbon support (which was deoxygenated using the single-step high-temperature deoxygenation technique #2 described in Example 2 before the platinum is deposited) was heated at various temperatures in 10% $H_2$ and 90% argon for about 2 hours. The catalyst then was used to catalyze the N-(phosphonomethyl)iminodiacetic acid oxidation reaction. The reaction was conducted in a 250 ml glass reactor using 5 g N-(phosphonomethyl)iminodiacetic acid, 0.157% catalyst (dry basis), 200 g total reaction mass, a temperature of 80° C., a pressure of 0 psig, and an oxygen flow rate of 150 ml/min.

The results are shown in Table 7. Increasing the reduction temperature from 125° C. to 600° C. reduces the amount of noble metal leaching and increases the formaldehyde oxidation activity during the oxidation reaction of N-(phosphonomethyl)iminodiacetic acid into Glyphosate.

TABLE 7

Effects of Reduction Temperature

| Reduction Temperature (° C.) | Pt in Soln. (normalized[1]) | $CH_2O$ (normalized[2]) | C/O Ratio | O/Pt Ratio |
|---|---|---|---|---|
| 125 | 1.00 | 0.41 | 26 | 13 |
| 200 | 0.44 | 0.80 | 27 | 14 |
| 400 | 0.18 | 0.93 | 42 | 10 |
| 500 | 0.14 | 0.95 | 32 | 14 |
| 600 | 0.06 | 1.00 | 40 | 11 |

[1]A normalized value of 1.00 corresponds to the highest amount of Pt observed in solution during this experiment.
[2]A normalized value of 1.00 corresponds to the highest formaldehyde activity during this experiment.

Example 10

Washing the Catalyst with Ammonia

An unreduced catalyst (6.22 g) consisting of 5% platinum on an activated carbon support (which was deoxygenated using the single-step high-temperature deoxygenation technique #2 described in Example 2 before the platinum was deposited onto the support) was slurried in 500 ml of water for 30 minutes. Afterward, the pH of the slurry was adjusted to 9.5 with diluted aqueous ammonia, and the slurry was stirred for one hour, with aqueous ammonia being periodically added to maintain the pH at 9.5. The resulting slurry was filtered and washed once with about 300 ml of water. The wet cake then was dried at 125° C. under vacuum for about 12 hours. This catalyst was heated at 640° C. for 11 hours in 10% $H_2$ and 90% argon, and then compared with two other catalysts consisting of 5% platinum on NUCHAR activated carbon: (a) one reduced at room temperature with $NaBH_4$ (see Example 12 for protocol), and (b) one heated at 640° C. in 10% $H_2$ and 90% argon for 11 hours. The reactions were the same as those in Example 5.

The results are shown in Table 8. Platinum leaching was the lowest with the catalyst which was washed with ammonia before high-temperature hydrogen reduction.

TABLE 8

Effects of Ammonia Washing

| Catalyst | $CH_2O$ (mg/g)[1] | $HCO_2H$ (mg/g) | NMG (mg/g) | Pt in soln. (µg/g) |
|---|---|---|---|---|
| $NH_3$-washed, High-Temp., $H_2$-reduced | 10.62 | 28.79 | 0.83 | 0.50 |
| High-temp., $H_2$-reduced | 14.97 | 27.82 | 1.38 | 4.64 |
| Room-Temp., $NaBH_4$-reduced | 28.51 | 70.16 | 2.59 | 8.64 |

[1]These quantities are per gram Glyphosate produced.

Example 11

Use of a Less Oxidizing Noble Metal Precursor

Platinum was deposited on an activated carbon support using diamminedinitrito platinum (II). Approximately 20 g of an activated carbon support was deoxygenated using the single-step high-temperature deoxygenation technique #2 described in Example 2. Next, it was slurried in 2 L of water for 2 hours. Approximately 51.3 g of a 3.4% solution of diamminedinitrito platinum (II), diluted to 400 g with water, then was added dropwise over a period of 3–4 hours. After addition was complete, stirring was continued for 90 more minutes. The pH was re-adjusted to 10.5 by adding diluted aqueous NaOH, and stirring was conducted for 10–14 more hours. The slurry then was filtered and washed with a plentiful amount of water until the filtrate reached constant conductivity. The wet cake was dried at 125° C. under vacuum for 10–24 hours. The resulting catalyst was heated at 640° C. for 4–6 hours in 10% $H_2$ and 90% argon.

A control was prepared using $H_2PtCl_6$ to deposit platinum onto the same carbon. The control was heated under the same conditions as the catalyst prepared using diamminedinitrito platinum (II).

These catalysts were compared while catalyzing the N-(phosphonomethyl)iminodiacetic acid oxidation reaction. The reaction conditions were the same as those in Example 5.

The catalyst prepared using diamminedinitrito platinum (II) showed less leaching than the control. Only 1.21 µg platinum per gram of Glyphosate produced leached into solution, which was about three times better than the control.

Example 12

Reducing the Catalyst Surface Using $NaBH_4$

The purpose of this example is to demonstrate the effects of reducing the catalyst using $NaBH_4$.

Approximately 5 g of an activated carbon support (which was deoxygenated using the single-step high-temperature deoxygenation technique #2 described in Example 2 before the platinum was deposited onto the support) was slurried with 85 ml of distilled water in a 250 ml round bottom flask. The slurry was stirred in a vacuum for about 1 hour. Next, 0.706 g of $H_2PtCl_6$ in 28 ml of distilled water was added to the slurry at a rate of about 1 ml per 100 seconds with the vacuum still being applied. After stirring overnight in the vacuum, the reactor was brought to atmospheric pressure by admitting a flow of $N_2$. After allowing the slurry to settle, approximately 30 ml of colorless supernatant was decanted. The remaining slurry was transferred to a 100 ml Teflon round bottom. At this point, the pH was adjusted to 12.2 with 0.3 g of NaOH. Then, 2.3 ml of $NaBH_4$ in 14 M NaOH was added at 0.075 ml/min. Subsequently, the resulting slurry was stirred for one hour, filtered, and washed five times with 50 ml of distilled water. The catalyst then was dried at 125° C. and 6 mmHg for 12 hours.

The resulting catalyst was used to catalyze the N-(phosphonomethyl)iminodiacetic acid oxidation. The reaction was conducted in a 300 ml stainless steel reactor using 0.5% catalyst, 8.2% N-(phosphonomethyl)iminodiacetic acid, a total reaction mass of 180 g, a pressure of 65 psig, a temperature of 90° C., an agitation rate of 900 rpm, and an oxygen feed rate of 72 ml/min.

A control experiment also was conducted at the same reaction conditions using 5.23% platinum on an activated carbon support (which was deoxygenated using the single-step high-temperature deoxygenation technique #2 described in Example 2 before the platinum was deposited onto the support).

Table 9 shows the results using the $NaBH_4$-reduced catalyst, and Table 10 shows the results of the control experiment. Reducing with $NaBH_4$ reduced the amount of noble metal leaching. It also reduced the amount of formaldehyde and NMG after a period of use.

TABLE 9

Results Using Catalyst Treated with $NaBH_4$

| Run # | 1 | 2 | 3 | 4 | 5 | 6 |
|---|---|---|---|---|---|---|
| Glyphosate (%) | 5.79 | 5.81 | 5.75 | 5.74 | 5.79 | 5.77 |
| NPMIDA (%) | 0.23 | 0.08 | 0.13 | 0.22 | 0.13 | 0.13 |
| $CH_2O$ (mg/g glyph) | 28.5 | 31.5 | 47.8 | 38.8 | 41.6 | 45.8 |
| $HCO_2H$ (mg/g glyph) | 70.2 | 90.5 | 100.5 | 96.6 | 98.8 | 99.0 |
| AMPA/MAMPA (%) | 0.02 | 0.01 | 0.01 | 0.01 | 0.01 | 0.01 |
| NMG (mg/g glyph) | 2.6 | 3.6 | 3.6 | 4.2 | 4.7 | 4.7 |
| Pt in Soln. (µg/g glyph.) | 8.64 | 8.60 | 5.22 | 6.96 | 6.91 | 5.20 |
| % of Pt Lost | 0.20 | 0.20 | 0.12 | 0.16 | 0.16 | 0.12 |

TABLE 10

Results Using Catalyst which was not treated with $NaBH_4$

| Run # | 1 | 2 | 3 | 4 | 5 | 6 |
|---|---|---|---|---|---|---|
| Glyphosate (%) | 5.36 | 5.63 | 5.37 | 5.50 | 5.56 | 5.59 |
| NPMIDA (%) | 0.18 | 0.15 | 0.25 | 0.21 | 0.18 | 0.23 |
| $CH_2O$ (%) | 20.9 | 23.6 | 38.4 | 44.2 | 47.7 | 58.3 |
| $HCO_2H$ (%) | 27.8 | 63.8 | 96.5 | 98.4 | 102.2 | 102.0 |
| AMPA/MAMPA (%) | 0.04 | 0.02 | 0.04 | 0.02 | 0.02 | 0.03 |
| NMG (mg/g glyph) | 1.5 | 3.0 | 5.4 | 6.9 | 10.6 | 7.3 |
| Pt in Soln ($\mu$g/g glyph.) | 63.6 | 62.2 | 44.7 | 34.6 | 28.8 | 28.6 |
| % of Pt Lost | 1.30 | 1.34 | 0.92 | 0.73 | 0.61 | 0.61 |

Example 13

Use of Bismuth as a Catalyst-Surface Promoter

A 500 g solution was prepared consisting of $10^{-3}$ M $Bi(NO_3)_3.5H_2O$ in $10^{-3}$ M formic acid solution. This solution was added to 500 g of a 5% formaldehyde solution containing 6.0 g of 5% platinum on an activated carbon support. The solution was stirred at 40° C. under $N_2$ overnight and then filtered with a Buchner funnel. An aliquot was dried and subsequently analyzed by X-ray fluorescence. The catalyst had a loss on drying ("LOD") of 63%. The dry catalyst was found to contain approximately 3% bismuth and 4% platinum.

The following were placed into a 300 ml stainless steel autoclave: 16.4 g of N-(phosphonomethyl)iminodiacetic acid; 4.16 g of an activated carbon catalyst, 0.68 g of the above catalyst consisting of 3% bismuth /4% platinum on its surface, and 179.4 g of water. The reaction was conducted at a pressure of 65 psig, a temperature of 90° C., an oxygen flow rate of 38 ml/min., and a stir rate of 900 rpm. The reaction was allowed to proceed until the N-(phosphonomethyl)iminodiacetic acid was depleted. The product solution was separated from the catalyst via filtration and the solution was neutralized with 6 g of 50% NaOH solution. The catalyst was recycled with no purge through 5 runs. Analysis of the product solution was done for each run. Two controls also were conducted in the same manner as above except that the 0.68 g of the Bi/Pt/carbon catalyst was omitted.

The results are shown in Table 11. The runs having the Bi/Pt/carbon catalyst produced lower levels of formaldehyde, formic acid, and NMG in the product.

Example 14

Depositing a Tin Promoter on a Carbon Support

An activated carbon (20 g) was slurried in about 2 L of water. Next, 0.39 g of $SnCl_2.2H_2O$ was dissolved in 500 g of 0.5% $HNO_3$. The solution was added dropwise to the carbon slurry. After all the solution was added, the slurry was stirred for 2 hours. The pH then was adjusted to 9.5, and the slurry was stirred for a few more hours. Next, the slurry was filtered and washed with a plentiful amount of water until the filtrate reached a constant conductivity. The wet cake was dried at 125° C. under vacuum to give 1% tin on carbon. Following drying, the 1% tin on carbon was calcined in argon at 500° C. for 6 hours.

To deposit platinum onto the carbon support, 5 g of the 1% tin on carbon first was slurried in about 500 ml of water. Then 0.705 g of $H_2PtCl_6$ was dissolved in about 125 ml of water and added dropwise. After all the $H_2PtCl_6$ solution was added, the slurry was stirred for 2.5 hours. The pH then was adjusted to 9.5 with diluted NaOH and stirring was continued for a few more hours. The slurry then was filtered and washed with a plentiful amount of water until the filtrate reached constant conductivity. The wet cake was dried at 125° C. under vacuum.

This technique produced a catalyst comprising 5% platinum and 1% tin on carbon.

Example 15

Depositing an Iron Promoter onto a Carbon Support

Approximately 5 g of activated carbon was slurried in about 500 ml of water. Next, 0.25 g of $FeCl_3.6H_2O$ was dissolved in 75 ml of water. The solution was added dropwise to the carbon slurry. After all the solution was added, the slurry was stirred for two hours. The slurry then was filtered and washed with a plentiful amount of water until the filtrate reached a constant conductivity. The wet cake was dried at 125° C. under vacuum to give 1% iron on carbon. Following drying, the 1% iron on carbon was calcined in argon at about 500° C. for 8 hours.

To deposit platinum onto the surface of the carbon support, 2.5 g of the 1% iron on carbon first was slurried in about 180 ml of water. Then, 0.355 g of $H_2PtCl_6$ was dissolved in about 70 ml of water and added dropwise. After all the solution was added, the slurry was stirred for three more hours. The pH then was adjusted to about 10.0 with diluted NaOH and stirring was continued for a few more

TABLE 11

NPMIDA Oxidation Results Using Pt/Bi/C Catalyst

| | CONTROL #1 | CONTROL #2 | 1ST RUN | 2ND RUN | 3RD RUN | 4TH RUN | 5TH RUN |
|---|---|---|---|---|---|---|---|
| Glyphosate (%) | 5.7 | 5.59 | 5.69 | 5.72 | 5.87 | 5.74 | 5.68 |
| NPMIDA (%) | ND | ND | 0.04 | 0.07 | 0.085 | 0.04 | 0.046 |
| AMPA (%) | 0.034 | 0.031 | 0.015 | 0.009 | 0.008 | DBNQ[1] | DBNQ |
| $CH_2O$ (mg/g glyph. prod.) | 142 | 138 | 28 | 31 | 34 | 38 | 42 |
| $HCO_2H$ (mg/g glyph. prod.) | 56 | 57 | DBNQ | 7 | 14 | 17 | 23 |
| AMPA/MAMPA (%) | 0.047 | 0.041 | 0.021 | 0.014 | 0.013 | 0.014 | 0.013 |
| NMG (mg/g glyph. prod.) | 16.3 | 19.3 | 0.7 | 0.9 | 1.4 | 2.3 | 2.6 |

[1]DBNQ = detectable, but not quantified hours. Next, the slurry was filtered and washed with a plentiful amount of water until the filtrate reached a constant conductivity. The wet cake was dried at 125° C. under vacuum.

This technique produces a catalyst comprising 5% platinum and 1% iron on carbon.

Example 16

Effect of Presence of Noble Metal on the Surface of the Carbon Support

This example shows the advantages of using a carbon support having a noble metal on its surface for effecting the oxidation of N-(phosphonomethyl)iminodiacetic acid rather than a carbon-only catalyst having no noble metal on its surface.

The N-(phosphonomethyl)iminodiacetic acid oxidation reaction was conducted in the presence of a carbon-only catalyst which was deoxygenated using the single-step high-temperature deoxygenation technique #2 described in Example 2. The reaction was carried out in a 300 ml stainless steel reactor using 0.365% catalyst, 8.2% N-phosphonomethyl)iminodiacetic acid, a total reaction mass of 200 g, a pressure of 65 psig, a temperature of 90° C., an agitation rate of 900 rpm, and an oxygen feed rate of 38 ml/min.

Table 12 shows the reaction times (i.e., the time for at least 98% of the N-(phosphonomethyl)iminodiacetic acid to be consumed) of 5 cycles for the carbon-only catalyst. Table 12 also shows the reaction times for the two Pt-on-carbon catalysts in Example 12 over 6 cycles under the reaction conditions described Example 12. As may be seen from Table 12, the deactivation of the carbon-only catalyst per cycle generally tends to be greater (i.e., the reaction times tend to increase more per cycle) than the deactivation of the carbon catalysts which had a noble metal on their surfaces. The deactivation particularly appears to be less where the catalyst has been reduced with $NaBH_4$ after the noble metal was deposited onto the surface. Without being bound by any particular theory, it is believed that the deactivation of the catalyst reduced with $NaBH_4$ was less than the deactivation of the other Pt-on-carbon catalyst because the platinum on the $NaBH_4$ catalyst leached less than the platinum on the other Pt-on-carbon catalyst. See Example 12, Tables 9 & 10.

TABLE 12

Results Using Catalyst which was not treated with $NaBH_4$

| Run # | 1 | 2 | 3 | 4 | 5 | 6 |
|---|---|---|---|---|---|---|
| Run Time for Carbon-Only Catalyst (min.) | 45.4 | 55.0 | 64.4 | 69.8 | 75.0 | |
| Run Time for 5% platinum on Carbon Catalyst which was Reduced w/ $NaBH_4$ (min.) | 35.1 | NA[1] | NA | 35.2 | 35.8 | 35.8 |
| Run Time for 5.23% platinum on Carbon Catalyst (min.) | 40.4 | 42.0 | 44.2 | 44.1 | 44.9 | 52.7 |

[1]Not available due to temperature problems.

Example 17

The Effect of Using a Catalyst Comprising a Noble Metal Alloyed with a Catalyst-Surface Promoter This example shows the advantages of a catalyst comprising platinum alloyed with iron.

1. Catalyst Comprising Platinum Alloyed with Iron

To prepare the catalyst comprising platinum alloyed with iron, approximately 10 grams of an activated carbon was slurried in about 180 ml of water. Next, 0.27 grams of $FeCl_3.6H_2O$ and 1.39 grams of $H_2PtCl_6$ hydrate were co-dissolved in about 60 ml of water. This solution was added dropwise to the carbon slurry over a period of about 30 minutes. During the addition, the pH of the slurry dropped and was maintained at from about 4.4 to about 4.8 using a dilute NaOH solution (i.e., a 1.0 to 2.5 molar solution of NaOH). Afterward, the slurry was stirred for 30 more minutes at a pH of about 4.7. The slurry then was heated under $N_2$ to 70° C. at a rate of about 2° C./min. while maintaining the pH at about 4.7. Upon reaching 70° C., the pH was raised slowly over a period of about 30 minutes to 6.0 with addition of the dilute NaOH solution. The stirring was continued for a period of about 10 min. until the pH became steady at about 6.0. The slurry was then cooled under $N_2$ to about 35° C. Subsequently, the slurry was filtered, and the cake was washed with approximately 800 ml of water 3 times. The cake was then dried at 125° C. under a vacuum. This produced a catalyst containing 5 wt. % platinum and 0.5 wt. % iron on carbon upon heating at 690° C. in 20% $H_2$ and 80% Ar for 1–6 hr.

This catalyst was analyzed via electron microscopy, as described in more detail in Example 19. An image obtained through TEM of the carbon support showed that the alloyed metal particles were highly dispersed and uniformly distributed throughout the carbon support (the white dots represent the metal particles; and the variations in the background intensity are believed to represent the change of the local density of the porous carbon). The average size of the particles was about 3.5 nm, and the average distance between particles was about 20 nm. A high energy resolution X-ray spectra from an individual metal particle of the catalyst showed that both platinum and iron peaks were present (the copper peaks originated from the scattering of the copper grids). Quantitative analysis of the high energy resolution X-ray spectra from different individual metal particles showed that the composition of the particles, within experimental error, did not vary with the size or the location of the metal particles on the catalyst surface.

2. Catalyst in which Platinum was Less Alloyed with Iron

To prepare the Pt/Fe/C catalyst in which the platinum was less alloyed with iron (i.e., this catalyst has less platinum alloyed with iron than does the first catalyst described in this example), the platinum and iron were deposited sequentially onto the surface of the carbon support. Approximately 5 grams of an activated carbon was slurried in about 500 ml of water. The pH was adjusted to about 5.0 with 1N HCl. Next, about 0.25 grams of $FeCl_3.6H_2O$ was dissolved in 75 ml of water. This solution was added dropwise to the carbon slurry over a period of about 60 min. After all the solution was added, the slurry was stirred for about 2 hours. The pH was adjusted to 9.5 with the dilute NaOH solution, and the slurry was stirred for a few more hours. Afterward, the slurry was filtered and washed with a plentiful amount of water. The wet cake was dried at 125° C. under vacuum to produce 1 wt. % iron on carbon. Following drying, this 1 wt. % iron on carbon was reduced with an atmosphere containing 20% $H_2$ and 80% Ar at 635° C. for 1–6 hr. About 2.5 grams of this 1 wt. % iron on carbon was slurried in 250 ml of water. Next, about 0.36 grams of $H_2PtCl_6$ hydrate was dissolved in 65 ml of water, which, in turn, was added dropwise to the slurry over a period of about 60 min. After all the solution was added, the slurry was stirred for 2 hours. The slurry then was filtered and washed with a plentiful amount of water. The cake was then re-slurried in 450 ml of water. After adjusting the pH of the slurry to 9.5 with the dilute NaOH solution, the slurry was stirred for about 45 min. Next, the slurry was filtered and washed once with 450 ml of water. The wet cake was the dried at 125° C. under vacuum. This produced a catalyst containing 5 wt. % platinum and 1 wt. % iron on carbon upon reduction by heating to a temperature of 660° C. in an atmosphere containing 20% $H_2$ and 80% Ar for 1–6 hr.

3. Comparison of the Two Catalysts

These two catalysts were compared while catalyzing the N-(phosphonomethyl)iminodiacetic acid oxidation reaction. The reaction conditions were the same as those in Example 5. Table 13 shows the results. The first catalyst described in this example (i.e., the catalyst comprising a greater amount of platinum alloyed with iron) had greater stability with respect to $CH_2O$ & $HCO_2H$ activities; the second catalyst described in this example (i.e., the catalyst comprising a lower amount of platinum alloyed with iron) deactivated rapidly. In addition, the first catalyst retained almost half of its iron content over 25 cycles, while the second catalyst lost most of its iron in the first cycle.

solution (i.e., a 1.0 to 2.5 molar solution of NaOH), and the slurry was stirred for a few more hours. Next, the slurry was filtered and washed with a plentiful amount of water until the filtrate reached a constant conductivity. The wet cake was dried at 125° C. under vacuum. This produced 0.9 wt. % tin on carbon. About 6 grams of this 0.9 wt. % tin on carbon was slurried in about 500 ml of water. Then approximately 0.23 grams of $Fe(NO_3)_3.9H_2O$ and 0.85 grams of $H_2PtCl_6$ were co-dissolved in about 150 ml of water and added dropwise to the slurry. After all the solution was added, the slurry was stirred for 4 hours, and then filtered to remove excess iron (~80 wt. %). The wet cake was re-slurried in 480 ml of water. After the pH of the slurry was adjusted to 9–10 with the dilute NaOH solution, the slurry was stirred for a few more hours. Next, the slurry was filtered and washed with a plentiful amount of water until the filtrate reached a constant conductivity. The wet cake was dried at 125° C. under vacuum. This produced a catalyst containing 4.9 wt. % Pt, 0.9 wt. % tin and 0.1 wt. % iron on carbon upon high-temperature reduction by heating at 700–750° C. in 20% $H_2$ and 80% Ar for 1–6 hr.

Example 19

Electron Microscopy Characterization of Catalysts

Electron microscopy techniques were used to analyze the size, spatial distribution, and composition of the metal particles of catalysts prepared in Example 17. Before analyzing the catalyst, the catalyst was first embedded in an EM Bed 812 resin (Electron Microscopy Sciences, Fort Wash-

TABLE 13

Comparison of Catalyst Having Pt/Fe Alloy with Catalyst Having Less Pt/Fe Alloy

|  | cycle 1 | cycle 2 | cycle 3 | cycle 4 | cycle 5 | cycle 6 | cycle 7 | cycle 8 | cycle 9 | cycle 10 | cycle 11 | cycle 12 | cycle 13 |
|---|---|---|---|---|---|---|---|---|---|---|---|---|---|
| Alloyed Pt & Fe |  |  |  |  |  |  |  |  |  |  |  |  |  |
| $CH_2O$ (mg/g glyph. prod.) | 10.49 |  | 9.23 |  | 6.04 |  | 4.92 |  | 4.44 |  | 5.08 |  | 5.24 |
| $HCO_2H$ (mg/g glyph. prod.) | 19.91 |  | 29.64 |  | 27.84 |  | 25.62 |  | 27.99 |  | 29.73 |  | 28.95 |
| NMG (mg/g glyph. prod.) | 0.22 |  | 0.44 |  | 0.28 |  | 0 |  | 0 |  | 0 |  | 0 |
| Pt in soln. (μg/g glyph. prod.) | 5.08 |  | 4.87 |  | 3.6 |  | 3.06 |  |  |  |  |  |  |
| % of Fe Lost | 44 |  | 1.9 |  | 1.2 |  | 0.8 |  |  |  |  |  |  |
| Less alloyed Pt & Fe |  |  |  |  |  |  |  |  |  |  |  |  |  |
| $CH_2O$ (mg/g glyph. prod.) | 10.16 | 10.7 | 12.24 | 13.56 | 14.68 |  |  |  |  |  |  |  |  |
| $HCO_2H$ (mg/g glyph. prod.) | 27.23 | 37.72 | 45.01 | 54.57 | 61.14 |  |  |  |  |  |  |  |  |
| NMG (mg/g glyph. prod.) | 0 | 0.98 | 1.23 | 1.77 | 2 |  |  |  |  |  |  |  |  |
| Pt in soln. (μg/g glyph. prod.) | 3.83 | 3.36 | 3.54 | 3.44 | 3.32 |  |  |  |  |  |  |  |  |
| % of Fe Lost | 86 | 3.2 | 1.4 | 1.8 | 1.4 |  |  |  |  |  |  |  |  |

Example 18

Preparation of a Pt/Fe/Sn on Carbon Catalyst

Approximately 10 grams of an activated carbon was slurried in about 90 ml of water. Next, about 0.2 g of $SnCl_2.2H_2O$ was dissolved in 250 ml of 0.025 M HCl. The solution was added dropwise to the carbon slurry. After all the solution was added, the slurry was stirred for 3 hr. The pH then was slowly adjusted to 9.0 with a diluted NaOH ington, Pa.). The resin was then polymerized at about 60° C. for approximately 24 hr. The resulting cured block was ultramicrotomed into slices having a thickness of about 50 μm. These slices were then transferred to 200 mesh copper grids for electron microscopy observation.

High-resolution analytical electron microscopy experiments were carried out in a Vacuum Generators dedicated scanning transmission electron microscope (model no. VG HB501, Vacuum Generators, East Brinstead, Sussex, England) with an image resolution of less than 0.3 nm. The microscope was operated at 100 kV. The vacuum in the specimen chamber area was below about $10^{-6}$ Pa. A digital image acquisition system (ES Vision Data Acquisition System, EmiSpec Sys., Inc., Tempe, Ariz.) was used to obtain high-resolution electron microscopy images. A windowless energy dispersive X-ray spectrometer (Link LZ-5 EDS Windowless Detector, Model E5863, High Wycombe, Bucks, England) was used to acquire high energy resolution X-ray spectra from individual metal particles. Because of its high atomic-number sensitivity, high-angle annular dark-field (HAADF) microscopy was used to observe the metal particles. An electron probe size of less than about 0.5 nm was used to obtain the HAADF images, and a probe size of less than about 1 nm was used to obtain high energy resolution X-ray spectra.

Example 20

Effect of a Supplemental Promoter

This example shows the use and advantages of mixing a supplemental promoter with a carbon-supported, noble-metal-containing oxidation catalyst.

A. Comparison of Effects on a NPMIDA Oxidation Reaction Caused by Mixing a Carbon-Supported Noble-Metal-Containing Catalyst with Various Amounts and Sources of Bismuth Several single batch N-(phosphonomethyl)iminodiacetic acid oxidation reactions were conducted. In each reaction, a different source and a different amount of bismuth were added to the reaction medium. The source of bismuth was either $(BiO)_2CO_3$, $Bi(NO_3)_3.5H_2O$, or $Bi_2O_3$. The amount of bismuth used corresponded to a bismuth to N-(phosphonomethyl)iminodiacetic acid mass ratio of 1:10,000; 1:2,000; or 1:1,000. A control was also conducted wherein no bismuth was added.

Each N-(phosphonomethyl)iminodiacetic acid oxidation reaction was conducted in the presence of a catalyst containing 5% by weight platinum and 0.5% by weight iron (this catalyst was prepared using a method similar to that described in Example 17). The reaction was carried out in a 1000 ml stainless steel reactor (Autoclave Engineers, Pittsburgh, Pa.) using 2.5 g catalyst (0.5% by weight of the total reaction mass), 60.5 g N-(phosphonomethyl)iminodiacetic acid (12.1% by weight of the total reaction mass), 1000 ppm formaldehyde, 5000 ppm formic acid, a total reaction mass of 500 g, a pressure of 110 psig, a temperature of 100° C., and an agitation rate of 1000 rpm. The oxygen feed rate for the first 22 minutes was 392 ml/min., and then 125 ml/min. until the N-(phosphonomethyl)iminodiacetic acid was essentially depleted.

Table 14 shows the results. In all the runs where a bismuth compound was added, the formaldehyde, formic acid, and NMG levels were less than those observed in the control.

TABLE 14

Direct Addition of Various Sources and Amounts of Bismuth

| Amt. & source of Bi Added | Glyph. (%)** | NPMIDA (%)** | $CH_2O$ (mg/g)*** | $HCO_2H$ (mg/g)*** | AMPA/ MAMPA (mg/g)*** | NMG (mg/g)*** | Run Time (min.) |
|---|---|---|---|---|---|---|---|
| 0 (control) | 8.2 | ND | 4.0 | 22.5 | 9.4 | 2.0 | 39.3 |
| 0.0074 g $(BiO)_2CO_3$ (100 ppm*) | 8.1 | ND | 2.6 | 3.8 | 10.9 | ND | 54.1 |
| 0.037 g $(BiO)_2CO_3$ (500 ppm) | 7.8 | ND | 1.8 | 1.4 | 14.5 | ND | 58.2 |
| 0.074 g $(BiO)_2CO_3$ (1000 ppm) | 7.7 | ND | 2.0 | 1.3 | 16.4 | ND | 60.2 |
| 0.0141 g $Bi(NO_3)_3 5H_2O$ (100 ppm) | 8.1 | ND | 2.4 | 3.0 | 11.2 | ND | 53.2 |
| 0.070 g $Bi(NO_3)_3 5H_2O$ (500 ppm) | 7.7 | ND | 1.9 | 1.4 | 14.4 | ND | 58.5 |
| 0.141 g $Bi(NO_3)_3 5H_2O$ (1000 ppm) | 7.6 | ND | 2.0 | 1.2 | 16.2 | ND | 59.2 |
| 0.0067 g $Bi_2O_3$ (100 ppm) | 8.1 | ND | 2.5 | 3.5 | 13.9 | ND | 48 |
| 0.034 g $Bi_2O_3$ (500 ppm) | 7.6 | ND | 2.0 | 1.4 | 15.1 | ND | 58.7 |
| 0.067 g $Bi_2O_3$ (1000 ppm) | 7.6 | ND | 2.0 | 1.2 | 17.3 | ND | 60.6 |

*ppm means a ratio of Bi to N-(phosphonomethyl)iminodiacetic acid equaling 1:1,000,000
**(mass ÷ total reaction mass) × 100%
***mg ÷ grams of glyphosate produced
"ND" means none detected B. Effect of Bismuth Addition on Subsequent NPMIDA Oxidation Batches Contacted with the Catalyst Four 6-run experiments (i.e., during each of the 4 experiments, 6 batch reactions were conducted in sequence) were conducted to determine the effect of (1) the initial bismuth addition on reaction runs subsequent to the initial bismuth addition, and (2) adding additional bismuth in one or more of the subsequent reaction runs.

All 4 experiments were conducted using a catalyst containing 5% by weight platinum and 0.5% by weight iron (this catalyst was prepared using a method similar to that described in Example 17). During each 6-run experiment, the same catalyst was used in each of the 6 runs (i.e., after the end of a run, the reaction product solution was separated and removed from the catalyst, and a new batch of N-(phosphonomethyl)iminodiacetic acid was then combined with the catalyst to begin a new run). The reaction was carried out in a 1000 ml stainless steel reactor (Autoclave Engineers) using 2.5 g catalyst (0.5% by weight of the total reaction mass), 60.5 g N-(phosphonomethyl)iminodiacetic acid (12.1% by weight of the total reaction mass), 1000 ppm formaldehyde, 5000 ppm formic acid, a total reaction mass of 500 g, a pressure of 110 psig, a temperature of 100° C., and an agitation rate of 1000 rpm. The oxygen feed rate for the first 22 minutes was 392 ml/min., and then 125 ml/min. until the N-(phosphonomethyl)iminodiacetic acid was essentially depleted.

In the control experiment, no bismuth was introduced into the reaction zone during any of the 6 runs. In the three other experiments, 0.034 grams of bismuth(III) oxide (i.e., $Bi_2O_3$) were introduced into the reaction medium at the beginning of the first reaction run. In one of these experiments, the bismuth oxide was only introduced into the reaction zone at the beginning of the first reaction run. In another experiment, 0.034 g of bismuth(III) oxide was introduced into the reaction medium at the beginning of the first and fourth reaction runs. In the final experiment, 0.034 g of bismuth (III) oxide was introduced into the reaction medium at the beginning of all 6 reaction runs.

Tables 15, 16, 17, and 18 show the results. The one-time addition of the bismuth oxide (data shown in Table 16) tended to give the same beneficial effects as adding the bismuth oxide every three runs (data shown in Table 17) or even every run (data shown in Table 18).

TABLE 15

Control Experiment: 6-Run NPMIDA Oxidation Reaction with No Bismuth Addition

| Sample (unless otherwise indicated, taken after approx. all NPMIDA consumed) | Run 1 | Run 2 | Run 3 | Run 4 | Run 5 | Run 6 |
|---|---|---|---|---|---|---|
| Glyphosate (%)* | 8.2 | 8.4 | 8.4 | 8.5 | 8.5 | 8.4 |
| NPMIDA (%)* | ND | 0.006 | 0.008 | ND | ND | ND |
| $CH_2O$ (mg/g)** | 3.1 | 2.4 | 2.0 | 2.6 | 3.2 | 3.8 |
| $HCO_2H$ (mg/g)** | 16 | 23 | 22 | 25 | 30 | 40 |
| AMPA/MAMPA (mg/g)** | 7.5 | 6.9 | 6.3 | 5.5 | 5.8 | 5.9 |
| NMG (mg/g)** | 0.5 | 1.7 | 1.4 | 1.6 | 2.8 | 4.9 |
| Time (min.) | 48.5 | 43.5 | 54.5 | 52.8 | 54.1 | 51.7 |

*(mass ÷ total reaction mass) × 100%
**mg ÷ grams of glyphosate produced
"ND" means none detected

TABLE 16

6-Run NPMIDA Oxidation Reaction with Bismuth Addition at Beginning of First Run

| Sample (unless otherwise indicated, taken after approx. all NPMIDA consumed) | Run 1 | Run 2 | Run 3 | Run 4 | Run 5 | Run 6 |
|---|---|---|---|---|---|---|
| Glyphosate (%)* | 7.8 | 8.6 | 8.5 | 8.6 | 8.6 | 7.7 |
| NPMIDA (%)* | ND | ND | ND | ND | ND | 0.005 |
| $CH_2O$ (mg/g)** | 2.4 | 2.7 | 2.1 | 2.6 | 3.1 | 3.9 |
| $HCO_2H$ (mg/g)** | DBNQ | DBNQ | DBNQ | DBNQ | DBNQ | DBNQ |
| AMPA/MAMPA (mg/g)** | 15 | 11 | 10 | 9.9 | 8.6 | 10 |
| NMG (mg/g)** | ND | ND | ND | ND | ND | ND |
| Time (min.) | 60.1 | 62.4 | 64.1 | 62.6 | 66.9 | 62 |

*(mass ÷ total reaction mass) × 100%
**mg ÷ grams of glyphosate produced
"ND" means none detected
"DBNQ" means detected, but not quantified

TABLE 17

6-Run NPMIDA Oxidation Reaction with Bismuth Addition at Beginning of 1st and 4th Runs

| Sample (unless otherwise indicated, taken after approx. all NPMIDA consumed) | Run 1 | Run 2 | Run 3 | Run 4 | Run 5 | Run 6 |
|---|---|---|---|---|---|---|
| Glyphosate (%)* | 7.8 | 8.4 | 8.5 | 8.5 | 8.5 | 8.6 |
| NPMIDA (%)* | ND | ND | ND | ND | ND | ND |
| CH$_2$O (mg/g)** | 2.3 | 2.6 | 2.6 | 3.2 | 3.6 | 3.5 |
| HCO$_2$H (mg/g)** | 3.4 | 3.1 | 3.2 | 2.9 | 3.3 | 3.5 |
| AMPA/MAMPA (mg/g)** | 14 | 11 | 10 | 11 | 9.3 | 8.9 |
| NMG (mg/g)** | ND | ND | ND | ND | ND | ND |
| Time (min.) | 57.4 | 63.2 | 64.3 | 64.9 | 66 | 64.5 |

*(mass ÷ total reaction mass) × 100%
**mg ÷ grams of glyphosate produced
"ND" means none detected

TABLE 18

6-Run NPMIDA Oxidation Reaction with Bismuth Addition at Beginning of Every Run

| Sample (unless otherwise indicated, taken after approx. all NPMIDA consumed) | Run 1 | Run 2 | Run 3 | Run 4 | Run 5 | Run 6 |
|---|---|---|---|---|---|---|
| Glyphosate (%)* | 7.8 | 8.5 | 8.2 | 8.3 | 8.3 | 8.3 |
| NPMIDA (%)* | ND | ND | ND | ND | ND | ND |
| CH$_2$O (mg/g)** | 2.4 | 2.8 | 3.2 | 2.9 | 3.4 | 4.0 |
| HCO$_2$H (mg/g)** | ND | ND | ND | ND | ND | ND |
| AMPA/MAMPA (mg/g)** | 14 | 12 | 11 | 12 | 10 | 9.7 |
| NMG (mg/g)** | ND | ND | ND | ND | ND | ND |
| Time (min.) | 56.4 | 62.4 | 64.8 | 62.8 | 66 | 66.1 |

*(mass ÷ total reaction mass) × 100%
**mg ÷ grams of glyphosate produced
"ND" means none detected

C. Effect of a One-Time Bismuth Addition Over 20 NPMIDA Oxidation Runs Using a Platinum/Iron/Carbon Catalyst Two 20-run experiments were conducted to determine the effect of a one-time bismuth addition on 20 N-(phosphonomethyl)iminodiacetic acid oxidation reaction runs.

Both experiments were conducted using a catalyst containing 5% by weight platinum and 0.5% by weight iron (this catalyst was prepared using a similar method to the method described in Example 17). During each experiment, the same catalyst was used in each of the 20 runs. The reaction was carried out in a 1000 ml stainless steel reactor (Autoclave Engineers) using 2.5 g catalyst (0.5% by weight of the total reaction mass), 60.5 g N-(phosphonomethyl)iminodiacetic acid (12.1% by weight of the total reaction mass), 1000 ppm formaldehyde, 5000 ppm formic acid, a total reaction mass of 500 g, a pressure of 110 psig, a temperature of 100° C., and an agitation rate of 1000 rpm. The oxygen feed rate for the first 22 minutes was 392 ml/min., and then 125 ml/min. until the N-(phosphonomethyl)iminodiacetic acid was essentially depleted. In the control experiment, no bismuth was introduced into the reaction zone during any of the 20 runs. In the other experiment, 0.034 grams of bismuth(III) oxide was introduced into the reaction medium at the beginning of the first reaction run.

FIG. 15 compares the resulting formic acid concentration profiles. The one-time introduction of bismuth into the reaction zone decreased the formic acid concentration over all 20 runs.

D. Effect of a One-Time Bismuth Addition over 30 NPMIDA Oxidation Runs Using a Platinum/Tin/Carbon Catalyst Two 30-run experiments were conducted to determine the effect of a one-time bismuth addition on 30 N-(phosphonomethyl)iminodiacetic acid oxidation reaction runs.

Both experiments were conducted using a catalyst containing 5% by weight platinum and 1% by weight tin (this catalyst was prepared using a method similar to that described in Example 18). During each experiment, the same catalyst was used in each of the 30 runs. Each run was carried out in a 300 ml reactor (made of alloy metal, Hastelloy C, Autoclave Engineers) using 1.35 g catalyst (0.75% by weight of the total reaction mass), 21.8 g N-(phosphonomethyl)iminodiacetic acid (12.1% by weight of the total reaction mass), 1000 ppm formaldehyde, 5000 ppm formic acid, a total reaction mass of 180 g, a pressure of 90 psig, a temperature of 100° C., and an agitation rate of 900 rpm. The oxygen feed rate for the first 26 minutes was 141 ml/min., and then 45 ml/min. until the N-(phosphonomethyl)iminodiacetic acid was essentially depleted. In the control experiment, no bismuth was introduced into the reaction zone during any of the 30 runs. In the other experiment, 0.012 grams of bismuth (III) oxide was introduced into the reaction medium at the beginning of the first reaction run.

Figure 16:
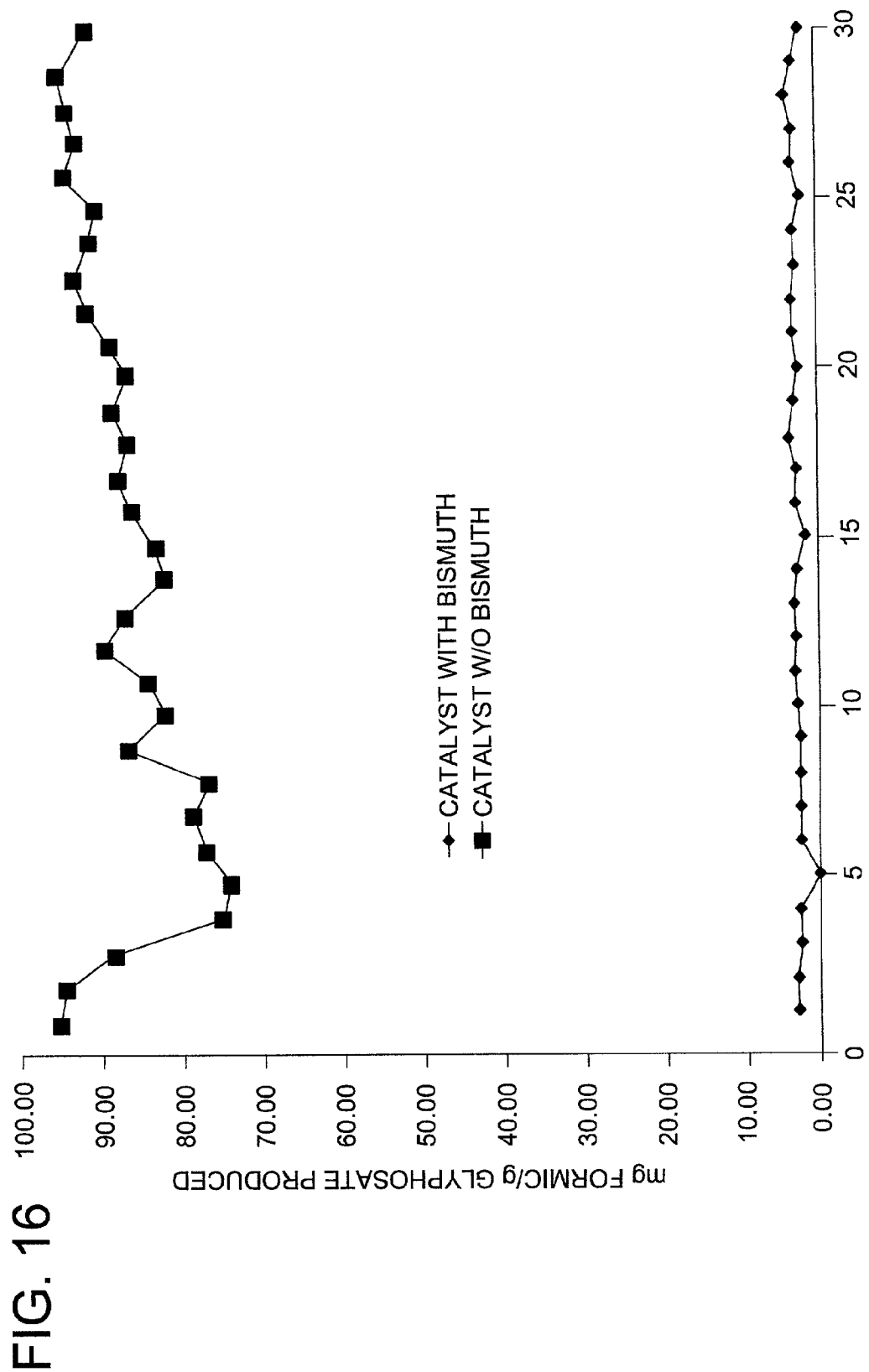
FIG. 16 shows the effect on the formic acid by-product concentration profile over 30 batch reaction runs caused by a one-time introduction of bismuth oxide directly into an N-(phosphonomethyl)iminodiacetic acid oxidation reaction mixture. Here, the catalyst concentration in the reaction mixture was 0.75% by weight, and the catalyst contained 5% by weight platinum and 1% by weight tin.
Figure 17:
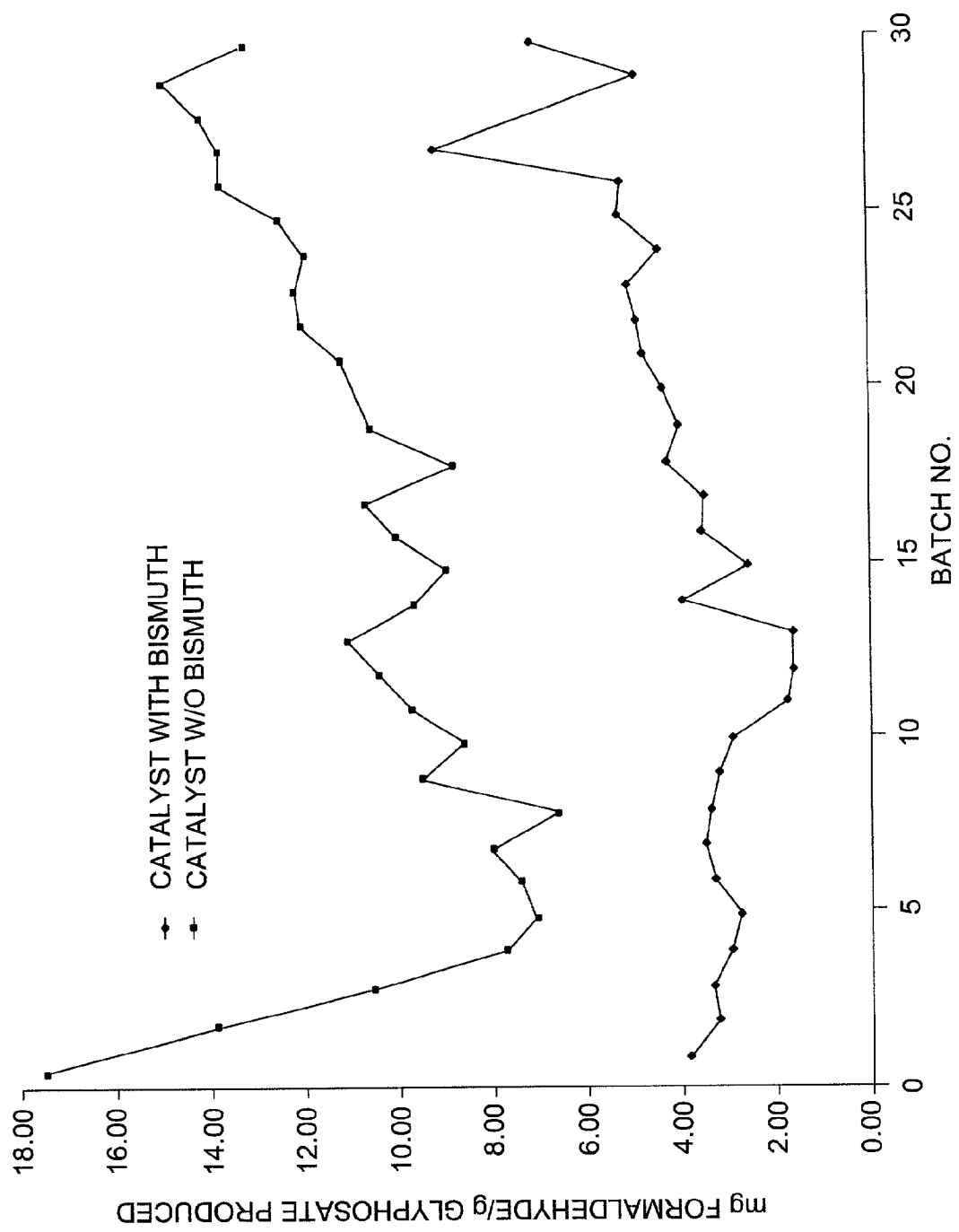
FIG. 17 shows the effect on the formaldehyde by-product concentration profile over 30 batch reaction runs caused by a one-time introduction of bismuth oxide directly into an N-(phosphonomethyl)iminodiacetic acid oxidation reaction mixture. Here, the catalyst concentration in the reaction mixture was 0.75% by weight, and the catalyst contained 5% by weight platinum and 1% by weight tin.
Figure 18:
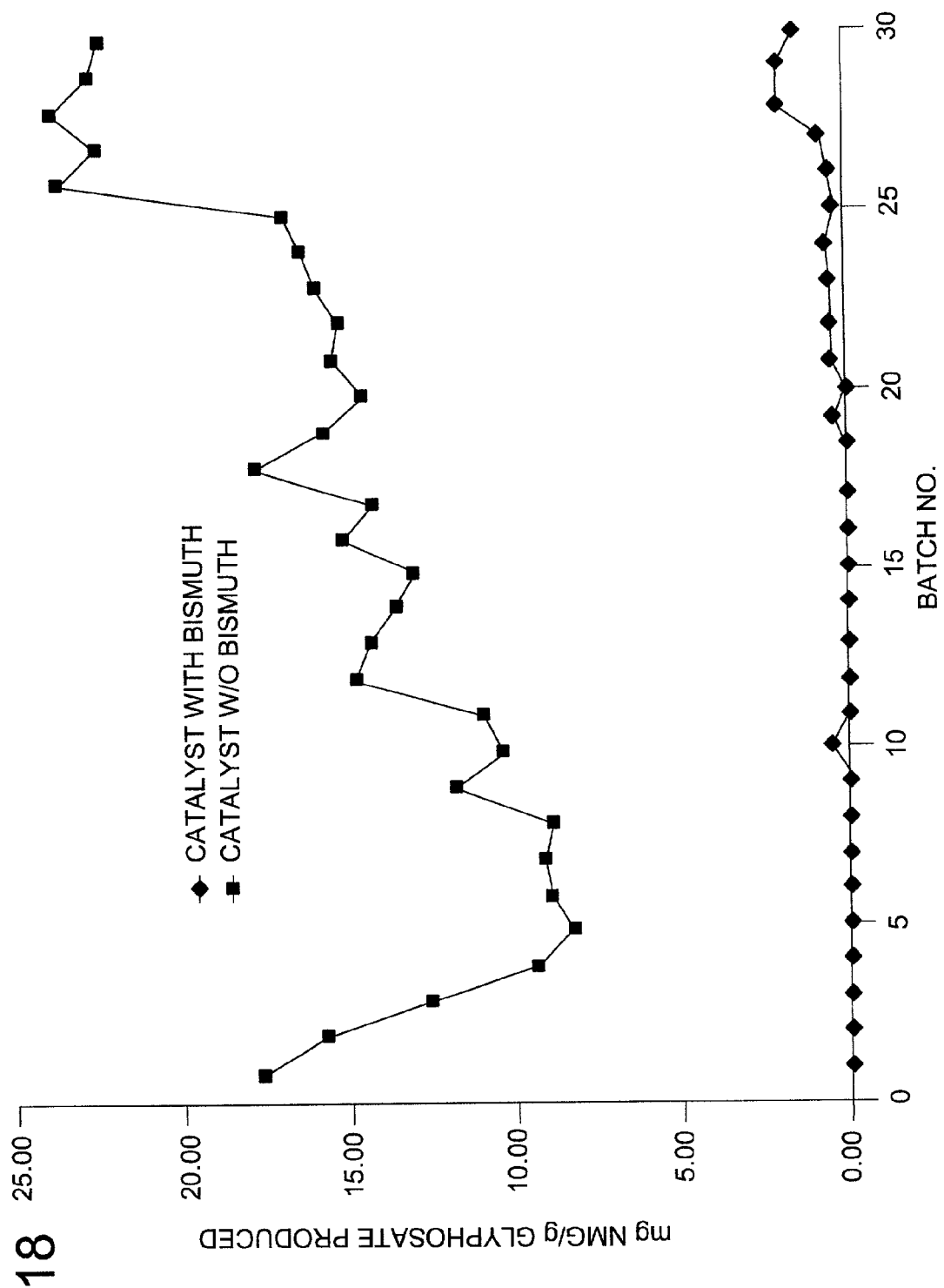
FIG. 18 shows the effect on the N-methyl-N-(phosphonomethyl)glycine (NMG) by-product concentration profile over 30 batch reaction runs caused by a one-time introduction of bismuth oxide directly into an N-(phosphonomethyl) iminodiacetic acid oxidation reaction mixture. Here, the catalyst concentration in the reaction mixture was 0.75% by weight, and the catalyst contained 5% by weight platinum and 1% by weight tin.

FIG. 16 compares the resulting formic acid concentration profiles, FIG. 17 compares the resulting formaldehyde concentration profiles, and FIG. 18 compares the resulting NMG concentration profiles. Even after 30 runs, the one-time introduction of bismuth into the reaction zone decreased the formic acid concentration by 98%, the formaldehyde concentration by 50%, and the NMG concentration by 90%.

E. Effect of Adding Bismuth to a Pt/Fe/C Catalyst that was Previously Used in 132 Batch NPMIDA Oxidation Reactions A 14-run experiment was conducted to determine the effect mixing bismuth with a used Pt/Fe/C catalyst. Before this experiment, the catalyst had been used to catalyze 129 batch N-(phosphonomethyl)iminodiacetic acid oxidation reactions. The fresh catalyst (i.e., the catalyst before it was used in the previous 129 N-(phosphonomethyl)iminodiacetic acid oxidation runs) was prepared using a method similar to the method described in Example 17, and contained 5% by weight platinum and 0.5% by weight iron.

The 14 N-(phosphonomethyl)iminodiacetic acid oxidation reaction runs were carried out in a 300 ml reactor (made of alloy metal, Hastelloy C, Autoclave Engineers) using 0.9 g of spent catalyst (0.5% by weight), 21.8 g N-(phosphonomethyl)iminodiacetic acid (12.1% by weight), 1000 ppm formaldehyde, 5000 ppm formic acid, a total reaction mass of 180 g, a pressure of 90 psig, a temperature of 100° C., and an agitation rate of 900 rpm. The oxygen feed rate for the first 26 minutes was 141 ml/min., and then 45 ml/min. until the N-(phosphonomethyl)iminodiacetic acid was essentially depleted. At the beginning of the 4th run, 0.012 grams of bismuth(III) oxide was introduced into the reaction zone.

Figure 19:
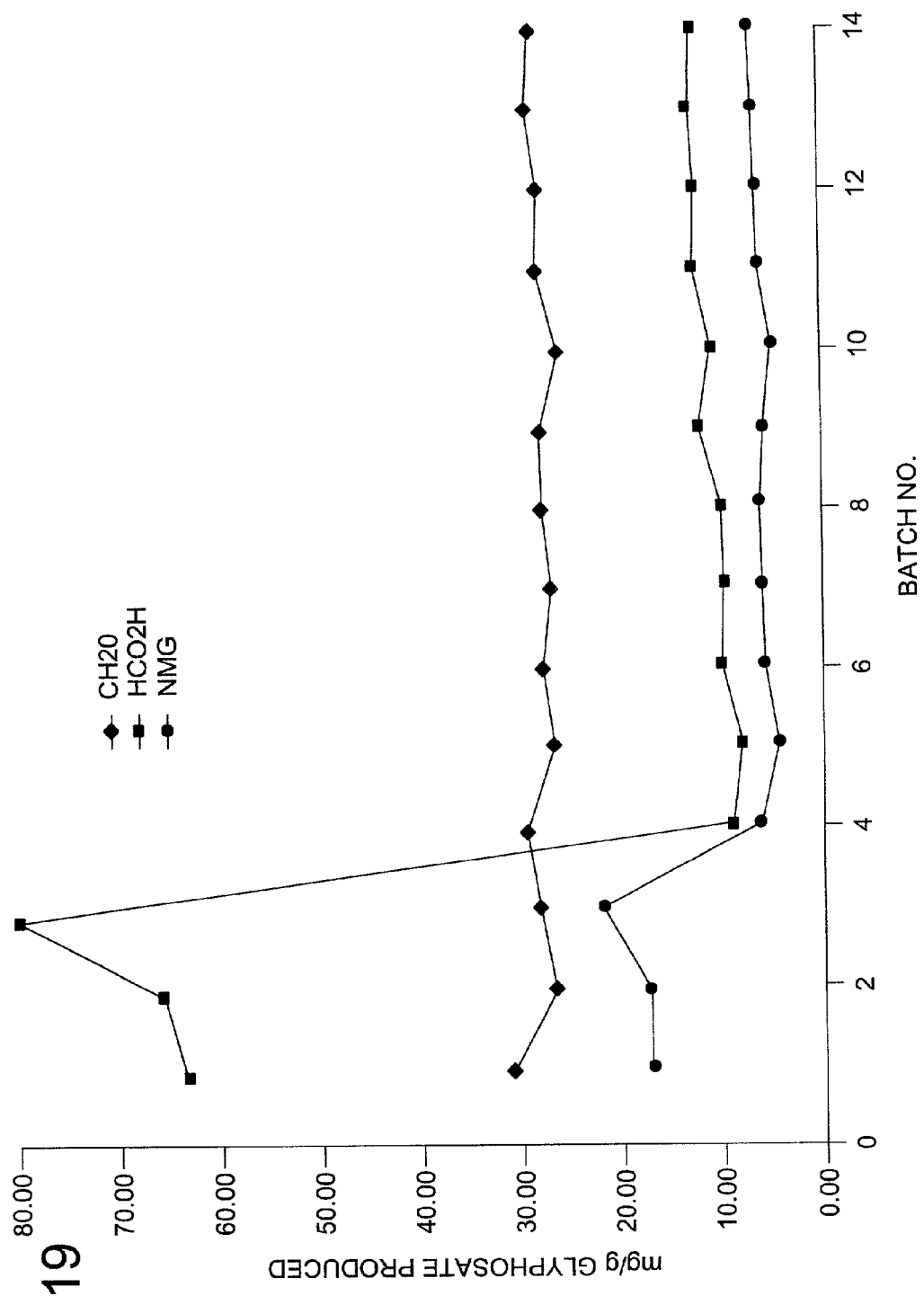
FIG. 19 shows the effect on formic acid, formaldehyde, and N-methyl-N-(phosphonomethyl)glycine (NMG) production during an N-(phosphonomethyl)iminodiacetic acid oxidation reaction caused by mixing bismuth oxide with an oxidation catalyst that had been used in 133 previous batch N-(phosphonomethyl)iminodiacetic acid oxidation reaction runs. Here, the catalyst comprised 5% by weight platinum and 0.5% by weight iron on a carbon support.

FIG. 19 shows the effects that the bismuth addition at the 4th run had on the formic acid, formaldehyde, and NMG by-product production.

F. Effect of Adding Bismuth to a Pt/Sn/C Catalyst that was Previously Used in 30 Batch NPMIDA Oxidation Reactions An 11-run experiment was conducted to determine the effect of mixing bismuth with a used Pt/Sn/C catalyst. The catalyst had previously been used to catalyze 30 batch N-(phosphonomethyl)iminodiacetic acid oxidation reactions. The fresh catalyst (i.e., the catalyst before it was used in the previous 30 N-(phosphonomethyl)iminodiacetic acid oxidation runs) was prepared using a method similar to that described in Example 18, and contained 5% by weight platinum and 1% by weight tin.

The 11 N-(phosphonomethyl)iminodiacetic acid oxidation reaction runs were carried out in a 300 ml reactor (made of alloy metal, Hastelloy C, Autoclave Engineers) using 1.35 g of used catalyst (0.75% by weight of the total reaction mass), 21.8 g N-(phosphonomethyl)iminodiacetic acid (12.1% by weight of the total reaction mass), 1000 ppm formaldehyde, 5000 ppm formic acid, a total reaction mass of 180 g, a pressure of 90 psig, a temperature of 100° C., and an agitation rate of 900 rpm. The oxygen feed rate for the first 26 minutes was 141 ml/min., and then 45 ml/min. until the N-(phosphonomethyl)iminodiacetic acid was essentially depleted. At the beginning of the 4th run, 0.012 grams of bismuth(III) oxide was introduced into the reaction zone.

Figure 20:
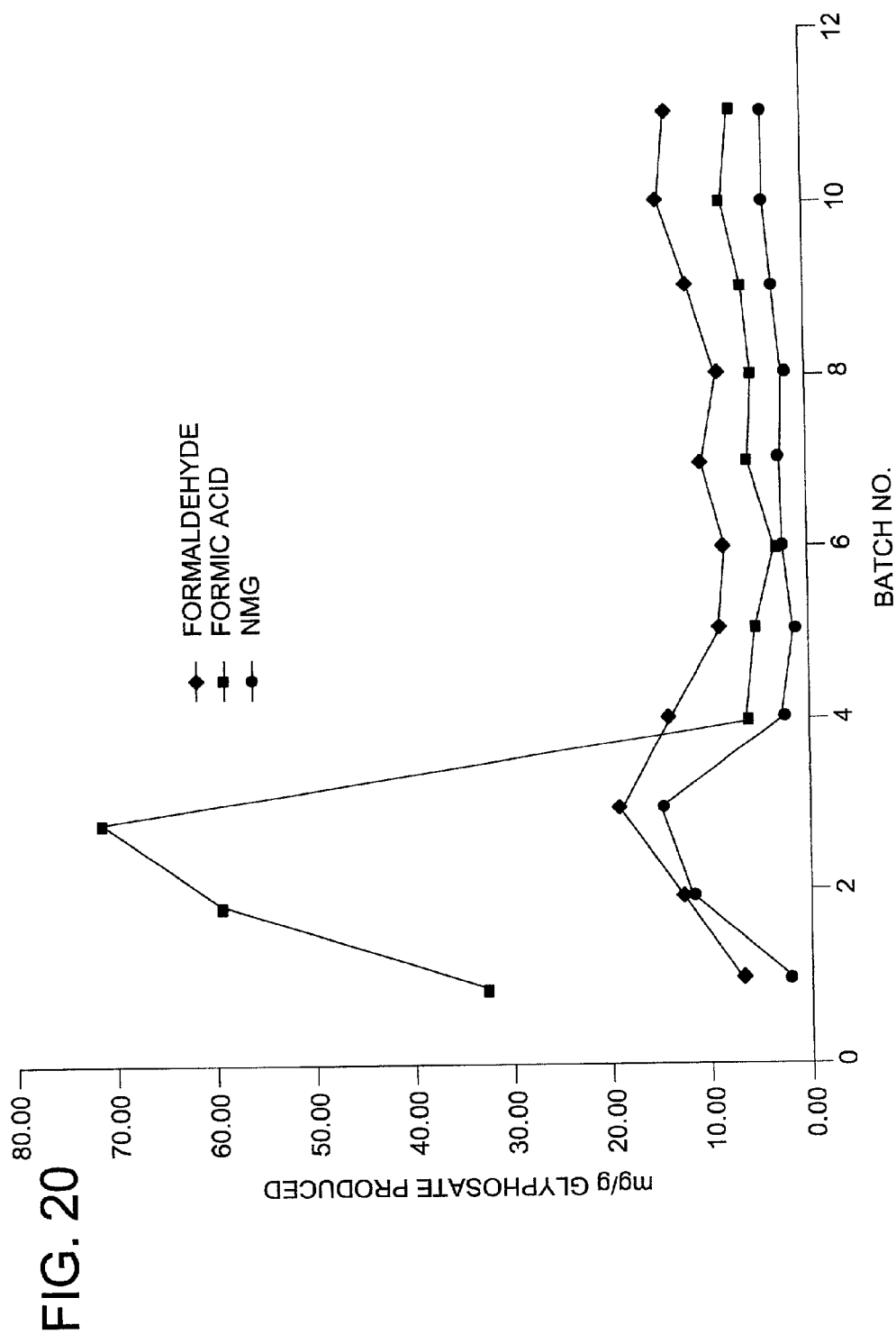
FIG. 20 shows the effect on formic acid, formaldehyde, and N-methyl-N-(phosphonomethyl)glycine (NMG) production during an N-(phosphonomethyl)iminodiacetic acid oxidation reaction caused by mixing bismuth oxide with an oxidation catalyst that had been used in 30 previous batch N-(phosphonomethyl)iminodiacetic acid oxidation reaction runs. Here, the catalyst comprised 5% by weight platinum and 1% by weight tin on a carbon support.

FIG. 20 shows the effects that the bismuth addition at the 4th run had on the formic acid, formaldehyde, and NMG by-product production.

G. Effect of Bismuth Addition on over 100 Subsequent NPMIDA Oxidation Batches Contacted with the Catalyst Two 125-run experiments were conducted to determine the effect of bismuth addition on over 100 subsequent reaction runs using the same catalyst.

Both experiments were conducted using a catalyst containing 5% by weight platinum and 1% by weight tin (this catalyst was prepared using a method similar to that described in Example 18). During each experiment, the same catalyst was used in all the runs. The reaction was carried out in a stirred tank reactor using 0.75% catalyst (by weight of the total reaction mass), 12.1% N-(phosphonomethyl)iminodiacetic acid (by weight of the total reaction mass), a pressure of 128 psig, and a temperature of 100° C. The oxygen feed rate for the first part of each batch reaction (the exact amount of time varied with each batch from 14.9 to 20.3 minutes, with times closer to 14.9 minutes being used for the earlier batches, and times closer to 20.3 minutes being used for the later batches) was 1.3 mg/min. per gram total reaction mass, and then 0.35 mg/min. per gram total reaction mass until the N-(phosphonomethyl)iminodiacetic acid was essentially depleted. A portion of the reaction product from each batch was evaporated off and returned to the reactor as a source of formaldehyde and formic acid to act as sacrificial reducing agents in the next batch reaction. The amounts of formaldehyde and formic acid recycled back to the reactor ranged from 100 to 330 ppm, and from 0 ppm to 2300 ppm (0 to 200 ppm formic acid after 25 batches following the addition of bismuth(III) oxide), respectively.

In the control experiment, no bismuth was introduced into the reaction zone during any of the 125 runs. In the other experiment, the catalyst was first used to catalyze 17 batches of N-(phosphonomethyl)iminodiacetic acid. After catalyzing the 17th batch, the catalyst was substantially separated from the reaction product, and the resulting catalyst mixture was transferred to a catalyst holding tank where 9.0 mg of bismuth(III) oxide per gram of catalyst were introduced into the catalyst mixture. The catalyst was then used to catalyze the oxidation of 107 subsequent batches of N-(phosphonomethyl)iminodiacetic acid.

Figure 21:
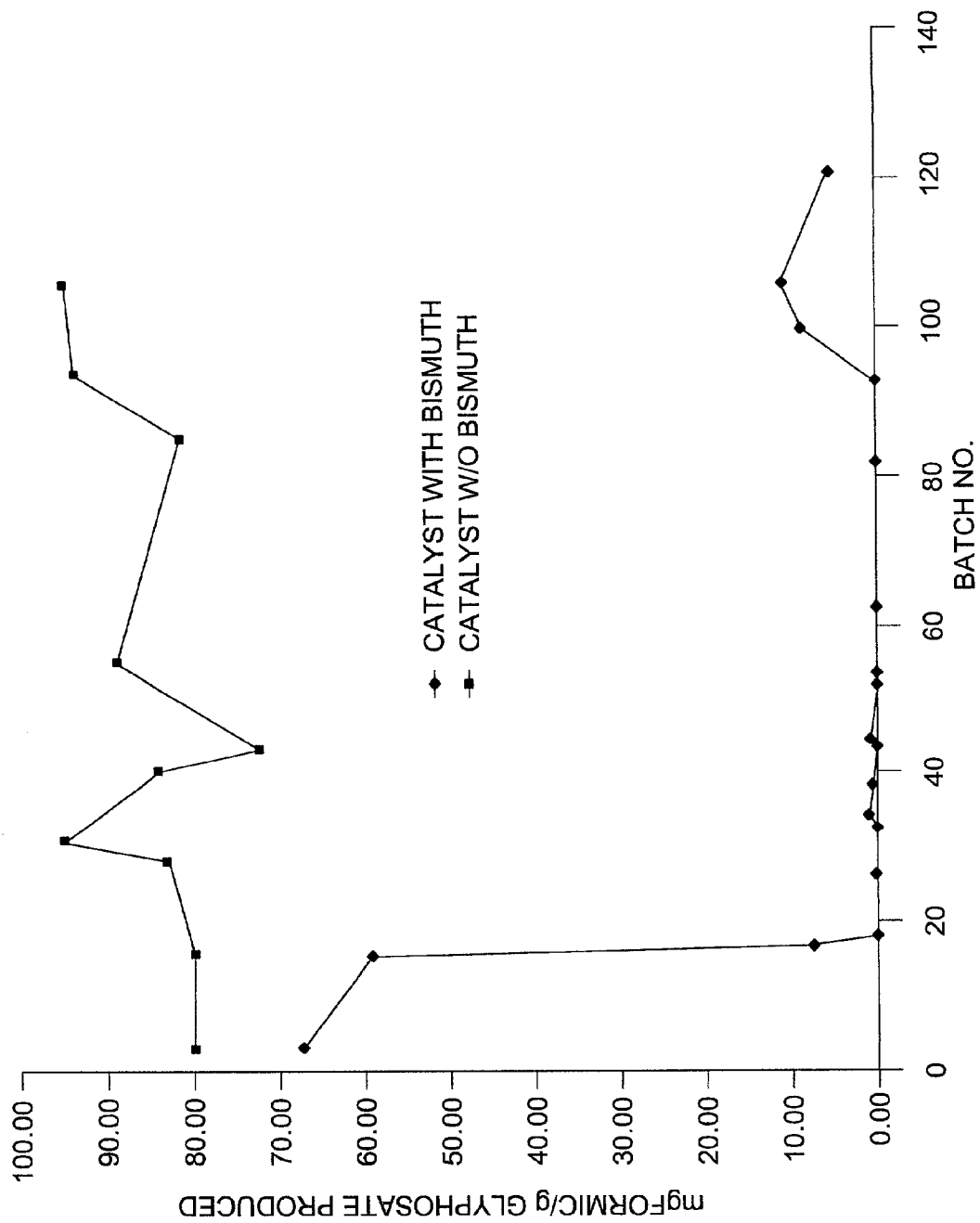
FIG. 21 shows the effect on the formic acid by-product concentration profile over 107 batch reaction runs caused by a one-time mixing of bismuth oxide with a catalyst containing 5% by weight platinum and 1% by weight tin.
Figure 22:
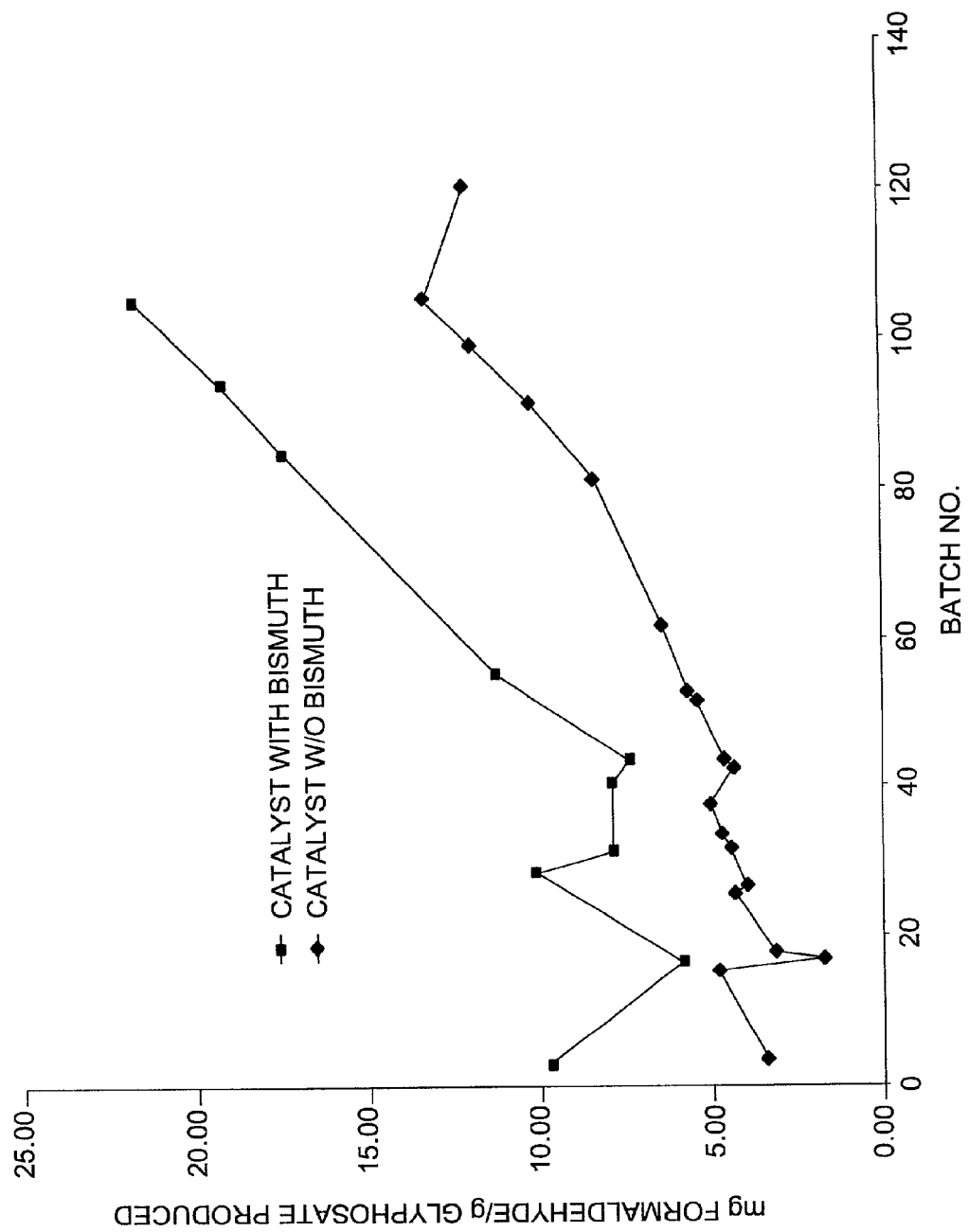
FIG. 22 shows the effect on the formaldehyde by-product concentration profile over 107 batch reaction runs caused by a one-time mixing of bismuth oxide with a catalyst containing 5% by weight platinum and 1% by weight tin.
Figure 23:
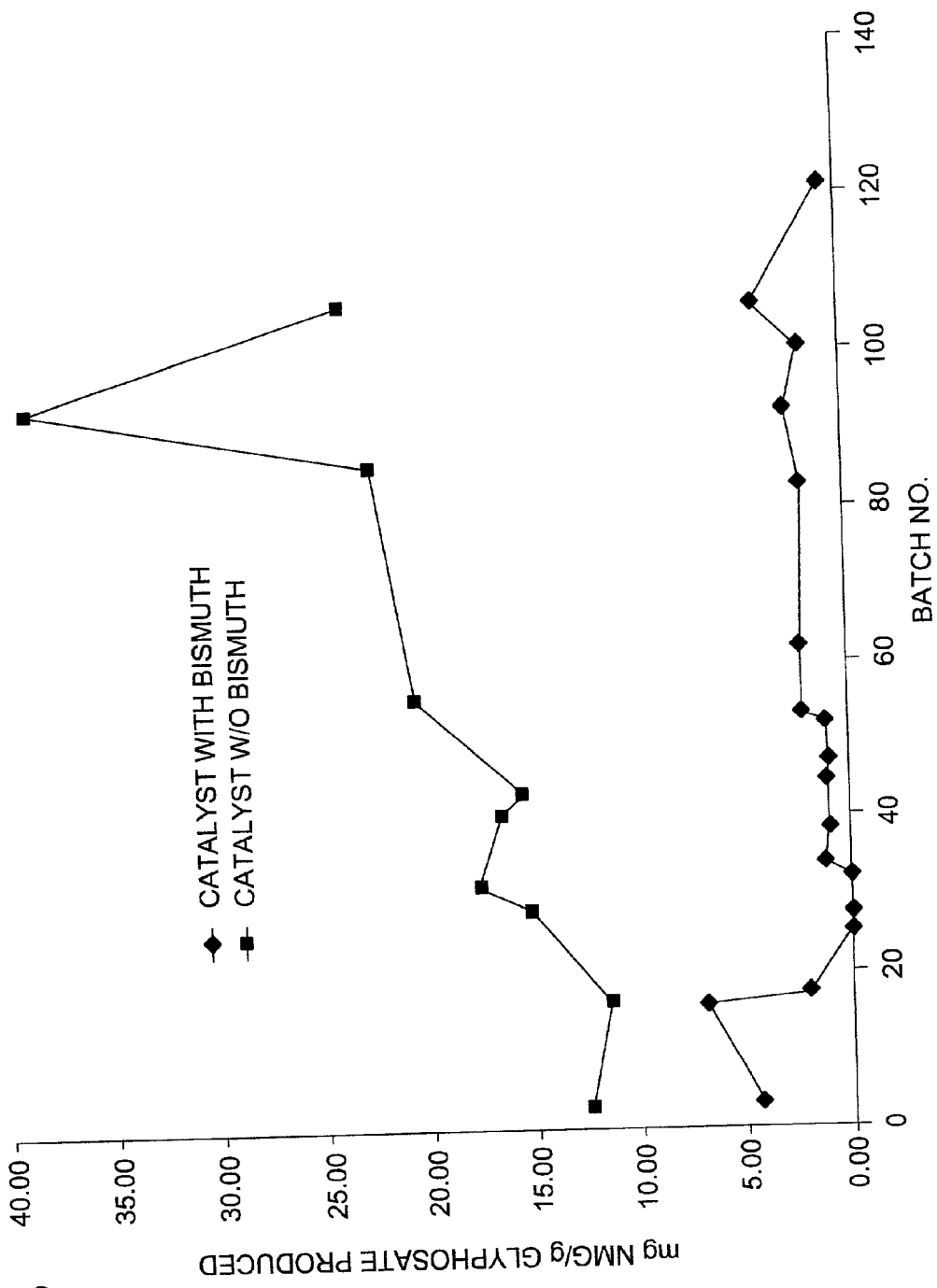
FIG. 23 shows the effect on the N-methyl-N-(phosphonomethyl)glycine (NMG) by-product concentration profile over 107 reaction runs caused by a one-time mixing of bismuth oxide with a catalyst containing 5% by weight platinum and 1% by weight tin.

FIG. 21 compares the resulting formic acid concentration profiles, FIG. 22 compares the resulting formaldehyde concentration profiles, and FIG. 23 compares the resulting NMG concentration profiles. Even after 107 runs, the one-time introduction of bismuth into a mixture with the catalyst decreased the formic acid and NMG concentrations by roughly 90%.

Example 21

Continuous Oxidation of NPMIDA to Glyphosate with Partially Spent Catalyst and the Use of a Supplemental Promoter This example demonstrates the continuous oxidation of N-(phosphonomethyl) iminodiacetic acid ("NPMIDA") to N-(phosphonomethyl)glycine ("glyphosate") in a continuous oxidation reactor system utilizing a previously used catalyst and a supplemental promoter. The experiment was designed to simulate the conditions that might prevail in a first reaction zone, particularly where crystallizer mother liquor containing reaction product is recycled to the reaction zone.

The reaction was performed in a continuous reactor system utilizing a 2-liter Hastelloy C autoclave (Autoclave Engineers Inc., Pittsburgh, Pa.). The reactor was equipped with an agitator having a 1.25" diameter six-blade turbine impeller, which was operated at 1600 RPM. The liquid level in the reactor was monitored using a Drexelbrook Universal III™ Smart Level™, with a teflon-coated sensing element. An internal cooling coil was utilized to control the temperature within the reactor during the course of the reaction.

During operation, the reactor was continuously fed an aqueous slurry feed material containing NPMIDA and a gaseous stream of oxygen. The oxygen was introduced into the reaction medium through a frit located near the impeller. A liquid product stream containing the product N-phosphonomethyl)glycine ("glyphosate") was continuously withdrawn from the reactor through a frit, which allowed any catalyst charged to the reactor to remain in the reaction medium. The product gas stream (containing $CO_2$ and unreacted oxygen) was continuously vented from the reactor headspace.

The reaction was begun by charging an aqueous slurry feed material (1420 grams) and catalyst (29.3 grams or about 2 wt % catalyst in reaction mass) to the reactor. The aqueous slurry feed material contained NPMIDA (7.53% by weight), glyphosate (2.87% by weight), formaldehyde (2127 ppm by weight) and formic acid (3896 ppm by weight). The feed slurry also contained NaCl (about 450 ppm by weight) to mimic low level chloride impurity typically present in commercially available NPMIDA. The catalyst, which was prepared by a method similar to that described in Example 17 above, comprised platinum (5% by weight) and iron (0.5% by weight) on a particulate carbon support. The catalyst had been previously used under conditions similar to those described in Example 20.

Figure 24:
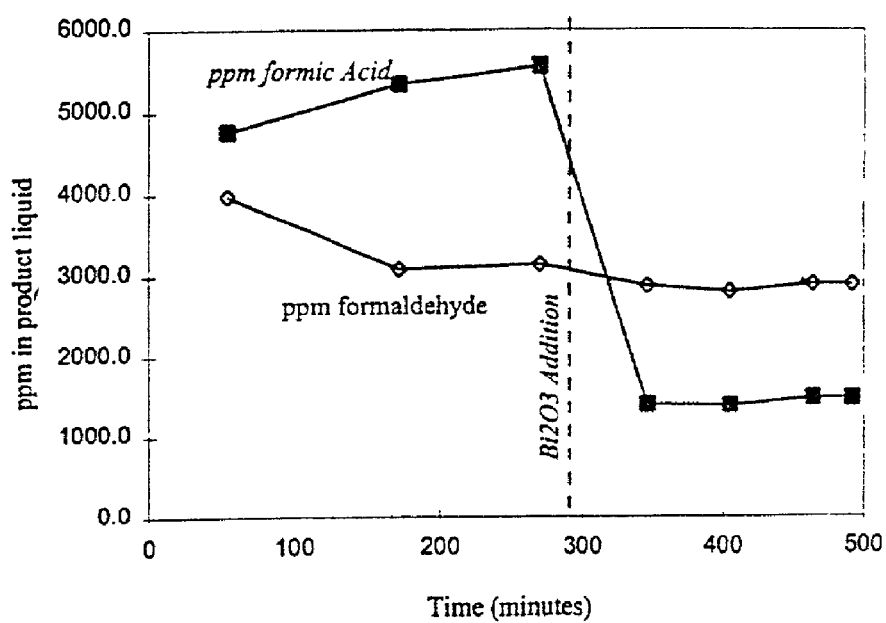
FIG. 24 shows profiles of formaldehyde and formic acid in the product liquid of Example 21.

The reactor was sealed to prevent any liquid inlet or outlet flow. The reaction mixture was heated to about 105° C. and brought to a pressure of about 100 psig with nitrogen. Oxygen flow (1000 sccm) was initiated and the reaction was run with no liquid inlet or outlet flow for about 15 minutes. After this initial 15 minutes, slurry feed (70.4 g/min) was initiated, and reaction liquid was continuously withdrawn to maintain a constant reactor level as indicated by the Drexelbrook level indicator described above. After about 55 minutes, the oxygen flow was lowered slightly to 800 sccm. After about 280 minutes of operation at an oxygen flow of 800 sccm, $Bi_2O_3$ (0.0336 grams) was injected into the reactor as a supplemental promoter. The liquid product was analyzed with HPLC. Analytical results of the continuous oxidation reaction are shown in Table 19 below. Also, FIG. 24 shows profiles for formaldehyde and formic acid in the product liquid while the oxygen flow was 800 sccm.

TABLE 19

Oxidation Results from HPLC for Example 21

| Time (min)[1] | NPMIDA (wt %) | Glyphosate (wt %) | Formaldehyde (ppm) | Formic Acid (ppm) |
|---|---|---|---|---|
| 55 | 0.85 | 7.74 | 3977 | 4758 |
| 172 | 1.43 | 7.48 | 3078 | 5338 |
| 270 | 1.37 | 7.52 | 3137 | 5545 |
| 347 | 2.41 | 6.87 | 2872 | 1395 |
| 405 | 2.42 | 6.97 | 2801 | 1385 |
| 464 | 2.48 | 6.99 | 2887 | 1474 |
| 492 | 2.27 | 7.01 | 2881 | 1472 |

[1]Time after slurry feed started.

Example 22

Continuous Oxidation of NPMIDA to Glyphosate in the Presence of a Previously Used Pt/Fe/C Catalyst This example demonstrates the continuous oxidation of NPMIDA to glyphosate using a previously used heterogeneous particulate catalyst. The experiment was designed to simulate the conditions that might prevail in a first reaction zone of a continuous reactor system, particularly where crystallizer mother liquor containing reaction product is recycled to the reaction zone.

The experiment was conducted in a continuous reactor system similar to that described in Example 21 above. The reaction was begun by charging an aqueous slurry feed material (1424 grams) and a heterogeneous particulate catalyst (29.3 grams or about 2% catalyst by weight of reaction mass) to the reactor. The aqueous slurry feed material contained NPMIDA (7.01% by weight), glyphosate (2.88% by weight), formaldehyde (2099.9 ppm by weight) and formic acid (4690 ppm by weight). The slurry feed also contained NaCl (about 450 ppm by weight) to mimic low level chloride impurity typically present in commercially available NPMIDA. The catalyst was prepared by a method similar to that described in Example 17 above and comprised platinum (5% by weight) and iron (0.5% by weight) on a particulate carbon support. The catalyst had been previously used under conditions similar to those described in Example 20.

Figure 25:
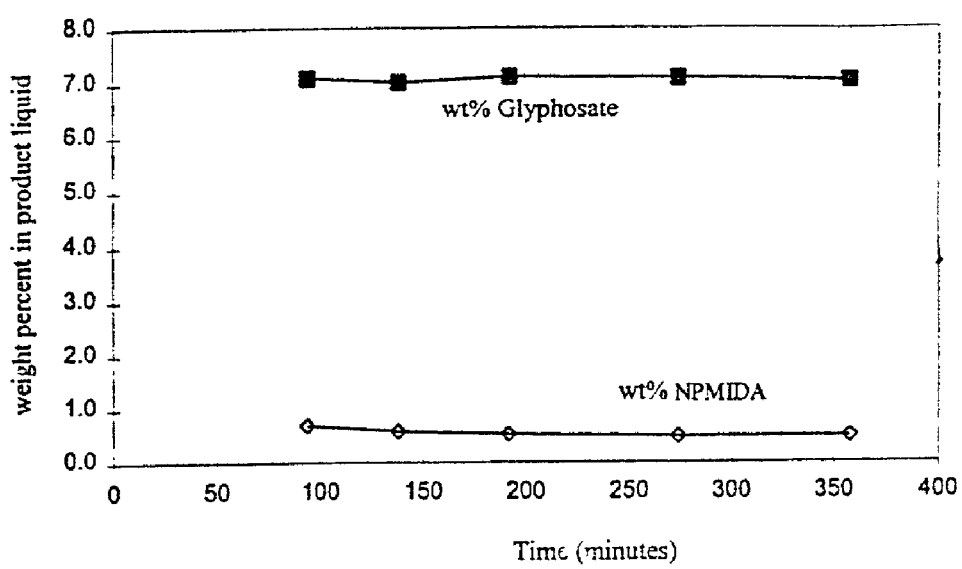
FIG. 25 shows profiles of glyphosate and N-(phosphonomethyl)iminodiacetic acid in the product liquid of Example 22.

The reactor was sealed to prevent any liquid inlet or outlet flow. The reaction mixture was heated to about 107° C. and brought to a pressure of about 100 psig with nitrogen. Oxygen flow (900 sccm) was initiated and the reaction was run with no liquid inlet or outlet flow for about 13 minutes. After this initial 13 minutes, slurry feed (70.4 g/min) was initiated, and reaction liquid was continuously withdrawn to maintain a constant reactor level as indicated by the Drexelbrook level indicator described in Example 21 above. The liquid product was analyzed with HPLC. Analytical results for the continuous oxidation reaction are shown in Table 20 below. Profiles for glyphosate produced and NPMIDA reactant remaining in the product liquid are shown in FIG. 25.

TABLE 20

Oxidation Results for Example 22

| Time (min)[1] | NPMIDA (wt %) | Glyphosate (wt %) |
|---|---|---|
| 94 | 0.67 | 7.10 |
| 138 | 0.55 | 7.02 |
| 192 | 0.50 | 7.12 |
| 274 | 0.46 | 7.09 |
| 358 | 0.47 | 7.06 |

[1]Time after slurry feed started.

Example 23

Continuous Oxidation of NPMIDA to Glyphosate in the Presence of a Pt/Fe/C Catalyst This example demonstrates the continuous oxidation of NPMIDA to glyphosate in the presence of a fresh Pt/Fe/C heterogeneous particulate catalyst (at a relatively low catalyst concentration) over an extended period of time. The experiment was designed to simulate the conditions that might prevail in a first reaction zone, particularly where crystallizer mother liquor containing reaction product is recycled to the reaction zone.

The experiment was conducted in a continuous reactor system similar to that described in Example 21 above. The reaction was begun by charging the reactor with an aqueous slurry feed material (1447 grams) and a heterogeneous particulate catalyst (3.63 grams or about 0.25 wt % catalyst in reaction mass). The aqueous slurry feed material contained NPMIDA (3.45% by weight), glyphosate (1.55% by weight), formaldehyde (1140 ppm by weight) and formic acid (2142 ppm by weight). The feed slurry also contained NaCl (about 450 ppm) to mimic low level chloride impurity typically present in commercially available NPMIDA. The catalyst was prepared by a method similar to that described in Example 17 above and comprised platinum (5% by weight) and iron (0.5% by weight) on a particulate carbon support. The catalyst had not been previously used.

Figure 26:
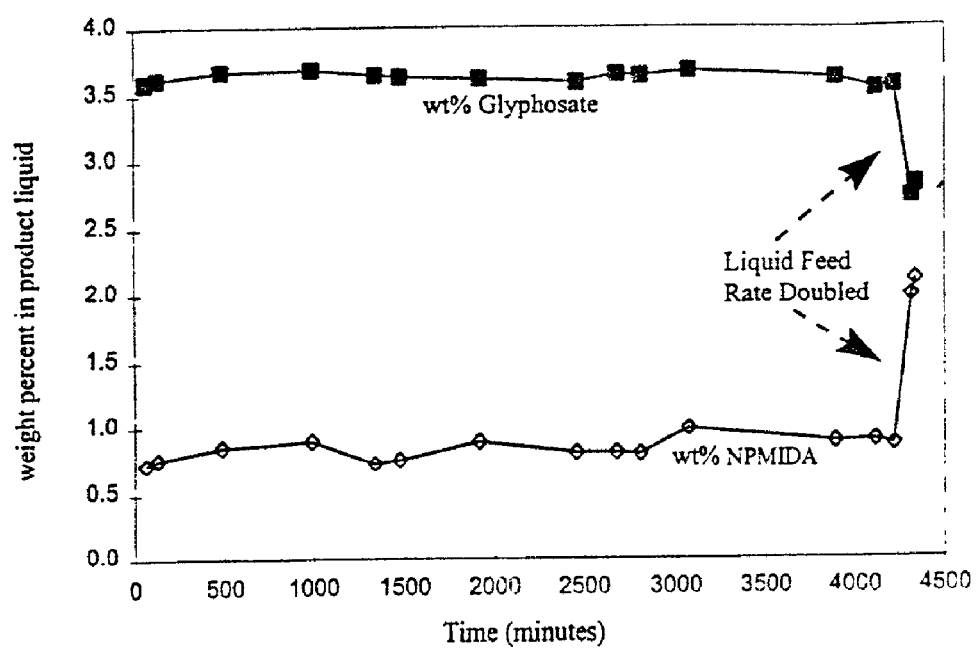
FIG. 26 shows profiles of glyphosate and N-(phosphonomethyl)iminodiacetic acid in the product liquid of Example 23.

The reactor was sealed to prevent any liquid inlet or outlet flow. The reaction mixture was heated to about 100° C. and brought to a pressure of about 100 psig with nitrogen. Oxygen flow (300 sccm) was initiated and the reaction was run with no liquid inlet or outlet flow for about 22 minutes. After the initial 22 minutes, slurry feed (70.4 g/min) was initiated, and reaction liquid was continuously withdrawn to maintain a constant reactor level as indicated by the Drexelbrook level indicator described in Example 21 above. The reactor system was allowed to run for about 4300 minutes, after which time the liquid flow rate was doubled to effectively reduce the reactor liquid residence time by a factor of two. The liquid product was analyzed with HPLC. Analytical results for the continuous oxidation are shown in Table 21 below. Profiles for glyphosate produced and NPMIDA reactant remaining in the product liquid are shown in FIG. 26.

TABLE 21

Oxidation Results for Example 23

| Time (min)[1] | NPMIDA (wt %) | Glyphosate (wt %) |
|---|---|---|
| 66 | 0.72 | 3.59 |
| 130 | 0.76 | 3.61 |
| 488 | 0.85 | 3.67 |
| 994 | 0.89 | 3.68 |
| 1343 | 0.73 | 3.65 |
| 1476 | 0.76 | 3.63 |
| 1918 | 0.89 | 3.61 |
| 2458 | 0.81 | 3.59 |
| 2679 | 0.81 | 3.65 |
| 2807 | 0.80 | 3.63 |
| 3072 | 0.98 | 3.67 |
| 3893 | 0.88 | 3.62 |
| 4113 | 0.89 | 3.54 |
| 4215 | 0.86 | 3.56 |
| 4314 | 1.99 | 2.73 |
| 4334 | 2.11 | 2.82 |

[1]Time after slurry feed started.

Example 24

Continuous Oxidation of NPMIDA to Glyphosate in Two Stirred Tank Reactors in Series This example demonstrates the continuous oxidation of NPMIDA to glyphosate in a continuous reactor system comprising two stirred tank reactors staged in series.

Figure 27:
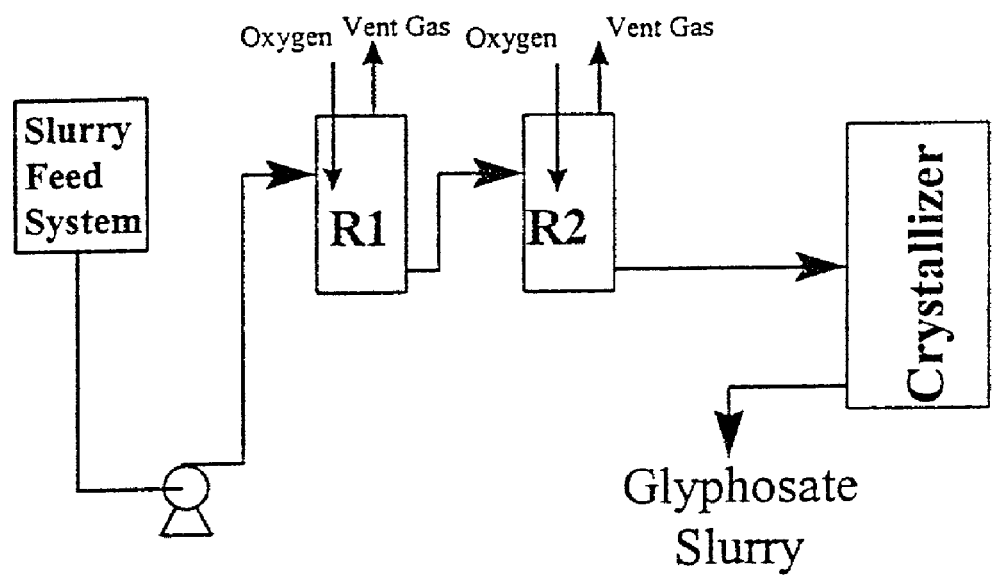
FIG. 27 is a block flow diagram for the continuous reactor system used in Example 24.

Referring to FIG. 27, the experiment was conducted in a continuous reactor system comprising two reactors and a crystallizer. The two reactors (each 1 gallon stainless steel autoclaves from Autoclave Engineers, Inc., Pittsburgh, Pa.) were operated continuously as stirred tank reactors in series. The continuous reactor system was arranged so that aqueous slurry feed material was continuously introduced into the first reaction zone (reactor R1). Liquid effluent was continuously withdrawn from R1 and introduced into the second reaction zone (reactor R2). Liquid effluent was continuously withdrawn from R2 and introduced into the crystallizer for product recovery of a glyphosate slurry. Oxygen was fed independently to each reaction zone, while product gas was vented from each reactor independently. Oxygen gas was introduced into R1 through a frit located near an agitator impeller (2" turbine blade impeller). Oxygen gas was introduced into R2 in the headspace above the liquid level and a DISPERSIMAX type 2.5" impeller was utilized to effectively back-mix the headspace gas into the reaction zone. The temperature of the reaction mass in each reactor was controlled by an internal cooling coil. Liquid effluent was removed from R1 via a frit, which allowed the heterogeneous catalyst to remain in R1. Similarly, liquid effluent was removed from R2 via a frit to maintain the heterogeneous catalyst inside of R2. The reaction mass/volume in each reactor was maintained constant.

The continuous reactor system was started up in a manner similar to that described in Example 21 above in that the reactors were started in batch mode with liquid flow through the system initiated shortly afterward. The feed material was an aqueous slurry containing NPMIDA (about 7.6% by weight), glyphosate (about 2.8% by weight), formaldehyde (about 2200 ppm by weight) and formic acid (about 4500 ppm by weight). A low level of NaCl (about 450 ppm) was also added to the feed to mimic chloride impurity typically present in commercially available NPMIDA. The catalyst was prepared by a method similar to that described in Example 17 above and comprised platinum (5% by weight) and iron (0.5% by weight) on a particulate carbon support. Aqueous slurry feed material and catalyst were charged to each reactor to give about 2% by weight catalyst concentration in each reactor, where the target total reactor masses were 2693 grams and 1539 grams respectively for R1 and R2.

The operating conditions are summarized in Table 22 below. Analytical results for the aqueous slurry feed composition, R1 liquid and gas effluent, and R2 liquid and gas effluent, which were analyzed by HPLC, are shown in Table 23 below.

TABLE 22

Summary of Operating Conditions for Example 24.

| | R1 | R2 |
|---|---|---|
| Catalyst Concentration in reactor: | 2 wt % | 2 wt % |
| Agitator RPM: | 1000 | 1200 |
| Liquid Flow: | 128 ml/min | 128 ml/min |
| Pressure: | 116 psig | 90 psig |
| Oxygen Flow Rate: | ~1840 sccm | ~390 sccm |
| Temperature: | 100° C. | 105° C. |
| Reaction Mass: | 2693 g | 1539 g |
| Impeller Type: | radial (2") | DISPERSIMAX (2.5") |

TABLE 23

Oxidation Results for Example 24.

| Elapsed Time (hrs) | NPMIDA (wt %) | Glyphosate (wt %) | Formaldehyde (ppm) | Formic Acid (ppm) |
|---|---|---|---|---|
| Reactor Feed | | | | |
| | 8.13 | 2.98 | 2348.5 | 5562.6 |
| 1.3 | 7.50 | 2.84 | 2290.0 | 4620.9 |
| 2.5 | 7.45 | 2.74 | 2244.2 | 4515.9 |
| 3.6 | 7.45 | 2.74 | 2244.2 | 4515.9 |
| 4.5 | 7.45 | 2.74 | 2244.2 | 4515.9 |
| 5.5 | 7.79 | 2.84 | 2271.0 | 4590.0 |
| 6.5 | 7.79 | 2.84 | 2271.0 | 4590.0 |

TABLE 23-continued

Oxidation Results for Example 24.

| Elapsed Time (hrs) | NPMIDA (wt %) | Glyphosate (wt %) | Formaldehyde (ppm) | Formic Acid (ppm) |
|---|---|---|---|---|
| 7.5 | 7.57 | 2.81 | 2286.8 | 4584.9 |
| 8.8 | 7.57 | 2.81 | 2286.8 | 4584.9 |
| First Reactor (R1) Outlet | | | | |
| 1.3 | 0.38 | 7.15 | 385.4 | 6115.1 |
| 2.5 | 0.41 | 6.65 | 328.1 | 4297.7 |
| 3.6 | 1.18 | 6.83 | 300.2 | 4841.8 |
| 4.5 | 0.79 | 6.56 | 307.2 | 4746.3 |
| 5.5 | 1.07 | 6.81 | 317.1 | 5193.0 |
| 6.5 | 0.88 | 6.48 | 323.6 | 5045.8 |
| 7.5 | 0.90 | 6.50 | 315.6 | 4976.0 |
| 8.8 | 1.38 | 6.42 | 323.0 | 5305.2 |
| Second Reactor (R2) Outlet | | | | |
| 1.3 | 0.03 | 6.84 | 475.9 | 3680.4 |
| 2.5 | 0.00 | 6.96 | 194.7 | 1048.1 |
| 3.6 | 0.02 | 7.23 | 424.0 | 3702.4 |
| 4.5 | 0.00 | 6.97 | 534.4 | 3006.4 |
| 5.5 | 0.00 | 7.27 | 1025.5 | 6176.5 |
| 6.5 | 0.00 | 6.89 | 1524.2 | 5471.0 |
| 7.5 | 0.01 | 6.97 | 1663.9 | 5468.1 |
| 8.8 | 0.03 | 7.07 | 1883.0 | 5808.2 |

Example 25

Continuous Oxidation of NPMIDA to Glyphosate in Two Stirred Tank Reactors in Series This example demonstrates the continuous oxidation of NPMIDA to glyphosate in a continuous reactor system comprising two stirred tank reactors in series where the liquid effluent from the second reactor is sent to a crystallizer for glyphosate recovery and the resulting mother liquor is recycled from the crystallizer back to the first reactor as part of the reactor feed.

Figure 28:
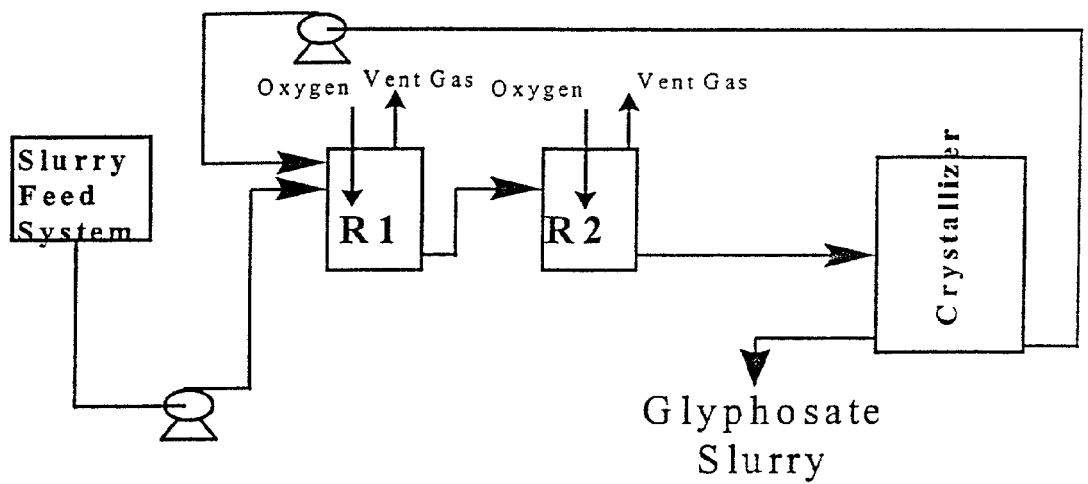
FIG. 28 is a block flow diagram for the continuous reactor system used in Example 25.

Referring to FIG. 28, Example 25 was conducted in a continuous reactor system similar to that described in Example 24 above, except that mother liquor from the crystallizer was recycled back to the first reactor R1. The continuous reactor system was started up in a manner similar to that described in Example 21 above in that the reactors were started in batch mode with liquid flow through the system initiated shortly afterward. The crystallizer (30 L) was initially charged with an aqueous slurry feed material comprising NPMIDA (0.16% by weight), glyphosate (2.0% by weight), formaldehyde (2754 ppm by weight) and formic acid (5637 ppm by weight) and was operated at about 60° C. and 1 atm pressure. The slurry feed system was charged with an aqueous slurry feed material comprising NPMIDA (about 25% by weight). The catalyst used was similar to the heterogeneous particulate catalyst used in Example 24.

Aqueous slurry and catalyst were charged to each reactor to give about 2% by weight catalyst concentration in each reactor, where the target total reactor masses were 2693 grams and 1539 grams respectively for R1 and R2. After the initial batch runs, liquid flow through the system was initiated. Liquid entering R1 comprised the aqueous slurry feed material (about 40 ml/min) and mother liquor recycle (about 80 ml/min) from the crystallizer. The liquid level in each reactor was controlled during the run to maintain a constant reaction mass in each reactor, targeting hydraulic residence times of 21 minutes and 12.2 minutes in R1 and R2, respectively, and giving a total liquid flow through the system of about 120 ml/min.

The operating conditions are summarized in Table 24 below. The liquid product was analyzed with HPLC. Analytical results for the aqueous slurry feed composition, R1 liquid effluent, and R2 liquid effluent are shown in Table 25 below. The elapsed time refers to the time period after which continuous liquid flow was initiated.

TABLE 24

Summary of Operating Conditions for Example 25.

| | R1 | R2 |
|---|---|---|
| Catalyst Concentration in reactor: | 2 wt % | 2 wt % |
| Agitator RPM: | 1015 | 1005 |
| Combined Liquid Flow Through System: | 121 ml/min | 121 ml/min |
| Pressure: | 116 psig | 89 psig |
| Oxygen Flow Rate: | ~1660 sccm | ~280 sccm |
| Temperature: | 100° C. | 106° C. |
| Reaction Mass: | 2545 g | 1592 g |
| Impeller Type: | radial (2") | DISPERSIMAX 2.5" |

TABLE 25

Oxidation Results for Example 25.

| Elapsed Time (hrs) | NPMIDA (wt %) | Glyphosate (wt %) | Formaldehyde (ppm) | Formic Acid (ppm) |
|---|---|---|---|---|
| First Reactor (R1) Outlet | | | | |
| 1.3 | 1.50 | 6.99 | 849.8 | 3202.0 |
| 2.9 | 0.45 | 8.16 | 1053.5 | 2789.3 |
| 4.1 | 0.62 | 8.40 | 1199.4 | 3178.0 |
| 5.0 | 0.65 | 8.07 | 1240.8 | 3348.6 |
| 6.1 | 1.21 | 7.51 | 1294.7 | 3701.1 |
| Second Reactor (R2) Outlet | | | | |
| 1.3 | 2.11 | 6.50 | 374.2 | 1682.3 |
| 2.9 | 0.27 | 8.02 | 501.0 | 2171.4 |
| 4.1 | 0.15 | 8.55 | 451.0 | 2678.0 |
| 5.0 | 0.12 | 8.49 | 564.4 | 3107.5 |
| 6.1 | 0.19 | 8.02 | 577.3 | 3505.7 |

Example 26

Continuous Oxidation of NPMIDA to Glyphosate in the Presence of a Pt/Sn/C Catalyst This example demonstrates the continuous oxidation of NPMIDA to glyphosate in the presence of a Pt/Sn/C heterogeneous particulate catalyst in a stirred tank reactor. The experiment was designed to simulate conditions that might prevail in a second reaction zone of a continuous reactor system.

The experiment was conducted in a continuous reactor system comprising a 500 ml Hastelloy C autoclave (Autoclave Engineers, Inc., Pittsburgh, Pa.). The reactor was equipped with an agitator having a 1.25" diameter radial six-blade turbine impeller. The liquid level in the reactor was monitored using a level indicator similar to that described in Example 21 above. An internal cooling coil was utilized to control the temperature within the reactor during the course of the reaction.

During operation, the reactor was continuously fed a gaseous stream of oxygen and an aqueous slurry feed material containing NPMIDA. The oxygen was introduced into the reaction medium through a frit located near the impeller. A liquid product stream containing glyphosate product was continuously withdrawn from the reactor through a frit, which allowed any catalyst charged to the reactor to remain in the reaction medium. The withdrawn liquid product stream was mixed in-line with a basic solution capable of dissolving glyphosate. The product gas stream (containing $CO_2$ and unreacted oxygen) was continuously vented from the reactor headspace.

The continuous reactor system was started up in a manner similar to that described in Example 21 above in that the reactor was started in batch mode with liquid flow through the system initiated shortly afterward. The aqueous slurry feed material comprised NPMIDA (2.46% by weight), glyphosate (3.72% by weight), formaldehyde (1381 ppm by weight) and formic acid (6485 ppm by weight). The catalyst was prepared by a method similar to that described in Example 14 above and comprised platinum (5% by weight) and tin (1.0% by weight) on a particulate carbon support.

The operating conditions are summarized in Table 26 below. The liquid product was analyzed with HPLC. Analytical data from the oxidation run are shown in Table 27 below.

TABLE 26

Summary of Operating Conditions for Example 26.

| | |
|---|---|
| Catalyst Concentration in Reaction Mass: | 1 wt % |
| Agitator RPM: | 1000 |
| Liquid Flow: | 30.8 ml/min |
| Pressure: | 100 psig |
| Gas Flow Rate: | 270 sccm |
| Temperature: | 100° C. |
| Reaction Mass: | 300 g |

TABLE 27

Oxidation Results for Example 26.

| Feed Composition | | |
|---|---|---|
| — | NPMIDA (wt %) | Glyphosate (wt %) |
| — | 2.46 | 3.72 |
| Reactor Effluent | | |
| Elapsed Time (mins) | NPMIDA (wt %) | Glyphosate (wt %) |
| 120 | 0.07 | 5.47 |
| 1200 | 0.09 | 5.58 |
| 2500 | 0.12 | 5.45 |
| 3500 | 0.15 | 5.47 |

Example 27

Continuous Oxidation of NPMIDA to Glyphosate in the Presence of a Pt/Sn/C Catalyst This example demonstrates the continuous oxidation of NPMIDA to glyphosate in the presence of a Pt/Sn/C heterogeneous particulate catalyst in a stirred tank reactor. The experiment was designed to simulate conditions that might prevail in a second reaction zone of a continuous reactor system. Also, the oxygen flow rate was varied to illustrate the impact of various oxygen flow rates on conversion.

The experiment was conducted in a continuous reactor system similar to the reactor system described in Example 26 above. During operation, the reactor was continuously fed a gaseous stream of oxygen and an aqueous slurry feed material containing NPMIDA. The oxygen was introduced into the reaction medium through a frit located near the impeller. A liquid product stream containing glyphosate product was continuously withdrawn from the reactor through a frit, which allowed any catalyst charged to the reactor to remain in the reaction medium. The withdrawn liquid product stream was mixed in-line with a basic solution capable of dissolving glyphosate. The product gas stream (containing $CO_2$ and unreacted oxygen) was continuously vented from the reactor headspace.

The continuous reactor system was started up in a manner similar to that described in Example 21 above in that the reactor was started in batch mode with liquid flow through the system initiated shortly afterward. The aqueous slurry feed material comprised NPMIDA (about 2.8% by weight), glyphosate (about 4.2% by weight), formaldehyde (about 1425 ppm by weight) and formic acid (about 6570 ppm by weight). The catalyst was prepared by a method similar to that described in Example 14 above and comprised platinum (5% by weight) and tin (1.0% by weight) on a particulate carbon support.

The operating conditions are summarized in Table 28 below. During the course of this experiment, the oxygen flow rate to the reactor was ramped up and ramped back down over the range of from 75 to 300 sccm. The liquid product was analyzed with HPLC. Analytical data from the continuous oxidation are shown in Table 29 below.

TABLE 28

Operating Conditions for Example 27

| | |
|---|---|
| Catalyst Concentration in reactor: | 1 wt % |
| Agitator RPM: | 1000 |
| Liquid Flow: | 30 ml/min |
| Pressure: | 100 psig |
| Oxygen Flow Rate: | variable (75–300 sccm) |
| Temperature: | 100° C. |
| Reaction Mass: | 300 g |
| Impeller Type: | radial (1.25") |

TABLE 29

Oxidation Results for Example 27

| Elapsed Time (hrs) | NPMIDA (wt %) | Glyphosate (wt %) | Formaldehyde (ppm) | Formic Acid (ppm) | O2 Flow (sccm) |
|---|---|---|---|---|---|
| Feed Composition | | | | | |
|  | 2.83 | 4.17 | 1425.1 | 6569.8 |  |
| Reactor Outlet Composition | | | | | |
| 0.0 | 1.1 | 4.59 | 1699.5 | 5463.1 | 74.7 |
| 0.4 | 1.8 | 4.86 | 1543.7 | 6067.0 | 49.7 |
| 0.7 | 1.98 | 4.74 | 1431.7 | 6020.5 | 49.8 |
| 1.0 | 2.02 | 4.90 | 1478.1 | 6105.2 | 52.7 |
| 1.4 | 1.97 | 4.80 | 1474.0 | 6209.0 | 54.7 |
| 1.7 | 1.91 | 4.73 | 1441.3 | 5806.0 | 54.7 |
| 2.0 | 1.67 | 4.93 | 1588.8 | 6006.9 | 74.7 |
| 2.4 | 1.54 | 5.03 | 1590.2 | 6135.3 | 74.7 |
| 2.7 | 1.63 | 5.20 | 1625.7 | 6280.1 | 74.7 |
| 3.0 | 1.64 | 5.19 | 1591.5 | 6015.1 | 74.8 |
| 3.4 | 1.61 | 5.00 | 1547.8 | 5834.7 | 74.7 |
| 3.7 | 1.61 | 5.12 | 1541.0 | 5864.8 | 74.7 |
| 4.0 | 1.58 | 5.15 | 1566.9 | 5791.0 | 74.7 |
| 4.4 | 1.61 | 5.23 | 1565.6 | 6274.6 | 74.7 |
| 4.7 | 0.66 | 6.01 | 2099.7 | 6337.5 | 149.8 |
| 5.0 | 0.51 | 6.20 | 2109.3 | 6036.9 | 149.6 |
| 5.4 | 0.46 | 5.81 | 1976.8 | 5688.5 | 149.8 |
| 5.7 | 0.47 | 6.04 | 2094.3 | 5849.7 | 149.8 |
| 6.0 | 0.45 | 6.04 | 2109.3 | 5785.5 | 149.8 |
| 6.4 | 0.45 | 6.15 | 2157.1 | 6101.1 | 149.8 |
| 6.7 | 0.41 | 5.70 | 2016.4 | 5489.1 | 149.8 |
| 7.0 | 0.38 | 5.38 | 1907.1 | 5213.1 | 149.8 |
| 7.4 | 0.41 | 5.79 | 2056.0 | 5531.4 | 149.8 |
| 7.7 | 0.44 | 6.26 | 2230.9 | 5949.5 | 149.8 |
| 8.0 | 0.35 | 6.43 | 2337.4 | 6083.4 | 166.0 |
| 8.4 | 0.48 | 6.09 | 2356.6 | 6147.6 | 210.6 |
| 8.7 | 0.33 | 6.37 | 2665.3 | 6464.5 | 224.9 |
| 9.0 | 0.34 | 6.24 | 2684.4 | 6308.8 | 224.9 |
| 9.4 | 0.36 | 6.30 | 2741.8 | 6412.6 | 224.9 |
| 9.7 | 0.19 | 6.58 | 2680.3 | 6340.2 | 224.7 |
| 10.0 | 0.22 | 6.54 | 2530.1 | 6367.5 | 224.7 |
| 10.4 | 0.20 | 6.52 | 2560.1 | 6256.9 | 224.7 |
| 10.7 | 0.18 | 5.51 | 2163.9 | 5241.8 | 224.7 |
| 11.0 | 0.22 | 6.37 | 2502.7 | 6202.2 | 224.7 |
| 11.4 | 0.23 | 6.73 | 2648.9 | 6449.5 | 224.7 |
| 11.7 | 0.20 | 6.35 | 2517.8 | 6131.2 | 224.7 |
| 12.0 | 0.16 | 5.11 | 1987.7 | 4889.4 | 224.7 |
| 12.4 | 0.20 | 6.04 | 2430.3 | 5877.1 | 224.7 |
| 12.7 | 0.13 | 6.67 | 2777.3 | 6276.0 | 299.7 |
| 13.0 | 0.13 | 6.73 | 2844.3 | 6349.8 | 299.7 |
| 13.4 | 0.15 | 6.61 | 2808.8 | 6204.9 | 299.7 |
| 13.7 | 0.08 | 5.57 | 2323.8 | 5144.8 | 299.7 |
| 14.0 | 0.10 | 6.61 | 2704.9 | 6215.9 | 299.8 |
| 14.4 | 0.14 | 6.80 | 2774.6 | 5810.1 | 299.8 |
| 14.7 | 0.13 | 6.89 | 2845.6 | 6147.6 | 299.8 |
| 15.0 | 0.12 | 6.86 | 2871.6 | 6232.3 | 299.8 |
| 15.3 | 0.11 | 6.53 | 2745.9 | 5874.3 | 299.8 |
| 15.7 | 0.13 | 6.28 | 2668.0 | 5654.4 | 299.8 |
| 16.0 | 0.15 | 6.86 | 2923.5 | 6360.7 | 299.8 |
| 16.3 | 0.16 | 6.86 | 2970.0 | 6702.2 | 299.8 |
| 16.7 | 0.17 | 6.57 | 2874.3 | 6459.0 | 224.8 |
| 17.0 | 0.23 | 6.53 | 2789.6 | 6508.2 | 224.8 |
| 17.3 | 0.24 | 6.57 | 2822.4 | 6403.0 | 224.8 |
| 17.7 | 0.25 | 6.63 | 2822.4 | 6580.2 | 224.8 |
| 18.0 | 0.23 | 6.39 | 2736.3 | 6385.3 | 224.8 |
| 18.3 | 0.22 | 6.19 | 2668.0 | 6189.9 | 224.8 |
| 18.7 | 0.23 | 6.53 | 2811.5 | 6546.5 | 224.8 |
| 19.0 | 0.24 | 6.52 | 2792.4 | 6445.4 | 224.8 |
| 19.3 | 0.24 | 6.20 | 2655.7 | 6138.0 | 224.8 |
| 19.7 | 0.35 | 6.49 | 2752.7 | 6278.7 | 224.8 |
| 20.0 | 0.48 | 6.23 | 2572.4 | 6460.4 | 149.8 |
| 20.3 | 0.53 | 6.15 | 2513.7 | 6030.1 | 149.8 |
| 20.7 | 0.50 | 6.34 | 2542.4 | 6143.5 | 149.8 |
| 21.0 | 0.51 | 6.31 | 2527.3 | 6113.4 | 149.8 |
| 21.3 | 0.48 | 6.31 | 2527.3 | 6050.6 | 149.8 |
| 21.7 | 0.48 | 6.42 | 2523.2 | 5885.3 | 149.8 |
| 22.0 | 0.46 | 6.16 | 2430.3 | 5655.8 | 149.8 |
| 22.3 | 0.48 | 6.38 | 2521.9 | 6032.8 | 149.8 |
| 22.7 | 0.45 | 6.12 | 2426.2 | 5695.4 | 149.8 |

TABLE 29-continued

Oxidation Results for Example 27

| Elapsed Time (hrs) | NPMIDA (wt %) | Glyphosate (wt %) | Formaldehyde (ppm) | Formic Acid (ppm) | O2 Flow (sccm) |
|---|---|---|---|---|---|
| 23.0 | 0.46 | 6.26 | 2480.9 | 5868.9 | 149.8 |
| 23.3 | 1.18 | 6.20 | 2117.5 | 6220.0 | 74.8 |
| 23.7 | 1.30 | 5.87 | 1956.3 | 5970.0 | 74.8 |
| 24.0 | 1.61 | 5.68 | 1916.7 | 5909.9 | 74.8 |
| 24.3 | 1.50 | 5.61 | 1795.1 | 5720.0 | 74.8 |
| 24.7 | 1.61 | 5.85 | 1847.0 | 5862.0 | 74.8 |
| 25.0 | 1.68 | 5.87 | 1908.5 | 6599.8 | 74.8 |
| 25.3 | 1.69 | 5.83 | 1868.9 | 6653.0 | 74.8 |
| 25.7 | 1.60 | 5.57 | 1773.2 | 6460.4 | 74.8 |
| 26.0 | 1.71 | 5.75 | 1837.4 | 6577.9 | 74.8 |
| 26.3 | 1.60 | 5.46 | 1751.4 | 6299.2 | 74.8 |
| 26.7 | 1.65 | 5.71 | 1827.9 | 6416.7 | 74.8 |
| 27.0 | 1.64 | 5.60 | 1811.5 | 6433.1 | 74.8 |
| 27.3 | 1.63 | 5.63 | 1826.5 | 6297.8 | 74.8 |

Example 28

Continuous Oxidation of NPMIDA to Glyphosate in Two Stirred Tank Reactors in Series This example demonstrates the continuous oxidation of NPMIDA to glyphosate in a continuous reactor system comprising two stirred tank reactors in series. In this example, the particulate heterogenous catalyst was transferred from the first reactor to the second reactor. The catalyst exited the second reactor with the second reactor liquid effluent, was separated by filtration, and recycled back to the first reactor zone.

Figure 29:
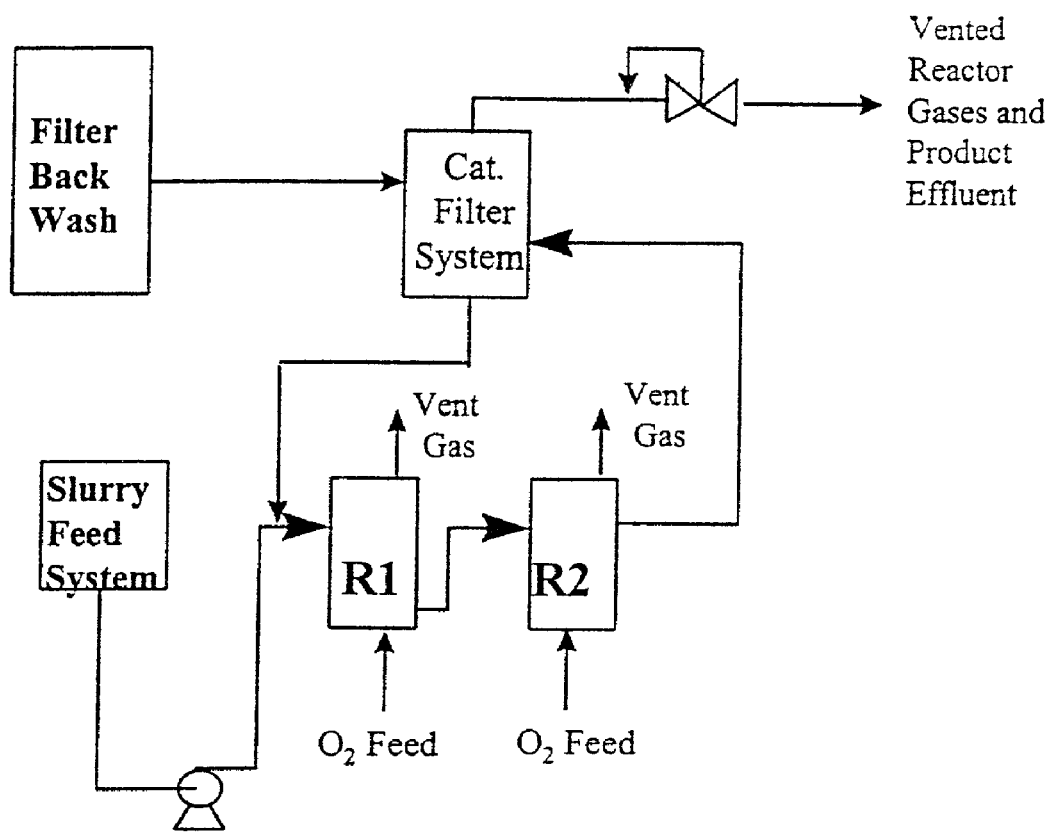
FIG. 29 is a block flow diagram for the continuous reactor system used in Example 28.

Referring to FIG. 29, the reaction was performed in a continuous reactor system comprising two stirred tank reactors, a slurry feed system and a catalyst filtration system. The two reactors (each 1 gallon stainless steel autoclaves from Autoclave Engineers, Inc., Pittsburgh, Pa.) were operated continuously as stirred tank reactors in series. Oxygen was fed to each respective reactor. Liquid effluent was withdrawn from the first reactor (R1) through a dip-tube which allowed for catalyst to be entrained with the liquid effluent from R1 to the second reactor (R2). Some reaction product gases were also entrained in the dip-tube from R1 to R2, and other reaction product gases in R1 were vented from the reactor. Similarly, liquid effluent was withdrawn from R2 through a dip-tube, which allowed for catalyst and some reaction product gases to be removed with the effluent. R2 liquid effluent which contained the catalyst was transferred to a catalyst filtration system. The catalyst filtration system generated an uninterrupted flow of catalyst-free filtrate as product. A filter back wash was fed to the catalyst filtration system to wash the filtered catalyst back to R1 in a continuous fashion. Oxygen was introduced into R1 and R2 through frits which were each located near an agitator impeller (2" turbine blade impeller in both R1 and R2). An internal cooling coil was used to control the temperature in each reactor.

An aqueous slurry feed material containing about 25% by weight NPMIDA was fed to the reactor at a rate of about 50 ml/min. The filter back wash contained NPMIDA (about 3% by weight), glyphosate (about 0.1% by weight), formaldehyde (about 3000 ppm by weight), and formic acid (about 7000 ppm by weight). The filter back wash was returned to R1 at a rate of about 100 ml/min. The catalyst was prepared by a method similar to that described in Example 17 above and comprised platinum (5% by weight) and iron (0.5% by weight) on a particulate carbon support. Catalyst was charged to the reactor system to provide an initial concentration of about 1% by weight catalyst. The reactor system was started up in a manner similar to that described in Example 24 in that the reactors were started in batch mode with liquid flow through the system initiated shortly thereafter.

The operating conditions are summarized in Table 30 below. The liquid product was analyzed with HPLC. Oxidation results are shown in Table 31 below. Table 31 gives data describing the inlet stream composition into R1 (including the combined from the catalyst filtration back-wash and the aqueous slurry feed) and liquid effluent compositions for R1 and R2.

TABLE 30

Summary of Operating Conditions for Example 28

| | R1 | R2 |
|---|---|---|
| Catalyst Concentration in reactor: | ~1 wt % | ~1 wt % |
| Agitator RPM: | ~1000 | ~1000 |
| Liquid Flow (combined through reactors): | ~150 ml/min | ~150 ml/min |
| Pressure: | 120–140 psig | 120–140 psig |
| Oxygen Flow Rate: | 2000–2500 sccm | ~400 sccm |
| Temperature: | ~100–105° C. | ~105° C. |
| Reaction Mass: | ~2950 g | ~1726 g |
| Impeller Type: | radial (2") | radial (2") |

TABLE 31

Oxidation Results for Example 28

| Elapsed Time (hrs) | NPMIDA (wt %) | Glyphosate (wt %) | Formaldehyde (ppm) | Formic Acid (ppm) |
|---|---|---|---|---|
| Feed Composition | | | | |
| 20.9 | 8.08 | 1.81 | 1778.0 | 4650.0 |
| 23.8 | 8.38 | 1.80 | 1757.2 | 4400.5 |
| 30.3 | 8.54 | 1.77 | 1518.5 | 4560.5 |
| 33.8 | 8.55 | 1.78 | 1522.8 | 4573.5 |
| First Reactor (R1) Outlet | | | | |
| 20.9 | 3.50 | 7.87 | 668.0 | 4384.2 |
| 23.8 | 3.44 | 7.32 | 651.6 | 4425.4 |
| 30.3 | 2.87 | 8.43 | 756.7 | 5057.3 |
| 33.8 | 2.71 | 8.39 | 798.8 | 5206.4 |
| Second Reactor (R2) Outlet | | | | |
| 20.9 | 2.55 | 8.04 | 302.5 | 3382.5 |
| 23.8 | 3.27 | 7.71 | 258.7 | 3791.2 |
| 30.3 | 0.40 | 6.98 | — | 4017.3 |
| 33.8 | 1.81 | 8.24 | 312.5 | 3945.7 |

Example 29

Continuous Oxidation of NPMIDA to Glyphosate in the Presence of a Pt/Sn/C Catalyst This example demonstrates the continuous oxidation of NPMIDA to glyphosate in the presence of a Pt/Sn/C heterogeneous particulate catalyst. The experiment was designed to simulate reaction conditions that might prevail in a first stirred tank reaction zone of a continuous reactor system.

The experiment was conducted in continuous reactor system similar to that described in Example 26 with the exception that a 1000 ml Hastelloy C autoclave was used. The reactor was equipped with an agitator having a 1.25" diameter radial six-blade turbine impeller. The liquid level in the reactor was monitored using a level indicator similar to that used in Example 21. An internal cooling coil was utilized to control the temperature within the reactor during the course of the reaction.

During operation, the reactor was continuously fed a gaseous stream of oxygen and an aqueous slurry feed material containing NPMIDA. The oxygen was introduced into the reaction medium through a frit located near the impeller. A liquid product stream containing glyphosate product was continuously withdrawn from the reactor through a frit, which allowed any catalyst charged to the reactor to remain in the reaction medium. The withdrawn liquid product stream was then mixed in-line with a basic solution capable of dissolving glyphosate. The product gas stream (containing $CO_2$ and unreacted oxygen) was continuously vented from the reactor headspace.

The aqueous slurry feed material comprised NPMIDA (about 7.7% by weight), formaldehyde (about 3000 ppm by weight) and formic acid (about 6100 ppm by weight). The catalyst was prepared by a method similar to that described in Example 14 above and comprised platinum (5% by weight) and tin (1.0% by weight) on a particulate carbon support. The continuous reactor system was started up in a manner similar to that described in Example 21 above in that the reactor was started in batch mode with liquid flow through the system initiated shortly thereafter. The operating conditions are summarized in Table 32 below. Analytical data from the continuous oxidation are shown in Table 33 below.

TABLE 32

Summary of Operating Conditions for Example 29.

| Catalyst Concentration in reactor: | 1 wt % |
| Agitator RPM: | 1000 |
| Liquid Flow: | 30.8 ml/min |
| Pressure: | 100 psig |
| Oxygen Flow Rate: | 647 sccm |
| Temperature: | 100° C. |
| Reaction Mass: | 725 g |
| Impeller Type: | radial (1.25") |

TABLE 33

Oxidation Results for Example 29.

| Feed Composition | |
|---|---|
| NPMIDA (wt %) | Glyphosate (wt %) |
| 7.73 | 0.00 |

| Reactor Outlet | | |
|---|---|---|
| Elapsed Time (hrs) | NPMIDA (wt %) | Glyphosate (wt %) |
| 0.0 | 0.04 | 1.35 |
| 0.5 | 0.29 | 4.42 |
| 1.0 | 0.34 | 4.91 |
| 1.5 | 0.41 | 5.18 |
| 2.0 | 0.58 | 5.55 |
| 2.5 | 0.97 | 6.50 |

Example 30

Continuous Oxidation of NPMIDA to Glyphosate in the Presence of a Pt/Sn/C Catalyst This example demonstrates the continuous oxidation of NPMIDA to glyphosate in the presence of a Pt/Sn/C heterogeneous particulate catalyst in a continuous reactor system having a single reaction zone.

The experiment was conducted in a continuous reactor system similar to that described in Example 27 above comprising a 500 ml Hastelloy C autoclave (Autoclave Engineers, Inc., Pittsburgh, Pa.). The reactor was equipped with an agitator having a 1.25" diameter radial six-blade turbine impeller. The liquid level in the reactor was monitored using a level indicator similar to that described in Example 21 above. An internal cooling coil was utilized to control the temperature within the reactor during the course of the reaction.

During operation, the reactor was continuously fed a gaseous stream of oxygen and an aqueous slurry feed material containing NPMIDA. The oxygen was introduced into the reaction medium through a frit located near the impeller. A liquid product stream containing glyphosate product was continuously withdrawn from the reactor through a frit, allowing any catalyst charged to the reactor to remain in the reaction medium. The product gas stream (containing $CO_2$ and unreacted oxygen) was continuously vented from the reactor headspace.

The continuous reactor system was started up in a manner similar to that described in Example 21 above in that the reactor was started in batch mode with liquid flow through the system initiated shortly afterward. The aqueous slurry feed material comprised NPMIDA (about 2.9 wt %). The catalyst was prepared by a method similar to that described in Example 14 above and comprised platinum (5% by weight) and tin (1.0% by weight) on a particulate carbon support. The operating conditions are summarized below in Table 34. The liquid product was analyzed with HPLC. Analytical data from the continuous oxidation are shown in Table 35 below.

TABLE 34

Summary of Operating Conditions for Example 30

| | |
|---|---|
| Catalyst Concentration in reactor: | 1 wt % |
| Agitator RPM: | 1000 |
| Liquid Flow: | 15.3 ml/min |
| Pressure: | 100 psig |
| Oxygen Flow Rate: | 150 sccm |
| Temperature: | 95° C. |
| Reaction Mass: | 300 g |
| Impeller Type: | radial (1.25") |

TABLE 35

Oxidation Results for Example 30

| Elapsed Time (hrs) | NPMIDA (wt %) | Glyphosate (wt %) | Formaldehyde (ppm) | Formic Acid (ppm) |
|---|---|---|---|---|
| 0.0 | 2.87 | 0.00 | 4.6 | 14.9 |
| 0.3 | 2.94 | 0.01 | 13.4 | 18.9 |
| 0.7 | 2.01 | 0.79 | 760.4 | 563.1 |
| 1.0 | 0.12 | 2.07 | 1893.6 | 1566.6 |
| 1.3 | 0.07 | 2.32 | 1953.6 | 1713.4 |
| 1.7 | 0.01 | 2.27 | 2111.1 | 1497.2 |
| 2.0 | 0.00 | 2.27 | 2167.1 | 1487.9 |
| 2.3 | 0.00 | 2.26 | 2155.1 | 1509.2 |
| 2.7 | 0.00 | 2.26 | 2183.1 | 1495.9 |
| 3.0 | 0.00 | 2.27 | 2189.8 | 1549.3 |
| 3.3 | 0.00 | 2.27 | 2195.1 | 1535.9 |
| 3.7 | 0.00 | 2.28 | 2196.5 | 1538.6 |
| 4.0 | 0.04 | 2.26 | 2184.5 | 1522.6 |
| 4.3 | 0.03 | 2.26 | 2184.5 | 1474.5 |
| 4.4 | 0.00 | 2.26 | 2177.8 | 1478.5 |

Example 31

Continuous Oxidation of NPMIDA to Glyphosate in the Presence of a Pt/Sn/C Catalyst This example demonstrates the continuous oxidation of NPMIDA to glyphosate in the presence of a Pt/Sn/C heterogeneous particulate catalyst. The experiment was designed to illustrate the impact of pressure, liquid and gas flow on conversion of NPMIDA to glyphosate.

The experiment was conducted in a continuous reactor system comprising a 500 ml Hastelloy C autoclave (Autoclave Engineers Inc.) similar to that described in Example 30. The reactor was equipped with an agitator having a 1.25" diameter radial six-blade turbine impeller. The liquid level in the reactor was monitored using a level indicator similar to that used in Example 21. An internal cooling coil was utilized to control the temperature within the reactor during the course of the reaction.

During operation, the reactor was continuously fed a gaseous stream of oxygen and an aqueous slurry feed material containing NPMIDA. The oxygen was introduced into the reaction medium through a frit located near the impeller. A liquid product stream containing glyphosate product was continuously withdrawn from the reactor through a frit, allowing any catalyst charged to the reactor to remain in the reaction medium. The product gas stream (containing $CO_2$ and unreacted oxygen) was continuously vented from the reactor headspace.

The aqueous slurry feed material comprised NPMIDA (about 3.0% by weight), formaldehyde (about 1000 ppm by weight) and formic acid (about 5100 ppm by weight). The catalyst was prepared by a method similar to that described in Example 14 above and comprised platinum (5% by weight) and tin (1.0% by weight) on a particulate carbon support.

The continuous reactor system was started up in a manner similar to that described in Example 21 above in that the reactor was started in batch mode with liquid flow through the system initiated shortly thereafter. During the course of the experiment, the oxygen flow rate to the reactor was ramped up and ramped back down over the range of 75 to 300 sccm. The operating conditions are summarized below in Table 36. The liquid product was analyzed with HPLC. Analytical data from the continuous oxidation are shown in Table 37 below.

TABLE 36

Summary of Operating Conditions for Example 31

| | |
|---|---|
| Catalyst Concentration in reactor: | 1 wt % |
| Agitator RPM: | 1000 |
| Liquid Flow: | variable (see data) |
| Pressure: | variable (see data) |
| Oxygen Flow Rate: | variable (see data) |
| Temperature: | 100° C. |
| Reaction Mass: | 300 g |
| Impeller Type: | radial (1.25") |

TABLE 37

Oxidation Results for Example 31

| Time (min) | Liquid Feed Rates (ml/min) | Pressure (psig) | O$_2$ Flow Rate (sccm) | GI (wt %) | Gly (wt %) | HCHO (ppm) | HCOOH (ppm) | NMG (ppm) | NFG (ppm) | AMPA (ppm) | MAMPA (ppm) | % CO$_2$ in Off-gas |
|---|---|---|---|---|---|---|---|---|---|---|---|---|
| 0 | 50 | 100.2 | 149.6 | 0.69 | 1.40 | 1713 | 4901 | 26 | 167 | 20 | 11 | 66 |
| 21 | 50 | 100.1 | 149.6 | 0.88 | 1.35 | 1756 | 5247 | 31 | 139 | 12 | 12 | 74 |
| 42 | 50 | 99.9 | 149.6 | 0.92 | 1.34 | 1709 | 5342 | 19 | 136 | 9 | 8 | 76 |
| 63 | 50 | 99.9 | 149.6 | 0.90 | 1.34 | 1671 | 5293 | 23 | 133 | 9 | 12 | 78 |
| 84 | 50 | 100.1 | 149.6 | 0.91 | 1.40 | 1709 | 5411 | 23 | 135 | 9 | 13 | 79 |
| 105 | 50 | 100 | 149.6 | 0.81 | 1.41 | 1685 | 5311 | 21 | 128 | 12 | 12 | 82 |
| 126 | 50 | 99.9 | 149.6 | 0.84 | 1.42 | 1686 | 5416 | 24 | 128 | 11 | 12 | 84 |
| 147 | 50 | 100 | 149.6 | 0.85 | 1.42 | 1685 | 5365 | 21 | 126 | 9 | 12 | 84 |
| 168 | 50 | 100 | 149.6 | 0.88 | 1.41 | 1650 | 5357 | 20 | 120 | 9 | 12 | 85 |
| 189 | 50 | 100 | 149.6 | 0.87 | 1.42 | 1651 | 5344 | 19 | 117 | 9 | 9 | 85 |
| 210 | 50 | 100.1 | 149.6 | 0.94 | 1.36 | 1607 | 5312 | 20 | 115 | 8 | 9 | 83 |
| 231 | 35 | 100 | 149.6 | 0.38 | 1.56 | 1312 | 4661 | 21 | 136 | 15 | 12 | 87 |
| 252 | 35 | 100.6 | 149.6 | 0.45 | 1.84 | 1799 | 5456 | 24 | 173 | 18 | 11 | 83 |
| 273 | 35 | 100 | 149.6 | 0.33 | 1.93 | 1794 | 5456 | 33 | 213 | 29 | 19 | 80 |
| 294 | 35 | 99.9 | 149.6 | 0.32 | 1.88 | 1785 | 5335 | 13 | 199 | 27 | — | 85 |
| 315 | 35 | 100.1 | 149.6 | 0.31 | 1.90 | 1834 | 5388 | 30 | 205 | 27 | 13 | 85 |
| 336 | 35 | 100.2 | 149.6 | 0.30 | 1.90 | 1866 | 5398 | 32 | 184 | 26 | 19 | 84 |
| 357 | 35 | 100 | 149.6 | 0.36 | 1.92 | 1887 | 5421 | 35 | 182 | 26 | 19 | 84 |
| 378 | 35 | 100 | 149.6 | 0.33 | 1.92 | 1884 | 5322 | 31 | 175 | 27 | 17 | 83 |
| 399 | 35 | 100 | 149.6 | 0.36 | 1.92 | 1906 | 5366 | 33 | 176 | 26 | 18 | 83 |
| 420 | 35 | 99.8 | 149.6 | 0.35 | 1.95 | 1932 | 5386 | 33 | 177 | 27 | 19 | 83 |
| 441 | 35 | 100 | 149.6 | 0.34 | 1.93 | 1950 | 5331 | 33 | 174 | 29 | 18 | 83 |
| 462 | 35 | 100.1 | 149.6 | 0.33 | 1.90 | 1956 | 5248 | 33 | 170 | 31 | 18 | 83 |
| 483 | 20 | 100.2 | 149.6 | 0.04 | 2.18 | 1547 | 4205 | 9 | 233 | 188 | -52 | 77 |
| 504 | 20 | 100.2 | 149.6 | 0.01 | 2.15 | 1656 | 4325 | 10 | 231 | 304 | 75 | 68 |
| 525 | 20 | 100 | 149.6 | 0.01 | 2.19 | 1756 | 4613 | 12 | 239 | 329 | 80 | 66 |
| 546 | 20 | 99.9 | 149.6 | 0.01 | 2.15 | 1799 | 4703 | 12 | 233 | 324 | 84 | 64 |
| 567 | 20 | 100 | 149.6 | 0.01 | 2.13 | 1822 | 4743 | 15 | 226 | 319 | 79 | 63 |
| 588 | 20 | 100 | 149.6 | 0.02 | 2.10 | 1839 | 4750 | 16 | 229 | 309 | 80 | 62 |
| 614 | — | 99.9 | 149.6 | | | — | — | — | — | — | — | 61 |
| 635 | — | 100.1 | 149.6 | | | | | | | | | 61 |
| 656 | — | 99.9 | 149.6 | | | — | — | — | — | — | — | 60 |
| 677 | 50 | 100 | 149.6 | 0.52 | 1.79 | 2379 | 5668 | 27 | 181 | 66 | 23 | 64 |
| 698 | 35 | 99.8 | 149.6 | 0.66 | 1.14 | 1563 | 4079 | 20 | 88 | 12 | 13 | 70 |
| 719 | 35 | 100 | 149.6 | 0.29 | 1.95 | 2271 | 5382 | 34 | 180 | 38 | 18 | 80 |
| 740 | 35 | 99.5 | 149.6 | 0.27 | 2.00 | 2334 | 5428 | 35 | 183 | 39 | 19 | 79 |
| 761 | 35 | 100.8 | 0 | | | — | — | — | — | — | — | 54 |
| 782 | 35 | 100.1 | 0 | 2.76 | 0.10 | 980 | 4930 | 12 | 13 | 0 | 8 | 53 |
| 803 | 35 | 99.7 | 150 | 1.67 | 1.07 | 1344 | 4074 | 8 | 97 | 5 | 9 | 17 |
| 824 | 35 | 100.2 | 150 | 0.65 | 1.71 | 2002 | 5269 | 20 | 148 | 17 | 12 | 59 |
| 845 | 35 | 100.2 | 150 | 0.55 | 1.79 | 2218 | 5499 | 24 | 151 | 23 | 14 | 68 |
| 979 | 35 | 99.6 | 199.8 | 0.02 | 1.93 | 2271 | 4947 | 20 | 174 | 832 | 32 | 44 |
| 1047 | 35 | 100 | 199.8 | 0.38 | 1.90 | 2342 | 5881 | 29 | 152 | 25 | 20 | 43 |
| 1067 | 35 | 100 | 199.8 | 0.19 | 2.05 | 2532 | 5723 | 34 | 162 | 50 | 22 | 56 |
| 1086 | 35 | 99.9 | 199.8 | 0.17 | 2.02 | 2663 | 5615 | 35 | 164 | 57 | 25 | 57 |
| 1106 | 35 | 100 | 199.8 | 0.19 | 2.02 | 2703 | 5584 | 36 | 163 | 55 | 25 | 56 |
| 1126 | 35 | 100.2 | 199.8 | 0.19 | 2.05 | 2797 | 5672 | 37 | 165 | 54 | 26 | 55 |
| 1145 | 35 | 100.1 | 199.8 | 0.22 | 1.99 | 2783 | 5551 | 37 | 158 | 48 | 24 | 54 |
| 1165 | 35 | 100.1 | 199.8 | 0.23 | 1.99 | 2813 | 5567 | 36 | 161 | 45 | 26 | 54 |
| 1186 | 35 | 100.1 | 199.8 | 0.24 | 2.01 | 2835 | 5605 | 35 | 158 | 44 | 25 | 53 |
| 1205 | 35 | 100 | 199.8 | 0.25 | 2.01 | 2880 | 5592 | 36 | 162 | 45 | 25 | 53 |
| 1225 | 35 | 100.2 | 199.8 | 0.25 | 2.00 | 2839 | 5535 | 35 | 158 | 43 | 24 | 52 |
| 1244 | 35 | 100.1 | 199.8 | 0.25 | 1.96 | 2809 | 5478 | 35 | 156 | 43 | 23 | 53 |
| 1274 | 20 | 100.1 | 199.8 | 0.00 | 2.05 | 1740 | 4227 | 8 | 197 | 444 | 92 | 52 |
| 1296 | 20 | 100 | 199.8 | 0.00 | 2.07 | 1955 | 4675 | 16 | 208 | 439 | 86 | 48 |
| 1317 | 20 | 100 | 199.8 | 0.00 | 2.05 | 1872 | 4701 | 12 | 172 | 439 | 92 | 48 |
| 1337 | 20 | 99.8 | 199.8 | 0.00 | 2.05 | 1688 | 4991 | 15 | 213 | 402 | 87 | 47 |
| 1354 | 20 | 100.2 | 199.8 | 0.00 | 2.07 | 2005 | 4982 | 14 | 217 | 417 | 86 | 46 |
| 1374 | 20 | 100.3 | 199.8 | 0.00 | 2.10 | 2122 | 5160 | 19 | 219 | 418 | 72 | 46 |
| 1444 | 20 | 99.9 | 199.8 | 0.00 | 2.09 | 2183 | 5228 | 21 | 220 | 369 | 93 | 44 |
| 1464 | 20 | 99.5 | 199.8 | 0.00 | 2.10 | 2127 | 5183 | 17 | 224 | 407 | 89 | 44 |
| 1484 | 35 | 100 | 199.8 | 0.22 | 2.05 | 2966 | 5982 | 50 | 184 | 69 | 30 | 47 |
| 1504 | 35 | 100.1 | 199.8 | 0.28 | 1.95 | 2930 | 5759 | 37 | 163 | 38 | 28 | 49 |
| 1524 | 35 | 99.8 | 199.8 | 0.34 | 1.93 | 3041 | 5728 | 48 | 158 | 38 | 22 | 47 |
| 1544 | 35 | 100 | 199.8 | 0.36 | 1.99 | 3003 | 5685 | 30 | 150 | 38 | 22 | 47 |

TABLE 37-continued

Oxidation Results for Example 31

| Time (min) | Liquid Feed Rates (ml/min) | Pressure (psig) | O$_2$ Flow Rate (sccm) | GI (wt %) | Gly (wt %) | HCHO (ppm) | HCOOH (ppm) | NMG (ppm) | NFG (ppm) | AMPA (ppm) | MAMPA (ppm) | % CO$_2$ in Off-gas |
|---|---|---|---|---|---|---|---|---|---|---|---|---|
| 1564 | 35 | 99.4 | 199.8 | 0.15 | 2.15 | 2965 | 5668 | 34 | 162 | 63 | 27 | 57 |
| 1584 | 35 | 100 | 199.8 | 0.26 | 2.00 | 3027 | 5687 | 45 | 167 | 46 | 27 | 52 |
| 1604 | 35 | 100.2 | 199.8 | 0.26 | 2.00 | 3020 | 5647 | 39 | 165 | 44 | 26 | 50 |
| 1624 | 35 | 129.7 | 199.8 | 0.15 | 2.07 | 3116 | 5613 | 42 | 168 | 68 | 30 | 51 |
| 1644 | 35 | 130 | 199.8 | 0.14 | 2.07 | 3146 | 5571 | 41 | 169 | 70 | 30 | 51 |
| 1664 | 35 | 130.1 | 199.8 | 0.16 | 2.06 | 3166 | 5599 | 41 | 168 | 63 | 30 | 50 |
| 1684 | 35 | 129.9 | 199.8 | 0.15 | 2.07 | 3199 | 5626 | 41 | 170 | 64 | 30 | 50 |
| 1704 | 35 | 129.8 | 199.8 | 0.16 | 2.07 | 3179 | 5640 | 41 | 168 | 58 | 30 | 49 |
| 1724 | 35 | 130 | 199.8 | 0.17 | 2.06 | 3189 | 5674 | 40 | 165 | 58 | 27 | 48 |
| 1744 | 35 | 129.8 | 199.8 | 0.19 | 2.02 | 3178 | 5669 | 41 | 164 | 54 | 28 | 48 |
| 1764 | 35 | 129.8 | 199.8 | 0.20 | 2.00 | 3179 | 5625 | 41 | 163 | 52 | 26 | 47 |
| 1784 | 35 | 130 | 199.8 | 0.30 | 1.99 | 2839 | 5551 | 31 | 161 | 55 | 22 | 52 |
| 1804 | 35 | 130.2 | 199.8 | 0.20 | 2.01 | 2657 | 5350 | 30 | 159 | 68 | 31 | 56 |
| 1824 | 35 | 130 | 199.8 | 0.10 | 2.14 | 2844 | 5516 | 31 | 177 | 100 | 38 | 56 |
| 1844 | 35 | 130 | 199.8 | 0.10 | 2.13 | 2822 | 5474 | 30 | 337 | 99 | 37 | 57 |
| 1864 | 35 | 130 | 150 | 0.20 | 2.05 | 2711 | 5517 | 35 | 313 | 64 | 29 | 62 |
| 1884 | 35 | 129.9 | 150 | 0.23 | 2.08 | 2754 | 5580 | 30 | 314 | 42 | 23 | 65 |
| 1904 | 35 | 130.4 | 150 | 0.36 | 1.90 | 2561 | 5336 | 32 | 274 | 36 | 20 | 66 |
| 1924 | 35 | 129.4 | 150 | 0.43 | 1.89 | 2691 | 5498 | 31 | 275 | 33 | 18 | 64 |
| 1944 | 35 | 130 | 150 | 0.22 | 2.09 | 2583 | 5419 | 40 | 314 | 77 | 31 | 73 |
| 1964 | 35 | 130 | 150 | 0.28 | 1.99 | 2789 | 5505 | 35 | 294 | 42 | 22 | 68 |
| 1984 | 35 | 130.2 | 150 | 0.27 | 1.98 | 2885 | 5510 | 35 | 292 | 43 | 23 | 65 |
| 2004 | 35 | 129.9 | 150 | 0.27 | 1.99 | 2926 | 5529 | 34 | 295 | 42 | 25 | 64 |
| 2024 | 35 | 130.1 | 150 | 0.24 | 2.02 | 2960 | 5525 | 37 | 301 | 44 | 27 | 63 |
| 2044 | 35 | 130.2 | 150 | 0.25 | 2.04 | 2989 | 5607 | 35 | 313 | 44 | 25 | 62 |
| 2064 | 35 | 129.7 | 150 | 0.30 | 1.98 | 2995 | 5549 | 34 | 299 | 40 | 21 | 62 |
| 2084 | 35 | 129.9 | 150 | 0.28 | 1.99 | 3033 | 5588 | 35 | 305 | 40 | 23 | 61 |
| 2104 | 20 | 130.4 | 200 | 0.18 | 2.10 | 2637 | 5240 | 25 | 307 | 229 | 62 | 54 |
| 2124 | 20 | 130 | 200 | 0.00 | 2.12 | 2078 | 4637 | 13 | 283 | 634 | 93 | 48 |
| 2144 | 20 | 129.7 | 200 | 0.00 | 2.20 | 2171 | 4975 | 14 | 332 | 686 | 114 | 46 |
| 2164 | 20 | 129.8 | 200 | 0.00 | 2.12 | 2299 | 5001 | 24 | 219 | 606 | 100 | 45 |
| 2184 | 20 | 129.7 | 200 | 0.00 | 2.13 | 2237 | 4955 | 20 | 230 | 692 | 110 | 46 |
| 2204 | 20 | 130.1 | 200 | 0.00 | 2.14 | 2260 | 5044 | 19 | 238 | 695 | 123 | 46 |
| 2224 | 20 | 130.4 | 200 | 0.00 | 2.12 | 2319 | 5014 | 23 | 230 | 662 | 111 | 45 |
| 2244 | 20 | 129.7 | 200 | 0.00 | 2.14 | 2386 | 5142 | 25 | 235 | 644 | 116 | 44 |
| 2264 | 20 | 129.9 | 200 | 0.00 | 2.12 | 2525 | 5172 | 34 | 231 | 516 | 124 | 42 |
| 2284 | 20 | 130 | 150 | 0.00 | 2.19 | 2428 | 5249 | 24 | 244 | 595 | 116 | 49 |
| 2304 | 20 | 130.3 | 150 | 0.01 | 2.10 | 2396 | 5058 | 31 | 225 | 460 | 89 | 53 |
| 2324 | 20 | 129.8 | 150 | 0.03 | 1.89 | 2401 | 4766 | 40 | 182 | 285 | 72 | 52 |
| 2344 | 20 | 129.7 | 150 | 0.01 | 2.15 | 2565 | 5195 | 37 | 231 | 377 | 84 | 51 |
| 2364 | 20 | 129.9 | 150 | 0.01 | 2.13 | 2490 | 5064 | 34 | 225 | 403 | 89 | 54 |
| 2384 | 20 | 129.9 | 150 | 0.01 | 2.10 | 2382 | 4983 | 30 | 224 | 444 | 88 | 55 |
| 2404 | 20 | 129.7 | 150 | 0.01 | 2.17 | 2409 | 5063 | 26 | 228 | 450 | 84 | 54 |
| 2424 | 20 | 129.7 | 150 | 0.01 | 2.18 | 2501 | 5178 | 30 | 234 | 418 | 83 | 54 |
| 2444 | 20 | 130.3 | 150 | 0.01 | 2.14 | 2668 | 5358 | 47 | 231 | 328 | 75 | 52 |

Example 32

Continuous Oxidation of NPMIDA to Glyphosate in the Presence of a Pt/Fe/C Catalyst This example demonstrates the continuous oxidation of NPMIDA to glyphosate in the presence of a Pt/Fe/C heterogeneous particulate catalyst in a stirred tank reactor. The experiment was designed to simulate conditions that might prevail in a first reaction zone of a continuous oxidation reactor system.

The experiment was conducted in a continuous reactor system similar to that used in Example 29 where the reactor comprised a 1000 ml Hastelloy C autoclave. The reactor was equipped with an agitator having a 1.25" diameter radial six-blade turbine impeller. The liquid level in the reactor was monitored using a level indicator similar to that used in Example 21. An internal cooling coil was utilized to control the temperature within the reactor during the course of the reaction.

During operation, the reactor was continuously fed an aqueous slurry feed material comprising NPMIDA and a gaseous stream of oxygen. The oxygen was introduced into the reaction medium through a frit located near the impeller. A liquid product stream containing glyphosate product was continuously withdrawn from the reactor through a frit, which allowed any catalyst charged to the reactor to remain in the reaction medium. The product gas stream (containing $CO_2$ and unreacted oxygen) was continuously vented from the reactor headspace.

The aqueous slurry feed material fed to the reactor comprised NPMIDA (9.9% by weight), glyphosate (1.3% by weight), formaldehyde (3600 ppm by weight) and formic acid (6200 ppm by weight). The catalyst was prepared by a method similar to that described in Example 17 above and comprised platinum (5% by weight) and iron (0.5% by weight) on a particulate carbon support. The continuous reactor system was started up in a manner similar to that described in Example 21 above in that the reactor was started in batch mode with liquid flow through the system initiated shortly afterward. The operating conditions are summarized in Table 38 below. The liquid product was analyzed with HPLC. Analytical data from the continuous oxidation are shown in Table 39 below.

TABLE 38

Summary of Operating Conditions for Example 32

| | |
|---|---|
| Catalyst Concentration in reactor: | 1 wt % |
| Agitator RPM: | 1000 |
| Liquid Flow: | 35 ml/min |
| Pressure: | 100 psig |
| Oxygen Flow Rate: | 630 sccm |
| Temperature: | 100° C. |
| Reaction Mass: | 725 g |
| Impeller Type: | radial (1.25") |

TABLE 39

Oxidation Results for Example 32

| Time (min) | NPMIDA (wt %) | Glyphosate (wt %) |
|---|---|---|
| 60 | 0.12 | 5.16 |
| 90 | 0.05 | 6.34 |
| 151 | 0.03 | 3.64 |
| 181 | 0.32 | 6.06 |
| 211 | 0.35 | 6.33 |
| 241 | 0.34 | 6.23 |
| 271 | 0.27 | 6.06 |
| 301 | 0.32 | 6.22 |
| 331 | 0.31 | 6.22 |
| 362 | 0.28 | 6.25 |
| 392 | 0.29 | 6.08 |
| 422 | 0.30 | 6.22 |
| 452 | 0.25 | 6.17 |
| 482 | 0.03 | 5.59 |
| 512 | 0.01 | 4.03 |
| 542 | 0.04 | 4.42 |
| 573 | 0.18 | 4.84 |
| 603 | 0.15 | 5.69 |
| 633 | 0.23 | 5.85 |
| 663 | 0.32 | 6.37 |

Example 33

Continuous Oxidation of NPMIDA to Glyphosate in the Presence of a Pt/Fe/C Catalyst This example demonstrates the continuous oxidation of NPMIDA to glyphosate in the presence of a Pt/Fe/C heterogeneous particulate catalyst in a stirred tank reactor. The experiment was designed to simulate conditions that might prevail in a second reaction zone of a continuous reactor system.

The experiment was conducted in a continuous reactor system similar to that used in Example 29 where the reactor comprised a 1000 ml Hastelloy C autoclave. The reactor was equipped with an agitator having a 1.25" diameter radial six-blade turbine impeller. The liquid level in the reactor was monitored using a level indicator similar to that used in Example 21. An internal cooling coil was utilized to control the temperature within the reactor during the course of the reaction.

During operation, an aqueous slurry feed material comprising NPMIDA and a gaseous stream of oxygen were continuously introduced to the reactor system. The oxygen was introduced into the reaction medium through a frit located near the impeller. A liquid product stream comprising glyphosate product was continuously withdrawn from the reactor through a frit, which allowed any catalyst charged to the reactor to remain in the reaction medium. The product gas stream (containing $CO_2$ and unreacted oxygen) was continuously vented from the reactor headspace.

The aqueous slurry feed material contained NPMIDA (1.9% by weight), glyphosate (6.7% by weight), formaldehyde (2400 ppm by weight), formic acid (4600 ppm by weight), NMG (280 ppm by weight), AMPA (400 ppm by weight) and MAMPA (200 ppm by weight). The catalyst was prepared by a method similar to that described in Example 17 above and comprised platinum (5% by weight) and iron (0.5% by weight) on a particulate carbon support. The continuous reactor system was started up in a manner similar to that described in Example 21 above in that the reactor was started in batch mode before initiating liquid flow through the system, which commenced shortly thereafter. The operating conditions are summarized in Table 40 below. The liquid product was analyzed with HPLC and analytical data from the continuous oxidation are shown in Table 41.

TABLE 40

Summary of Operating Conditions for Example 33

| | |
|---|---|
| Catalyst Concentration in reactor: | 1 wt % |
| Agitator RPM: | 1000 |
| Liquid Flow: | 60.4 ml/mm |
| Pressure: | Variable (see data) |
| Oxygen Flow Rate: | Variable (see data) |
| Temperature: | 100° C. |
| Reaction Mass: | 725 g |
| Impeller Type: | radial (1.25") |

TABLE 41

Oxidation Results for Example 33

| Time min | Pres. (psig) | $O_2$ Flow (sccm) | NPMIDA (wt %) | Glyphosate (wt %) | HCHO (ppm) | HCOOH (ppm) |
|---|---|---|---|---|---|---|
| 0 | 100 | 225 | 1.52 | 5.72 | 951 | 2822 |
| 60 | 100 | 225 | 0.48 | 7.55 | 1127 | 4404 |
| 121 | 100 | 225 | 0.47 | 7.62 | 1219 | 4419 |
| 181 | 100 | 225 | 0.46 | 7.57 | 1272 | 4442 |
| 241 | 100 | 225 | 0.45 | 7.63 | 1301 | 4434 |
| 302 | 100 | 225 | 0.45 | 7.74 | 1351 | 4590 |
| 362 | 100 | 315 | 0.19 | 7.68 | 1467 | 4230 |
| 422 | 100 | 315 | 0.10 | 7.65 | 1518 | 3739 |
| 482 | 100 | 315 | 0.10 | 7.77 | 1633 | 3756 |
| 543 | 100 | 315 | 0.10 | 7.77 | 1684 | 3714 |
| 603 | 100 | 315 | 0.11 | 7.75 | 1671 | 3741 |
| 663 | 99 | 315 | 0.10 | 7.78 | 1724 | 3721 |
| 724 | 100 | 292 | 0.13 | 7.75 | 1706 | 3840 |
| 784 | 100 | 292 | 0.13 | 7.84 | 1758 | 3905 |
| 844 | 100 | 292 | 0.13 | 7.76 | 1748 | 3908 |
| 904 | 100 | 292 | 0.11 | 7.81 | 1608 | 3884 |
| 965 | 100 | 292 | 0.11 | 7.75 | 1659 | 3901 |
| 1025 | 100 | 292 | 0.11 | 7.91 | 1703 | 3973 |
| 1085 | 100 | 292 | 0.11 | 8.05 | 1819 | 4108 |
| 1145 | 100 | 270 | 0.15 | 7.82 | 1681 | 4120 |
| 1206 | 100 | 270 | 0.14 | 7.74 | 1687 | 4438 |
| 1266 | 100 | 270 | 0.16 | 7.52 | 1850 | 4063 |
| 1326 | 100 | 270 | 0.13 | 7.42 | 1754 | 3962 |
| 1748 | 100 | 247 | 0.64 | 6.77 | 1566 | 4025 |
| 1809 | 100 | 247 | 0.65 | 7.70 | 1572 | 4266 |
| 1869 | 100 | 247 | 0.65 | 7.52 | 1545 | 4313 |
| 1929 | 100 | 247 | 0.67 | 7.54 | 1612 | 4473 |

TABLE 41-continued

Oxidation Results for Example 33

| Time min | Pres. (psig) | O₂ Flow (sccm) | NPMIDA (wt %) | Glyphosate (wt %) | HCHO (ppm) | HCOOH (ppm) |
|---|---|---|---|---|---|---|
| 1989 | 100 | 247 | 0.63 | 7.50 | 1620 | 4436 |
| 2050 | 100 | 247 | 0.59 | 7.59 | 1640 | 4500 |
| 2110 | 100 | 225 | 0.59 | 7.18 | 1562 | 4321 |
| 2170 | 100 | 225 | 0.68 | 7.50 | 1639 | 4517 |
| 2261 | 100 | 225 | 0.66 | 7.60 | 1659 | 4551 |
| 2351 | 100 | 225 | 0.59 | 7.41 | 1677 | 4519 |
| 2411 | 100 | 360 | 0.16 | 7.86 | 1907 | 4157 |
| 2472 | 100 | 360 | 0.16 | 7.86 | 2039 | 4040 |
| 2532 | 100 | 360 | 0.10 | 7.89 | 2028 | 3664 |
| 2592 | 100 | 360 | 0.09 | 7.98 | 2045 | 3635 |
| 2653 | 100 | 360 | 0.10 | 7.82 | 2150 | 3628 |
| 2713 | 70 | 360 | 0.11 | 8.47 | 2036 | 4008 |
| 2773 | 71 | 360 | 0.08 | 7.55 | 1338 | 2920 |

Example 34

Continuous Oxidation of NPMIDA to Glyphosate in the Presence of a Pt/Fe/C Catalyst This example demonstrates the continuous oxidation of NPMIDA to glyphosate in the presence of a Pt/Fe/C heterogeneous particulate catalyst in a fixed bed reactor. The experiment was designed to mimic a small initial section of a fixed bed reactor with gas and liquid feeds entering co-currently.

The experiment was performed in a continuous reactor system comprising a vertical stainless steel tubular reactor (2.2 cm inside diameter; 61.5 cm length; 215 ml volume). The gas and liquid feeds entered the tubular reactor at the top and flowed down through the reactor. The reactor was filled with a mixture of catalyst (50 g) and glass Raschig rings (6 mm). The catalyst comprised 2% by weight platinum and 0.2% by weight iron on ⅛-inch carbon granule supports. The reactor was heated to about 90° C. with a heated water feed and brought to a pressure of about 100 psig with nitrogen. After the reactor reached a temperature of 90° C., water and nitrogen flow were stopped and the liquid feed and oxygen feed were initiated.

The liquid feed was fed to the top of the reactor at 90° C. and comprised an aqueous slurry feed material containing NPMIDA (3.00% by weight) and formic acid (0.54% by weight). Oxygen was fed to the top of the reactor with the reactor pressure maintained at 100 psig. The liquid and oxygen feed rates were varied in a series of four experiments as indicated in Table 42 below. In each experiment, the system was allowed to equilibrate for at least one half hour before samples were collected at the column exit and analyzed for formic acid and glyphosate.

TABLE 42

Effluent Analysis Under Different Operating Conditions for Example 34

| Liquid Flow (ml/min) | Oxygen Flow (sccm) | % Glyphosate | % Formic Acid | % Formaldehyde |
|---|---|---|---|---|
| 100 | 100 | 0.11 | 0.47 | ~0.011 |
| 100 | 200 | 0.13 | 0.46 | ~0.014 |
| 50 | 100 | 0.24 | 0.38 | ~0.018 |
| 25 | 100 | 0.41 | 0.33 | ~0.026 |

Example 35

Figure 30:
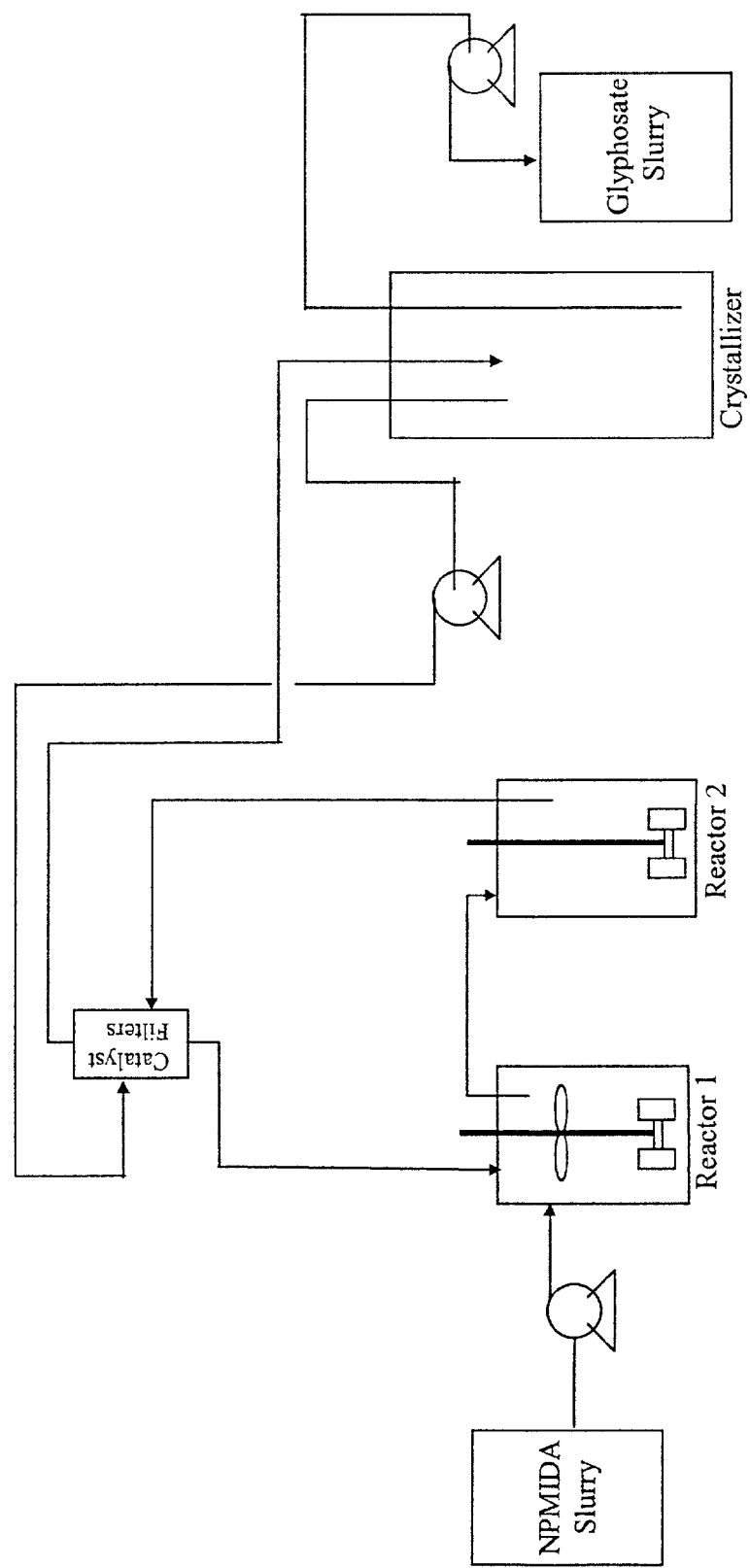
FIG. 30 is a block flow diagram for the continuous reactor system used in Example 35.

Continuous Oxidation of NPMIDA to Glyphosate in Two Stirred Tank Reactors in Series with Catalyst Recycle and Crystallizer Recycle This example demonstrates the continuous oxidation of NPMIDA to glyphosate in the presence of a heterogeneous particulate catalyst slurry in a continuous reactor system comprising two stirred tank reactors staged in series. The reactor system was similar to that shown in FIG. 30. The two stirred tank reactors (R1 and R2) were as described in Example 24 except that the impeller configuration of R2 was not operated in a DISPERSIMAX mode. The catalyst was continuously filtered from the reaction mixture effluent withdrawn from R2 using a back-pulse filter system comprising parallel filter bodies and the separated catalyst was recycled to R1. Crystalline N-(phosphonomethyl)glycine product was recovered from the filtrate in a crystallizer (30 L) and the mother liquor from the crystallizer was recycled to R1.

The heterogeneous particulate catalyst was prepared by a method similar to that described in Example 17 above and comprised platinum (5% by weight) and iron (0.5% by weight) on a particulate carbon support. In this example, the particulate heterogeneous catalyst was transferred from R1 to R2 with the effluent from R1 including some entrained gas. The catalyst exited R2 with the reactor effluent, was separated in the back-pulse filter, and recycled back to R1. The back-pulse catalyst filter also acted as a liquid gas separator for the effluent from R2. The filtrate from the back-pulse catalyst filter was sent to a crystallizer for recovery of crystalline N-(phosphonomethyl)glycine product. The resulting mother liquor from the crystallizer was used to back-pulse the catalyst filter bodies and recycled to R1 with the separated catalyst.

The operating conditions for R1 and R2 are summarized in Table 43. R1 and R2 were charged initially as shown in Table 43 and oxygen was introduced concurrent with the NPMIDA feed. The NPMIDA feed comprised an aqueous slurry feed material containing from about 12.5% to about 15% NPMIDA and mother liquor recycle from the catalyst filters to give an effective combined feed to R1. The effective combined feed to R1 was introduced initially at 4.3 wt % and later increased to 5.2 wt %. Bismuth oxide was added throughout the run to increase the formic acid destruction rate. Bismuth oxide was added in a batchwise fashion to R1 (~5 mg per addition) and also in a continuous fashion by addition to the NPMIDA slurry feed (4–25 mg per 20 kg of NPMIDA slurry). The frequency and amount of bismuth oxide added to the slurry feed is listed in Table 44. The aqueous slurry feed to R1 (including the component from the crystallizer mother liquor recycled with the catalyst), R1 reactor effluent and R2 reactor effluent were analyzed by HPLC. The HPLC analytical results are presented in Table 45.

TABLE 43

Operating Conditions for the Continuous Oxidation Reactor System of Example 35

| Initial Reactor Charge | R1 | R2 |
|---|---|---|
| Catalyst | 0.8 wt % | 0.8 wt % |
| NPMIDA | 0.8 wt % | 0.3 wt % |
| Glyphosate | 5.0 wt % | 5.0 wt % |
| formaldehyde | 500 ppm | 500 ppm |

TABLE 43-continued

Operating Conditions for the Continuous Oxidation Reactor System of Example 35

| Initial Reactor Charge | R1 | R2 |
|---|---|---|
| formic acid | 2000 ppm | 2000 ppm |
| water | 2700 ml | 1500 ml |
| Operating Conditions | | |
| Catalyst Concentration[1] | 0.8–1.4 wt % | 0.8–1.4 wt % |
| Agitator RPM | 1000 | 600 |
| Total Liquid Flow into R1 | 147.4 g/min | 147.4 g/min |
| Pressure | 100 psig | 100 psig |
| Oxygen | 900–1700 sccm | 120–700 sccm |
| Temperature | 950–100° C. | 950–100° C. |
| Reaction Mass | 2950 g | 1725 g |
| Impeller Type | radial (2")[2] | radial (2")[2] |
| NPMIDA Slurry Flow Rate | 50 g/min | NA |
| RML Flow Rate[3] | 97.4 ml/min | NA |

[1]Initial catalyst charge was 0.8 wt %. During the run the catalyst loading was increased to 1.0 wt % at 69 hours, 1.2 wt % at 119 hours and 1.4 wt % at 143 hours.
[2]A downward pumping impeller was installed on the agitator shaft about half way up the liquid colunm.
[3]Crystallizer mother liquor (RML) was used to back pulse the catalyst filters and return filtered catalyst back to R1 with RML.

TABLE 44

Frequency and Amount of Bismuth Oxide Addition to Reactor System

| Elapsed Time (hrs) | Bismuth Oxide Addition |
|---|---|
| 19.4 | 12.5 mg to R1 with 50 ml $H_2O$ |
| 19.6 | 4.2 mg to 20 kg of NPMIDA slurry feed |
| 46.2 | 12.7 mg in R1 with 50 ml $H_2O$ |
| 102.3 | 12.8 mg to R1 with 50 ml $H_2O$ |
| | 4.7 mg to 20 kg of NPMIDA slurry feed |
| 139.3 | 12.4 mg to R1 with 50 ml $H_2O$ |
| | 4.1 mg to 20 kg of NPMIDA slurry feed |
| 159.3 | 13.3 mg to Ri with 50 ml $H_2O$ |
| | 4.0 mg to 20 kg of NPMIDA slurry feed |
| 165.7 | 16.4 mg to R1 with 50 ml $H_2O$ |
| | 16.9 mg to 20 kg of NPMIDA slurry feed |
| 172.0 | 25 mg to 20 kg of NPMIDA slurry feed |
| 215.9 | 12.3 mg to 20 kg of NPMIDA slurry feed |
| 370.7 | 16.7 mg to 20 kg of NPMIDA slurry feed |

TABLE 45

Analytical Results for Example 35

| Elapsed time (hrs) | Effective Combined R1 Feed | | | | R1 Exit | | | | R2 Exit | | | |
|---|---|---|---|---|---|---|---|---|---|---|---|---|
| | NPMIDA (wt %) | Gly (wt %) | HCHO (ppm) | HCOOH (ppm) | NPMIDA (wt %) | Gly (wt %) | HCHO (ppm) | HCOOH (ppm) | NPMIDA (wt %) | Gly (wt %) | HCHO (ppm) | HCOOH (ppm) |
| 9.0 | 4.4 | 1.07 | 417 | 1775 | 0.62 | 3.86 | 841 | 3058 | 0.54 | 3.96 | 449 | 3147 |
| 12.1 | 4.31 | 1.08 | 408 | 1857 | 0.36 | 3.88 | 927 | 3446 | 0.24 | 3.98 | 417 | 3448 |
| 16.9 | 4.30 | 1.12 | 497 | 2179 | 0.32 | 4.10 | 984 | 3507 | 0.18 | 4.13 | 418 | 3416 |
| 18.0 | 4.30 | 1.03 | 492 | 2179 | 0.34 | 4.04 | 951 | 3664 | 0.19 | 3.80 | 401 | 3414 |
| 20.5 | 4.33 | 1.03 | 480 | 1853 | 0.57 | 4.35 | 1010 | 2941 | 0.29 | 3.81 | 354 | 2213 |
| 22.0 | 4.34 | 1.13 | 494 | 2082 | 0.52 | 4.20 | 943 | 2790 | 0.32 | 4.18 | 406 | 3058 |
| 27.0 | 4.31 | 2.27 | 269 | 1368 | 0.45 | 4.62 | 1035 | 3147 | 0.23 | 4.53 | 445 | 2911 |
| 30.0 | 4.32 | 2.54 | 310 | 1491 | 0.48 | 5.31 | 1196 | 3331 | 0.26 | 5.54 | 596 | 3364 |
| 30.7 | 4.31 | 2.57 | 311 | 1646 | 0.44 | 5.34 | 1178 | 3369 | 0.21 | 5.61 | 567 | 3347 |
| 34.5 | 4.27 | 2.43 | 406 | 1882 | 0.12 | 5.51 | 1282 | 3156 | 0.09 | 5.41 | 824 | 3364 |
| 36.0 | 4.29 | 2.42 | 432 | 1887 | 0.18 | 5.37 | 1332 | 3299 | 0.14 | 5.40 | 920 | 3381 |
| 39.0 | 4.30 | 2.44 | 459 | 1969 | 0.19 | 5.67 | 1049 | 3704 | 0.19 | 5.45 | 1017 | 3684 |
| 46.0 | 4.36 | 2.55 | 483 | 2176 | 0.52 | 5.65 | 1660 | 4224 | 0.41 | 5.88 | 1106 | 4447 |
| 47.3 | 4.42 | 2.46 | 429 | 1677 | 0.74 | 5.88 | 1567 | 3528 | 0.62 | 5.55 | 909 | 2608 |
| 48.3 | 4.39 | 2.44 | 405 | 1864 | 0.64 | 5.44 | 1382 | 2809 | 0.54 | 5.47 | 819 | 3297 |
| 50.7 | 4.44 | 2.76 | 552 | 2225 | 0.45 | 5.50 | 1505 | 3417 | 0.26 | 5.61 | 805 | 3245 |
| 56.5 | 4.35 | 2.59 | 518 | 1827 | 0.09 | 5.35 | 1566 | 2807 | 0.00 | 5.64 | 724 | 2113 |
| 59.0 | 4.37 | 2.51 | 591 | 2165 | 0.15 | 5.21 | 1700 | 3368 | 0.06 | 5.32 | 993 | 3359 |
| 62.1 | 4.32 | 2.51 | 649 | 2284 | 0.22 | 5.18 | 1760 | 3495 | 0.10 | 5.36 | 1087 | 3520 |
| 65.0 | 4.29 | 2.54 | 704 | 2213 | 0.17 | 5.22 | 1890 | 3634 | 0.06 | 5.42 | 1178 | 3718 |
| 69.5 | 5.18 | 2.53 | 577 | 1805 | 0.21 | 5.42 | 1402 | 2211 | 0.19 | 5.38 | 710 | 2215 |
| 71.5 | 5.20 | 2.65 | 600 | 1898 | 0.35 | 5.74 | 1574 | 2468 | 0.22 | 5.88 | 881 | 2735 |
| 75.0 | 5.27 | 2.74 | 612 | 2134 | 0.56 | 5.08 | 1577 | 3240 | 0.40 | 6.06 | 958 | 3704 |
| 77.5 | 5.25 | 2.74 | 612 | 1828 | 0.44 | 5.84 | 1666 | 3256 | 0.27 | 6.06 | 952 | 2503 |
| 80.8 | 5.25 | 2.63 | 616 | 1802 | 0.46 | 5.75 | 1717 | 3406 | 0.26 | 5.90 | 961 | 2436 |
| 84.0 | 5.27 | 2.85 | 663 | 2114 | 0.50 | 5.84 | 1680 | 3328 | 0.31 | 6.47 | 1089 | 3437 |
| 87.0 | 5.27 | 2.63 | 656 | 2004 | 0.46 | 5.92 | 1735 | 3288 | 0.29 | 5.56 | 979 | 2897 |
| 91.0 | 5.26 | 2.47 | 687 | 1933 | 0.45 | 6.03 | 1924 | 3173 | 0.23 | 5.37 | 1012 | 2906 |
| 93.0 | 5.26 | 2.74 | 752 | 2122 | 0.45 | 6.10 | 1967 | 3706 | 0.23 | 6.37 | 1251 | 3605 |

TABLE 45-continued

Analytical Results for Example 35

| Elapsed time (hrs) | Effective Combined R1 Feed | | | | R1 Exit | | | | R2 Exit | | | |
|---|---|---|---|---|---|---|---|---|---|---|---|---|
| | NPMIDA (wt %) | Gly (wt %) | HCHO (ppm) | HCOOH (ppm) | NPMIDA (wt %) | Gly (wt %) | HCHO (ppm) | HCOOH (ppm) | NPMIDA (wt %) | Gly (wt %) | HCHO (ppm) | HCOOH (ppm) |
| 97.7 | 5.24 | 2.69 | 898 | 2684 | 0.45 | 5.94 | 2248 | 4651 | 0.19 | 6.20 | 1569 | 4428 |
| 105.0 | 5.23 | 2.61 | 968 | 2210 | 0.42 | 5.79 | 2195 | 3791 | 0.21 | 6.11 | 1478 | 3276 |
| 107.0 | 5.24 | 2.64 | 1001 | 2388 | 0.48 | 5.77 | 2265 | 3935 | 0.24 | 5.95 | 1558 | 3403 |
| 109.0 | 5.24 | 2.63 | 1031 | 2242 | 0.52 | 5.80 | 2255 | 3697 | 0.26 | 6.16 | 1629 | 3480 |
| 111.0 | 5.24 | 2.59 | 1031 | 2242 | 0.52 | 5.80 | 2255 | 3697 | 0.26 | 6.03 | 1629 | 3480 |
| 116.0 | 5.19 | 2.68 | 1213 | 2620 | 0.46 | 6.02 | 2634 | 4379 | 0.14 | 6.15 | 1976 | 4163 |
| 129.5 | 5.27 | 2.66 | 1328 | 3239 | 0.70 | 5.91 | 2952 | 6163 | 0.42 | 6.05 | 2400 | 6449 |
| 134.0 | 5.27 | 2.58 | 1332 | 2880 | 0.76 | 5.72 | 3014 | 5731 | 0.43 | 5.78 | 2415 | 5125 |
| 135.5 | 5.41 | 2.65 | 1310 | 2872 | 1.14 | 5.62 | 2848 | 4719 | 0.96 | 6.02 | 2336 | 5095 |
| 140.3 | 5.23 | 2.84 | 1268 | 3477 | 0.52 | 6.34 | 3494 | 5613 | 0.15 | 6.53 | 2604 | 5308 |
| 142.0 | 5.21 | 2.78 | 1248 | 3364 | 0.39 | 6.07 | 3429 | 5113 | 0.09 | 6.30 | 2529 | 4891 |
| 144.6 | 5.20 | 2.84 | 849 | 3154 | 0.25 | 6.29 | 1751 | 4150 | 0.03 | 6.52 | 1058 | 4117 |
| 152.5 | 5.23 | 2.62 | 1026 | 3065 | 0.34 | 5.67 | 2330 | 3998 | 0.16 | 5.70 | 1711 | 3788 |
| 153.5 | 5.19 | 2.63 | 1046 | 2580 | 0.37 | 5.67 | 2317 | 4048 | 0.14 | 5.75 | 1724 | 3726 |
| 156.5 | 5.19 | 2.72 | 1135 | 2962 | 0.46 | 5.84 | 2729 | 5120 | 0.16 | 6.07 | 2011 | 5137 |
| 158.3 | 5.19 | 2.61 | 1168 | 2920 | 0.48 | 5.85 | 2747 | 5363 | 0.14 | 5.66 | 2132 | 4980 |
| 160.5 | 5.24 | 2.71 | 1150 | 2696 | 0.63 | 5.86 | 2750 | 5035 | 0.32 | 6.06 | 2066 | 4156 |
| 161.5 | 5.19 | 2.78 | 1135 | 2729 | 0.51 | 6.09 | 2670 | 4389 | 0.15 | 6.32 | 2010 | 4277 |
| 163.5 | 5.18 | 2.89 | 1192 | 3068 | 0.54 | 6.13 | 2844 | 5696 | 0.10 | 6.73 | 2219 | 5528 |
| 167.1 | 5.22 | 2.73 | 1261 | 3250 | 0.67 | 5.50 | 2659 | 5220 | 0.28 | 6.14 | 2476 | 6197 |
| 170.0 | 5.14 | 2.77 | 1431 | 3625 | 0.45 | 5.93 | 3133 | 5555 | 0.03 | 6.45 | 2474 | 5485 |
| 173.0 | 5.12 | 2.64 | 1484 | 3346 | 0.28 | 5.27 | 3099 | 4459 | 0.01 | 5.73 | 2564 | 4327 |
| 176.3 | 5.15 | 2.68 | 1528 | 3489 | 0.56 | 5.50 | 3175 | 5094 | 0.12 | 5.95 | 2649 | 5136 |
| 179.8 | 5.15 | 2.74 | 1280 | 3225 | 0.55 | 5.78 | 3222 | 4716 | 0.11 | 6.16 | 2587 | 4164 |
| 183.5 | 5.17 | 2.73 | 1306 | 3247 | 0.74 | 5.93 | 3308 | 4556 | 0.19 | 6.13 | 2684 | 4245 |
| 188.0 | 5.15 | 2.64 | 1244 | 3043 | 0.54 | 5.61 | 3143 | 3924 | 0.14 | 5.78 | 2455 | 3491 |
| 189.5 | 5.14 | 2.60 | 1624 | 2184 | 0.37 | 5.97 | 3165 | 3278 | 0.09 | 6.12 | 2481 | 3057 |
| 190.5 | 5.14 | 2.62 | 1601 | 1858 | 0.38 | 5.99 | 3109 | 3059 | 0.09 | 6.03 | 2417 | 2358 |
| 196.0 | 5.14 | 2.60 | 1624 | 2184 | 0.37 | 5.97 | 3165 | 3278 | 0.09 | 6.12 | 2481 | 3057 |
| 199.0 | 5.14 | 2.62 | 1601 | 1858 | 0.38 | 5.99 | 3109 | 3059 | 0.09 | 6.03 | 2417 | 2358 |
| 201.5 | 5.14 | 2.70 | 1559 | 1600 | 0.28 | 5.74 | 2889 | 2528 | 0.08 | 6.24 | 2305 | 2110 |
| 203.5 | 5.13 | 2.65 | 1525 | 1522 | 0.29 | 6.01 | 3001 | 2260 | 0.07 | 6.11 | 2241 | 1898 |
| 205.5 | 5.14 | 2.63 | 1517 | 1439 | 0.30 | 5.95 | 2871 | 2104 | 0.10 | 6.05 | 2210 | 1590 |
| 207.5 | 5.13 | 2.90 | 1448 | 1130 | 0.23 | 5.95 | 2819 | 1786 | 0.06 | 6.15 | 2065 | 1319 |
| 209.5 | 5.14 | 2.77 | 1492 | 1010 | 0.28 | 6.10 | 2929 | 1839 | 0.10 | 6.34 | 2224 | 1275 |
| 211.5 | 5.14 | 2.69 | 1453 | 932 | 0.27 | 5.64 | 2774 | 1736 | 0.10 | 6.05 | 2082 | 986 |
| 219.5 | 5.14 | 2.64 | 1287 | 585 | 0.28 | 5.81 | 2554 | 1234 | 0.07 | 6.02 | 1858 | 819 |
| 221.5 | 5.14 | 2.91 | 1273 | 538 | 0.37 | 5.86 | 2605 | 1227 | 0.10 | 6.03 | 1860 | 748 |
| 223.5 | 5.15 | 2.64 | 1272 | 530 | 0.35 | 5.95 | 2558 | 1146 | 0.09 | 5.97 | 1846 | 751 |
| 225.5 | 5.16 | 2.71 | 1262 | 489 | 0.42 | 5.98 | 2573 | 1144 | 0.12 | 6.12 | 1869 | 688 |
| 227.5 | 5.15 | 2.79 | 1254 | 473 | 0.39 | 5.78 | 2500 | 1122 | 0.10 | 6.40 | 1841 | 629 |
| 229.5 | 5.12 | 2.58 | 1222 | 165 | 0.36 | 5.95 | 2505 | 1028 | 0.08 | 5.70 | 1806 | 608 |
| 231.5 | 5.15 | 2.82 | 1222 | 429 | 0.39 | 6.09 | 2550 | 948 | 0.11 | 6.36 | 1844 | 595 |
| 233.5 | 5.16 | 2.81 | 1214 | 425 | 0.40 | 6.05 | 2514 | 902 | 0.12 | 6.32 | 1816 | 581 |
| 242.5 | 5.16 | 2.64 | 1131 | 326 | 0.51 | 5.91 | 2372 | 867 | 0.09 | 5.85 | 1597 | 495 |
| 244.0 | 5.16 | 2.50 | 1105 | 313 | 0.56 | 5.98 | 2416 | 791 | 0.11 | 5.36 | 1499 | 450 |
| 245.5 | 5.20 | 2.82 | 1186 | 314 | 0.71 | 6.07 | 2441 | 791 | 0.25 | 6.43 | 1796 | 469 |
| 248.0 | 5.14 | 2.81 | 1150 | 303 | 0.48 | 5.95 | 2458 | 746 | 0.03 | 6.41 | 1660 | 432 |
| 249.3 | 5.16 | 2.81 | 1165 | 304 | 0.45 | 5.74 | 2310 | 699 | 0.10 | 6.41 | 1717 | 432 |
| 250.3 | 5.17 | 2.79 | 1162 | 303 | 0.52 | 6.10 | 2409 | 787 | 0.13 | 6.34 | 1707 | 429 |
| 251.5 | 5.18 | 2.75 | 1150 | 287 | 0.58 | 5.72 | 2250 | 701 | 0.16 | 6.17 | 1663 | 370 |
| 256.0 | 5.16 | 2.88 | 1101 | 254 | 0.60 | 5.66 | 2166 | 625 | 0.03 | 6.43 | 1619 | 391 |
| 258.0 | 5.17 | 2.87 | 1108 | 310 | 0.81 | 5.91 | 2239 | 651 | 0.11 | 6.50 | 1693 | 429 |
| 260.0 | 5.16 | 2.83 | 1093 | 300 | 0.73 | 5.78 | 2234 | 612 | 0.06 | 6.35 | 1638 | 394 |
| 262.0 | 5.15 | 2.79 | 1091 | 249 | 0.71 | 5.77 | 2270 | 640 | 0.07 | 6.41 | 1674 | 395 |
| 267.0 | 5.30 | 2.70 | 1062 | 213 | 1.33 | 5.29 | 2049 | 531 | 0.55 | 6.00 | 1645 | 315 |
| 270.0 | 5.25 | 2.84 | 1080 | 222 | 1.12 | 5.88 | 2226 | 587 | 0.35 | 6.51 | 1710 | 349 |
| 271.0 | 5.20 | 2.87 | 1069 | 224 | 0.95 | 5.91 | 2243 | 685 | 0.19 | 6.60 | 1669 | 358 |
| 273.2 | 5.21 | 2.87 | 1071 | 247 | 0.90 | 5.93 | 2207 | 586 | 0.20 | 6.61 | 1675 | 440 |
| 273.8 | 5.21 | 2.83 | 1076 | 231 | 0.90 | 5.82 | 2235 | 640 | 0.23 | 6.48 | 1696 | 383 |
| 275.5 | 5.21 | 2.90 | 1107 | 237 | 0.93 | 5.68 | 2167 | 596 | 0.20 | 6.72 | 1809 | 406 |
| 277.0 | 5.18 | 2.87 | 1100 | 270 | 0.91 | 6.28 | 2240 | 590 | 0.12 | 6.61 | 1785 | 527 |
| 278.2 | 5.19 | 2.89 | 1163 | 240 | 0.94 | 5.95 | 2339 | 632 | 0.11 | 6.76 | 1852 | 422 |
| 281.5 | 5.20 | 2.79 | 1186 | 281 | 0.92 | 6.08 | 2505 | 729 | 0.12 | 6.39 | 1936 | 571 |
| 284.5 | 5.19 | 2.71 | 1162 | 244 | 0.87 | 6.04 | 2630 | 708 | 0.07 | 6.09 | 1847 | 437 |
| 287.5 | 5.19 | 2.69 | 1179 | 269 | 0.84 | 6.02 | 2693 | 745 | 0.07 | 6.03 | 1908 | 529 |
| 292.5 | 5.13 | 2.64 | 1177 | 241 | 0.20 | 5.87 | 2679 | 653 | 0.07 | 5.96 | 1718 | 378 |
| 301.0 | 5.27 | 2.65 | 979 | 166 | 0.92 | 5.30 | 1839 | 406 | 0.45 | 5.86 | 1259 | 200 |
| 335.5 | 5.50 | 1.14 | 191 | 82 | 1.85 | 3.64 | 1200 | 505 | 1.48 | 4.21 | 703 | 302 |
| 339.8 | 5.10 | 1.34 | 226 | 74 | 0.15 | 4.84 | 1654 | 518 | 0.01 | 4.92 | 833 | 273 |
| 344.0 | 5.11 | 1.41 | 235 | 38 | 0.48 | 5.25 | 1824 | 480 | 0.04 | 5.20 | 868 | 142 |
| 347.5 | 5.12 | 1.44 | 285 | 68 | 0.33 | 4.96 | 1867 | 528 | 0.09 | 5.30 | 1050 | 252 |

TABLE 45-continued

Analytical Results for Example 35

| Elapsed time (hrs) | Effective Combined R1 Feed | | | | R1 Exit | | | | R2 Exit | | | |
|---|---|---|---|---|---|---|---|---|---|---|---|---|
| | NPMIDA (wt %) | Gly (wt %) | HCHO (ppm) | HCOOH (ppm) | NPMIDA (wt %) | Gly (wt %) | HCHO (ppm) | HCOOH (ppm) | NPMIDA (wt %) | Gly (wt %) | HCHO (ppm) | HCOOH (ppm) |
| 351.5 | 5.12 | 1.42 | 297 | 69 | 0.28 | 5.18 | 2003 | 474 | 0.07 | 5.24 | 1096 | 255 |
| 353.8 | 5.11 | 1.44 | 314 | 75 | 0.30 | 5.11 | 2115 | 753 | 0.05 | 5.29 | 1157 | 276 |
| 357.5 | 5.16 | 2.94 | 807 | 216 | 0.44 | 6.34 | 2417 | 757 | 0.16 | 6.74 | 1558 | 364 |
| 359.5 | 5.13 | 2.83 | 789 | 192 | 0.29 | 6.27 | 2553 | 943 | 0.04 | 6.34 | 1490 | 278 |
| 368.0 | 5.15 | 2.70 | 881 | 201 | 0.34 | 5.96 | 2792 | 694 | 0.13 | 5.85 | 1831 | 309 |
| 370.5 | 5.14 | 2.91 | 894 | 227 | 0.34 | 6.65 | 2897 | 950 | 0.09 | 6.64 | 1877 | 406 |
| 373.5 | 5.17 | 2.95 | 986 | 224 | 0.51 | 6.49 | 3084 | 542 | 0.19 | 6.77 | 2216 | 394 |
| 375.0 | 5.17 | 2.78 | 1425 | 270 | 0.43 | 6.46 | 3131 | 976 | 0.12 | 6.44 | 2291 | 563 |
| 378.3 | 5.14 | 2.76 | 1437 | 238 | 0.32 | 6.05 | 3273 | 940 | 0.03 | 6.34 | 2334 | 444 |
| 380.5 | 5.14 | 2.79 | 1425 | 226 | 0.21 | 6.13 | 3229 | 1021 | 0.00 | 6.48 | 2290 | 402 |
| 383.5 | 5.34 | 2.87 | 1853 | 272 | 0.95 | 6.57 | 3829 | 1031 | 0.59 | 6.55 | 3052 | 397 |
| 387.5 | 5.20 | 2.86 | 1868 | 275 | 0.25 | 6.09 | 3652 | 842 | 0.07 | 6.55 | 2787 | 476 |
| 389.5 | 5.22 | 2.82 | 1953 | 308 | 0.53 | 5.89 | 3833 | 1370 | 0.22 | 6.43 | 3115 | 476 |
| 391.0 | 5.28 | 2.91 | 2002 | 334 | 0.72 | 6.05 | 4118 | 1358 | 0.42 | 6.74 | 3295 | 574 |
| 392.0 | 5.26 | 2.91 | 2061 | 286 | 0.59 | 6.41 | 4047 | 1336 | 0.32 | 6.73 | 3273 | 485 |
| 395.0 | 5.19 | 2.83 | 2101 | 324 | 0.31 | 6.19 | 4022 | 1036 | 0.10 | 6.62 | 3221 | 582 |
| 398.5 | 5.16 | 2.76 | 2153 | 344 | 0.34 | 6.17 | 4219 | 1519 | 0.09 | 6.47 | 3353 | 649 |
| 399.5 | 5.16 | 2.78 | 2184 | 396 | 0.33 | 6.13 | 4262 | 1286 | 0.07 | 6.53 | 3466 | 840 |
| 401.5 | 5.15 | 2.78 | 2265 | 494 | 0.38 | 6.19 | 4323 | 1570 | 0.09 | 6.37 | 3609 | 1005 |
| 405.0 | 5.21 | 2.88 | 2383 | 563 | 0.65 | 6.21 | 4337 | 1470 | 0.27 | 6.63 | 3731 | 937 |
| 407.0 | 5.20 | 2.87 | 2409 | 635 | 0.61 | 6.30 | 4492 | 1922 | 0.25 | 6.58 | 3830 | 1202 |
| 409.6 | 5.20 | 2.70 | 2493 | 708 | 0.53 | 6.40 | 4498 | 1926 | 0.17 | 5.84 | 3854 | 1360 |
| 412.0 | 5.14 | 2.66 | 2438 | 723 | 0.27 | 5.66 | 4230 | 1874 | 0.02 | 6.04 | 3601 | 1387 |
| 413.5 | 5.15 | 2.67 | 2497 | 747 | 0.36 | 5.71 | 4355 | 2236 | 0.07 | 6.09 | 3819 | 1477 |
| 416.5 | 5.13 | 2.68 | 2553 | 985 | 0.39 | 5.78 | 4371 | 2351 | 0.06 | 6.17 | 3911 | 1804 |

Example 36

Figure 31:
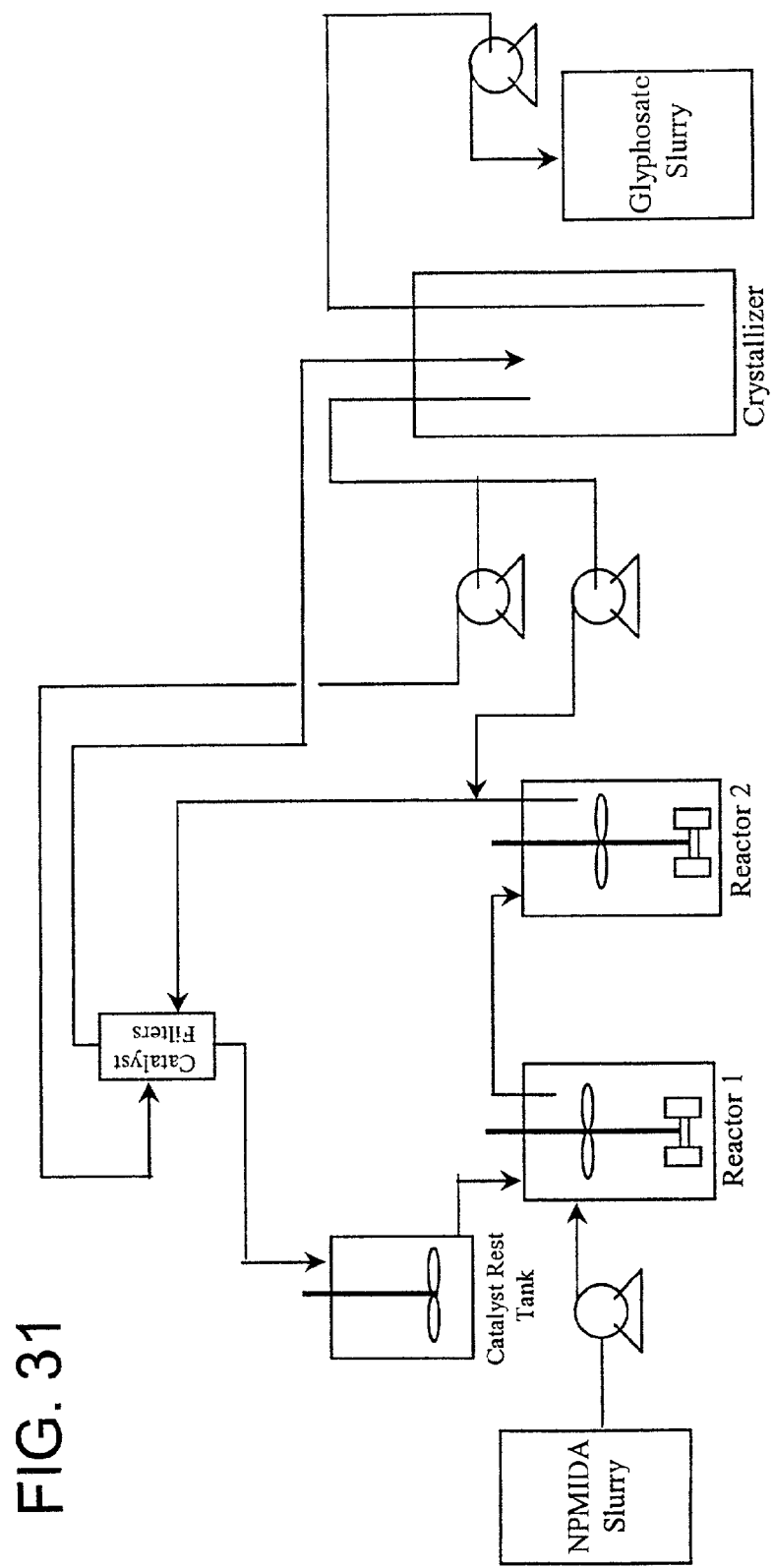
FIG. 31 is a block flow diagram for the continuous reactor system used in Example 36.

Continuous Oxidation of NPMIDA to Glyphosate in Two Stirred Tank Reactors in Series with Catalyst Recycle and Crystallizer Recycle This example demonstrates the continuous oxidation of NPMIDA to N-(phosphonomethyl)glycine in a continuous reactor system comprising two stirred-tank reactors staged in series utilizing a heterogeneous particulate catalyst slurry. The reactor system was similar to that shown in FIG. 31. The two stirred tank reactors (R1 and R2) were as described in Example 35 above. The catalyst was continuously filtered from the reaction mixture effluent withdrawn from R2 using a back-pulse filter system comprising parallel filter bodies and the separated catalyst was recycled to R1. Crystalline N-(phosphonomethyl)glycine product was recovered from the filtrate in a crystallizer (30 L) and the mother liquor from the crystallizer was recycled to R1. Additionally, a portion of the crystallizer mother liquor was added to the effluent from R2 as an effluent dilution stream (75–100 ml/min) to reduce the glyphosate concentration in the R2 effluent introduced to the back-pulse filter to reduce potential crystallization problems. Also, the reaction system further comprised a catalyst rest tank (500 ml Hastelloy C autoclave with an upward pumping impeller), which collected the separated catalyst prior to its re-introduction to R1. The catalyst rest tank was operated without level control and catalyst slurry was allowed to exit at the top of the vessel.

The heterogeneous particulate catalyst was prepared by a method similar to that described in Example 17 above and comprised platinum (5% by weight) and iron (0.5% by weight) on a particulate carbon support. In this example, the particulate heterogeneous catalyst was transferred from R1 to R2 with the effluent from R1 including some entrained gas. The catalyst exited R2 with the reactor effluent, was separated in the back-pulse filter, sent to the catalyst rest tank and recycled back to R1. The back-pulse catalyst filter also acted as a liquid gas separator for the effluent from R2. The filtrate from the back-pulse catalyst filter was sent to a crystallizer for recovery of crystalline N-(phosphonomethyl) glycine product. The resulting mother liquor from the crystallizer was used to back-pulse the catalyst filter bodies, as a diluent for the effluent from R2 passing to the catalyst filter bodies, and recycled to R1 with the separated catalyst.

The operating conditions for R1 and R2 are summarized in Table 46. R1 and R2 were charged initially as shown in Table 46 and oxygen was introduced concurrent with the NPMIDA feed. The NPMIDA feed comprised an aqueous slurry feed material containing from about 20% to about 20.5% NPMIDA and mother liquor recycle from the catalyst filters to give an effective combined feed to R1. The effective combined feed to R1 was introduced initially at 7 wt % and later increased to 7.7 wt %. Bismuth oxide was added throughout the run to increase the formic acid destruction rate. Bismuth oxide was added in a continuous fashion by addition to the NPMIDA slurry feed (3–12 mg per 20 kg of NPMIDA slurry). The frequency and amount of bismuth oxide added to the slurry feed is listed in Table 47. The aqueous slurry feed to R1 (including the component from the crystallizer mother liquor recycled with the catalyst), R1 reactor effluent and R2 reactor effluent were analyzed by HPLC. The HPLC analytical results are presented in Table 48.

TABLE 46

Operating Conditions for Example 36.

| Initial Reactor Charge | R1 | R2 |
|---|---|---|
| Catalyst | 1.6 wt % | 1.6 wt % |
| water | 2400 ml | 2400 ml |
| Operating Conditions | | |
| Catalyst Concentration[1] | 1.6–2.2 wt % | 1.6–2.2 wt % |
| Agitator RPM | 1000 | 1000 |
| Total Liquid Flow into R1 | 147.4 g/min | 147.4 g/min |
| Pressure | 100 psig | 100 psig |
| Oxygen | 1200–2750 sccm | 350–1200 sccm |
| Temperature | 105°–110° C. | 105°–110° C. |
| Reaction Mass | 2950 g | 2950 g |
| Impeller Type | radial (2")[2] | radial (2")[2] |
| NPMIDA Slurry Flow Rate | 50 g/min | NA |
| RML Flow Rate[3] | 97.4 ml/min | NA |

[1]Initial catalyst charge was 1.6 wt %. During the run the catalyst loading was increased to 1.7 wt % at 344 hours, 1.8 wt % at 354 hours, 1.9 wt % at 356 hours, 2.0 wt % at 359 hours, 2.1 wt% at 363 hours and 2.2 wt % at 366 hours.
[2]A downward pumping impeller was installed on the agitator shaft about half way up the liquid column.
[3]Crystallizer mother liquor (RML) was used to back pulse the catalyst filters and return filtered catalyst back to R1 with RML.

TABLE 47

Frequency and Amount of Bismuth Oxide Addition to NPMIDA Slurry Feed.

| Elapsed Time (hrs) | Bismuth Oxide Addition (to 20 kg of NPMIDA Slurry Feed) |
|---|---|
| 9.8 | 3 mg |
| 20.5 | 6 mg |
| 34.3 | 9 mg |
| 44.0 | 18 mg |
| 89.4 | 12 mg |
| 98.0 | 3 mg |
| 204.9 | 6 mg |
| 225.1 | 3 mg |
| 274.3 | 12 mg |

TABLE 48

Analytical Results for Example 36.

| Elapsed time (hrs) | Effective Combined R1 Feed | | | | R1 Exit | | | | R2 Exit | | | |
|---|---|---|---|---|---|---|---|---|---|---|---|---|
| | NPMIDA (wt %) | Gly (wt %) | HCHO (ppm) | HCOOH (ppm) | NPMIDA (wt %) | Gly (wt %) | HCHO (ppm) | HCOOH (ppm) | NPMIDA (wt %) | Gly (wt %) | HCHO (ppm) | HCOOH (ppm) |
| 2.2 | 8.03 | 1.84 | 185 | 1338 | 3.50 | 4.47 | 682 | 3378 | 3.03 | 4.54 | 456 | 3303 |
| 5.5 | 6.85 | 1.71 | 53 | 515 | 1.00 | 6.14 | 712 | 3816 | 0.20 | 6.88 | 215 | 2073 |
| 8.5 | 6.86 | 2.55 | 71 | 742 | 1.10 | 6.33 | 743 | 3742 | 0.22 | 6.84 | 230 | 2564 |
| 11.5 | 6.85 | 2.85 | 97 | 1044 | 1.01 | 7.05 | 842 | 4090 | 0.17 | 7.56 | 247 | 2609 |
| 14.5 | 6.84 | 2.28 | 95 | 1079 | 0.64 | 6.89 | 817 | 3927 | 0.12 | 7.48 | 216 | 2398 |
| 17.5 | 7.01 | 2.67 | 146 | 1441 | 1.44 | 6.38 | 849 | 4142 | 0.74 | 7.06 | 399 | 3494 |
| 20.5 | 7.12 | 2.72 | 188 | 1746 | 1.60 | 6.22 | 837 | 4323 | 0.70 | 6.86 | 388 | 3458 |
| 23.5 | 7.13 | 2.87 | 213 | 2115 | 1.30 | 6.82 | 892 | 4732 | 0.49 | 7.43 | 385 | 3674 |
| 26.5 | 7.01 | 3.00 | 201 | 1854 | 1.06 | 7.39 | 904 | 4871 | 0.13 | 7.67 | 298 | 2414 |
| 28.0 | 6.99 | 2.93 | 193 | 1827 | 1.04 | 6.79 | 951 | 4147 | 0.06 | 7.38 | 267 | 2303 |
| 30.0 | 7.00 | 2.96 | 204 | 1941 | 1.01 | 6.88 | 973 | 4621 | 0.10 | 7.50 | 311 | 2779 |
| 31.0 | 6.92 | 2.80 | 215 | 1888 | 1.31 | 6.81 | 1022 | 6357 | 0.18 | 7.57 | 385 | 3050 |
| 33.0 | 6.89 | 2.76 | 217 | 1721 | 1.09 | 6.45 | 975 | 4210 | 0.13 | 7.36 | 345 | 2629 |
| 35.0 | 6.87 | 2.75 | 226 | 1888 | 0.99 | 6.78 | 1198 | 4748 | 0.06 | 7.50 | 392 | 2761 |
| 36.5 | 6.87 | 2.66 | 270 | 1885 | 0.94 | 6.67 | 1422 | 4872 | 0.05 | 7.10 | 576 | 2747 |
| 37.5 | 6.87 | 2.78 | 299 | 2138 | 0.88 | 6.92 | 1617 | 5403 | 0.05 | 7.62 | 694 | 3804 |
| 40.0 | 7.73 | 2.72 | 423 | 2844 | 1.35 | 6.84 | 1867 | 6272 | 0.21 | 6.99 | 727 | 5318 |
| 43.0 | 7.75 | 2.87 | 419 | 3330 | 1.45 | 6.78 | 1871 | 6615 | 0.20 | 7.57 | 696 | 5672 |
| 44.8 | 7.75 | 2.86 | 726 | 3316 | 1.28 | 6.69 | 2207 | 6247 | 0.19 | 7.50 | 1262 | 5180 |
| 46.3 | 7.77 | 2.79 | 761 | 3106 | 1.72 | 6.99 | 2216 | 6140 | 0.29 | 7.20 | 1405 | 4303 |
| 48.0 | 7.79 | 2.89 | 768 | 3357 | 1.44 | 7.00 | 2309 | 6196 | 0.35 | 7.64 | 1437 | 5353 |
| 51.0 | 7.84 | 3.69 | 1033 | 4607 | 1.22 | 7.16 | 2348 | 5807 | 0.16 | 7.92 | 1379 | 4709 |
| 53.0 | 7.83 | 3.64 | 1002 | 4423 | 1.29 | 6.66 | 2323 | 5481 | 0.09 | 7.70 | 1249 | 3940 |
| 54.8 | 7.94 | 3.46 | 1066 | 4513 | 1.94 | 8.07 | 2234 | 5273 | 0.57 | 7.24 | 1497 | 3870 |
| 56.0 | 7.90 | 3.00 | 933 | 3216 | 2.04 | 6.92 | 2304 | 5384 | 0.57 | 7.84 | 1557 | 4666 |
| 57.0 | 7.85 | 2.89 | 915 | 2927 | 1.60 | 7.19 | 2307 | 5030 | 0.36 | 7.34 | 1473 | 3327 |
| 58.5 | 7.86 | 3.14 | 941 | 3065 | 1.81 | 7.14 | 2357 | 5248 | 0.34 | 8.04 | 1470 | 4184 |
| 60.5 | 7.85 | 3.40 | 940 | 3010 | 1.35 | 7.30 | 2399 | 4871 | 0.30 | 9.24 | 1468 | 3927 |
| 62.5 | 7.81 | 3.05 | 923 | 2729 | 1.34 | 7.34 | 2448 | 4730 | 0.16 | 8.00 | 1349 | 3329 |
| 64.0 | 7.82 | 3.02 | 934 | 2564 | 1.69 | 8.50 | 2420 | 4719 | 0.20 | 7.87 | 1401 | 2564 |
| 65.5 | 7.87 | 3.22 | 986 | 2829 | 1.63 | 7.69 | 2364 | 4381 | 0.42 | 8.80 | 1642 | 3791 |
| 67.0 | 7.78 | 2.75 | 866 | 2291 | 0.51 | 6.94 | 2377 | 3248 | 0.02 | 6.64 | 1085 | 1293 |

TABLE 48-continued

Analytical Results for Example 36.

| Elapsed time (hrs) | Effective Combined R1 Feed | | | | R1 Exit | | | | R2 Exit | | | |
|---|---|---|---|---|---|---|---|---|---|---|---|---|
| | NPMIDA (wt %) | Gly (wt %) | HCHO (ppm) | HCOOH (ppm) | NPMIDA (wt %) | Gly (wt %) | HCHO (ppm) | HCOOH (ppm) | NPMIDA (wt %) | Gly (wt %) | HCHO (ppm) | HCOOH (ppm) |
| 68.0 | 7.79 | 2.96 | 910 | 2616 | 0.99 | 7.33 | 2498 | 3884 | 0.09 | 7.58 | 1289 | 2801 |
| 69.0 | 7.81 | 3.00 | 920 | 2476 | 1.16 | 6.93 | 2543 | 3938 | 0.15 | 7.78 | 1334 | 2151 |
| 71.0 | 7.74 | 3.10 | 890 | 1969 | 1.18 | 7.18 | 2528 | 3862 | 0.12 | 8.12 | 1415 | 2796 |
| 73.3 | 7.75 | 3.14 | 906 | 1988 | 1.46 | 7.73 | 2547 | 4093 | 0.18 | 8.31 | 1493 | 2881 |
| 75.5 | 7.75 | 3.14 | 953 | 1960 | 1.53 | 7.15 | 2398 | 3595 | 0.17 | 8.29 | 1534 | 2773 |
| 77.8 | 7.73 | 3.12 | 933 | 1994 | 1.21 | 7.28 | 2424 | 3353 | 0.08 | 8.23 | 1441 | 2932 |
| 79.5 | 7.71 | 3.17 | 940 | 1725 | 1.29 | 7.16 | 2448 | 3237 | 0.07 | 7.96 | 1436 | 2264 |
| 81.0 | 7.72 | 3.01 | 937 | 1558 | 1.41 | 7.95 | 2438 | 2738 | 0.10 | 7.23 | 1421 | 1490 |
| 82.5 | 7.73 | 3.17 | 997 | 1709 | 1.46 | 7.07 | 2445 | 3090 | 0.13 | 8.12 | 1590 | 2294 |
| 84.0 | 7.73 | 3.07 | 1003 | 1546 | 1.49 | 7.89 | 2459 | 2579 | 0.15 | 7.67 | 1616 | 1536 |
| 86.8 | 7.73 | 3.11 | 1010 | 1509 | 1.57 | 8.16 | 2497 | 2442 | 0.11 | 7.84 | 1648 | 1364 |
| 88.5 | 7.72 | 3.27 | 1092 | 1500 | 1.46 | 7.44 | 2608 | 2896 | 0.09 | 8.57 | 1739 | 2048 |
| 90.0 | 7.75 | 3.48 | 1109 | 1518 | 2.04 | 7.73 | 2696 | 2969 | 0.21 | 9.50 | 1818 | 2129 |
| 91.5 | 7.75 | 3.08 | 1159 | 1529 | 1.91 | 7.44 | 2671 | 2935 | 0.20 | 7.86 | 1907 | 2219 |
| 93.0 | 7.74 | 3.23 | 1152 | 1340 | 1.74 | 8.07 | 2971 | 2964 | 0.14 | 8.54 | 1874 | 1342 |
| 94.5 | 7.73 | 3.71 | 1192 | 1425 | 1.56 | 7.77 | 3039 | 2883 | 0.10 | 9.01 | 1893 | 1899 |
| 98.5 | 7.66 | 1.67 | 264 | 233 | 1.28 | 6.26 | 2256 | 1985 | 0.05 | 7.73 | 1227 | 1082 |
| 100.0 | 7.65 | 1.54 | 160 | 166 | 1.02 | 6.42 | 1807 | 1496 | 0.02 | 7.16 | 742 | 769 |
| 101.5 | 7.65 | 1.54 | 146 | 153 | 0.97 | 6.58 | 1718 | 1927 | 0.01 | 7.13 | 678 | 709 |
| 104.5 | 7.65 | 1.45 | 122 | 151 | 0.71 | 6.01 | 1591 | 1739 | 0.02 | 6.73 | 566 | 699 |
| 107.5 | 7.68 | 1.42 | 118 | 175 | 1.10 | 5.71 | 1439 | 1698 | 0.14 | 6.59 | 549 | 811 |
| 111.5 | 7.75 | 1.54 | 130 | 196 | 1.39 | 6.20 | 1429 | 1854 | 0.46 | 7.15 | 603 | 909 |
| 113.0 | 7.75 | 2.70 | 190 | 164 | 1.23 | 5.67 | 1337 | 1717 | 0.08 | 6.71 | 520 | 479 |
| 114.2 | 7.84 | 3.10 | 237 | 310 | 1.98 | 7.39 | 1605 | 2358 | 0.48 | 8.55 | 740 | 1156 |
| 115.5 | 7.75 | 3.23 | 305 | 349 | 1.15 | 7.32 | 1662 | 2044 | 0.07 | 8.32 | 694 | 833 |
| 118.5 | 7.77 | 3.25 | 288 | 243 | 1.50 | 7.49 | 1701 | 1973 | 0.21 | 8.99 | 750 | 647 |
| 121.5 | 7.79 | 3.48 | 555 | 756 | 1.56 | 7.82 | 2111 | 2604 | 0.28 | 8.81 | 1093 | 1395 |
| 124.5 | 7.73 | 3.09 | 507 | 677 | 1.46 | 8.01 | 2239 | 2757 | 0.16 | 9.04 | 1122 | 1404 |
| 127.5 | 7.82 | 3.61 | 719 | 1064 | 1.57 | 7.64 | 2283 | 2755 | 0.49 | 8.99 | 1249 | 1530 |
| 133.5 | 7.71 | 3.22 | 835 | 1021 | 1.53 | 7.75 | 2507 | 2738 | 0.11 | 8.55 | 1400 | 1583 |
| 136.5 | 7.70 | 3.40 | 906 | 1090 | 1.29 | 7.78 | 2634 | 2961 | 0.09 | 8.72 | 1494 | 1626 |
| 139.5 | 7.77 | 3.55 | 1124 | 1181 | 1.48 | 6.26 | 2718 | 1929 | 0.36 | 8.74 | 2267 | 2129 |
| 142.5 | 7.88 | 3.50 | 1045 | 1064 | 1.68 | 7.72 | 2733 | 2985 | 0.54 | 8.75 | 1690 | 1569 |
| 145.5 | 7.77 | 3.60 | 1055 | 1194 | 1.53 | 8.07 | 2836 | 2997 | 0.07 | 9.05 | 1655 | 1557 |
| 149.0 | 7.72 | 3.52 | 1100 | 1359 | 1.32 | 7.62 | 2949 | 2913 | 0.06 | 8.81 | 1773 | 1666 |
| 152.0 | 7.71 | 3.34 | 1138 | 1302 | 1.25 | 7.62 | 3032 | 2408 | 0.11 | 8.79 | 1811 | 1602 |
| 155.0 | 7.72 | 3.62 | 1165 | 1354 | 1.79 | 8.32 | 2989 | 3128 | 0.19 | 9.16 | 1864 | 1584 |
| 158.5 | 7.71 | 3.98 | 1195 | 1164 | 1.35 | 8.02 | 3162 | 2902 | 0.10 | 8.92 | 1933 | 1641 |
| 161.5 | 7.70 | 3.47 | 1276 | 1193 | 1.34 | 7.75 | 3174 | 3005 | 0.12 | 8.89 | 2071 | 1691 |
| 164.5 | 7.73 | 3.13 | 1324 | 1059 | 1.40 | 7.82 | 3264 | 2969 | 0.13 | 7.42 | 2135 | 1263 |
| 167.5 | 7.71 | 3.38 | 1311 | 918 | 1.47 | 7.99 | 3378 | 3102 | 0.12 | 8.61 | 2089 | 1528 |
| 172.0 | 7.74 | 2.93 | 1427 | 1173 | 1.44 | 7.50 | 3428 | 2731 | 0.14 | 8.31 | 2223 | 1511 |
| 175.0 | 7.72 | 3.07 | 1480 | 1050 | 1.48 | 7.51 | 3555 | 2653 | 0.10 | 8.57 | 2314 | 1479 |
| 178.0 | 7.69 | 2.91 | 1474 | 1159 | 1.39 | 6.89 | 3347 | 2254 | 0.09 | 8.48 | 2319 | 1506 |
| 181.0 | 7.69 | 2.91 | 1505 | 1044 | 1.42 | 7.79 | 3573 | 2669 | 0.10 | 8.43 | 2322 | 1452 |
| 184.0 | 7.70 | 3.01 | 1525 | 1058 | 1.39 | 7.41 | 3572 | 2670 | 0.11 | 8.81 | 2268 | 1499 |
| 186.5 | 7.78 | 2.81 | 1802 | 2335 | 2.69 | 6.32 | 3714 | 6849 | 0.51 | 7.87 | 3550 | 7428 |
| 188.3 | 8.02 | 2.47 | 1418 | 3234 | 4.05 | 6.45 | 3407 | 8082 | 1.24 | 7.99 | 3294 | 8694 |
| 203.5 | 7.76 | 2.59 | 1303 | 2043 | 1.76 | 6.65 | 3365 | 4733 | 0.15 | 7.53 | 2552 | 3664 |
| 205.8 | 7.79 | 2.74 | 1397 | 2401 | 2.04 | 7.25 | 3564 | 5706 | 0.29 | 8.20 | 2988 | 5327 |
| 209.5 | 7.66 | 1.53 | 544 | 523 | 0.91 | 6.13 | 3720 | 4459 | 0.04 | 7.09 | 2525 | 2427 |
| 212.0 | 7.72 | 2.60 | 1454 | 1788 | 1.51 | 6.92 | 3834 | 4230 | 0.11 | 7.55 | 2802 | 2741 |
| 213.5 | 7.74 | 2.61 | 1439 | 1954 | 2.24 | 7.04 | 3462 | 4683 | 0.19 | 7.59 | 2732 | 3513 |
| 215.0 | 7.75 | 2.72 | 1819 | 2043 | 1.85 | 7.01 | 4071 | 4994 | 0.22 | 7.03 | 3126 | 3839 |
| 216.5 | 7.76 | 2.86 | 1769 | 2046 | 1.93 | 7.02 | 3577 | 4998 | 0.25 | 7.70 | 2892 | 3852 |
| 218.0 | 7.74 | 2.75 | 1959 | 2623 | 1.50 | 6.88 | 4035 | 5101 | 0.13 | 8.13 | 3122 | 3909 |
| 221.0 | 7.73 | 2.77 | 2080 | 2861 | 1.68 | 6.91 | 4039 | 5394 | 0.15 | 7.94 | 3284 | 4107 |
| 225.0 | 7.72 | 2.96 | 1808 | 2461 | 1.59 | 6.99 | 3427 | 5187 | 0.14 | 7.43 | 2706 | 3819 |
| 228.5 | 7.65 | 1.44 | 535 | 407 | 0.76 | 6.99 | 3674 | 2202 | 0.03 | 6.71 | 2484 | 1888 |
| 232.0 | 7.68 | 2.54 | 1208 | 524 | 1.12 | 7.01 | 2708 | 2686 | 0.13 | 7.24 | 1619 | 1724 |
| 236.5 | 7.70 | 2.98 | 2767 | 1236 | 1.20 | 7.53 | 2934 | 3346 | 0.11 | 8.46 | 1820 | 2154 |
| 238.5 | 7.71 | 2.95 | 2962 | 1256 | 1.51 | 7.51 | 3748 | 3631 | 0.17 | 8.31 | 2728 | 2246 |
| 242.0 | 7.73 | 2.93 | 1404 | 1146 | 1.48 | 7.14 | 3231 | 3767 | 0.17 | 7.55 | 2192 | 2064 |
| 245.5 | 7.74 | 3.00 | 1778 | 1657 | 1.44 | 7.19 | 3758 | 3684 | 0.13 | 8.22 | 2782 | 2247 |
| 248.0 | 7.72 | 3.00 | 1831 | 1739 | 1.47 | 7.24 | 3781 | 3763 | 0.14 | 8.39 | 2867 | 2397 |
| 250.0 | 7.72 | 2.96 | 1834 | 1733 | 1.57 | 8.02 | 3875 | 3928 | 0.15 | 8.20 | 2882 | 2372 |
| 252.3 | 7.69 | 3.08 | 1995 | 1421 | 1.47 | 7.53 | 4141 | 4229 | 0.13 | 8.50 | 3190 | 2405 |
| 255.0 | 7.70 | 3.17 | 2045 | 1699 | 1.60 | 7.64 | 4102 | 3635 | 0.15 | 8.74 | 3076 | 2601 |
| 258.0 | 7.72 | 2.92 | 1919 | 1898 | 1.57 | 7.39 | 3914 | 4148 | 0.14 | 8.08 | 2778 | 2428 |
| 261.0 | 7.72 | 2.98 | 1909 | 2016 | 1.54 | 7.24 | 3935 | 4109 | 0.13 | 8.09 | 2747 | 2603 |
| 262.5 | 7.73 | 2.97 | 1853 | 2044 | 1.76 | 7.30 | 3296 | 4404 | 0.15 | 8.06 | 2490 | 2731 |
| 264.0 | 7.73 | 2.92 | 1905 | 2125 | 1.83 | 7.41 | 3858 | 4367 | 0.16 | 8.22 | 2720 | 2828 |

TABLE 48-continued

Analytical Results for Example 36.

| Elapsed time (hrs) | Effective Combined R1 Feed | | | | R1 Exit | | | | R2 Exit | | | |
|---|---|---|---|---|---|---|---|---|---|---|---|---|
| | NPMIDA (wt %) | Gly (wt %) | HCHO (ppm) | HCOOH (ppm) | NPMIDA (wt %) | Gly (wt %) | HCHO (ppm) | HCOOH (ppm) | NPMIDA (wt %) | Gly (wt %) | HCHO (ppm) | HCOOH (ppm) |
| 270.0 | 7.73 | 2.93 | 1978 | 2269 | 1.86 | 7.15 | 3840 | 4415 | 0.15 | 8.30 | 3062 | 3498 |
| 273.0 | 7.71 | 3.01 | 1646 | 1713 | 1.81 | 6.97 | 3081 | 4619 | 0.13 | 7.97 | 2492 | 3091 |
| 276.0 | 7.72 | 2.95 | 1637 | 1751 | 1.87 | 6.95 | 3062 | 4531 | 0.16 | 7.99 | 2471 | 3038 |
| 279.0 | 7.72 | 2.94 | 1646 | 2020 | 1.95 | 6.90 | 3049 | 4576 | 0.14 | 7.99 | 2514 | 2600 |
| 282.0 | 7.74 | 2.99 | 1973 | 1741 | 1.67 | 7.02 | 3093 | 3462 | 0.16 | 8.05 | 2450 | 2548 |
| 285.0 | 7.69 | 2.96 | 1807 | 1438 | 1.53 | 7.23 | 3444 | 3660 | 0.08 | 8.11 | 2547 | 2352 |
| 288.0 | 7.70 | 2.98 | 1781 | 1464 | 1.46 | 7.13 | 3498 | 3683 | 0.10 | 7.97 | 2654 | 2359 |
| 291.0 | 7.69 | 2.92 | 1809 | 1371 | 1.55 | 7.10 | 3520 | 3793 | 0.11 | 8.03 | 2756 | 2450 |
| 294.0 | 7.69 | 2.89 | 1823 | 1357 | 1.52 | 7.13 | 3666 | 3750 | 0.10 | 7.96 | 2790 | 2399 |
| 297.0 | 7.70 | 2.88 | 1836 | 1377 | 1.82 | 6.98 | 3632 | 3747 | 0.14 | 7.92 | 2849 | 2492 |
| 300.0 | 7.69 | 2.89 | 1828 | 1358 | 1.71 | 6.85 | 3525 | 3640 | 0.11 | 7.95 | 2815 | 2406 |
| 303.0 | 7.71 | 2.86 | 1889 | 1468 | 1.93 | 6.87 | 3617 | 3802 | 0.14 | 7.78 | 2868 | 2505 |
| 306.0 | 7.71 | 2.85 | 1875 | 1453 | 1.72 | 6.65 | 3538 | 3657 | 0.11 | 7.71 | 2803 | 2435 |
| 309.0 | 7.68 | 2.80 | 1874 | 1356 | 1.60 | 6.70 | 3573 | 3731 | 0.09 | 7.72 | 2904 | 2512 |
| 312.0 | 7.70 | 2.80 | 2117 | 2129 | 1.96 | 6.83 | 3902 | 3753 | 0.13 | 8.04 | 3223 | 2603 |
| 315.0 | 7.70 | 2.89 | 2106 | 1744 | 1.85 | 6.94 | 3946 | 3545 | 0.10 | 8.96 | 3459 | 2368 |
| 318.0 | 7.72 | 2.85 | 2115 | 2025 | 2.21 | 6.89 | 3933 | 3772 | 0.16 | 8.23 | 3299 | 2731 |
| 321.0 | 7.72 | 2.84 | 2150 | 2177 | 2.24 | 6.73 | 3864 | 3918 | 0.16 | 8.20 | 3313 | 2989 |
| 324.0 | 7.73 | 2.82 | 2173 | 2207 | 2.21 | 6.69 | 3857 | 3817 | 0.15 | 8.27 | 3321 | 2920 |
| 327.0 | 7.73 | 2.94 | 2187 | 2244 | 2.27 | 6.69 | 3805 | 4088 | 0.17 | 8.19 | 3317 | 3221 |
| 330.0 | 7.74 | 2.95 | 2382 | 1790 | 2.46 | 6.76 | 4069 | 4402 | 0.23 | 8.14 | 3536 | 3297 |
| 333.0 | 7.78 | 3.05 | 2777 | 1942 | 2.52 | 6.67 | 4864 | 4586 | 0.21 | 8.48 | 4232 | 3341 |
| 337.0 | 7.75 | 3.07 | 2848 | 1987 | 2.19 | 7.20 | 5059 | 4908 | 0.15 | 8.35 | 4237 | 3434 |
| 339.5 | 7.75 | 2.97 | 2798 | 2025 | 2.35 | 6.66 | 4770 | 4719 | 0.20 | 8.06 | 4152 | 3552 |
| 342.5 | 7.75 | 3.07 | 2782 | 2105 | 2.39 | 6.98 | 4905 | 4929 | 0.18 | 8.36 | 4240 | 3636 |
| 344.0 | 7.75 | 3.07 | 2776 | 2564 | 2.37 | 6.90 | 4860 | 5242 | 0.17 | 8.43 | 4198 | 3899 |
| 346.0 | 7.71 | 2.97 | 2462 | 2316 | 1.56 | 7.34 | 4418 | 4337 | 0.08 | 8.16 | 3386 | 2732 |
| 348.0 | 7.72 | 3.01 | 2506 | 2515 | 1.98 | 7.00 | 4454 | 5019 | 0.12 | 8.34 | 3593 | 3655 |
| 350.3 | 7.71 | 2.97 | 2386 | 2328 | 1.90 | 7.19 | 4624 | 4795 | 0.11 | 8.17 | 3614 | 3321 |
| 352.3 | 7.71 | 3.00 | 2441 | 2387 | 1.95 | 6.96 | 4594 | 4764 | 0.13 | 8.27 | 3869 | 3596 |
| 354.3 | 7.70 | 3.05 | 2531 | 1888 | 2.13 | 7.03 | 4941 | 4936 | 0.14 | 8.27 | 3839 | 3312 |
| 356.3 | 7.68 | 2.97 | 2289 | 1874 | 1.39 | 7.62 | 4250 | 4101 | 0.06 | 8.53 | 3191 | 2754 |
| 358.3 | 7.67 | 3.04 | 2021 | 1415 | 1.05 | 8.15 | 4080 | 3814 | 0.03 | 8.49 | 2685 | 2026 |
| 365.0 | 7.68 | 3.48 | 1358 | 998 | 1.13 | 8.47 | 3195 | 3102 | 0.02 | 7.95 | 1949 | 1597 |
| 367.0 | 7.65 | 3.91 | 1266 | 1063 | 1.13 | 8.33 | 2825 | 3149 | 0.02 | 8.94 | 1612 | 1647 |
| 368.0 | 7.65 | 3.87 | 1217 | 1101 | 1.24 | 8.31 | 2475 | 3257 | 0.02 | 9.08 | 1737 | 1898 |

Example 37

Continuous Oxidation of NPMIDA to Glyphosate in a Fixed Bed Reactor Using a Pt/Fe/C Catalyst This example demonstrates the continuous oxidation of NPMIDA to glyphosate in the presence of a Pt/Fe/C heterogeneous particulate catalyst in a fixed bed reactor. The experiment was designed to simulate a small section of a fixed bed reactor with gas and liquid feeds entering co-currently.

The experiment was conducted in a continuous reactor system comprising a vertical stainless steel tubular reactor (1.56 cm ID, 60.5 cm in length, 116 ml volume). The gas and liquid feed streams entered the tubular reactor at the top and flowed down through the reactor. The reactor contained a Pt/Fe/C catalyst (42.3 g) comprising platinum (2% by weight) and iron (0.2% by weight) on 1.2 mm-diameter extruded carbon supports ranging from about 1 mm to about 9 mm in length. The reactor was heated to 90° C. with a heated water feed and brought to a pressure of 150 psig with nitrogen. After the reactor temperature reached 90° C., the water and nitrogen flow were stopped and the liquid and oxygen feeds were initiated.

The liquid feed (50 ml/min) comprised an aqueous slurry feed material containing NPMIDA (1.92% by weight), glyphosate (1.89% by weight), formic acid (0.26% by weight) and formaldehyde (0.15% by weight). Oxygen (200 sccm) was fed to the top of the reactor with the pressure maintained at 150 psig. After ten days of continuous operation, analysis of the reactor product showed 0.15% formaldehyde, 0.26% formic acid and 2.53% glyphosate.

Example 38

Continuous Oxidation of NPMIDA to Glyphosate in a Fixed Bed Reactor Using a Pt/Fe/C Catalyst This example demonstrates the continuous oxidation of NPMIDA to glyphosate in the presence of a Pt/Fe/C heterogeneous particulate catalyst in a fixed bed reactor with cocurrent upflow of gas and liquid reactants.

The experiment was conducted in a continuous oxidation reactor system comprising a vertical stainless steel tubular reactor as described in Example 37, except that reactants flowed up through the reaction zone. The reactor contained a Pt/Fe/C catalyst (42.3 g) comprising platinum (2% by weight) and iron (0.2% by weight) on 1.2 mm-diameter extruded carbon supports ranging from about 1 mm to about 9 mm in length. The reactor was heated to 90° C. with a heated water feed and brought to a pressure of 150 psig with nitrogen. After the reactor temperature reached 90° C., the water and nitrogen flow were stopped and the liquid and oxygen feeds were initiated.

The liquid feed (50 ml/min) comprised an aqueous slurry feed material containing NPMIDA (1.80% by weight), glyphosate (2.19% by weight), formic acid (0.26% by weight) and formaldehyde (0.14% by weight) and was fed to the bottom of the reactor at 90° C. Oxygen (200 sccm) was fed to the bottom of the reactor with the pressure maintained at 150 psig. After nineteen hours of continuous operation, analysis of the reactor product showed 0.13% formaldehyde, 0.16% formic acid and 2.42% glyphosate.

Example 39

Continuous Oxidation of NPMIDA Potassium Salt to Glyphosate Potassium Salt in a Fixed Bed Reactor Using a Pt/Fe/C Catalyst with Co-Current Upflow of Liquid and Gas Reactants This example demonstrates the continuous oxidation of NPMIDA potassium salt to glyphosate potassium salt in the presence of a Pt/Fe/C heterogeneous particulate catalyst in a fixed bed reactor with co-current upflow of liquid and gas reactants.

The experiment was conducted in a continuous oxidation reactor system comprising a vertical stainless steel tubular reactor as described in Example 37, except that reactants flowed up through the reaction zone. The reactor contained a Pt/Fe/C catalyst (42.3 g) comprising platinum (2% by weight) and iron (0.2% by weight) on 1.2 mm-diameter extruded carbon supports ranging from about 1 mm to about 9 mm in length. The reactor was heated to 90° C. with a heated water feed and brought to a pressure of 150 psig with nitrogen. After reaching 90° C., the water and nitrogen flow were stopped and the liquid and oxygen feeds were initiated.

The liquid feed (50 ml/min) comprised an aqueous slurry feed material containing NPMIDA as the potassium salt (22.9% by weight), glyphosate (0.09% by weight), formic acid (0.20% by weight) and formaldehyde (0.14% by weight), and was fed to the bottom of the reactor at 90° C. Oxygen (500 sccm) was fed to the bottom of the reactor with the pressure maintained at 150 psig. Analysis of the reactor product showed 0.35% formaldehyde, 0.20% formic acid and 1.56% glyphosate potassium salt.

Example 40

Comparison of Pt/Fe Catalyst Versus a Mixture of Pt/Fe and Pt/Fe/Te Catalysts

This example compares the conversion of NPMIDA to glyphosate in a continuous oxidation reactor system using a Pt/Fe heterogeneous particulate catalyst versus the conversion of NPMIDA to glyphosate in a continuous oxidation reactor system using a combination of Pt/Fe and Pt/Fe/Te heterogeneous particulate catalysts.

The reactions were conducted in a continuous reactor system utilizing a 2-liter Hastelloy C autoclave (Autoclave Engineers Inc., Pittsburgh, Pa.). The reactor was equipped with an agitator having a 1.25" diameter six-blade turbine impeller, which was operated at 1600 RPM. The liquid level in the reactor was monitored using a Drexelbrook Universal III™ Smart Level™, with a teflon-coated sensing element. An internal cooling coil was utilized to control the temperature within the reactor during the course of the reaction.

In the first experiment, the reactor was loaded with a Pt/Fe heterogenous particulate catalyst (2.18 g) and an aqueous slurry feed material (1448 g). The catalyst comprised platinum (5% by weight) and iron (0.5% by weight). The aqueous slurry feed material comprised NPMIDA (3.5% by weight), glyphosate (1.5% by weight), formaldehyde (1200 ppm by weight), and formic acid (2500 ppm by weight). The slurry feed also contained NaCl (580 ppm by weight) to mimic NaCl impurity.

The reactor was pressurized to 100 psi with nitrogen and heated to 100° C. Once at temperature, a continuous flow of gaseous oxygen was fed to the reactor without any liquid flow through the system. After 9 minutes, the continuous slurry feed was initiated at a rate of 70.4 g/min and a oxygen flow was continued as described in Table 49 below. A liquid product stream containing glyphosate product was continuously withdrawn from the reactor and analyzed by HPLC. Oxidation results are also presented in Table 49.

In the second experiment, the reactor was loaded with a Pt/Fe heterogenous particulate catalyst (1.09 g), a Pt/Fe/Te heterogeneous particulate catalyst (1.09 g) and an aqueous slurry feed material (1455 g). The Pt/Fe catalyst comprised platinum (5% by weight) and iron (0.5% by weight) and the Pt/Fe/Te catalyst comprised platinum (5% by weight), iron (0.5% by weight) and tellurium (0.2% by weight). The aqueous slurry feed material comprised NPMIDA (3.5% by weight), glyphosate (1.5% by weight), formaldehyde (1200 ppm by weight), and formic acid (2500 ppm by weight). The slurry feed also contained NaCl (580 ppm by weight) to mimic NaCl impurity.

The reactor was pressurized to 100 psi with nitrogen and heated to 100° C. Once at temperature, a continuous flow of gaseous oxygen was fed to the reactor without any liquid flow through the system. After 19 minutes, the continuous slurry feed was initiated at a rate of 70.4 g/min and oxygen flow was continued as described in Table 50 below. A liquid product stream containing glyphosate product was continuously withdrawn from the reactor and analyzed by HPLC. Oxidation results for the second experiment are also presented in Table 50.

TABLE 49

Oxidation Results for Pt/Fe catalyst (Experiment 1)

| Elapsed Time (min) | O₂ Flow (sccm) | feed NPMIDA (wt %) | exit NPMIDA (wt %) | feed Glyphosate (wt %) | exit Glyphosate (wt %) | feed CH₂O (ppm) | exit CH₂O (ppm) | feed HCOOH (ppm) | exit HCOOH (ppm) |
|---|---|---|---|---|---|---|---|---|---|
| 77.0 | 300.0 | 3.49 | 0.82 | 1.51 | 3.47 | 1098.9 | 2083.9 | 2118.7 | 4385.0 |
| 147.0 | 300.0 | 3.49 | 0.52 | 1.51 | 3.23 | 1098.9 | 1674.8 | 2118.7 | 4653.9 |
| 205.0 | 300.0 | 3.49 | 0.80 | 1.51 | 3.49 | 1098.9 | 2195.2 | 2118.7 | 4206.5 |
| 280.0 | 300.0 | 3.49 | 0.84 | 1.51 | 3.48 | 1098.9 | 2215.4 | 2118.7 | 4167.7 |
| 1212.0 | 300.0 | 3.49 | 1.07 | 1.51 | 3.40 | 1098.9 | 2344.2 | 2118.7 | 3991.1 |
| 1378.0 | 300.0 | 3.49 | 1.18 | 1.51 | 3.40 | 1098.9 | 2361.3 | 2118.7 | 3973.1 |
| 1447.0 | 300.0 | 3.49 | 1.17 | 1.51 | 3.38 | 1098.9 | 2347.3 | 2118.7 | 4008.4 |

TABLE 49-continued

Oxidation Results for Pt/Fe catalyst (Experiment 1)

| Elapsed Time (min) | $O_2$ Flow (sccm) | feed NPMIDA (wt %) | exit NPMIDA (wt %) | feed Glyphosate (wt %) | exit Glyphosate (wt %) | feed $CH_2O$ (ppm) | exit $CH_2O$ (ppm) | feed HCOOH (ppm) | exit HCOOH (ppm) |
|---|---|---|---|---|---|---|---|---|---|
| 1618.0 | 300.0 | 3.49 | 1.26 | 1.51 | 3.35 | 1098.9 | 2323.1 | 2118.7 | 3985.8 |
| 1795.0 | 300.0 | 3.49 | 1.35 | 1.51 | 3.31 | 1098.9 | 2356.2 | 2118.7 | 3896.4 |
| 2683.0 | 300.0 | 3.49 | 1.39 | 1.51 | 3.27 | 1098.9 | 2316.2 | 2118.7 | 3861.0 |
| 2789.0 | 300.0 | 3.49 | 1.45 | 1.51 | 3.30 | 1098.9 | 2353.9 | 2118.7 | 3871.0 |
| 2885.0 | 300.0 | 3.49 | 1.53 | 1.51 | 3.25 | 1098.9 | 2310.5 | 2118.7 | 3796.1 |
| 3071.0 | 450.0 | 3.49 | 0.98 | 1.51 | 3.43 | 1098.9 | 2520.4 | 2118.7 | 3935.2 |
| 3180.0 | 700.0 | 3.49 | 0.88 | 1.51 | 3.55 | 1098.9 | 2653.0 | 2118.7 | 4086.1 |

TABLE 50

Oxidation Results for Pt/Fe and Pt/Fe/Te catalysts (Experiment 2)

| Elapsed Time (min) | $O_2$ Flow (sccm) | feed NPMIDA (wt %) | exit NPMIDA (wt %) | feed Glyphosate (wt %) | exit Glyphosate (wt %) | feed $CH_2O$ (ppm) | exit $CH_2O$ (ppm) | feed HCOOH (ppm) | exit HCOOH (ppm) |
|---|---|---|---|---|---|---|---|---|---|
| 48.0 | 315.0 | 3.25 | 0.82 | 1.60 | 3.18 | 1222.1 | 940.17 | 2299.6 | 3757.3 |
| 156.0 | 330.0 | 3.25 | 0.75 | 1.60 | 3.15 | 1222.1 | 1087.2 | 2299.6 | 3975.6 |
| 210.0 | 365.0 | 3.25 | 0.57 | 1.60 | 3.27 | 1222.1 | 1200.9 | 2299.6 | 4114.4 |
| 281.0 | 410.0 | 3.25 | 0.46 | 1.60 | 3.39 | 1222.1 | 1306.9 | 2299.6 | 4182.9 |
| 339.0 | 410.0 | 3.25 | 0.67 | 1.60 | 3.35 | 1222.1 | 1306.5 | 2299.6 | 4191.2 |
| 626.0 | 400.0 | 3.25 | 0.92 | 1.60 | 3.30 | 1222.1 | 1385.2 | 2299.6 | 4081.0 |
| 1295.0 | 425.0 | 3.25 | 1.10 | 1.60 | 3.15 | 1222.1 | 1289.0 | 2299.6 | 3910.2 |
| 1424.0 | 450.0 | 3.25 | 1.16 | 1.60 | 3.14 | 1222.1 | 1341.6 | 2299.6 | 3951.3 |
| 1548.0 | 450.0 | 3.25 | 1.13 | 1.60 | 3.07 | 1222.1 | 1292.0 | 2299.6 | 3948.4 |
| 1648.0 | 450.0 | 3.25 | 1.16 | 1.60 | 3.17 | 1222.1 | 1264.6 | 2299.6 | 3916.0 |
| 1762.0 | 450.0 | 3.25 | 1.26 | 1.60 | 3.11 | 1222.1 | 1234.7 | 2299.6 | 3964.7 |
| 1820.0 | 500.0 | 3.25 | 1.08 | 1.60 | 3.08 | 1222.1 | 1200.8 | 2299.6 | 4065.8 |
| 2749.0 | 500.0 | 3.25 | 1.78 | 1.60 | 2.76 | 1222.1 | 1079.1 | 2299.6 | 3927.5 |
| 2857.0 | 500.0 | 3.25 | 1.92 | 1.60 | 2.75 | 1222.1 | 1065.1 | 2299.6 | 3926.3 |
| 2986.0 | 500.0 | 3.25 | 1.69 | 1.60 | 2.68 | 1222.1 | 1031.1 | 2299.6 | 3910.7 |
| 3118.0 | 500.0 | 3.25 | 1.81 | 1.60 | 2.64 | 1222.1 | 1009.7 | 2299.6 | 3892.2 |

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), Applicants note that unless the context requires otherwise, those words are used on the basis and clear understanding that they are to be interpreted inclusively, rather than exclusively, and that Applicants intend each of those words to be so interpreted in construing this entire specification.

We claim:

1. A process for making an N-(phosphonomethyl)glycine product, the process comprising:

introducing an aqueous feed stream comprising an N-(phosphonomethyl)iminodiacetic acid substrate into an oxidation reactor system;

oxidizing N-(phosphonomethyl)iminodiacetic acid substrate in the oxidation reactor system in the presence of an oxidation catalyst to produce a reaction product solution comprising N-(phosphonomethyl)glycine product;

dividing the reaction product solution into plural fractions comprising a primary fraction and a secondary fraction;

cooling the primary fraction as water is evaporated from the primary fraction under substantially adiabatic conditions by reducing the pressure to precipitate N-(phosphonomethyl)glycine product crystals from the primary fraction to produce a primary product slurry comprising precipitated N-(phosphonomethyl)glycine product crystals and a primary mother liquor; and precipitating N-(phosphonomethyl)glycine product crystals from an aqueous secondary crystallization feed mixture comprising N-(phosphonomethyl)glycine product contained in said secondary fraction to produce a secondary product slurry comprising precipitated N-(phosphonomethyl)glycine product crystals and a secondary mother liquor.

2. The process as set forth in claim 1 wherein water is evaporated from the aqueous secondary crystallization feed mixture to precipitate N-(phosphonomethyl)glycine product crystals from the aqueous secondary crystallization feed mixture.

3. The process as set forth in claim 1 wherein the evaporation cools the primary fraction to a temperature of from about 45° C. to about 80° C.

4. The process as set forth in claim 1 wherein from about 5% to about 30% by weight of the primary fraction is evaporated.

5. The process as set forth in claim 1 further comprising decanting primary mother liquor from the precipitated N-(phosphonomethyl)glycine product crystals in the primary product slurry.

6. The process as set forth in claim 5 further comprising recycling primary mother liquor decanted from the precipitated N-(phosphonomethyl)glycine product crystals in the primary product slurry to the oxidation reactor system for use as a source of process water.

7. The process as set forth in claim 6 wherein substantially all the primary mother liquor decanted from the precipitated N-(phosphonomethyl)glycine product crystals in the primary product slurry is recycled to the oxidation reactor system.

8. The process as set forth in claim 6 wherein the oxidation catalyst comprises a heterogenous catalyst comprising a noble metal deposited on a carbon support.

9. The process as set forth in claim 8 wherein the N-(phosphonomethyl)iminodiacetic acid substrate is oxidized in a liquid reaction medium in contact with the oxidation catalyst and the chloride ion concentration in the liquid reaction medium is maintained at no greater than about 500 ppm by weight.

10. The process as set forth in claim 9 wherein the chloride ion concentration in the liquid reaction medium is maintained at no greater than 300 ppm by weight.

11. The process as set forth in claim 10 wherein the chloride ion concentration in the liquid reaction medium is maintained at no greater than 100 ppm by weight.

12. The process as set forth in claim 9 wherein a source of the N-(phosphonomethyl)iminodiacetic acid substrate is used to prepare the aqueous feed stream introduced into the reactor system and the concentration of chloride ion in the N-(phosphonomethyl)iminodiacetic acid substrate source is less than about 5000 ppm by weight on a dry basis.

13. The process as set forth in claim 12 wherein the concentration of chloride ion in the N-(phosphonomethyl)iminodiacetic acid substrate source is less than about 3000 ppm by weight on a dry basis.

14. The process as set forth in claim 13 wherein the concentration of chloride ion in the N-(phosphonomethyl)iminodiacetic acid substrate source is less than about 2000 ppm by weight on a dry basis.

15. The process as set forth in claim 14 wherein the concentration of chloride ion in the N-(phosphonomethyl)iminodiacetic acid substrate source is less than about 1000 ppm by weight on a dry basis.

16. The process as set forth in claim 1 wherein the process further comprises purging secondary mother liquor for removal of by-products and impurities from the process.

17. The process as set forth in claim 16 wherein substantially all the secondary mother liquor is purged from the process.

18. The process as set forth in claim 1 wherein the primary fraction is from about 30% to about 85% of the reaction product solution.

19. The process as set forth in claim 18 wherein the primary fraction is from about 50% to about 80% of the reaction product solution.

20. The process as set forth in claim 19 wherein the primary fraction is from about 65% to about 75% of the reaction product solution.

21. The process as set forth in claim 18 wherein the reactor system comprises a first and a second oxidation reaction zone in series;
the aqueous feed stream is introduced into the first oxidation reaction zone;
N-(phosphonomethyl)iminodiacetic acid substrate is continuously oxidized in the first oxidation reaction zone to produce an intermediate reaction mixture comprising N-(phosphonomethyl)glycine product and unreacted N-(phosphonomethyl)iminodiacetic acid substrate;
an intermediate aqueous feed stream is introduced into the second oxidation reaction zone, the intermediate aqueous feed stream comprising N-(phosphonomethyl)glycine product obtained in the intermediate reaction mixture and unreacted N-(phosphonomethyl)iminodiacetic acid substrate;
N-(phosphonomethyl)iminodiacetic acid substrate is continuously oxidized in the second oxidation reaction zone to produce the reaction product solution comprising N-(phosphonomethyl)glycine product; and
the reaction product solution is divided into plural fractions comprising the primary and secondary fractions.

22. The process as set forth in claim 21 wherein the oxidation catalyst is in contact with a liquid reaction medium in each of the oxidation reaction zones.

23. The process as set forth in claim 22 wherein the oxidation catalyst comprises a heterogenous particulate catalyst.

24. The process as set forth in claim 23 wherein the heterogeneous particulate catalyst comprises a noble metal deposited on a particulate carbon support.

25. The process of claim 1 wherein evaporative cooling of said primary fraction comprises:
introducing an aqueous evaporation feed mixture into an evaporation zone, said aqueous feed mixture comprising said primary fraction;
evaporating water from said aqueous evaporation feed mixture in said evaporation zone in the presence of solid particulate N-(phosphonomethyl)glycine product, thereby producing a vapor phase comprising water vapor, precipitating N-(phosphonomethyl)glycine product from the aqueous liquid phase, and producing an evaporation product comprising N-(phosphonomethyl)glycine product solids and a primary mother liquor that is substantially saturated or supersaturated in N-(phosphonomethyl)glycine product; and
maintaining a ratio of particulate N-(phosphonomethyl) glycine product solids to primary mother liquor in said evaporation zone which exceeds the ratio of N-(phosphonomethyl)glycine product solids incrementally produced by the effects of evaporation to mother liquor incrementally produced thereby.

26. The process as set forth in claim 25 wherein said evaporation product is divided to provide an N-(phosphonomethyl)glycine product solids fraction that is relatively depleted in mother liquor and a primary mother liquor fraction that is relatively depleted in N-(phosphonomethyl) glycine product solids.

27. The process as set forth in claim 26 wherein maintaining said ratio of particulate N-(phosphonomethyl)glycine product solids to mother liquor in said evaporation zone comprises returning solids obtained in said solids fraction to said evaporation zone or retaining solids obtained in said solid fraction within said zone.

28. The process as set forth in claim 27 comprising:
introducing the aqueous evaporation feed mixture comprising said primary fraction into a vapor/liquid separation zone of said evaporation zone wherein the pressure is below the vapor pressure of said mixture, thereby allowing water to flash from the evaporation feed mixture, producing said vapor phase comprising water vapor, and precipitating N-(phosphonomethyl) glycine product from the aqueous liquid phase to produce a first slurry stream comprising particulate N-(phosphonomethyl)glycine product in a saturated or supersaturated mother liquor;

separating said vapor phase from said first slurry stream;

introducing said first slurry stream into a retention zone in which a supernatant liquid comprising a fraction of said mother liquor is separated from a second slurry stream comprising precipitated N-(phosphonomethyl)glycine product and mother liquor, said retention zone having an inlet for said first slurry, a decantation liquid exit for said supernatant liquid spaced above said inlet, and an exit for said second slurry spaced above said inlet but below said decantation liquid exit; and maintaining the relative rates at which said first slurry is introduced into said retention zone, said second slurry is drawn off through said second slurry exit and said supernatant liquid is drawn off through said decantation liquid exit such that the upward flow velocity in a lower region of said retention zone below said second slurry exit is sufficient to maintain precipitated N-(phosphonomethyl)glycine product in suspension in the liquid phase while the upward flow velocity in an upper region of said retention zone above said second slurry exit is below the sedimentation velocity of at least 80% by weight of the N-(phosphonomethyl)glycine product particles in said lower region.

29. The process as set forth in claim 28 wherein at least a portion of said second slurry stream is recirculated to said vapor/liquid separation zone.

30. The process as set forth in claim 29 wherein at least a portion of said second slurry stream and said primary fraction together comprise the aqueous evaporation feed mixture introduced into said vapor/liquid separation zone.

31. The process as set forth in claim 30 wherein a third slurry stream is removed from said lower region of said zone.

32. The process as set forth in claim 31 wherein the relative rates of the flow of said primary fraction to said vapor/liquid separation zone, recirculation of all or part of said second slurry stream to said vapor/liquid separation zone, withdrawal of said supernatant liquid from said decantation liquid exit, withdrawal of said third slurry stream from said lower region of said retention zone, and return to said evaporation zone of any liquid or solids bearing streams from any solids/liquid separations to which said third slurry may be subjected, are sufficient to establish a ratio of N-(phosphonomethyl)glycine product solids to mother liquor in said lower region of said zone that is higher than the ratio of precipitated solid N-(phosphonomethyl)glycine product incrementally produced by the effects of evaporation of said primary fraction to mother liquor incrementally produced thereby.

33. The process as set forth in claim 32 wherein the relative flow rates of said streams are controlled so that the N-(phosphonomethyl)glycine product solids concentration in said lower region of said zone is at least about twice the concentration of N-(phosphonomethyl)glycine product solids in the mixture of such solids and mother liquor that is or would be produced by flashing of said primary fraction in said vapor/liquid zone in the absence of said recirculated second slurry stream.

34. The process as set forth in claim 33 wherein solids are removed from said third slurry to produce a recycle liquid fraction which is recirculated to said vapor/liquid separation zone, whereby said aqueous evaporation feed mixture further comprises said recycle liquid fraction.

35. The process as set forth in claim 34 wherein both said primary fraction and said recycle liquid fraction are mixed with said second slurry stream prior to introduction into said vapor/liquid separation zone.

36. The process as set forth in claim 21 wherein said secondary fraction is introduced into a secondary reactor system comprising a tertiary oxidation reaction zone, unreacted N-(phosphonomethyl)iminodiacetic acid substrate contained in said secondary fraction being converted to N-(phosphonomethyl)glycine product in said tertiary oxidation reaction zone to produce a tertiary oxidation reaction mixture, said secondary crystallization feed mixture comprising N-(phosphonomethyl)glycine product contained in said tertiary oxidation reaction mixture.

37. The process as set forth in claim 35 wherein the relative flow rates of all of said streams, including said recycle liquid fraction, are controlled so that the solids content of the slurry in said lower region of said zone is at least about 12% by weight.

38. The process as set forth in claim 18 further comprising decanting primary mother liquor from the precipitated N-(phosphonomethyl)glycine product crystals in the primary product slurry.

39. The process as set forth in claim 38 further comprising recycling primary mother liquor to said oxidation reactor system for use as a source of water.

40. The process as set forth in claim 18 further comprising purging secondary mother liquor for removal of by-products and impurities from the process.

41. The process as set forth in claim 18 wherein said oxidation reactor system comprises a series of at least two continuous oxidation reaction zones, the process further comprising:

separating the oxidation catalyst from reaction product solution; and continuously recycling the separated oxidation catalyst to at least one of the oxidation reaction zones.

42. A process for making an N-(phosphonomethyl)glycine product, the process comprising:

introducing an aaueous feed stream comprising an N-(phosphonomethyl)iminodiacetic acid substrate into an oxidation reactor system;

oxidizing the N-(phosphonomethyl)iminodiacetic acid substrate in the oxidation reactor system in the presence of an oxidation catalyst to produce a reaction product solution containing N-(phosphonomethyl)glycine product;

cooling the reaction product solution as water is evaporated from the reaction product solution under substantially adiabatic conditions by reducing the pressure to precipitate N-(phosphonomethyl)glycine product crystals from the reaction product solution and produce a primary product slurry comprising precipitated N-(phosphonomethyl)glycine product crystals and a primary mother liguor;

separating precipitated N-(phosphonomethyl)glycine product from said primary mother liauor; and subiectinq the primary mother liquor to heat-driven evaporative crystallization to thereby evaporate water from the primary mother liquor, precipitate additional N-(phosphonomethyl)qlycine product crystals and produce a secondary mother liquor.

43. The process as set forth in claim 42 wherein the evaporation cools the reaction product solution to a temperature of from about 45° C. to about 80° C.

44. The process as set forth in claim 42 wherein from about 5% to about 30% by weight of the reaction product solution is evaporated.

45. The process as set forth in claim 42 wherein the process further comprises purging secondary mother liquor for removal of by-products and impurities from the process.

46. The process as set forth in claim 45 wherein substantially all the secondary mother liquor is purged from the process.

47. A process for making an N-(phosphonomethyl)glycine product, the process comprising:
introducing an aqueous feed stream comprising an N-(phosphonomethyl)iminodiacetic acid substrate into a primary oxidation reactor system comprising one or more oxidation reaction zones;
oxidizing N-(phosphonomethyl)iminodiacetic acid substrate in the primary oxidation reactor system to produce a reaction product solution comprising N-(phosphonomethyl)glycine product and unreacted N-(phosphonomethyl)iminodiacetic acid substrate;
dividing the reaction product solution into plural fractions comprising a primary fraction and a secondary oxidation reactor feed fraction;
precipitating N-(phosphonomethyl)glycine product crystals from the primary fraction to produce a primary product slurry comprising precipitated N-(phosphonomethyl)glycine product crystals and a primary mother liquor;
introducing the secondary oxidation reactor feed fraction into a secondary oxidation reactor system comprising one or more oxidation reaction zones;
oxidizing N-(phosphonomethyl)iminodiacetic acid substrate in the secondary oxidation reactor system to produce a secondary oxidation reactor effluent comprising N-(phosphonomethyl)glycine product; and
precipitating N-(phosphonomethyl)glycine product crystals from the secondary oxidation reactor effluent to produce a secondary product slurry comprising precipitated N-(phosphonomethyl)glycine product crystals and a secondary mother liquor.

48. The process as set forth in claim 47 wherein the primary fraction is cooled to precipitate N-(phosphonomethyl)glycine product crystals from the primary fraction and water is evaporated from the secondary oxidation reactor effluent to precipitate N-(phosphonomethyl)glycine product crystals from the secondary oxidation reactor effluent.

49. The process as set forth in claim 48 wherein the primary fraction is cooled as water is evaporated from the primary fraction by reducing the pressure.

50. The process as set forth in claim 49 wherein the water is evaporated from the primary fraction under substantially adiabatic conditions.

51. The process as set forth in claim 47 wherein the primary reactor system comprises multiple oxidation reaction zones in series.

52. The process as set forth in claim 51 wherein the reaction product solution is divided after the last oxidation reaction zone in the series.

53. The process as set forth in claim 51 wherein the reaction product solution is divided before the last oxidation reaction zone in the series and the primary fraction passes through at least one further oxidation reaction zone in the primary reactor system before precipitating N-(phosphonomethyl)glycine product crystals from the primary fraction.

54. The process as set forth in claim 47 wherein the primary reactor system comprises a single oxidation reaction zone.

55. The process as set forth in claim 47 wherein the secondary oxidation reactor system comprises a stirred tank reactor.

56. The process as set forth in claim 47 wherein the secondary oxidation reactor system comprises a fixed bed reactor.

57. The process as set forth in claim 56 wherein the fixed bed reactor is operated with cocurrent gas and liquid flows through the oxidation reaction zone.

58. The process as set forth in claim 56 wherein the fixed bed reactor is operated adiabatically.

59. The process as set forth in claim 47 wherein the secondary oxidation reactor feed fraction is cooled prior to introduction into the secondary oxidation reactor system.

60. A process for preparing an N-(phosphonomethyl)glycine product by oxidizing an N-(phosphonomethyl)iminodiacetic acid substrate, the process comprising:
introducing the N-(phosphonomethyl)iminodiacetic acid substrate into a liquid reaction medium within an oxidation reaction zone, the liquid reaction medium comprising the N-(phosphonomethyl)glycine product and having a particulate heterogeneous catalyst for the oxidation reaction suspended therein;
introducing an oxidizing agent into the oxidation reaction zone;
continuously oxidizing the N-(phosphonomethyl)iminodiacetic acid substrate in the liquid reaction medium within the oxidation reaction zone to form the N-(phosphonomethyl)glycine product;
continuously withdrawing a reaction mixture effluent from said oxidation reaction zone, the reaction mixture effluent comprising the N-(phosphonomethyl)glycine product;
continuously separating the particulate catalyst from the reaction mixture effluent to form a catalyst recycle stream comprising the separated catalyst; and
introducing at least a portion of the particulate catalyst contained in the catalyst recycle stream into said oxidation reaction zone.

61. The process as set forth in claim 60 wherein particulate catalyst contained in the catalyst recycle stream passes through at least one other oxidation reaction zone before being introduced into said oxidation reaction zone.

62. The process as set forth in claim 60 wherein particulate catalyst contained in the catalyst recycle stream is introduced directly into said oxidation reaction zone.

63. The process as set forth in claim 60 wherein the particulate catalyst is separated from the reaction mixture effluent in a catalyst filter to form the catalyst recycle stream and a filtrate substantially free of the particulate catalyst and comprising N-(phosphonomethyl)glycine product.

64. The process as set forth in claim 63 wherein the catalyst filter is adapted for continuous separation of the particulate catalyst from the reaction mixture effluent.

65. A process for the preparation of an N-(phosphonomethyl)glycine product comprising:
introducing an aqueous feed mixture comprising an N-(phosphonomethyl)iminodiacetic acid substrate into a liquid reaction medium;
catalytically oxidizing N (phosphonomethyl)iminodiacetic acid substrate in said aqueous liquid reaction medium in the presence of a heterogenous oxidation catalyst comprising a noble metal on carbon thereby producing a reaction mixture comprising N-(phosphonomethyl)glycine product;

cooling a primary crystallization feed mixture comprising N-(phosphonomethyl)glycine product produced in said reaction mixture, thereby precipitating N-(phosphonomethyl)glycine product and producing a primary mother liquor comprising N-(phosphonomethyl)glycine product;

separating precipitated N-(phosphonomethyl)glycine product from said primary mother liquor; and recycling primary mother liquor and introducing it into said liquid reaction medium wherein N-(phosphonomethyl)iminodiacetic acid substrate is oxidized to N-(phosphonomethyl)glycine product.

66. The process as set forth in claim 65 wherein said reaction mixture is divided into a primary fraction and a secondary fraction, said primary crystallization feed mixture comprising N-(phosphonomethyl)glycine product obtained in said primary fraction.

67. The process as set forth in claim 66 wherein N-(phosphonomethyl)glycine product is crystallized from a secondary crystallizer feed mixture comprising N-(phosphonomethyl)glycine product obtained in said secondary fraction, thereby producing a secondary mother liquor comprising N-(phosphonomethyl)glycine product and by-products of said oxidation reaction.

68. The process as set forth in claim 67 wherein an aqueous secondary reactor feed mixture, comprising N-(phosphonomethyl)glycine product obtained in said secondary fraction and unreacted N-(phosphonomethyl)iminodiacetic acid substrate contained therein, is introduced into a secondary oxidation zone wherein unreacted N-(phosphonomethyl)iminodiacetic acid substrate is oxidized to produce a secondary oxidation reaction mixture containing additional N-(phosphonomethyl)glycine product, said secondary crystallizer feed mixture comprising said secondary oxidation reaction mixture.

69. The process as set forth in claim 68 wherein said secondary oxidation zone comprises a fixed bed containing a catalyst for the oxidation.

70. The process as set forth in claim 67 wherein crystallization of N-(phosphonomethyl)glycine product from said primary crystallization feed mixture comprises evaporative cooling of said primary feed mixture.

71. The process as set forth in claim 70 wherein water constituting between about 5% and about 30% by weight of said primary crystallization feed mixture is removed in evaporative cooling thereof.

72. The process as set forth in claim 70 wherein said evaporative cooling is conducted substantially adiabatically.

73. The process as set forth in claim 71 wherein crystallization of said N-(phosphonomethyl)glycine product from said secondary crystallization feed mixture comprises heat-driven evaporative crystallization.

74. The process as set forth in claim 65 wherein N-(phosphonomethyl)iminodiacetic acid substrate is oxidized in said aqueous liquid reaction medium in a primary oxidation reaction zone, thereby producing a primary oxidation product, the process further comprising:

dividing said primary oxidation product into a finishing reaction feed mixture and a primary crystallization fraction, said primary crystallization feed mixture comprising said primary crystallization fraction;

introducing said finishing reaction feed mixture into a finishing reaction zone; and catalytically oxidizing residual N-(phosphonomethyl)iminodiacetic acid substrate contained in said finishing reaction feed mixture to N-(phosphonomethyl)glycine product to produce a finished reaction mixture.

75. The process as set forth in claim 74 wherein said primary oxidation product contains between about 0.5% and about 2% by weight unreacted N-(phosphonomethyl)iminodiacetic acid.

76. The process as set forth in claim 75 wherein a secondary crystallizer feed mixture comprising N-(phosphonomethyl)glycine product obtained in said finished reaction mixture is subjected to heat-driven evaporative crystallization, thereby precipitating N-(phosphonomethyl)glycine product and producing a secondary mother liquor comprising N-(phosphonomethyl)glycine product and by-products of the oxidation of N-(phosphonomethyl)iminodiacetic acid substrate.

77. The process as set forth in claim 65 wherein N-(phosphonomethyl)iminodiacetic acid substrate is continuously oxidized in the presence of said heterogenous oxidation catalyst, said heterogenous oxidation catalyst comprising a noble metal on a particulate carbon support.

78. A process for the preparation of an N-(phosphonomethyl)glycine product comprising:

introducing an aqueous feed mixture comprising an N-(phosphonomethyl)iminodiacetic acid substrate into a catalytic reactor system comprising one or more catalytic reaction zones;

catalytically oxidizing N-(phosphonomethyl)iminodiacetic acid substrate to N-(phosphonomethyl)glycine product in said catalytic reactor system to produce a product mixture comprising N-(phosphonomethyl)glycine product;

dividing said product mixture into a primary fraction and a secondary fraction comprising N-(phosphonomethyl) glycine product;

crystallizing N-(phosphonomethyl)glycine product from said primary fraction to produce a solid N-(phosphonomethyl)glycine product fraction and a primary mother liquor;

recycling primary mother liquor for use as a source of water in the preparation of said feed mixture; and purging at least a portion of the secondary fraction for removal of by-products and impurities from the process.

79. The process as set forth in claim 78 wherein substantially all of said primary mother liquor is recycled as a source of water in the preparation of said feed mixture.

80. The process as set forth in claim 78 wherein N-(phosphonomethyl)glycine is crystallized from said primary fraction by evaporative crystallization.

81. The process as set forth in claim 78 wherein N-(phosphonomethyl)glycine is crystallized from said secondary fraction by evaporative crystallization to produce additional solid N-(phosphonomethyl)glycine product and a secondary mother liquor, and secondary mother liquor is purged from the process for removal of by-products and impurities from the process.

82. The process as set forth in claim 81 wherein N-(phosphonomethyl)glycine is crystallized from said primary fraction by substantially adiabatic evaporative crystallization.

83. The process as set forth in claim 81 wherein said feed mixture is continuously introduced into said reactor system, a reaction zone within said system being substantially backmixed with respect to the liquid phase therein, the exothermic heat of reaction serving to heat the contents of the feed mixture to the reaction temperature prevailing in said back-mixed reaction zone.

84. The process as set forth in claim 83 wherein the catalyst for said reaction comprises a noble metal and is effective to oxidize $C_1$ by-products selected from the group consisting of formaldehyde and formic acid, the oxidation of said $C_1$ by-products further contributing to heating the contents of said aqueous feed mixture.

85. The process as set forth in claim 78 wherein N-(phosphonomethyl)iminodiacetic acid is oxidized in the presence of a heterogeneous catalyst comprising a noble metal, a fraction of noble metal is leached from said catalyst in said catalytic oxidation reactor system, leached noble metal contained in said primary fraction being returned to said catalytic reactor system in said primary mother liquor.

86. The process as set forth in claim 85 wherein leached noble metal contained in said recycle primary mother liquor inhibits further leaching of noble metal from said catalyst in said catalytic reactor system.

87. The process as set forth in claim 85 wherein a portion of leached noble metal contained in said recycle mother liquor is redeposited on the surface of said heterogeneous catalyst in said catalytic reactor system.

88. A continuous process for the catalytic oxidation of an N-(phosphonomethyl)iminodiacetic acid substrate to produce an N-(phosphonomethyl)glycine product, the process comprising:
introducing a liquid phase feed stream comprising an aqueous feed stream comprising the N-(phosphonomethyl)iminodiacetic acid substrate into a primary oxidation reaction zone, the primary oxidation reaction zone comprising a primary fixed bed containing an oxidation catalyst;
introducing an oxidizing agent into the primary oxidation reaction zone;
continuously oxidizing the N-(phosphonomethyl)iminodiacetic acid substrate to the N-(phosphonomethyl)glycine product in the primary oxidation reaction zone, thereby producing a primary reaction mixture comprising the N-(phosphonomethyl)glycine product and unreacted N-(phosphonomethyl)iminodiacetic acid substrate;
withdrawing the primary reaction mixture from the primary oxidation reaction zone; and
maintaining the difference in unit weight sensible heat content between said reaction mixture and said aqueous feed stream less than the exothermic reaction heat generated in the reaction zone per unit weight of the aqueous feed stream.

89. The process as set forth in claim 88 wherein maintaining the difference in unit weight sensible heat content between said reaction mixture and said aqueous feed stream less than the exothermic reaction heat generated in the reaction zone per unit weight of the aqueous feed stream comprises cooling of said fixed bed by indirect transfer of heat to a heat transfer or process fluid flowing through a conduit within or in contact with said bed.

90. The process as set forth in claim 88 wherein maintaining the difference in unit weight sensible heat content between said reaction mixture and said aqueous feed stream less than the exothermic reaction heat generated in the reaction zone per unit weight of the aqueous feed stream comprises introducing into said bed a recirculation fraction comprising N-(phosphonomethyl)glycine product produced in the reaction wherein said recirculation fraction has been cooled externally of said fixed bed.

91. The process as set forth in claim 90 comprising:
dividing the primary reaction mixture into a primary product fraction and a primary reactor circulation fraction;
passing the primary reaction mixture or the primary reactor recirculation fraction through a heat exchanger for removal of heat of oxidation of the N-(phosphonomethyl)iminodiacetic acid substrate; and
returning the primary reactor recirculation fraction to the primary oxidation reaction zone.

92. The process as set forth in claim 91 wherein said primary reaction mixture is passed through said heat exchanger before said primary reaction mixture is divided.

93. The process as set forth in claim 91 wherein the ratio of the volumetric flow rate of the primary reactor recirculation fraction to the volumetric flow rate of the primary product fraction is at least about 0.5:1.

94. The process as set forth in claim 93 wherein the ratio of the volumetric flow rate of the primary reactor recirculation fraction to the volumetric flow rate of the primary product fraction is from about 1:1 to about 10:1.

95. The process as set forth in claim 90 wherein the aqueous feed stream and the primary reactor recirculation fraction are mixed to produce a combined inlet stream, the liquid phase feed stream introduced into the oxidation reaction zone comprising said combined inlet feed stream.

96. The process as set forth in claim 95 wherein the aqueous feed stream comprises a slurry of N-(phosphonomethyl)iminodiacetic acid substrate in a substantially saturated aqueous solution of N-(phosphonomethyl)iminodiacetic acid substrate, and the primary reactor recirculation fraction has a lower N-(phosphonomethyl)iminodiacetic acid substrate content than the aqueous feed stream, whereby the combined inlet stream obtained by mixing the aqueous feed stream with the primary reactor recirculation fraction is substantially free of N-(phosphonomethyl)iminodiacetic acid substrate solids under the conditions prevailing at the liquid inlet region of the primary fixed bed.

97. The process as set forth in claim 96 wherein the aqueous feed stream comprises a slurry containing between about 8% and about 15% N-(phosphonomethyl)iminodiacetic acid substrate and the primary reactor recirculation fraction comprises a solution containing between about 0.5% and about 5% by weight N-(phosphonomethyl)iminodiacetic acid substrate.

98. The process as set forth in claim 88 further comprising:
introducing a second reactor feed mixture comprising at least a portion of the primary product fraction into a second oxidation reaction zone, the second oxidation reaction zone comprising a second fixed bed containing an oxidation catalyst;
introducing an oxidizing agent into the second oxidation reaction zone; and
continuously oxidizing the N-(phosphonomethyl)iminodiacetic acid substrate and a by-product $C_1$ compound in the second oxidation reaction zone to produce a second reaction product mixture containing N-(phosphonomethyl)glycine product.

99. The process as set forth in claim 98 wherein at least 95% of the N-(phosphonomethyl)iminodiacetic acid substrate contained in the aqueous feed stream is oxidized in the primary and second oxidation reaction zones.

100. The process as set forth in claim 99 wherein at least 98% of the N-(phosphonomethyl)iminodiacetic acid substrate contained in the aqueous feed stream is oxidized in the primary and second oxidation reaction zones.

101. The process as set forth in claim 88 wherein the primary fixed bed in the primary oxidation reaction zone contains a noble metal on carbon catalyst.

102. The process as set forth in claim 98 wherein the second fixed bed in the second oxidation reaction zone contains a noble metal on carbon catalyst and the primary fixed bed in the primary oxidation reaction zone consists essentially of carbon catalyst, or contains a noble metal on carbon catalyst having a lower noble metal content than the noble metal on carbon catalyst in the second fixed bed.

103. The process as set forth in claim 98 further comprising:
introducing at least a portion of the second reaction mixture into a third oxidation reaction zone comprising a fixed bed containing an oxidation catalyst;
introducing an oxidizing agent into the third oxidation reaction zone; and
continuously oxidizing a by-product $C_1$ compound in the third oxidation reaction zone to produce a third reaction product mixture containing N-(phosphonomethyl)glycine product.

104. The process as set forth in claim 103 further comprising oxidizing the N-(phosphonomethyl)iminodiacetic acid substrate in the third oxidation reaction zone.

105. The process as set forth in claim 103 wherein the fixed bed in the third oxidation reaction zone contains a noble metal on carbon catalyst, reaction in the third oxidation reaction zone comprising catalytic oxidation of $C_1$ compound remaining in the second reaction mixture.

106. The process as set forth in claim 103 wherein the liquid phase reacting mixture passes through the third fixed bed in substantially plug flow and substantially without recirculation of said third reaction product mixture or other effluent therefrom.

107. The process as set forth in claim 106 wherein the third oxidation reaction zone is operated substantially without back-mixing of the liquid phase reacting mixture.

108. The process as set forth in claim 101 wherein the fixed bed in the primary oxidation reaction zone contains a noble metal on carbon catalyst, a $C_1$ compound being oxidized in the primary oxidation reaction zone.

109. The process as set forth in claim 98 wherein the liquid phase reacting mixture passes through the second fixed bed in substantially plug flow and substantially without recirculation of said second reaction product mixture or other effluent therefrom.

110. The process as set forth in claim 98 wherein the second oxidation reaction zone is operated substantially without back-mixing of the liquid phase reacting mixture.

111. The process as set forth in claim 98 further comprising transferring heat of reaction generated in the second oxidation reaction zone to a cooling fluid.

112. The process as set forth in claim 98 wherein the second oxidation reaction zone operates substantially adiabatically.

113. The process as set forth in claim 88 wherein the oxidizing agent is an $O_2$-containing gas and the integrated average oxygen partial pressure over the liquid phase flow path in the primary oxidation reaction zone is at least about 50 psia.

114. The process as set forth in claim 113 wherein the integrated average oxygen partial pressure over the liquid phase flow path in the primary oxidation reaction zone is at least about 100 psia.

115. The process as set forth in claim 113 wherein the oxygen concentration of the gas phase at the gas exit of the primary oxidation reaction zone is between about 20% and about 30% by volume.

116. The process as set forth in claim 113 wherein oxygen utilization in the primary oxidation reaction zone is between about 50% and about 95%.

117. The process as set forth in claim 88 wherein the integrated average temperature of the liquid phase across the liquid phase flow path through the primary oxidation reaction zone is between about 80° C. and about 130° C.

118. The process as set forth in claim 88 wherein the integrated average temperature of the liquid phase across the liquid phase flow path through the primary oxidation reaction zone is between about 105° C. and about 120° C.

119. The process as set forth in claim 88 wherein the ratio of catalyst surface area to volume of liquid phase reacting mixture in the primary fixed bed is from about 100 to about 6000 $m^2/cm^3$.

120. The process as set forth in claim 119 wherein the ratio of catalyst surface area to volume of liquid phase reacting mixture in the primary fixed bed is from about 200 to about 2000 $m^2/cm^3$.

121. The process as set forth in claim 88 wherein the oxidizing agent is an $O_2$-containing gas and the liquid phase and the gas phase flow co-currently through the primary fixed bed.

122. The process as set forth in claim 88 wherein the oxidizing agent is an $O_2$-containing gas and the liquid phase and the gas phase flow countercurrently through the primary fixed bed.

123. The process as set forth in claim 88 wherein the catalyst activity within the primary fixed bed varies along the liquid phase flow path through the reactor, the activity of the catalyst in an upstream section of the primary fixed bed with respect to the direction of liquid phase flow being lower than the catalyst activity in a downstream section.

124. A process for the catalytic oxidation of an N-(phosphonomethyl)iminodiacetic acid substrate to produce an N-(phosphonomethyl)glycine product, the process comprising:
introducing an aqueous feed stream comprising the N-(phosphonomethyl)iminodiacetic acid substrate into the first of a series of oxidation reaction zones, each of the series of oxidation reaction zones comprising an oxidation catalyst;
oxidizing the N-(phosphonomethyl)iminodiacetic acid substrate to the N-(phosphonomethyl)glycine product in the first oxidation reaction zone to produce an intermediate oxidation reaction product comprising the N-(phosphonomethyl)glycine product and by-product formaldehyde and/or formic acid;
introducing the intermediate oxidation reaction product into a second oxidation reaction zone comprising a fixed bed containing a noble metal on carbon catalyst; and
oxidizing by-product formaldehyde and/or formic acid in the second oxidation reaction zone.

125. The process as set forth in claim 124 wherein the first and second oxidation reaction zones comprise continuous oxidation reaction zones, the aqueous feed stream being continuously or intermittently introduced into the first oxidation reaction zone, the intermediate oxidation product being continuously or intermittently withdrawn from the first oxidation reaction zone and continuously or intermittently introduced into the second oxidation reaction zone.

126. The process as set forth in claim 125 wherein the intermediate oxidation reaction product is cooled prior to being introduced into the second oxidation reaction zone.

127. The process as set forth in claim 126 wherein each of the oxidation reaction zones comprises a fixed bed containing a catalyst for the oxidation of N-(phosphonomethyl)iminodiacetic acid substrate to N-(phosphonomethyl)glycine product, each except the last of the series producing an intermediate reaction product which is introduced into the next succeeding oxidation reaction zone in the series, and a final reaction product comprising N-(phosphonomethyl)glycine product being withdrawn from the last of the oxidation reaction zones.

128. The process as set forth in claim 127 wherein the series comprises more than two oxidation reaction zones, the intermediate reaction product exiting each of the first two of the oxidation reaction zones being cooled before being introduced into the next succeeding oxidation reaction zone.

129. The process as set forth in claim 128 wherein the intermediate reaction product exiting each of the oxidation reaction zones is cooled before being introduced into the next succeeding oxidation reaction zone.

130. The process as set forth in claim 128 wherein said aqueous feed stream contains at least about 15% by weight of a water-soluble salt of N-(phosphonomethyl)iminodiacetic acid on an acid equivalent basis and said final reaction product contains at least about 12% by weight of a water-soluble salt of N-(phosphonomethyl)glycine on an acid equivalent basis.

131. The process as set forth in claim 130 wherein said aqueous feed stream contains at least about 25% by weight of a water-soluble salt of N-(phosphonomethyl)iminodiacetic acid on an acid equivalent basis and said final oxidation reaction product contains at least about 20% by weight of a water-soluble salt of N-(phosphonomethyl)glycine on an acid equivalent basis.

132. The process as set forth in claim 131 wherein said aqueous feed stream contains at least about 35% by weight of a water-soluble salt of N-(phosphonomethyl)iminodiacetic acid on an acid equivalent basis and said final oxidation reaction product contains at least about 28% by weight of a water-soluble salt of N-(phosphonomethyl)glycine on an acid equivalent basis.

133. The process as set forth in claim 130 wherein said final oxidation reaction product is concentrated by removal of water therefrom.

134. The process as set forth in claim 133 wherein said final oxidation reaction product is introduced into a flash evaporation zone wherein the pressure is lower than the vapor pressure of said final oxidation reaction product at the temperature at which it exits the last of said series of reactors.

135. The process as set forth in claim 124 wherein the first oxidation reaction zone comprises a substantially back-mixed oxidation reaction zone within a continuous stirred tank reactor.

136. A continuous process for the catalytic oxidation of an N-(phosphonomethyl)iminodiacetic acid substrate to produce an N-(phosphonomethyl)glycine product, the process comprising:
introducing an aqueous feed stream comprising the N-(phosphonomethyl)iminodiacetic acid substrate into an oxidation reaction zone comprising a fixed bed containing an oxidation catalyst;
introducing an $O_2$-containing gas into the oxidation reaction zone; and
continuously oxidizing the N-(phosphonomethyl)iminodiacetic acid substrate to the N-(phosphonomethyl)glycine product in the oxidation reaction zone, thereby producing an oxidation reaction mixture comprising the N-(phosphonomethyl)glycine product, the ratio of the mass flow rate of the liquid phase to the mass flow rate of gas phase in the fixed bed being between about 20 and about 800.

137. A continuous process for the catalytic oxidation of an N-(phosphonomethyl)iminodiacetic acid substrate to produce an N-(phosphonomethyl)glycine product, the process comprising:
introducing an aqueous feed stream comprising the N-(phosphonomethyl)iminodiacetic acid substrate into an oxidation reaction zone comprising a fixed bed containing an oxidation catalyst;
introducing an $O_2$-containing gas into the oxidation reaction zone; and
continuously oxidizing the N-(phosphonomethyl)iminodiacetic acid substrate to N-(phosphonomethyl)glycine product in the oxidation reaction zone, thereby producing an oxidation reaction mixture comprising the N-(phosphonomethyl)glycine product, the volumetric ratio of the liquid phase holdup in the fixed bed to the total bed volume being between about 0.1 and about 0.5.

138. A continuous process for the catalytic oxidation of an N-(phosphonomethyl)iminodiacetic acid substrate to produce an N-(phosphonomethyl)glycine product, the process comprising:
introducing an aqueous feed stream comprising the N-(phosphonomethyl)iminodiacetic acid substrate into an oxidation reaction zone comprising a fixed bed containing an oxidation catalyst;
introducing an $O_2$-containing gas into the oxidation reaction zone; and
continuously oxidizing the N-(phosphonomethyl)iminodiacetic acid substrate to the N-(phosphonomethyl)glycine product in the oxidation reaction zone, thereby producing an oxidation reaction mixture comprising the N-(phosphonomethyl)glycine product, the partial pressure of oxygen at the liquid exit of the fixed bed being not greater than about 100 psia.

139. The process as set forth in claim 138 wherein the partial pressure of oxygen at the liquid exit of the fixed bed is between about 10 and about 50 psia.

140. A continuous process for the catalytic oxidation of an N-(phosphonomethyl)iminodiacetic acid substrate to produce an N-(phosphonomethyl)glycine product, the process comprising:
introducing an aqueous teed stream comprising the N-(phosphonomethyl)iminodiacetic acid substrate into an oxidation reaction zone comprising a fixed bed containing an oxidation catalyst;
introducing an $O_2$-containing gas into the oxidation reaction zone; and
continuously oxidizing the N-(phosphonomethyl)iminodiacetic acid substrate to the N-(phosphonomethyl)glycine product in the oxidation reaction zone, thereby producing an oxidation reaction mixture comprising the N-(phosphonomethyl)glycine product, the partial pressure of oxygen being not greater than about 50 psia at any location in the fixed bed at which the concentration of N-(phosphonomethyl)iminodiacetic acid substrate in the liquid phase is lower than about 0.1 ppm.

141. The process as set forth in claim 140 wherein the partial pressure of oxygen is not greater than about 50 psia at any location in the fixed bed at which the concentration of N-(phosphonomethyl)iminodiacetic acid substrate in the liquid phase is lower than about 0.2 ppm.

142. A continuous process for the catalytic oxidation of an N-(phosphonomethyl)iminodiacetic acid substrate to produce an N-(phosphonomethyl)glycine product, the process comprising:
introducing an aqueous feed stream comprising the N-(phosphonomethyl)iminodiacetic acid substrate into an oxidation reaction zone comprising a fixed bed containing an oxidation catalyst, the ratio of catalyst surface area to liquid holdup in the fixed bed being between about 100 and about 6000 $m^2/cm^3$;
introducing an oxidizing agent into the oxidation reaction zone; and
continuously oxidizing the N-(phosphonomethyl)iminodiacetic acid substrate to the N-(phosphonomethyl)glycine product in the oxidation reaction zone, thereby producing an oxidation reaction mixture comprising the N-(phosphonomethyl)glycine product.

143. The process as set forth in claim 142 wherein the ratio of catalyst surface area to liquid holdup in the fixed bed is between about 200 and about 2000 $m^2/cm^3$.

144. The process as set forth in claim 143 wherein the ratio of catalyst surface area to liquid holdup in the fixed bed is between about 400 and about 1500 $m^2/cm^3$.

145. The process as set forth in claim 143 wherein the catalyst comprises platinum on carbon and the platinum loading on the catalyst is less than 70% of the loading required to provide equivalent productivity in lbs. N-(phosphonomethyl)glycine product per hour per pound of catalyst at the same temperature in a continuous stirred tank reactor utilizing a platinum on carbon a slurry catalyst.

146. The process as set forth in claim 143 wherein the catalyst comprises a platinum on carbon catalyst containing less than 3 wt % platinum.

147. The process as set forth in claim 142 wherein the integrated average partial pressure of oxygen along the liquid flow path in the fixed bed is at least about 50 psia.

148. The process as set forth in claim 142 wherein the integrated average temperature of the liquid phase in the fixed bed is between about 80° C. and about 130° C.

149. The process as set forth in claim 142 wherein the partial pressure of oxygen is not greater than about 50 psia at any location in the fixed bed at which the concentration of N-(phosphonomethyl)iminodiacetic acid substrate in the liquid phase is lower than about 0.1 ppm.

150. The process as set forth in claim 149 wherein the partial pressure of oxygen is not greater than about 50 psia at any location in the fixed bed at which the concentration of N-(phosphonomethyl)iminodiacetic acid substrate in the liquid phase is lower than about 0.2 ppm.

151. A process as set forth in claim 142 wherein the oxygen utilization in the oxidation reaction zone is between about 50% and about 95%.

152. A continuous process for the catalytic oxidation of an N-(phosphonomethyl)iminodiacetic acid substrate to produce an N-(phosphonomethyl)glycine product, the process comprising:
introducing an aqueous feed stream comprising the N-(phosphonomethyl)iminodiacetic acid substrate into an oxidation reaction zone comprising a fixed bed containing an oxidation catalyst;
introducing an $O_2$-containing gas into the oxidation reaction zone; and
continuously oxidizing the N-(phosphonomethyl)iminodiacetic acid substrate to the N-(phosphonomethyl) glycine product in the oxidation reaction zone, thereby producing an oxidation reaction mixture comprising the N-(phosphonomethyl)glycine product, the integrated average partial pressure of oxygen along the liquid flow path in the fixed bed being at least about 50 psia and the integrated average temperature of the liquid phase in the fixed bed being between about 80° C. and about 130° C.

153. The process as set forth in claim 152 wherein the integrated average partial pressure of oxygen along the liquid flow path in the fixed bed is at least about 100 psia and the integrated average temperature of the liquid phase in the fixed bed is between about 105° C. and about 120° C.

154. The process as set forth in claim 152 wherein the oxygen partial pressure at the liquid exit of the fixed bed is not greater than about 100 psia.

155. The process as set forth in claim 152 wherein the oxygen partial pressure is not greater than about 50 psia at any location in the fixed bed wherein the concentration of N-(phosphonomethyl)iminodiacetic acid substrate in the liquid phase is lower than about 0.1 ppm.

156. A continuous process for the catalytic oxidation of an N-(phosphonomethyl)iminodiacetic acid substrate to produce an N-(phosphonomethyl)glycine product, the process comprising:
introducing an aqueous feed stream comprising the N-(phosphonomethyl)iminodiacetic acid substrate into an oxidation reaction zone comprising a fixed bed containing oxidation catalyst bodies and other means for promoting gas/liquid mass transfer;
introducing an $O_2$-containing gas into the oxidation reaction zone; and
continuously oxidizing the N-(phosphonomethyl)iminodiacetic acid substrate to the N-(phosphonomethyl) glycine product in the oxidation reaction zone, thereby producing an oxidation reaction mixture comprising the N-(phosphonomethyl)glycine product.

157. The process as set forth in claim 156 wherein said other means for promoting gas/liquid mass transfer comprises inert packing.

158. The process as set forth in claim 157 wherein said packing functions as a diluent for the catalyst, thereby modulating the activity of the catalyst bed.

159. The process as set forth in claim 158 wherein the activity of the catalyst bed varies in the direction of fluid flow as a function of variation of the surface area of the catalyst bodies relative to the surface area of the inert packing in said direction.

160. The process as set forth in claim 157 wherein said inert packing is selected from the group consisting of rings, saddles and structured packing.

161. A continuous process for the catalytic oxidation of an N-(phosphonomethyl)iminodiacetic acid substrate to produce an N-(phosphonomethyl)glycine product, the process comprising:
introducing a liquid phase feed stream comprising an aqueous feed mixture comprising the N-(phosphonomethyl)iminodiacetic acid substrate into a primary oxidation reaction zone, the primary oxidation reaction zone comprising a fixed bed containing an oxidation catalyst;
introducing an oxidizing agent into the primary oxidation reaction zone;
continuously oxidizing the N-(phosphonomethyl)iminodiacetic acid substrate to the N-(phosphonomethyl) glycine product in the primary oxidation reaction zone, thereby producing a liquid phase exit stream comprising a primary reaction mixture comprising the N-(phosphonomethyl)glycine product and unreacted N-(phosphonomethyl)iminodiacetic acid substrate; and withdrawing said liquid phase exit stream from the primary oxidation reaction zone, the rate of introduction of said liquid phase feed stream and withdrawal of said liquid phase exit stream being such that the liquid phase hourly space velocity in said fixed bed based on total bed volume is between about 0.5 hr$^{-1}$ and about 20 hr$^{-1}$.

162. The process as set forth in claim 161 wherein the liquid phase hourly space velocity in said fixed bed is between about 3 hr$^{-1}$ and about 20 hr$^{-1}$.

163. The process as set forth in claim 161 wherein the conversion of N-(phosphonomethyl)iminodiacetic acid substrate to N-(phosphonomethyl)glycine product within said fixed bed is at least about 50%.

164. The process as set forth in claim 161 wherein said liquid hourly space velocity in said fixed bed is between about 0.5 hr$^{-1}$ and about 5 hr$^{-1}$ and the conversion of N-(phosphonomethyl)iminodiacetic acid substrate to N-(phosphonomethyl)glycine product within said fixed bed is at least about 95%.

165. The process as set forth in claim 161 wherein the residual N-(phosphonomethyl)iminodiacetic acid substrate in said primary oxidation reaction mixture is not greater than about 0.2 ppm.

166. A process as set forth in claim 165 wherein said aqueous feed mixture contains at least about 15% by weight of a water-soluble salt of N-(phosphonomethyl)iminodiacetic acid on an acid equivalent basis, and wherein a final reaction mixture is produced which contains at least about 12% by weight of a water-soluble salt of N-(phosphonomethyl)glycine on an acid equivalent basis, said final oxidation reaction mixture comprising said primary oxidation reaction mixture, a primary product comprising a fraction of said primary oxidation reaction mixture, or a further reaction mixture obtained by introducing said primary reaction mixture or said primary product fraction into a secondary reaction system comprising one or more additional reaction zones for further oxidation of N-(phosphonomethyl)iminodiacetic acid substrate to N-(phosphonomethyl)glycine product and/or oxidation of formaldehyde or formic acid.

167. The process as set forth in claim 166 wherein said aqueous feed mixture contains at least about 25% by weight of a water-soluble salt of N-(phosphonomethyl)iminodiacetic acid on an acid equivalent basis and said final oxidation reaction mixture contains at least about 20% by weight of a water-soluble salt of N-(phosphonomethyl)glycine on an acid equivalent basis.

168. The process as set forth in claim 167 wherein said aqueous feed mixture contains at least about 35% by weight of a water-soluble salt of N-(phosphonomethyl)iminodiacetic acid on an acid equivalent basis and said final oxidation reaction mixture contains at least about 28% by weight of a water-soluble salt of N-(phosphonomethyl)glycine on an acid equivalent basis.

169. The process as set forth in claim 166 wherein final oxidation reaction mixture is concentrated by removal of water therefrom.

170. The process as set forth in claim 169 wherein said final oxidation reaction mixture is introduced into a flash evaporation zone wherein the pressure is lower than the vapor pressure of said final oxidation reaction mixture at the temperature at which it exits said primary reactor or said secondary reaction system.

171. The process as set forth in claim 169 wherein removal of water from said final oxidation reaction mixture produces a concentrated solution containing at least about 40% by weight of a water-soluble salt of N-(phosphonomethyl)glycine on an acid equivalent basis.

172. The process as set forth in claim 161 wherein the temperature of said liquid phase exit stream from said primary reaction zone is maintained below a reference autogenous adiabatic reaction temperature that would result from absorption by said primary reaction mixture of the heat of reaction generated in said primary reaction zone in the absence of any measure to maintain a lower exit temperature.

173. The process as set forth in claim 172 wherein maintaining the temperature of said liquid phase exit stream below said reference temperature comprises cooling of said fixed bed by indirect transfer of heat to a cooling fluid comprising a heat transfer or process fluid flowing through a conduit within or in contact with said bed.

174. The process as set forth in claim 173 wherein said fixed bed is disposed within the shell or tube side of a shell and tube heat exchanger, said cooling fluid being passed through the other side of the exchanger.

175. The process as set forth in claim 174 wherein said fixed bed comprises multiple component beds separately disposed in the tubes of a shell and tube heat exchanger, said aqueous feed mixture and oxidizing agent being distributed among said component beds for conversion therein of said N-(phosphonomethyl)iminodiacetic acid substrate to said N-(phosphonomethyl)glycine product, said cooling fluid flowing through the shell side of said heat exchanger.

176. The process as set forth in claim 174 wherein said fixed bed is contained within the shell of a shell and tube heat exchanger.

177. The process as set forth in claim 174 wherein said fixed bed comprises a noble metal on carbon catalyst, and the liquid phase reacting mixture passes in substantially plug flow through said fixed bed within said heat exchanger, thereby promoting oxidation of by-product formaldehyde and/or formic acid therein.

178. The process as set forth in claim 172 wherein maintaining the temperature of said liquid phase exit stream below said reference temperature comprises introducing into said fixed bed a recirculation fraction comprising N-(phosphonomethyl)glycine produced in the reaction wherein said recirculation fraction has been cooled externally of said fixed bed, said liquid phase feed stream comprising said aqueous feed mixture and said recirculation fraction.

179. The process as set forth in claim 178 comprising:
dividing the liquid phase exit stream into a primary product fraction and a primary reactor recirculation fraction;
passing the liquid phase exit stream or the primary reactor recirculation fraction through a heat exchanger for removal of heat of oxidation of the N-(phosphonomethyl)iminodiacetic acid substrate; and
returning the primary reactor recirculation fraction to the primary oxidation reaction zone.

180. The process as set forth in claim 179 wherein said liquid phase exit stream is passed through said heat exchanger before said liquid phase exit stream is divided.

181. The process as set forth in claim 161 wherein said catalyst comprises a platinum on carbon catalyst comprising not greater than 3% platinum on a total catalyst basis.

182. A continuous process for the catalytic oxidation of an N-(phosphonomethyl)iminodiacetic acid substrate to produce an N-(phosphonomethyl)glycine product, comprising:
　introducing a first component feed stream comprising an N-(phosphonomethyl)iminodiacetic acid substrate into the first of a series of continuous reaction zones, each of said series of reaction zones comprising an oxidation catalyst;
　introducing an oxidant into said first of said series of reaction zones;
　catalytically oxidizing said substrate in said first reaction zone to produce an intermediate reaction mixture containing N-(phosphonomethyl)glycine product;
　transferring the intermediate reaction mixture exiting said first reaction zone to the second of said series of reaction zones;
　catalytically oxidizing said substrate in each of said series of reaction zones;
　withdrawing an intermediate reaction mixture from each of said reaction zones;
　introducing into each succeeding reaction zone the intermediate reaction mixture produced in the preceding reaction zone;
　introducing an additional component feed stream into each of one or more of said reaction zones succeeding said first reaction zone in said series, each said additional feed stream comprising an N-(phosphonomethyl)iminodiacetic acid substrate;
　introducing an oxidant into one or more said reaction zones succeeding said first reaction zone in said series; and
　withdrawing a final reaction product from the last in said series of reaction zones.

183. A process as set forth in claim 182 wherein an additional component feed stream comprising an N-(phosphonomethyl)iminodiacetic acid substrate is introduced into each of said series of reaction zones.

184. A process as set forth in claim 182 wherein an oxidant is introduced into each of said series of reaction zones.

185. A process as set forth in claim 184 wherein there are at least three continuous reaction zones in said series.

186. A process as set forth in claim 182 wherein one or more of said additional component feed streams contains solid N-(phosphonomethyl)iminodiacetic acid substrate.

187. A process as set forth in claim 182 wherein said N-(phosphonomethyl)iminodiacetic acid substrate comprises a water-soluble salt of N-(phosphonomethyl)iminodiacetic acid and the average concentration of said salt among said component feed streams is such that said final reaction product contains at least about 10% by weight of a water-soluble salt of N-(phosphonomethyl)glycine on an acid equivalent basis.

188. A process as set forth in claim 187 wherein said average concentration of said salt in said component feed streams is such that the final reaction product contains at least about 20% by weight of a water-soluble salt of N-(phosphonomethyl)glycine on an acid equivalent basis.

189. A process as set forth in claim 188 wherein said average concentration of said salt in said component feed streams is such that the final reaction product contains at least about 28% by weight of a water-soluble salt of N-(phosphonomethyl)glycine on an acid equivalent basis.

190. A process set forth in claim 182 wherein the final reaction product is concentrated by removal of water therefrom.

191. A process as set forth in claim 190 wherein said final reaction product is introduced into a flash evaporation zone wherein the pressure is lower than the vapor pressure of said final reaction product at the temperature at which it exits the last in said series of reaction zones.

192. A process as set forth in claim 190 wherein said N-(phosphonomethyl)iminodiacetic acid substrate comprises a water-soluble salt of N-(phosphonomethyl)iminodiacetic acid and removal of water from said final oxidation reaction product produces a concentrated solution containing at least about 40% by weight of a water-soluble salt of N-(phosphonomethyl)glycine on an acid equivalent basis.

193. A process for preparing an N-(phosphonomethyl)glycine product by oxidizing an N-(phosphonomethyl)iminodiacetic acid substrate, the process comprising:
　introducing an aqueous feed stream comprising the N-(phosphonomethyl)iminodiacetic acid substrate into a liquid reaction medium within an oxidation reaction zone provided by an ejector nozzle loop reactor, the oxidation reaction zone being substantially back-mixed in the liquid phase and containing a heterogenous particulate catalyst for the oxidation reaction suspended in the liquid reaction medium, the catalyst comprising a noble metal deposited on a particulate carbon support, the liquid reaction medium comprising the N-(phosphonomethyl)glycine product;
　introducing an oxidizing agent into the oxidation reaction zone;
　continuously oxidizing the N-(phosphonomethyl)iminodiacetic acid substrate in the oxidation reaction zone to form the N-(phosphonomethyl)glycine product; and
　continuously withdrawing a reaction mixture effluent comprising the N-(phosphonomethyl)glycine product from the oxidation reaction zone.

194. The process as set forth in claim 193 wherein the oxidizing agent is an $O_2$-containing gas and is introduced simultaneously with the aqueous feed stream into the oxidation reaction zone through an ejector nozzle of the ejector nozzle loop reactor.

195. A process for preparing an N-(phosphonomethyl)glycine product by oxidizing an N-(phosphonomethyl)iminodiacetic acid substrate, the process comprising:
　introducing an aqueous feed stream comprising the N-(phosphonomethyl)iminodiacetic acid substrate into a liquid reaction medium within an oxidation reaction zone provided by a continuous stirred tank reactor, the oxidation reaction zone being substantially back-mixed in the liquid phase and containing a heterogenous particulate catalyst for the oxidation reaction suspended in the liquid reaction medium, the catalyst comprising a noble metal deposited on a particulate carbon support, the liquid reaction medium comprising the N-(phosphonomethyl)glycine product;
　introducing an oxidizing agent into the oxidation reaction zone;
　continuously oxidizing the N-(phosphonomethyl)iminodiacetic acid substrate in the oxidation reaction zone to form the N-(phosphonomethyl)glycine product; and
　continuously withdrawing a reaction mixture effluent comprising the N-(phosphonomethyl)glycine product from the oxidation reaction zone, the reaction mixture effluent withdrawn from the oxidation reaction zone being substantially free of the particulate catalyst, the stirred tank reactor comprising an internal catalyst filter for preventing the particulate catalyst from being withdrawn from the oxidation reaction zone with the reaction mixture effluent.

196. A process for preparing an N-(phosphonomethyl) glycine product by oxidizing an N-(phosphonomethyl)iminodiacetic acid substrate, the process comprising:

introducing an aqueous feed stream comprising the N-(phosphonomethyl)iminodiacetic acid substrate into a liquid reaction medium within an oxidation reaction zone provided by a continuous stirred tank reactor, the oxidation reaction zone being substantially back-mixed in the liquid phase and containing a heterogenous particulate catalyst for the oxidation reaction suspended in the liquid reaction medium, the catalyst comprising a noble metal deposited on a particulate carbon support, the liquid reaction medium comprising the N-(phosphonomethyl)glycine product;

introducing an oxidizing agent into the oxidation reaction zone;

continuously oxidizing the N-(phosphonomethyl)iminodiacetic acid substrate in the oxidation reaction zone to form the N-(phosphonomethyl)glycine product;

continuously withdrawing a reaction mixture effluent comprising the N-(phosphonomethyl)glycine product and the particulate catalyst from the oxidation reaction zone;

separating the particulate catalyst from the reaction mixture effluent to form a catalyst recycle stream comprising the separated particulate catalyst; and introducing at least a portion of the particulate catalyst contained in the catalyst recycle stream into the oxidation reaction zone.

197. The process as set forth in claim 196 wherein catalyst is purged from the catalyst recycle stream.

198. The process as set forth in claim 197 wherein fresh catalyst is added to the catalyst recycle stream.

199. The process as set forth in claim 196 wherein the particulate catalyst is separated from the reaction mixture effluent in a catalyst filter to form the catalyst recycle stream and a filtrate substantially free of the particulate catalyst and comprising the N-(phosphonomethyl)glycine product.

200. The process as set forth in claim 199 wherein the catalyst filter is adapted for continuous separation of particulate catalyst from the reaction mixture effluent.

201. The process as set forth in claim 200 wherein the catalyst filter is a continuous cross-flow filter.

202. The process as set forth in claim 200 wherein the catalyst filter is a continuous back-pulse filter.

203. The process as set forth in claim 202 wherein the back-pulse filter comprises a filter element and a portion of the filtrate is used to back-pulse the filter element and remove separated catalyst from the filter element.

204. The process as set forth in claim 202 wherein the reaction mixture effluent further comprises dissolved $CO_2$, the reaction mixture effluent being passed through a flash tank before being introduced into the catalyst filter to lower the pressure on the reaction mixture effluent and remove dissolved $CO_2$ from the reaction mixture effluent.

205. The process as set forth in claim 202 wherein at least a portion of the particulate catalyst contained in the catalyst recycle stream passes through a catalyst holding tank before being introduced into the oxidation reaction zone.

206. The process as set forth in claim 205 wherein the catalyst holding tank is substantially free of $O_2$.

207. The process as set forth in claim 206 further comprising introducing a non-oxidizing gas into the catalyst holding tank.

208. The process as set forth in claim 206 wherein the residence time of the recycled catalyst in the catalyst holding tank is at least about 2 minutes.

209. The process as set forth in claim 199 wherein the filtrate comprises unreacted N-(phosphonomethyl)iminodiacetic acid substrate, the process further comprising:

continuously introducing the filtrate into a second oxidation reaction zone;

introducing an oxidizing agent into the second oxidation reaction zone; and continuously oxidizing the N-(phosphonomethyl)iminodiacetic acid substrate in the second oxidation reaction zone to form additional N-(phosphonomethyl)glycine product.

210. The process as set forth in claim 209 wherein the second oxidation reaction zone is substantially back-mixed in the liquid phase.

211. The process as set forth in claim 210 wherein the second oxidation reaction zone is provided by a second stirred tank reactor.

212. The process as set forth in claim 210 wherein the second oxidation reaction zone is provided by an ejector nozzle loop reactor.

213. The process as set forth in claim 209 wherein the second oxidation reaction zone is provided by a fixed bed reactor.

214. A process for preparing an N-(phosphonomethyl) glycine product by oxidizing an N-(phosphonomethyl)iminodiacetic acid substrate in a reactor system, the process comprising:

introducing an aqueous feed stream comprising the N-(phosphonomethyl)iminodiacetic acid substrate into a first oxidation reaction zone provided by an ejector nozzle loop reactor, the first oxidation reaction zone being substantially back-mixed in the liquid phase and containing a heterogenous particulate catalyst for the oxidation reaction suspended in a liquid reaction medium comprising the N-(phosphonomethyl)iminodiacetic acid substrate;

introducing an oxidizing agent into the first oxidation reaction zone;

continuously oxidizing the N-(phosphonomethyl)iminodiacetic acid substrate in the first oxidation reaction zone to form the N-(phosphonomethyl)glycine product;

continuously withdrawing an intermediate reaction mixture effluent comprising the N-(phosphonomethyl)glycine product and unreacted N-(phosphonomethyl)iminodiacetic acid substrate from the first oxidation reaction zone;

continuously introducing an intermediate aqueous teed stream into a second oxidation reaction zone containing a catalyst for the oxidation reaction, the intermediate aqueous feed stream comprising N-(phosphonomethyl) glycine product and unreacted N-(phosphonomethyl) iminodiacetic acid substrate obtained in the intermediate reaction mixture effluent;

introducing an oxidizing agent into the second oxidation reaction zone;

continuously oxidizing the N-(phosphonomethyl)iminodiacetic acid substrate in the second oxidation reaction zone to form additional N-(phosphonomethyl)glycine product; and continuously withdrawing a reaction mixture effluent comprising the N-(phosphonomethyl)glycine product from the second oxidation reaction zone.

215. A process for preparing an N-(phosphonomethyl) glycine product by oxidizing an N-(phosphonomethyl)iminodiacetic acid substrate in a reactor system, the process comprising:

introducing an aqueous feed stream comprising the N-(phosphonomethyl)iminodiacetic acid substrate into a first oxidation reaction zone provided by a continuous stirred tank reactor, the first oxidation reaction zone being substantially back-mixed in the liquid phase and containing a heterogenous particulate catalyst for the oxidation reaction suspended in a liquid reaction medium comprising the N-(phosphonomethyl)iminodiacetic acid substrate;

introducing an $O_2$-containing gas into the first oxidation reaction zone;

continuously oxidizing the N-(phosphonomethyl)iminodiacetic acid substrate in the first oxidation reaction zone to form the N-(phosphonomethyl)glycine product;

continuously withdrawing an intermediate reaction mixture effluent comprising the N-(phosphonomethyl)glycine product and unreacted N-(phosphonomethyl)iminodiacetic acid substrate from the first oxidation reaction zone;

continuously introducing an intermediate aqueous feed stream into a second oxidation reaction zone provided by an ejector nozzle loop reactor, the second oxidation reaction zone being substantially back-mixed in the gas and liquid phases and containing a heterogenous particulate catalyst for the oxidation reaction suspended in a liquid reaction medium comprising the N-(phosphonomethyl)iminodiacetic acid substrate, the intermediate aqueous feed stream comprising N-(phosphonomethyl)glycine product and unreacted N-(phosphonomethyl)iminodiacetic acid substrate obtained in the intermediate reaction mixture effluent;

introducing an $O_2$-containing gas into the second oxidation reaction zone;

continuously oxidizing the N-(phosphonomethyl)iminodiacetic acid substrate in the second oxidation reaction zone to form additional N-(phosphonomethyl)glycine product; and continuously withdrawing a reaction mixture effluent comprising the N-(phosphonomethyl)glycine product from the second oxidation reaction zone.

216. A process for preparing an N-(phosphonomethyl) glycine product by oxidizing an N-(phosphonomethyl)iminodiacetic acid substrate in a reactor system, the process comprising:

introducing an aqueous feed stream comprising the N-(phosphonomethyl)iminodiacetic acid substrate into a first oxidation reaction zone provided by a first continuous stirred tank reactor, the first oxidation reaction zone being substantially back-mixed in the liquid phase and containing a heterogenous particulate catalyst for the oxidation reaction comprising a noble metal deposited on a particulate carbon support and suspended in a liquid reaction medium comprising the N-(phosphonomethyl)iminodiacetic acid substrate, the carbon support exhibiting a particle size distribution such that about 95% of the catalyst particles are from about 3 to about 100 $\mu$m in their largest dimensions, the concentration of the particulate catalyst within the first oxidation reaction zone being from about 0.1 to about 10 wt. % based on the total weight of catalyst and the liquid reaction medium in the oxidation reaction zone;

introducing an oxidizing agent into the first oxidation reaction zone;

continuously oxidizing the N-(phosphonomethyl)iminodiacetic acid substrate in the first oxidation reaction zone to form the N-(phosphonomethyl)glycine product;

continuously withdrawing an intermediate reaction mixture effluent comprising the N-(phosphonomethyl)glycine product and unreacted N-(phosphonomethyl)iminodiacetic acid substrate from the first oxidation reaction zone;

continuously introducing an intermediate aqueous feed stream into a second oxidation reaction zone provided by a second continuous stirred tank reactor, the second oxidation reaction zone being substantially back-mixed in the liquid phase and containing a heterogenous particulate catalyst for the oxidation reaction comprising a noble metal deposited on a particulate carbon support and suspended in a liquid reaction medium comprising the N-(phosphonomethyl)iminodiacetic acid substrate, the carbon support exhibiting a particle size distribution such that about 95% of the catalyst particles are from about 3 to about 100 $\mu$m in their largest dimension, the concentration of the particulate catalyst within the second oxidation reaction zone being from about 0.1 to about 10 wt. % based on the total weight of catalyst and the liquid reaction medium in the oxidation reaction zone, the intermediate aqueous feed stream comprising N-(phosphonomethyl)glycine product and unreacted N-(phosphonomethyl)iminodiacetic acid substrate obtained in the intermediate reaction mixture effluent;

introducing an oxidizing agent into the second oxidation reaction zone;

continuously oxidizing the N-(phosphonomethyl)iminodiacetic acid substrate in the second oxidation reaction zone to form additional N-(phosphonomethyl)glycine product;

continuously withdrawing a reaction mixture effluent comprising the N-(phosphonomethyl)glycine product and the particulate catalyst from the second oxidation reaction zone; and separating the particulate catalyst from the reaction mixture effluent withdrawn from the second oxidation reaction zone to form a catalyst recycle stream comprising the separated catalyst.

217. The process as set forth in claim 216 further comprising introducing at least a portion of the particulate catalyst contained in the catalyst recycle stream into at least one of the first and second oxidation reaction zones.

218. The process as set forth in claim 217 wherein the particulate catalyst is separated from the reaction mixture effluent in a catalyst filter to form the catalyst recycle stream and a filtrate substantially free of the particulate catalyst and comprising the N-(phosphonomethyl)glycine product.

219. The process as set forth in claim 218 wherein the catalyst filter is adapted for continuous separation of particulate catalyst from the reaction mixture effluent.

220. The process as set forth in claim 219 wherein the catalyst filter is a continuous back-pulse filter.

221. The process as set forth in claim 220 wherein the back-pulse filter comprises a filter element and a portion of the filtrate is used to back-pulse the filter element and remove separated catalyst from the filter element.

222. The process as set forth in claim 220 wherein at least a portion of the particulate catalyst contained in the catalyst recycle stream passes through a catalyst holding tank before being introduced into at least one of the first and second oxidation reaction zones.

223. The process as set forth in claim 222 wherein the catalyst holding tank is substantially free of $O_2$.

224. The process as set forth in claim 223 further comprising introducing a non-oxidizing gas into the catalyst holding tank.

225. The process as set forth in claim 223 wherein the residence time of the recycled catalyst in the catalyst holding tank is at least about 2 minutes.

226. The process as set forth in claim 217 wherein at least a portion of the particulate catalyst contained in the catalyst recycle stream is introduced into the first oxidation reaction zone concurrently with the N-(phosphonomethyl)iminodiacetic acid substrate.

227. The process as set forth in claim 217 wherein at least a portion of the particulate catalyst contained in the catalyst recycle stream is introduced into the second oxidation reaction zone concurrently with the unreacted N-(phosphonomethyl)iminodiacetic acid substrate obtained in the intermediate aqueous reaction mixture effluent.

228. The process as set forth in claim 217 wherein a portion of the particulate catalyst contained in the catalyst recycle stream is introduced into the first oxidation reaction zone concurrently with the N-(phosphonomethyl)iminodiacetic acid substrate and another portion of the particulate catalyst contained in the catalyst recycle stream is introduced into the second oxidation reaction zone concurrently with the unreacted N-(phosphonomethyl)iminodiacetic acid substrate obtained in the intermediate aqueous reaction mixture effluent.

229. The process as set forth in claim 217 wherein catalyst is purged from the catalyst recycle stream.

230. The process as set forth in claim 229 wherein fresh catalyst is added to the catalyst recycle stream.

231. A process for preparing an N-(phosphonomethyl)glycine product by oxidizing an N-(phosphonomethyl)iminodiacetic acid substrate in a reactor system, the process comprising:

introducing an aqueous feed stream comprising the N-(phosphonomethyl)iminodiacetic acid substrate into a first oxidation reaction zone provided by a first continuous stirred tank reactor, the first oxidation reaction zone being substantially back-mixed in the liquid phase and containing a heterogenous particulate catalyst for the oxidation reaction comprising a noble metal deposited on a particulate carbon support and suspended in a liquid reaction medium comprising the N-(phosphonomethyl)iminodiacetic acid substrate, the carbon support exhibiting a particle size distribution such that about 95% of the catalyst particles are from about 3 to about 100 $\mu$m in their largest dimensions, the concentration of the particulate catalyst within the first oxidation reaction zone being from about 0.1 to about 10 wt. % based on the total weight of catalyst and the liquid reaction medium in the oxidation reaction zone;

introducing an oxidizing agent into the first oxidation reaction zone;

continuously oxidizing the N-(phosphonomethyl)iminodiacetic acid substrate in the first oxidation reaction zone to form the N-(phosphonomethyl)glycine product;

continuously withdrawing an intermediate reaction mixture effluent comprising the N-(phosphonomethyl)glycine product, unreacted N-(phosphonomethyl)iminodiacetic acid substrate and the particulate catalyst from the first oxidation reaction zone;

separating the particulate catalyst from the intermediate reaction mixture effluent withdrawn from the first oxidation reaction zone to form a catalyst recycle stream comprising the separated catalyst;

introducing at least a portion of the particulate catalyst contained in the catalyst recycle stream into the first oxidation reaction zone concurrently with the N-(phosphonomethyl)iminodiacetic acid substrate;

continuously introducing an intermediate aqueous feed stream into a second oxidation reaction zone provided by a second continuous stirred tank reactor, the second oxidation reaction zone being substantially back-mixed in the liquid phase and containing a heterogenous particulate catalyst for the oxidation reaction comprising a noble metal deposited on a particulate carbon support and suspended in a liquid reaction medium comprising the N-(phosphonomethyl)iminodiacetic acid substrate, the carbon support exhibiting a particle size distribution such that about 95% of the catalyst particles are from about 3 to about 100 $\mu$m in their largest dimension, the concentration of the particulate catalyst within the second oxidation reaction zone being from about 0.1 to about 10 wt. % based on the total weight of catalyst and the liquid reaction medium in the oxidation reaction zone, the intermediate aqueous feed stream comprising N-(phosphonomethyl)glycine product and unreacted N-(phosphonomethyl)iminodiacetic acid substrate obtained in the intermediate reaction mixture effluent;

introducing an oxidizing agent into the second oxidation reaction zone;

continuously oxidizing the N-(phosphonomethyl)iminodiacetic acid substrate in the second oxidation reaction zone to form additional N-(phosphonomethyl)glycine product; and continuously withdrawing a reaction mixture effluent comprising the N-(phosphonomethyl)glycine product from the second oxidation reaction zone.

232. The process as set forth in claim 231 wherein the particulate catalyst is separated from the intermediate reaction mixture effluent in a catalyst filter to form the catalyst recycle stream and a filtrate substantially free of the particulate catalyst and comprising the N-(phosphonomethyl)glycine product and the intermediate aqueous feed stream introduced into the second oxidation reaction zone comprises the filtrate.

233. The process as set forth in claim 232 wherein the reaction mixture effluent withdrawn from the second oxidation reaction zone further comprises the particulate catalyst, the process further comprising separating the particulate catalyst from the reaction mixture effluent withdrawn from the second oxidation reaction zone to form a second catalyst recycle stream comprising the separated catalyst.

234. The process as set forth in claim 233 wherein the particulate catalyst is separated from the reaction mixture effluent in a second catalyst filter to form the second catalyst recycle stream and a second filtrate substantially free of the particulate catalyst and comprising the N-(phosphonomethyl)glycine product.

235. The process as set forth in claim 234 further comprising introducing at least a portion of the particulate catalyst contained in the second catalyst recycle stream into at least one of the first and second oxidation reaction zones.

236. The process as set forth in claim 235 wherein at least a portion of the particulate catalyst contained in the second catalyst recycle stream is introduced into the second oxidation reaction zone concurrently with the unreacted N-(phosphonomethyl)iminodiacetic acid substrate obtained in the intermediate reaction mixture effluent.

237. The process as set forth in claim 236 wherein the average age of the catalyst in the first oxidation reaction zone is different from the average age of the catalyst in the second oxidation reaction zone.

238. The process as set forth in claim 237 wherein the average age of the catalyst in the first oxidation reaction zone is greater than the average age of the catalyst in the second oxidation reaction zone.

239. The process as set forth in claim 237 wherein the average age of the catalyst in the first oxidation reaction zone is less than the average age of the catalyst in the second oxidation reaction zone.

240. The process as set forth in claim 234 wherein the catalyst filters are adapted for continuous separation of particulate catalyst from the intermediate reaction mixture effluent and the reaction mixture effluent.

241. A process for preparing an N-(phosphonomethyl) glycine product by oxidizing an N-(phosphonomethyl)iminodiacetic acid substrate in a reactor system, the process comprising:

introducing an aqueous feed stream comprising the N-(phosphonomethyl)iminodiacetic acid substrate into a first oxidation reaction zone provided by a first continuous stirred tank reactor, the first oxidation reaction zone being substantially back-mixed in the liquid phase and containing a heterogenous particulate catalyst for the oxidation reaction comprising a noble metal deposited on a particulate carbon support and suspended in a liquid reaction medium comprising the N-(phosphonomethyl)iminodiacetic acid substrate, the carbon support exhibiting a particle size distribution such that about 95% of the catalyst particles are from about 3 to about 100 $\mu$m in their largest dimensions, the concentration of the particulate catalyst within the first oxidation reaction zone being from about 0.1 to about 10 wt. % based on the total weight of catalyst and the liquid reaction medium in the oxidation reaction zone;

introducing an oxidizing agent into the first oxidation reaction zone;

continuously oxidizing the N-(phosphonomethyl)iminodiacetic acid substrate in the first oxidation reaction zone to form the N-(phosphonomethyl)glycine product;

cooling the liquid reaction medium in the first oxidation reaction zone;

continuously withdrawing an intermediate reaction mixture effluent comprising the N-(phosphonomethyl)glycine product and unreacted N-(phosphonomethyl)iminodiacetic acid substrate from the first oxidation reaction zone;

continuously introducing an intermediate aqueous feed stream into a second oxidation reaction zone operated adiabatically and provided by a second continuous stirred tank reactor, the second oxidation reaction zone being substantially back-mixed in the liquid phase and containing a heterogenous particulate catalyst for the oxidation reaction comprising a noble metal deposited on a particulate carbon support and suspended in a liquid reaction medium comprising the N-(phosphonomethyl)iminodiacetic acid substrate, the carbon support exhibiting a particle size distribution such that about 95% of the catalyst particles are from about 3 to about 100 $\mu$m in their largest dimension, the concentration of the particulate catalyst within the second oxidation reaction zone being from about 0.1 to about 10 wt. % based on the total weight of catalyst and the liquid reaction medium in the oxidation reaction zone, the intermediate aqueous feed stream comprising N-(phosphonomethyl)glycine product and unreacted N-(phosphonomethyl)iminodiacetic acid substrate obtained in the intermediate reaction mixture effluent;

introducing an oxidizing agent into the second oxidation reaction zone;

continuously oxidizing the N-(phosphonomethyl)iminodiacetic acid substrate in the second oxidation reaction zone to form additional N-(phosphonomethyl)glycine product; and continuously withdrawing a reaction mixture effluent comprising the N-(phosphonomethyl)glycine product from the second oxidation reaction zone.

242. A process for preparing an N-(phosphonomethyl) glycine product by oxidizing an N-(phosphonomethyl)iminodiacetic acid substrate in a reactor system, the process comprising:

introducing an aqueous feed stream comprising the N-(phosphonomethyl)iminodiacetic acid substrate into a first oxidation reaction zone provided by a first continuous stirred tank reactor, the first oxidation reaction zone being substantially back-mixed in the liquid phase and containing a heterogenous particulate catalyst for the oxidation reaction comprising a noble metal deposited on a particulate carbon support and suspended in a liquid reaction medium comprising the N-(phosphonomethyl)iminodiacetic acid substrate, the carbon support exhibiting a particle size distribution such that about 95% of the catalyst particles are from about 3 to about 100 $\mu$m in their largest dimensions, the concentration of the particulate catalyst within the first oxidation reaction zone being from about 0.1 to about 10 wt. % based on the total weight of catalyst and the liquid reaction medium in the oxidation reaction zone;

introducing an oxidizing agent into the first oxidation reaction zone;

continuously oxidizing the N-(phosphonomethyl)iminodiacetic acid substrate in the first oxidation reaction zone to form the N-(phosphonomethyl)glycine product;

cooling the liquid reaction medium in the first oxidation reaction zone;

continuously withdrawing an intermediate reaction mixture effluent comprising the N-(phosphonomethyl)glycine product and unreacted N-(phosphonomethyl)iminodiacetic acid substrate from the first oxidation reaction zone;

continuously introducing an intermediate aqueous feed stream into a second oxidation reaction zone provided by a second continuous stirred tank reactor, the second oxidation reaction zone being substantially back-mixed in the liquid phase and containing a heterogenous particulate catalyst for the oxidation reaction comprising a noble metal deposited on a particulate carbon support and suspended in a liquid reaction medium comprising the N-(phosphonomethyl)iminodiacetic acid substrate, the carbon support exhibiting a particle size distribution such that about 95% of the catalyst particles are from about 3 to about 100 $\mu$m in their largest dimension, the concentration of the particulate catalyst within the second oxidation reaction zone being from about 0.1 to about 10 wt. % based on the total weight of catalyst and the liquid reaction medium in the oxidation reaction zone, the intermediate aqueous feed stream comprising N-(phosphonomethyl)glycine product and unreacted N-(phosphonomethyl)iminodiacetic acid substrate obtained in the intermediate reaction mixture effluent;

introducing an oxidizing agent into the second oxidation reaction zone;

continuously oxidizing the N-(phosphonomethyl)iminodiacetic acid substrate in the second oxidation reaction zone to form additional N-(phosphonomethyl)glycine product;

cooling the liquid reaction medium in the second oxidation reaction zone; and continuously withdrawing a reaction mixture effluent comprising the N-(phosphonomethyl)glycine product from the second oxidation reaction zone.

243. The process as set forth in claim 242 wherein the liquid reaction medium in the second oxidation reaction zone is cooled in an external heat transfer recirculation loop comprising a heat exchanger associated with the second stirred tank reactor.

244. The process as set forth in claim 242 wherein the temperature of the liquid reaction medium in the first oxidation reaction zone is maintained at from about 95° C. to about 105° C. and the temperature of the liquid reaction medium in the second oxidation reaction zone is maintained at from about 100° C. to about 105° C.

245. The process as set forth in claims 1, 42, 47, 60, 65, 78, 88, 124, 136, 137, 138, 140, 142, 152, 156, 161, 182, 193, 195, 196, 214, 215, 216, 231, 241 or 242 wherein the N-(phosphonomethyl)glycine product comprises N-(phosphonomethyl)glycine, the process further comprising converting the N-(phosphonomethyl)glycine to a salt thereof.

246. The process as set forth in claim 245 wherein the N-(phosphonomethyl)glycine is converted to a salt selected from the group consisting of alkali metal salts, alkanolamine salts, alkyl amine salts and alkyl sulfonium salts of N-(phosphonomethyl)glycine.

247. The process as set forth in claim 246 wherein the N-(phosphonomethyl)glycine is converted to the potassium salt of N-(phosphonomethyl)glycine.

248. The process as set forth in claim 246 wherein the N-(phosphonomethyl)glycine is converted to the monoethanolamine salt of N-(phosphonomethyl)glycine.

249. The process as set forth in claim 246 wherein the N-(phosphonomethyl)glycine is converted to the isopropylamine salt of N-(phosphonomethyl)glycine.

* * * * *

UNITED STATES PATENT AND TRADEMARK OFFICE
CERTIFICATE OF CORRECTION

PATENT NO. : 7,015,351 B2
APPLICATION NO. : 09/863885
DATED : March 21, 2006
INVENTOR(S) : Haupfear et al.

It is certified that error appears in the above-identified patent and that said Letters Patent is hereby corrected as shown below:

Column 9, Line 65: "N-phosphonomethyl)iminodiacetic" should read
-- N-(phosphonomethyl)iminodiacetic --.

Column 11, Line 35: "withe" should read -- with --.

Column 22, Line 44: "reformation" should read -- re-formation --.

Column 25, Line 44: "preforming" should read -- pre-forming --.

Column 28, Line 67: "N-methyl-N-phosphonomethyl)glycine" should
read -- N-methyl-N-(phosphonomethyl)glycine --.

Column 34, Line 49: "with a such a metal" should read -- with such a metal --.

Column 42, Line 23: "flash tank may 17" should read -- flash tank 17 may --.

Column 43, Line 29: "to" should be deleted.

Column 43, Line 56: "particularly" should read -- (particularly --.

Column 48, Line 48: "reactor Conversion" should read -- reactor. Conversion --.

Column 52, Line 30: "stream 21 *a*" should read -- stream 21*a* --.

Column 63, Line 18: "fixed be" should read -- fixed bed --.

Column 92, Line 59: "N-(phosphonomethyl)imino" should read
-- N-(phosphonomethyl)iminodiacetic --.

Column 101, Line 27: "N-phosphonomethyl)iminodiacetic"
should read -- N-(phosphonomethyl)iminodiacetic --.

Column 137, Table 43, Line 20: Both Temperatures listed as
"950-100°C" should read -- 95°-100°C --.

Column 138, Table 44, Line 20: "Ri" should read -- R1 --.

Column 148, Line 40: "(200 seem)" should read -- (200 sccm) --.

CERTIFICATE OF CORRECTION (continued)
U.S. Pat. No. 7,015,351 B2

Column 156, Claim 42, Line 41: "aaueous" should read -- aqueous --.

Column 156, Claim 42, Line 59: "liauor" should read -- liquor --.

Column 166, Claim 140, Line 51: "teed" should read -- feed --.

Column 174, Claim 214, Line 48: "teed" should read -- feed --.

Signed and Sealed this

Twenty-third Day of March, 2010

David J. Kappos
*Director of the United States Patent and Trademark Office*